(12) United States Patent
Fung et al.

(10) Patent No.: US 11,224,435 B2
(45) Date of Patent: Jan. 18, 2022

(54) DEVICES AND METHODS FOR LEFT ATRIAL APPENDAGE CLOSURE

(71) Applicant: SentreHEART, Inc., Redwood City, CA (US)

(72) Inventors: Gregory W. Fung, Redwood Shores, CA (US); Robert L. Clark, III, Hayward, CA (US); Russell A. Seiber, Cullowhee, NC (US); Russell Pong, Newark, CA (US); Arnold M. Escano, San Jose, CA (US)

(73) Assignee: SentreHEART LLC, Redwood City, CA (US)

( * ) Notice: Subject to any disclaimer, the term of this patent is extended or adjusted under 35 U.S.C. 154(b) by 0 days.

(21) Appl. No.: 15/713,376

(22) Filed: Sep. 22, 2017

(65) Prior Publication Data

US 2018/0085130 A1    Mar. 29, 2018

Related U.S. Application Data

(60) Provisional application No. 62/399,228, filed on Sep. 23, 2016.

(51) Int. Cl.
*A61B 17/12* (2006.01)
*A61B 90/00* (2016.01)
(Continued)

(52) U.S. Cl.
CPC .... *A61B 17/12122* (2013.01); *A61B 17/0057* (2013.01); *A61B 17/0218* (2013.01);
(Continued)

(58) Field of Classification Search
CPC .......... A61B 2017/00358; A61B 2017/00575; A61B 2017/12018; A61B 17/0057;
(Continued)

(56) References Cited

U.S. PATENT DOCUMENTS

| | | |
|---|---|---|
| 3,677,597 A | 7/1972 | Stipek |
| 3,703,169 A | 11/1972 | Ouchi |

(Continued)

FOREIGN PATENT DOCUMENTS

| | | |
|---|---|---|
| EP | 0 317 490 A2 | 5/1989 |
| EP | 0 598 219 B1 | 5/1994 |

(Continued)

OTHER PUBLICATIONS

International Search Report dated Dec. 4, 2017, for PCT Application No. PCT/US2017/053069, filed on Sep. 22, 2017, 2 pages.

(Continued)

*Primary Examiner* — Diane D Yabut
*Assistant Examiner* — Christina C Lauer
(74) *Attorney, Agent, or Firm* — Cooley LLP

(57) ABSTRACT

Closure devices and methods for ligating tissue, such as the left atrial appendage, generally, include an elongate body having a first lumen therethrough, a snare loop assembly, a vacuum tube, and an imaging device. The snare loop assembly may include a snare and a suture loop releasably coupled to the snare and may at least partially extend from a distal end of the elongate body. The vacuum tube may be slidably positioned within the first lumen to extend through the snare loop assembly. The imaging device may be disposed within the lumen of the vacuum tube.

20 Claims, 65 Drawing Sheets

(51) Int. Cl.
*A61B 17/02* (2006.01)
*A61B 17/00* (2006.01)
*A61B 17/128* (2006.01)
*A61B 17/30* (2006.01)
*A61M 29/00* (2006.01)
*A61B 17/04* (2006.01)
*A61B 90/30* (2016.01)
*A61B 17/122* (2006.01)

(52) U.S. Cl.
CPC ........ *A61B 17/1285* (2013.01); *A61B 90/361* (2016.02); *A61B 17/0467* (2013.01); *A61B 17/0485* (2013.01); *A61B 17/122* (2013.01); *A61B 17/12013* (2013.01); *A61B 2017/00053* (2013.01); *A61B 2017/00243* (2013.01); *A61B 2017/00358* (2013.01); *A61B 2017/306* (2013.01); *A61B 2090/306* (2016.02); *A61B 2090/309* (2016.02); *A61B 2090/3614* (2016.02); *A61B 2090/3782* (2016.02); *A61B 2090/3925* (2016.02); *A61B 2090/3937* (2016.02); *A61B 2090/3966* (2016.02); *A61M 29/00* (2013.01)

(58) Field of Classification Search
CPC ........ A61B 17/12122; A61B 17/32056; A61B 17/12009; A61B 17/122; A61B 17/12013
See application file for complete search history.

(56) References Cited

U.S. PATENT DOCUMENTS

| | | |
|---|---|---|
| 3,841,685 A | 10/1974 | Kolodziej |
| 4,018,229 A | 4/1977 | Komiya |
| 4,217,891 A | 8/1980 | Carson |
| 4,369,768 A | 1/1983 | Vukovic |
| 4,428,375 A | 1/1984 | Ellman |
| 4,579,348 A | 1/1986 | Jones |
| 4,596,530 A | 6/1986 | McGlinn |
| 4,706,655 A | 11/1987 | Krauter |
| 4,759,348 A | 7/1988 | Cawood |
| 4,934,340 A | 6/1990 | Ebling et al. |
| 5,108,406 A | 4/1992 | Lee |
| 5,144,942 A | 9/1992 | Decarie et al. |
| 5,163,949 A | 11/1992 | Bonutti |
| 5,176,691 A | 1/1993 | Pierce |
| 5,234,455 A | 8/1993 | Mulhollan |
| 5,279,539 A | 1/1994 | Bohan et al. |
| 5,281,238 A | 1/1994 | Chin et al. |
| 5,312,423 A | 5/1994 | Rosenbluth et al. |
| 5,336,229 A | 8/1994 | Noda |
| 5,336,231 A | 8/1994 | Adair |
| 5,373,840 A | 12/1994 | Knighton |
| 5,403,331 A | 4/1995 | Chesterfield et al. |
| 5,417,697 A | 5/1995 | Wilk et al. |
| 5,465,731 A | 11/1995 | Bell et al. |
| 5,494,240 A | 2/1996 | Waugh |
| 5,540,711 A | 7/1996 | Kieturakis et al. |
| 5,545,178 A | 8/1996 | Kensey et al. |
| 5,676,636 A | 10/1997 | Chin |
| 5,681,278 A | 10/1997 | Igo et al. |
| 5,683,348 A | 11/1997 | Diener |
| 5,699,748 A | 12/1997 | Linskey, Jr. et al. |
| 5,735,877 A | 4/1998 | Pagedas |
| 5,741,281 A | 4/1998 | Martin |
| 5,766,151 A | 6/1998 | Valley et al. |
| 5,769,863 A | 6/1998 | Garrison |
| 5,800,414 A | 9/1998 | Cazal |
| 5,814,052 A | 9/1998 | Nakao et al. |
| 5,855,586 A | 1/1999 | Habara et al. |
| 5,865,791 A | 2/1999 | Whayne et al. |
| 5,893,869 A | 4/1999 | Barnhart et al. |
| 5,906,579 A | 5/1999 | Vander Salm et al. |
| 5,906,620 A | 5/1999 | Nakao et al. |
| 5,908,429 A | 6/1999 | Yoon |
| RE36,269 E | 8/1999 | Wright |
| 5,931,787 A | 8/1999 | Dietz et al. |
| 5,947,953 A | 9/1999 | Ash et al. |
| 5,957,936 A | 9/1999 | Yoon et al. |
| 5,961,440 A | 10/1999 | Schweich, Jr. et al. |
| 6,045,570 A | 4/2000 | Epstein et al. |
| 6,067,942 A | 5/2000 | Fernandez |
| 6,071,281 A | 6/2000 | Burnside et al. |
| 6,152,936 A | 11/2000 | Christy et al. |
| 6,210,416 B1 | 4/2001 | Chu et al. |
| 6,221,007 B1 | 4/2001 | Green |
| 6,312,404 B1 | 11/2001 | Agro et al. |
| 6,423,051 B1 | 7/2002 | Kaplan et al. |
| 6,488,689 B1 | 12/2002 | Kaplan et al. |
| 6,789,509 B1 | 9/2004 | Motsinger |
| 7,041,111 B2 | 5/2006 | Chu |
| 7,226,458 B2 | 6/2007 | Kaplan et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,610,104 B2 | 10/2009 | Kaplan et al. |
| 7,618,425 B2 | 11/2009 | Yamamoto et al. |
| 7,736,347 B2 | 6/2010 | Kaplan et al. |
| 7,828,810 B2 | 11/2010 | Liddicoat et al. |
| 7,846,168 B2 | 12/2010 | Liddicoat et al. |
| 7,918,865 B2 | 4/2011 | Liddicoat et al. |
| 7,967,808 B2 | 6/2011 | Fitzgerald et al. |
| 8,157,818 B2 | 4/2012 | Gartner et al. |
| 8,469,983 B2 | 6/2013 | Fung et al. |
| 8,636,767 B2 | 1/2014 | McClain |
| 8,647,367 B2 * | 2/2014 | Kassab ............ A61B 17/00491 604/509 |
| 8,715,302 B2 | 5/2014 | Ibrahim et al. |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,974,473 B2 | 3/2015 | Kaplan et al. |
| 8,986,278 B2 | 3/2015 | Fung et al. |
| 8,986,325 B2 | 3/2015 | Miller et al. |
| 8,996,133 B2 | 3/2015 | Kaplan et al. |
| 9,089,324 B2 | 7/2015 | McCaw et al. |
| 9,144,431 B2 | 9/2015 | Friedman et al. |
| 9,186,174 B2 | 11/2015 | Krishnan et al. |
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,408,608 B2 | 8/2016 | Clark et al. |
| 9,463,024 B2 | 10/2016 | Kiser et al. |
| 9,486,281 B2 | 11/2016 | Fung et al. |
| 9,498,206 B2 | 11/2016 | Fung et al. |
| 9,498,223 B2 | 11/2016 | Miller et al. |
| 9,522,006 B2 | 12/2016 | Liddicoat et al. |
| 9,668,671 B2 | 6/2017 | Friedman et al. |
| 9,724,105 B2 | 8/2017 | Kaplan et al. |
| 9,848,898 B2 | 12/2017 | Friedman et al. |
| 9,907,954 B2 | 3/2018 | Kassab et al. |
| 9,936,956 B2 | 4/2018 | Fung et al. |
| 10,045,784 B2 | 8/2018 | Friedman et al. |
| 10,052,168 B2 | 8/2018 | Krishnan |
| 10,130,369 B2 | 11/2018 | Fung et al. |
| 10,251,650 B2 | 4/2019 | Clark et al. |
| 10,258,408 B2 | 4/2019 | Fung et al. |
| 10,292,710 B2 | 5/2019 | Clark et al. |
| 10,405,919 B2 | 9/2019 | Fung et al. |
| 10,716,571 B2 | 7/2020 | Fung et al. |
| 10,799,241 B2 | 10/2020 | Fung et al. |
| 10,799,288 B2 | 10/2020 | Fung et al. |
| 10,806,460 B2 | 10/2020 | Liddicoat et al. |
| 10,959,734 B2 | 3/2021 | Fung et al. |
| 10,959,752 B2 | 3/2021 | Fung et al. |
| 10,966,725 B2 | 4/2021 | Miller et al. |
| 11,020,122 B2 | 6/2021 | Miller et al. |
| 11,026,690 B2 | 6/2021 | Fung et al. |

(56) References Cited

U.S. PATENT DOCUMENTS

| | | | |
|---|---|---|---|
| 2002/0016564 A1* | 2/2002 | Courtney | A61B 17/22 604/96.01 |
| 2002/0103492 A1 | 8/2002 | Kaplan et al. | |
| 2002/0111637 A1 | 8/2002 | Kaplan et al. | |
| 2002/0147456 A1 | 10/2002 | Diduch et al. | |
| 2004/0059352 A1 | 3/2004 | Burbank et al. | |
| 2004/0102804 A1 | 5/2004 | Chin | |
| 2004/0116943 A1 | 6/2004 | Brandt et al. | |
| 2004/0162579 A1 | 8/2004 | Foerster | |
| 2004/0225300 A1 | 11/2004 | Goldfarb et al. | |
| 2004/0260273 A1 | 12/2004 | Wan | |
| 2005/0043743 A1 | 2/2005 | Dennis | |
| 2005/0080454 A1 | 4/2005 | Drews et al. | |
| 2006/0004323 A1 | 1/2006 | Chang et al. | |
| 2006/0020336 A1 | 1/2006 | Liddicoat | |
| 2006/0100545 A1 | 5/2006 | Ayala et al. | |
| 2006/0200169 A1 | 9/2006 | Sniffin | |
| 2006/0253128 A1 | 11/2006 | Sekine et al. | |
| 2006/0253129 A1 | 11/2006 | Liddicoat et al. | |
| 2007/0038229 A1 | 2/2007 | del la Torre | |
| 2007/0088369 A1 | 4/2007 | Shaw et al. | |
| 2007/0100405 A1 | 5/2007 | Thompson et al. | |
| 2007/0135822 A1 | 6/2007 | Onuki et al. | |
| 2007/0156217 A1 | 7/2007 | Kaplan et al. | |
| 2007/0156220 A1 | 7/2007 | Kaplan et al. | |
| 2007/0270637 A1 | 11/2007 | Takemoto et al. | |
| 2008/0065156 A1 | 3/2008 | Hauser et al. | |
| 2008/0097489 A1 | 4/2008 | Goldfarb et al. | |
| 2008/0177179 A1 | 7/2008 | Stubbs et al. | |
| 2008/0269782 A1 | 10/2008 | Stefanchik et al. | |
| 2008/0294175 A1* | 11/2008 | Bardsley | A61B 17/12009 606/113 |
| 2009/0043317 A1 | 2/2009 | Cavanaugh et al. | |
| 2010/0204716 A1 | 8/2010 | Stewart et al. | |
| 2011/0112569 A1* | 5/2011 | Friedman | A61B 5/042 606/205 |
| 2011/0276075 A1 | 11/2011 | Fung et al. | |
| 2011/0282250 A1 | 11/2011 | Fung et al. | |
| 2011/0295060 A1 | 12/2011 | Zenati et al. | |
| 2012/0095434 A1* | 4/2012 | Fung | A61B 17/3421 604/500 |
| 2012/0323262 A1 | 12/2012 | Ibrahim et al. | |
| 2012/0330351 A1 | 12/2012 | Friedman et al. | |
| 2013/0144311 A1* | 6/2013 | Fung | A61B 17/12013 606/139 |
| 2014/0018831 A1 | 1/2014 | Kassab et al. | |
| 2014/0171733 A1 | 6/2014 | Sternik | |
| 2014/0222138 A1 | 8/2014 | Machold et al. | |
| 2014/0316385 A1 | 10/2014 | Longoria et al. | |
| 2014/0336572 A1 | 11/2014 | Heisei et al. | |
| 2014/0336676 A1 | 11/2014 | Pong et al. | |
| 2014/0364901 A1 | 12/2014 | Kiser et al. | |
| 2014/0364907 A1 | 12/2014 | White et al. | |
| 2014/0371741 A1 | 12/2014 | Longoria et al. | |
| 2015/0018853 A1 | 1/2015 | Friedman et al. | |
| 2015/0173765 A1 | 1/2015 | Friedman et al. | |
| 2015/0157328 A1 | 6/2015 | Miller et al. | |
| 2015/0182225 A1 | 7/2015 | Morejohn et al. | |
| 2015/0190135 A1 | 7/2015 | Ibrahim et al. | |
| 2015/0223813 A1 | 8/2015 | Willisamson et al. | |
| 2015/0250482 A1 | 9/2015 | Slaughter et al. | |
| 2015/0272618 A1 | 10/2015 | Fung et al. | |
| 2015/0313633 A1 | 11/2015 | Gross et al. | |
| 2015/0374380 A1 | 12/2015 | Miller et al. | |
| 2016/0008001 A1 | 1/2016 | Winkler et al. | |
| 2016/0008061 A1 | 1/2016 | Fung et al. | |
| 2016/0022273 A1 | 1/2016 | Kassab | |
| 2016/0074043 A1 | 3/2016 | Friedman et al. | |
| 2016/0106421 A1 | 4/2016 | Eliachar et al. | |
| 2016/0120549 A1 | 5/2016 | Fung et al. | |
| 2016/0235412 A1 | 8/2016 | Liddicoat et al. | |
| 2016/0249932 A1 | 9/2016 | Rogers et al. | |
| 2016/0310144 A1 | 10/2016 | Kimura et al. | |
| 2016/0317155 A1 | 11/2016 | Kimura et al. | |
| 2016/0346028 A1 | 12/2016 | Rogers et al. | |
| 2017/0119435 A1 | 5/2017 | Gross et al. | |
| 2017/0128075 A1 | 5/2017 | Friedman et al. | |
| 2017/0209141 A1 | 7/2017 | Fung et al. | |
| 2017/0245866 A1 | 8/2017 | Kiser et al. | |
| 2017/0290591 A1 | 10/2017 | Liddicoat et al. | |
| 2017/0290592 A1 | 10/2017 | Miller et al. | |
| 2017/0325819 A1 | 11/2017 | Kaplan et al. | |
| 2018/0000485 A1 | 1/2018 | Ad | |
| 2018/0036514 A1 | 2/2018 | Kassab et al. | |
| 2018/0193635 A1 | 7/2018 | Kassab et al. | |
| 2018/0303488 A1 | 10/2018 | Hill | |
| 2018/0310941 A1 | 11/2018 | Fung et al. | |
| 2018/0325523 A1 | 11/2018 | Friedman et al. | |
| 2019/0125350 A1 | 5/2019 | Fung et al. | |
| 2019/0262067 A1 | 8/2019 | Fung et al. | |
| 2019/0274690 A1 | 9/2019 | Clark et al. | |
| 2019/0290285 A1 | 9/2019 | Liddicoat et al. | |
| 2019/0298376 A1 | 10/2019 | Clark et al. | |
| 2019/0298382 A1 | 10/2019 | Fung et al. | |
| 2021/0015483 A1 | 1/2021 | Fung et al. | |

FOREIGN PATENT DOCUMENTS

| | | |
|---|---|---|
| EP | 0 705 566 A1 | 4/1996 |
| EP | 1 010 397 A | 6/2000 |
| EP | 1685802 A1 | 8/2006 |
| JP | H-07-299073 A | 11/1995 |
| JP | 11-507262 A | 6/1999 |
| JP | 2003-225241 A | 8/2003 |
| JP | 2005-110860 A | 4/2005 |
| JP | 2005-296645 A | 10/2005 |
| WO | WO-96/40356 A1 | 12/1996 |
| WO | WO-98/17187 A1 | 4/1998 |
| WO | WO-00/16850 A1 | 3/2000 |
| WO | WO-2004/066828 A2 | 8/2004 |
| WO | WO-2005/034802 A2 | 4/2005 |
| WO | WO-2008/017080 A2 | 2/2008 |
| WO | WO-2008/121278 A2 | 10/2008 |
| WO | WO-2009/039191 A2 | 3/2009 |
| WO | WO-2016/005902 A1 | 1/2016 |
| WO | WO-2017/109923 A1 | 6/2017 |
| WO | WO-2019/191316 | 10/2019 |

OTHER PUBLICATIONS

Written Opinion of the International Search Report dated Dec. 4, 2017, for PCT Application No. PCT/US2017/053069, filed on Sep. 22, 2017, 4 pages.

Afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

(56) References Cited

OTHER PUBLICATIONS

Benjamin, B.A. et al. (1994). "Effect of Bilateral Atrial Appendectomy on Postprandial Sodium Excretion in Conscious Monkeys," *Society for Experimental Biology and Medicine* 2006: 1 page.
Beygui, F. et al. (2005, e-pub. Oct. 21, 2005). "Multimodality Imaging of Percutaneous Closure of the Left Atrial Appendage," *Clinical Vignette*, 1 page.
Bisleri, G. et al. (Jun. 3, 2005). "Innovative Monolateral Approach for Closed-Chest Atrial Fibrillation Surgery," *The Annals of Thoracic Surgery* 80:e22-e25.
Björk, V.O. et al. (Aug. 1961). "Sequelae of Left Ventricular Puncture with Angiocardiography," *Circulation* 24:204-212.
Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.
Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.
Bonanomi, G. et al. (Jan. 1, 2003). "Left Atrial Appendectomy and Maze," *Journal of the American College of Cardiology* 41(1):169-171.
Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.
Botham, R.J. et al. (May 1959). "Pericardial Tamponade Following Percutaneous Left Ventricular Puncture," *Circulation* 19:741-744.
Brock, R. et al. (1956). "Percutaneous Left Ventricular Puncture in the Assessment of Aortic Stenosis," *Thorax* 11:163-171.
Burke, R.P. et al. (1992). "Improved Surgical Approach to Left Atrial Appendage Aneurysm," *Journal of Cardiac Surgery* 7(2):104-107.
Canaccord Adams (Aug. 11, 2008). "A-Fib: Near A Tipping Point," 167 pages.
Chung, M.K. (Jul. 2003). "Current Clinical Issues in Atrial Fibrillation," *Cleveland Clinic Journal of Medicine* 70(Supp. 3):S6-S11.
Coffin, L.H. (Jun. 1985). "Use of the Surgical Stapler to Obliterate the Left Atrial Appendage," *Surgery, Gynecology & Obstetric* 160:565-566.
Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.
Costa, R. et al. (2006). "Bi-Atrial Subxiphoid Epicardial Pacemaker in Superior Vena Cava Syndrome," *Arq. Bras. Cardiol.* 87:e45-e47.
Cox, J.L. et al. (Apr. 1991). "The Surgical Treatment of Atrial Fibrillation: IV. Surgical Technigue," *J. Thorac. Cardiovasc. Surg.* 101(4):584-592.
Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.
Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.
Cox, J.L. et al. (Nov. 1999). "Impact of the Maze Procedure on the Stroke Rate in Patients with Atrial Fibrillation," *J. Thorac. Cardiovasc. Surg.* 118:833-840.
Cox, J.L. et al. (2004). "The Role of Surgical Intervention in the Management of Atrial Fibrillation," *Texas Heart Institute Journal* 31(3):257-265.
Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.
D'Avila, A. et al. (Apr. 2003). "Pericardial Anatomy for the Interventional Electrophysiologist," *Journal of Cardiovascular Electrophysiology* 14(4):422-430.
D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.
Demaria, A.N. et al. (Dec. 17, 2003). "Highlights of the Year JACC 2003," *Journal of the American College of Cardiology* 42(12):2156-2166.
Deneu, S. et al. (Jul. 11, 1999). "Catheter Entrapment by Atrial Suture During Minimally Invasive Port-access Cardiac Surgery," *Canadian Journal of Anesthesia* 46(10):983-986.
Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.
Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.
Donnino, R. et al. (2007). "Left Atrial Appendage Thrombus Outside of a 'Successful' Ligation," *European Journal of Echocardiography* pp. 1-2.
Dullum, M.K.C. et al. (1999). "Xyphoid MIDCAB: Report of the Technique and Experience with a Less Invasive MIDCAB Procedure," *Heart Surgery Forum* 2(1):77-81.
Feinberg, W.M. et al. (Mar. 13, 1995). "Prevalence, Age Distribution, and Gender of Patients With Atrial Fibrillation," *Arch Intern Med* 155:469-473.
Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.
Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr et al. (Apr. 1986). "Complications of Transluminal Angioplasty," *Radiology* 159:201-208.
Gillinov, A.M. (2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta In Aortography and Renal Arteriography," *Annals of Surgery* 132(5):944-958.
Gottlieb, L.K. et al. (Sep. 12, 1994). "Anticoagulation in Atrial Fibrillation," *Arch Intern Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Journal of the American Heart Association* 19(8):937-941.
Halperin, J.L. et al. (Oct. 1, 2003). "Obliteration of the Left Atrial Appendage for Prevention of Thromboembolism," *Journal of the American College of Cardiology* 42(7):1259-1261.
Hammill, S.C. (May 2006). "Epicardial Ablation: Reducing the Risks," *J. Cardiovasc. Electrophysiol.* 17:550-552.

(56) References Cited

OTHER PUBLICATIONS

Hara, H. et al. (Jan. 2008). "Percutaneous Left Atrial Appendage Obliteration," *JACC: Cardiovascular Imagin* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (2001). "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," *presented at* the Canadian Cardiovascular Congress 2003, Toronto, Canada, Abstract No. 666, 2 pages.
Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.
Hein, R. et al. (2005). "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.
Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
Inoue, Y. et al. (Jul.-Aug. 1997). "Video Assisted Thoracoscopic and Cardioscopic Radiofrequency Maze Ablation," *Asaio Journal* 43(4):334-337, Abstract Only.
Jaïs, P. et al. (2003). "Radiofrequency Ablation for Atrial Fibrillation," *European Society of Cardiology* 5(Supplement H):H34-H39.
Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.
Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.
Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.
Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.
Kerut, E.K. et al. (Jul. 2008). "Anatomy of the Left Atrial Appendage," *Echocardiography* 25(6):669-673.
Khargi, K. et al. (2005). "Surgical Treatment of Atrial Fibrillation: A Systematic Review," *European Journal of Cardiothoracic Surgery* 27:258-265.

Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.
Kistler, P.M. et al. (May 2007). "The Left Atrial Appendage: Not Just an Innocent Bystander," *J. Cardiovasc Electrophysiol* 18(5):465-466.
Klein, H. et al. (Apr. 1990). "The Implantable Automatic Cardioverter-Defibrillator," *Herz* 15(2):111-125, Abstract Only.
Kolb, C. et al. (Feb. 2004). "Incidence of Antitachycardia Therapy Suspension Due to Magnet Reversion in Implantable Cardioverter Defibrillators," *Pace* 27:221-223.
Krikorian, J.G. et al. (Nov. 1978). "Pericardiocentesis," *Am. J. Med.* 65(5):808-814.
Krum, D. et al. (2004). "Visualization of Remnants of the left Atrial Appendage Following Epicardial Surgical Removal," *Heart Rhythm* 1:249.
Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.
Lacomis, J.M. et al. (2007, e-pub. Oct. 17, 2007). "Dynamic Multidimensional Imaging of the Human Left Atrial Appendage," *Europace* 9:1134-1140.
Lee, R. et al. (1999). "The Closed Heart MAZE: A Nonbypass Surgical Technique," *The Annals of Thoracic Surgery* 67:1696-1702.
Levinson, M.L. et al. (1998). "Minimally Invasive Atrial Septal Defect Closure Using the Subxyphoid Approach," *Heart Surg. Forum* 1(1):49-53, Abstract Only.
Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.
Li, H. (2007). "Magnet Decoration, Beautiful But Potentially Dangerous For Patients with Implantable Pacemakers or Defibrillators," *Heart Rhythm* 4(1):5-6.
Lindsay, B.D. (1996). "Obliteration of the Left Atrial Appendage: A Concept Worth Testing," *The Annals of Thoracic Surgery* 61:515.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.
Macris, M. et al. (Jan. 1999). "Minimally Invasive Access of the Normal Pericardium: Initial Clinical Experience with a Novel Device," *Clin. Cardiol.* 22(Suppl. I):I-36-I-39.
Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-Jan. 17, 22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measure and Emergency Management," *Ches Surg Clin N Am.* 7(2):213-226, Abstract Only.
McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.
McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.
McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.
Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.

(56) References Cited

OTHER PUBLICATIONS

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.

Morris, J.J. Jr. (1979). "Transvenous versus Transthoracic Cardiac Pacing," Chapter 16 in *Cardiac Pacing: A Concise Guide to Clinical Practice*, pp. 239-245.

Mráz, T. et al. (Apr. 2007). "Role of Echocardiography in Percutaneous Occlusion of the left Atrial Appendage," *Echocardiography* 24(4):401-404.

Naclerio, E.A. et al. (1979). "Surgical Techniques for Permanent Ventricular Pacing," Chapter 10 in *Cardiac Pacing: A Concise Guide to Clinical Practice*, pp. 145-168.

Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.

Odell, J.A. et al. (1996). "Thorascopic Obliteration of the Left Atrial Appendage: Potential for Stroke Reduction?" *Ann. Thorac. Surg.* 61:565-569.

O'Donnell, M. et al. (2005). "Emerging Therapies for Stroke Prevention in Atrial Fibrillation," *European Heart Journal* 7(Supplement C):C19-C27.

Omran, H. et al. (1997). "Left Atrial Appendage Function in Patients with Atrial Flutter," *Heart* 78:250-254.

Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part2):624-630.

Ostermayer, S. et al. (2003). "Percutaneous Closure of the Left Atrial Appendage," *Journal of Interventional Cardiology* 16(6):553-556.

Ota, T. et al. (2006). "Epicardial Atrial Ablation Using a Novel Articulated Robotic Medical Probe via a Percutaneous Subxiphoid Approach," *National Institute of Health* 1(6):335-340.

Ota, T. et al. (Oct. 2007). "Impact of Beating Heart left Atrial Ablation on Left-sided Heart Mechanics," *The Journal of Thoracic and Cardiovascular Surgery* 134:982-988.

Pennec, P-Y. et al. (2003). "Assessment of Different Procedures for Surgical Left Atrial Appendage Exclusion," *The Annals of Thoracic Surgery* 76:2167-2168.

Perk, G. et al. (Aug. 2009). "Use of Real Time Three-Dimensional Transesophageal Echocardiography in Intracardiac Catheter Based Interventions," *J. Am Soc Echocardiogr* 22(8):865-882.

Pollick C. (Feb. 2000). "Left Atrial Appendage Myopathy," *Chest* 117(2):297-308.

Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.

Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.

Robicsek, F. (1987). "Closed-Chest Decannulation of Transthoracically Inserted Aortic Balloon Catheter without Grafting," *Journal of Cardiac Surgery* 2(2):327-329.

Ross, J. Jr. et al. (Jun. 3, 2008). "Transseptal Left Heart Catheterization: A 50-Year Odyssey," *Journal of the American College of Cardiology* 51(22):2107-2115.

Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.

Ruchat, P. et al. (2002). "Off-pump Epicardial Compartmentalization for Ablation of Atrial Fibrillation," *Interactive Cardio Vascular and Thoracic Surgery* 1:55-57.

Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *Journal of Cardiovascular Electrophysiology* 12(12):1411-1414.

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablation," *Circulation* 108:1329-1335.

Schweikert, R.A. et al. (2005). "Epicardial Access: Present and Future Applications for Interventional Electrophysiologists," Chapter 25 in *New Arrhythmia Technolqies*, Wang, P.J. ed., Blackwell Publishing, pp. 242-256.

Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Centricular Tachycardia," *Journal of Cardiovasc. Electrphsiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and

(56) References Cited

OTHER PUBLICATIONS

Blunts Sodium and Water Excretion During Volume Loading in Conscious Dogs," *Circulation Research* 70(4):724-732.
Stewart, S. (1974). "Placement of the Sutureless Epicardial Pacemaker Lead by the Subxiphoid Approach," *Ann. of Thoracic Surg.* 18(3):308-313.
Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.
Stokes, K. (Jun. 1990). "Implantable Pacing Lead Technology," *IEEE Engineering in Medicine and Biology* pp. 43-49.
Stöllberger, C. et al. (2000). "Is the Left Atrial Appendage Our Most Lethal Attachment?" *European Journal of Cardio-Thoracic Surgery* 18:625-626.
Stöllberger, C. et al. (Dec. 2003). "Elimination of the Left Atrial Appendage To Prevent Stroke or Embolism?: Anatomic, Physiologic, and Pathophysiologic Considerations," 124(6):2356-2362.
Stöllberger, C. et al. (2006). "Stroke Prevention by Means of Epicardial Occlusion of the Left Atrial Appendage," *Journal of Thoracic and Cardiovascular Surgery* 132(1):207-208.
Stöllberger, C. et al. (2007). "Arguments Against Left Atrial Appendage Occlusion for Stroke Prevention," *Stroke* 38:e77.
Stöllberger, C. et al. (2007). "Leave the Left Atrial Appendage Untouched for Stroke Prevention!" *Journal of Thoracic and Cardiovascular Surgery* 134(2):549-550.
Su, P. et al. (Sep. 2008, e-pub. May 8, 2007). "Occluding the Left Atrial Appendage: Anatomical Considerations," *Heart* 94(9):1166-1170.
Subramanian, V.A. (Jun. 1997). "Less Invasive Arterial CABG on a Beating Heart," *Ann. Thorac. Surg.* 63(6 Suppl.):S68-S71.
Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.
Suehiro, S. et al. (1995). "Echocardiography-Guided Pericardiocentesis With a Needle Attached to a Probe," *Ann. Thoracic Surg.* 61:741-742.
Sun, F. et al. (Feb. 2006). "Subxiphoid Access to Normal Pericardium with Micropuncture Set: Technical Feasibility Study in Pigs," *Radiology* 238(2):719-724.
Szili-Torok, T. et al. (2001). "Transseptal Left heart Catheterisation Guided by Intracardiac Echocardiography," *Heart* 86:e11-e15.
Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Institutional Experience," *Indian Heart Journal* 58(4):325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With New-Onset Atrial Fibrillation in the Community," *American Medical Association* 290(8):1049-1056.
Watkins, L. et al. (Nov. 1982). "Implantation of the Automatic Defibrillator: The Subxiphoid Approach," *Ann. of Thoracic Surg.* 34(5):515-520.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (Aug. 1991). "Atrial Fibrillation as an Independent Risk Factor For Stroke: The Framingham Study," *Stroke* 22(8):983-988.
Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion In Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
International Preliminary Report on Patentability dated Mar. 26, 2019, for PCT Application No. PCT/US2017/053069, filed on Sep. 22, 2017, 5 pages.
International Preliminary Report on Patentability dated Oct. 6, 2009, for PCT Application No. PCT/US2008/003938, filed on Mar. 25, 2008, 11 pages.
International Search Report dated Feb. 27, 2007, for PCT Application No. PCT/US2008/003938, filed on Mar. 25, 2008, 6 pages.
Written Opinion of the International Searching Authority dated Feb. 27, 2007, for PCT Application No. PCT/US2008/003938, filed on Mar. 25, 2008, 10 pages.
Non-Final Office Action dated Nov. 15, 2010, for U.S. Appl. No. 12/055,213, filed Mar. 25, 2008, 18 pages.
Non-Final Office Action dated Apr. 28, 2011, for U.S. Appl. No. 12/055,213, filed Mar. 25, 2008, 20 pages.
Final Office Action dated Oct. 28, 2011, for U.S. Appl. No. 12/055,213, filed Mar. 25, 2008, 15 pages.
Non-Final Office Action dated Sep. 18, 2013, for U.S. Appl. No. 12/055,213, filed Mar. 25, 2008, 15 pages.
Notice of Allowance dated Mar. 4, 2014, for U.S. Appl. No. 12/055,213, filed Mar. 25, 2008, 9 pages.
Extended European Search Report dated Mar. 1, 2013, for European Patent Application No. 12186090.2, filed on Mar. 25, 2008, 7 pages.
Non-Final Office Action dated Oct. 27, 2011, for U.S. Appl. No. 12/363,359, filed Jan. 30, 2009, 11 pages.
Final Office Action dated May 4, 2012, for U.S. Appl. No. 12/363,359, filed Jan. 30, 2009, 10 pages.
Non-Final Office Action dated Jun. 17, 2014, for U.S. Appl. No. 12/363,359, filed Jan. 30, 2009, 7 pages.

(56) References Cited

OTHER PUBLICATIONS

Final Office Action dated Nov. 14, 2014, for U.S. Appl. No. 12/363,359, filed Jan. 30, 2009, 10 pages.
Non-Final Office Action dated Sep. 10, 2015, for U.S. Appl. No. 12/363,359, filed Jan. 30, 2009, 12 pages.
Final Office Action dated Mar. 17, 2016, for U.S. Appl. No. 12/363,359, filed Jan. 30, 2009, 9 pages.
Notice of Allowance dated Jul. 29, 2016, for U.S. Appl. No. 12/363,359, filed Jan. 30, 2009, 8 pages.
Extended European Search Report dated Jul. 10, 2015, for European Patent Application No. 15153029.2, filed on Mar. 25, 2008, 6 pages.
Non-Final Office Action dated Nov. 9, 2011, for U.S. Appl. No. 12/363,381, filed Jan. 30, 2009, 10 pages.
Final Office Action dated May 16, 2012, for U.S. Appl. No. 12/363,381, filed Jan. 30, 2009, 8 pages.
Notice of Allowance dated Apr. 1, 2014, for U.S. Appl. No. 12/363,381, filed Jan. 30, 2009, 9 pages.
Notice of Allowance dated Dec. 29, 2014, for U.S. Appl. No. 12/363,381, filed Jan. 30, 2009, 9 pages.
Final Office Action dated Jun. 8, 2017, for U.S. Appl. No. 14/625,540, filed Feb. 18, 2015, 14 pages.
Final Office Action dated Sep. 6, 2018, for U.S. Appl. No. 14/625,540, filed Feb. 18, 2015, 15 pages.
Non-Final Office Action dated Dec. 2, 2016, for U.S. Appl. No. 14/625,540, filed Feb. 18, 2015, 19 pages.
Non-Final Office Action dated Jan. 26, 2018, for U.S. Appl. No. 14/625,540, filed Feb. 18, 2015, 15 pages.
Non-Final Office Action dated Mar. 27, 2019, for U.S. Appl. No. 14/625,540, filed Feb. 18, 2015, 14 pages.
Non-Final Office Action dated Mar. 15, 2019, for U.S. Appl. No. 15/634,982, filed Jun. 27, 2017, 10 pages.
Extended European Search Report dated Feb. 10, 2017, for EP Application No. 10759425.1, filed on Apr. 1, 2010, 7 pages.
Extended European Search Report dated Feb. 20, 2019, for EP Application No. 18211384.5, 8 pages.
International Search Report dated Jun. 1, 2010, for PCT Application No. PCT/US2010/029668, filed on Apr. 1, 2010, 2 pages.
Written Opinion of the International Searching Authority dated Jun. 1, 2010, for PCT Application No. PCT/US2010/029668, filed on Apr. 1, 2010, 8 pages.
International Preliminary Report on Patentability dated Apr. 10, 2011, for PCT Application No. PCT/US2010/029668, filed on Apr. 1, 2010, 9 pages.
Non-Final Office Action dated Mar. 29, 2013, for U.S. Appl. No. 12/752,873, filed Apr. 1, 2010, 15 pages.
Final Office Action dated Jan. 13, 2014, for U.S. Appl. No. 12/752,873, filed Apr. 1, 2010, 10 pages.
Non-Final Office Action dated Nov. 10, 2014, for U.S. Appl. No. 12/752,873, filed Apr. 1, 2010, 10 pages.
Notice of Allowance dated Jul. 22, 2015, for U.S. Appl. No. 12/752,873, filed Apr. 1, 2010, 8 pages.
Non-Final Office Action dated Jan. 12, 2018, for U.S. Appl. No. 14/928,836, filed Oct. 30, 2015, 11 pages.
Final Office Action dated Nov. 23, 2018, for U.S. Appl. No. 14/928,836, filed Oct. 30, 2015, 10 pages.
Non-Final Office Action dated May 30, 2019, for U.S. Appl. No. 14/928,836, filed Oct. 30, 2015, 10 pages.
Supplementary European Search Report dated Aug. 14, 2006, for EP Patent Application No. 00957904.6, filed on Aug. 29, 2000, 6 pages.
International Search Report dated Oct. 26, 2000, for PCT Application No. PCT/US2000/023727, filed on Aug. 29, 2000, 1 page.
Final Office Action dated Feb. 10, 2005, for U.S. Appl. No. 10/105,978, filed Mar. 25, 2002, 7 pages.
Final Office Action dated Mar. 14, 2006, for U.S. Appl. No. 10/105,978, filed Mar. 25, 2002, 8 pages.
Non-Final Office Action dated Jun. 17, 2004, for U.S. Appl. No. 10/105,978, filed Mar. 25, 2002, 6 pages.
Non-Final Office Action dated Aug. 18, 2004, for U.S. Appl. No. 10/105,978, filed Mar. 25, 2002, 6 pages.
Non-Final Office Action dated Jul. 20, 2005, for U.S. Appl. No. 10/105,978, filed Mar. 25, 2002, 6 pages.
Non-Final Office Action dated Jan. 25, 2007, for U.S. Appl. No. 10/105,978, filed Mar. 25, 2002, 9 pages.
Notice of Allowance dated Aug. 15, 2006, for U.S. Appl. No. 10/105,978, filed Mar. 25, 2002, 7 pages.
Notice of Allowance dated Sep. 18, 2007, for U.S. Appl. No. 10/105,978, filed Mar. 25, 2002, 2 pages.
Notice of Allowance dated Aug. 22, 2007, for U.S. Appl. No. 10/105,978, filed Mar. 25, 2002, 6 pages.
Supplemental Notice of Allowance dated Oct. 6, 2006, for U.S. Appl. No. 10/105,978, filed Mar. 25, 2002, 2 pages.
Final Office Action dated Aug. 31, 2011, for U.S. Appl. No. 11/944,522, filed Nov. 23, 2007, 7 pages.
Final Office Action dated Jan. 29, 2013, for U.S. Appl. No. 11/944,522, filed Nov. 23, 2007, 8 pages.
Final Office Action dated Jan. 7, 2014, for U.S. Appl. No. 11/944,522, filed Nov. 23, 2007, 9 pages.
Non-Final Office Action dated Jul. 10, 2012, for U.S. Appl. No. 11/944,522, filed Nov. 23, 2007, 8 pages.
Non-Final Office Action dated Apr. 12, 2010, for U.S. Appl. No. 11/944,522, filed Nov. 23, 2007, 6 pages.
Non-Final Office Action dated Dec. 15, 2010, for U.S. Appl. No. 11/944,522, filed Nov. 23, 2007, 6 pages.
Non-Final Office Action dated Aug. 9, 2013, for U.S. Appl. No. 11/944,522, filed Nov. 23, 2007, 8 pages.
Non-Final Office Action dated Jul. 1, 2014, for U.S. Appl. No. 11/944,522, filed Nov. 23, 2007, 9 pages.
Notice of Allowance dated Oct. 24, 2014, for U.S. Appl. No. 11/944,522, filed Nov. 23, 2007, 8 pages.
Notice of Allowance dated Dec. 26, 2013, for U.S. Appl. No. 13/160,441, filed Jun. 14, 2011, 9 pages.
Notice of Allowance dated Aug. 6, 2013, for U.S. Appl. No. 13/160,441, filed Jun. 14, 2011, 8 pages.
Notice of Allowance dated Apr. 13, 2017, for U.S. Appl. No. 14/604,632, filed Jan. 23, 2015, 7 pages.
Non-Final Office Action dated Jul. 2, 2019, for U.S. Appl. No. 15/669,637, filed Aug. 4, 2017, 9 pages.
Final Office Action dated Sep. 12, 2019, for U.S. Appl. No. 14/625,540, filed Feb. 18, 2015, 16 pages.
International Search Report and Written Opinion dated Aug. 19, 2019, for PCT Application No. PCT/US2019/024413, filed on Mar. 27, 2019, 19 pages.
Final Office Action dated Sep. 17, 2019, for U.S. Appl. No. 14/928,836, filed Oct. 30, 2015, 11 pages.
Final Office Action dated Sep. 26, 2019, for U.S. Appl. No. 15/634,982, filed Jun. 27, 2017, 7 pages.
Non-Final Office Action dated Mar. 20, 2020 for U.S. Appl. No. 14/625,540, filed Feb. 18, 2015, 15 pages.
Extended European Search Report dated May 11, 2020 for EP Application No. 17854032.4, 9 pages.
Notice of Allowance dated May 28, 2020 for U.S. Appl. No. 14/928,836, filed Oct. 30, 2015, 8 pages.
Notice of Allowance dated Jul. 13, 2020 for U.S. Appl. No. 14/928,836, filed Oct. 30, 2015, 3 pages.
Non-Final Office Action dated Jul. 29, 2020 for U.S. Appl. No. 15/634,982, filed Jun. 27, 2017, 9 pages.
Corrected Notice of Allowance dated Sep. 18, 2020 for U.S. Appl. No. 14/928,836, filed Oct. 30, 2015, 3 pages.
Notice of Allowance dated Dec. 3, 2020 for U.S. Appl. No. 14/625,540, filed Feb. 18, 2015, 10 pages.
Notice of Allowance dated Jan. 22, 2021 for U.S. Appl. No. 15/634,982, filed Jun. 27, 2017, 5 pages.

* cited by examiner

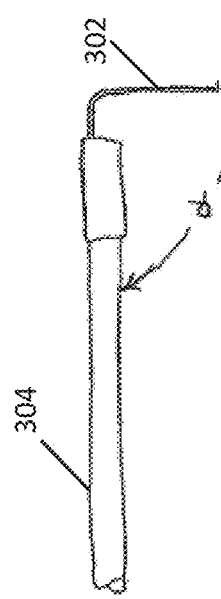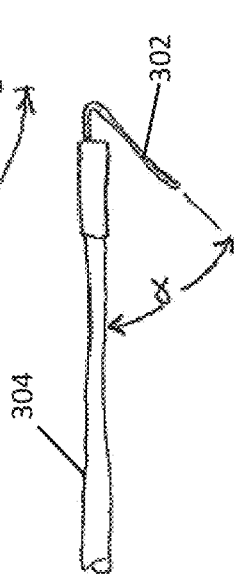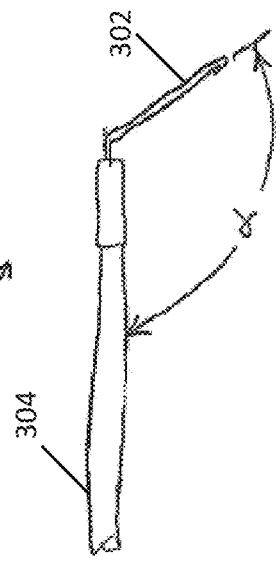

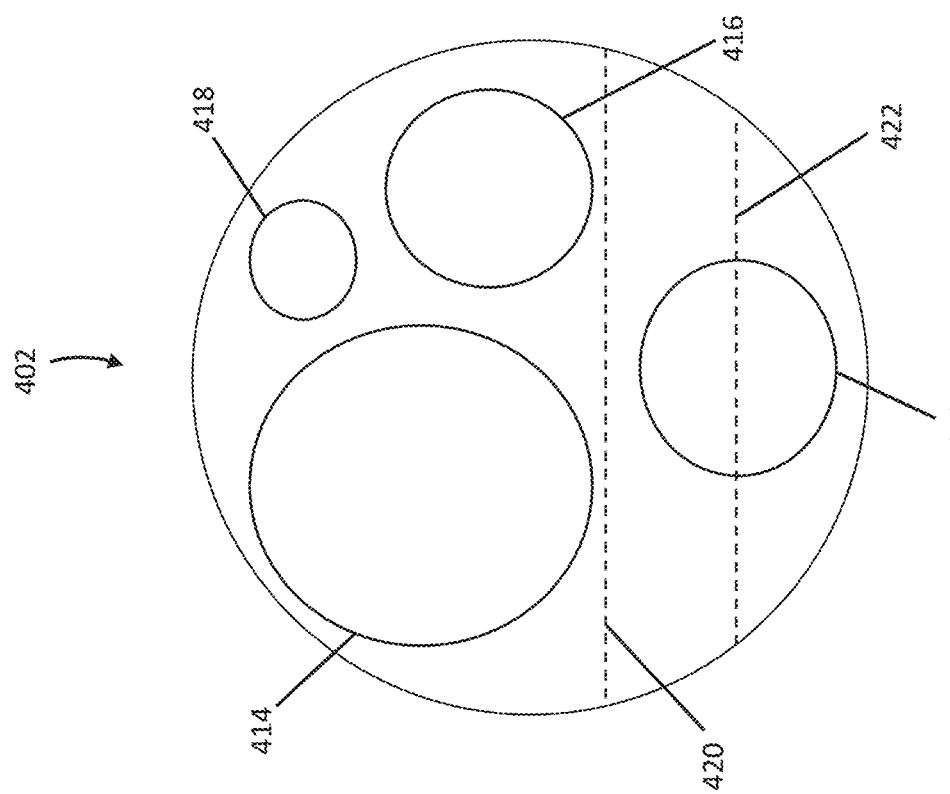

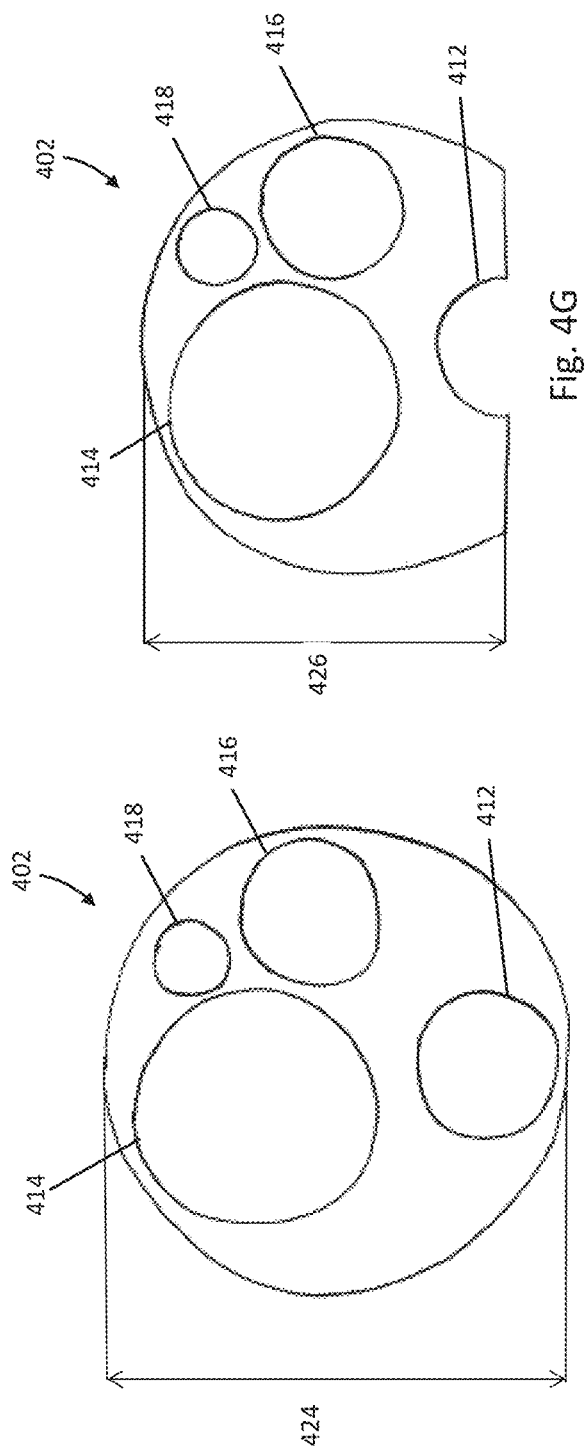

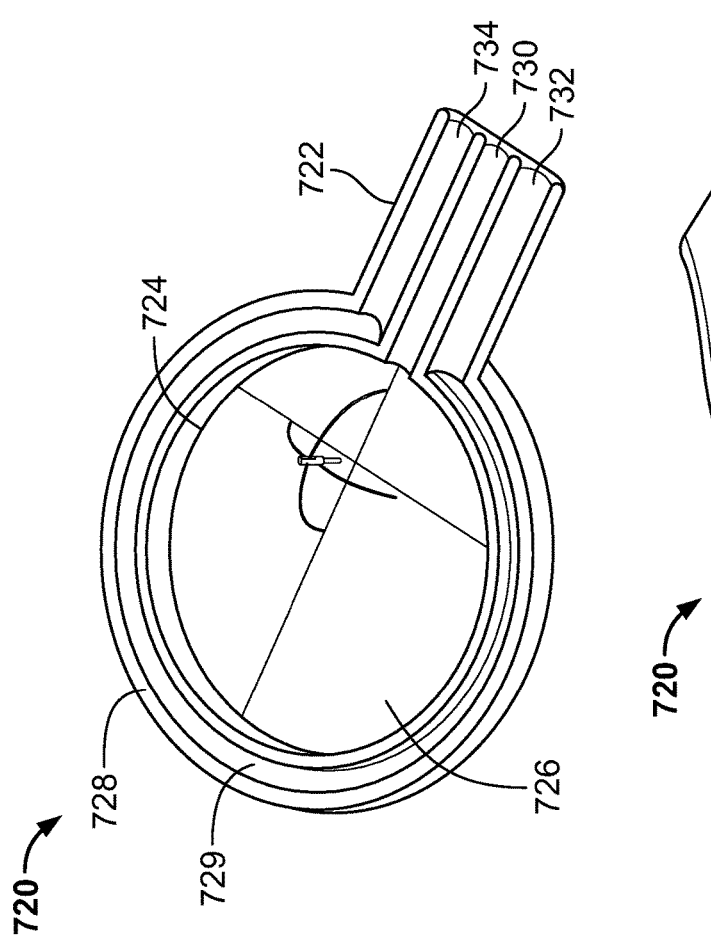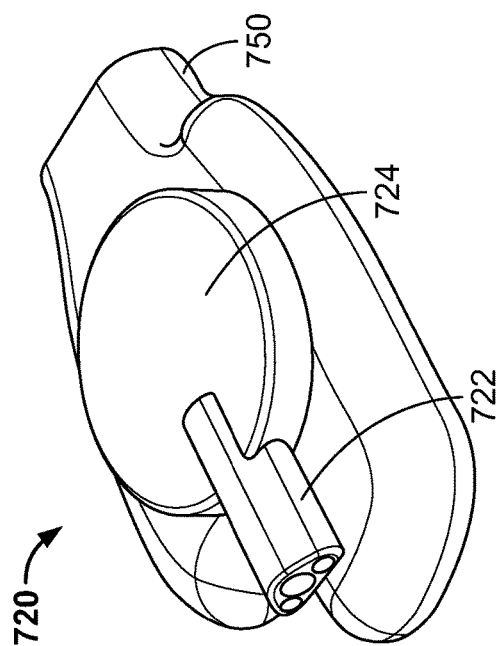

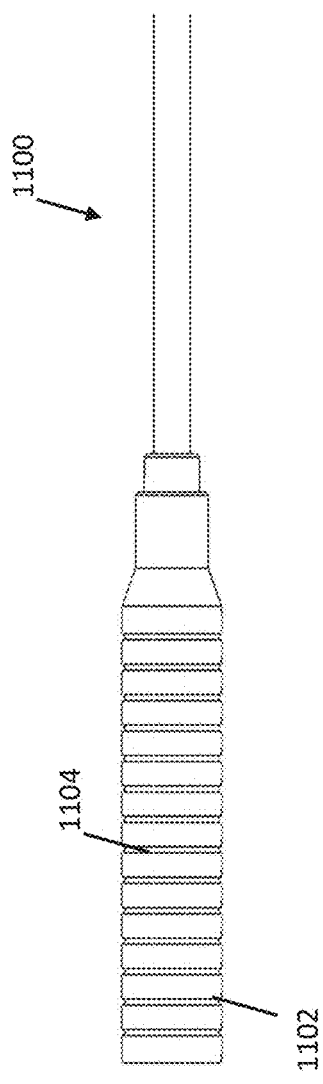
Fig. 11A
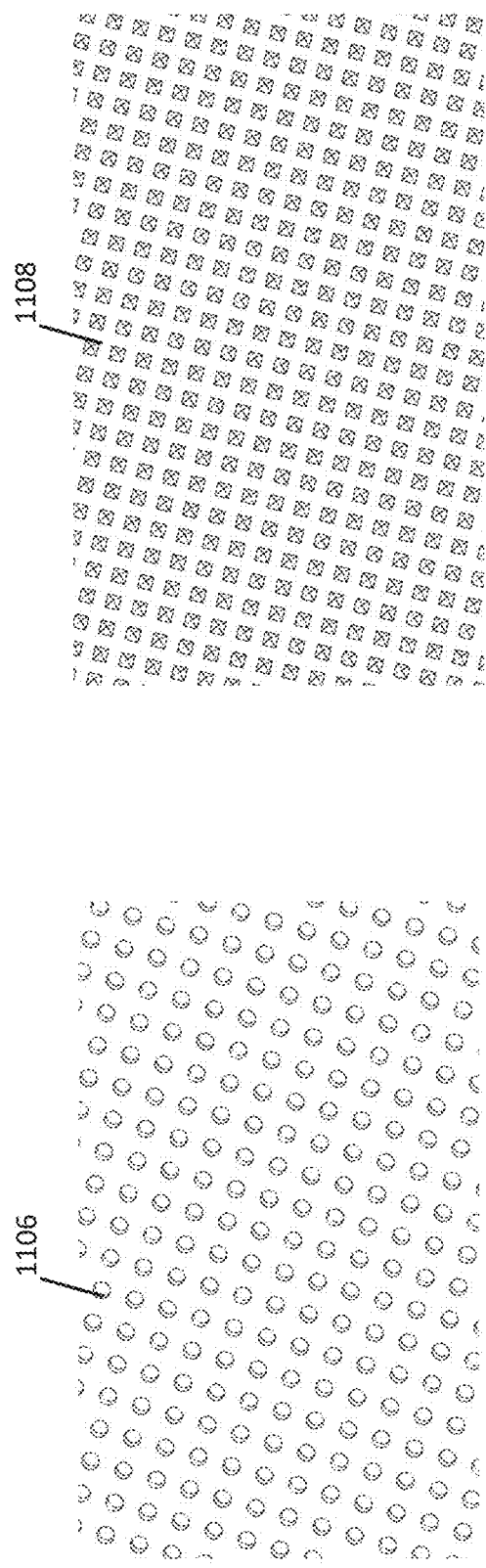
Fig. 11C
Fig. 11B

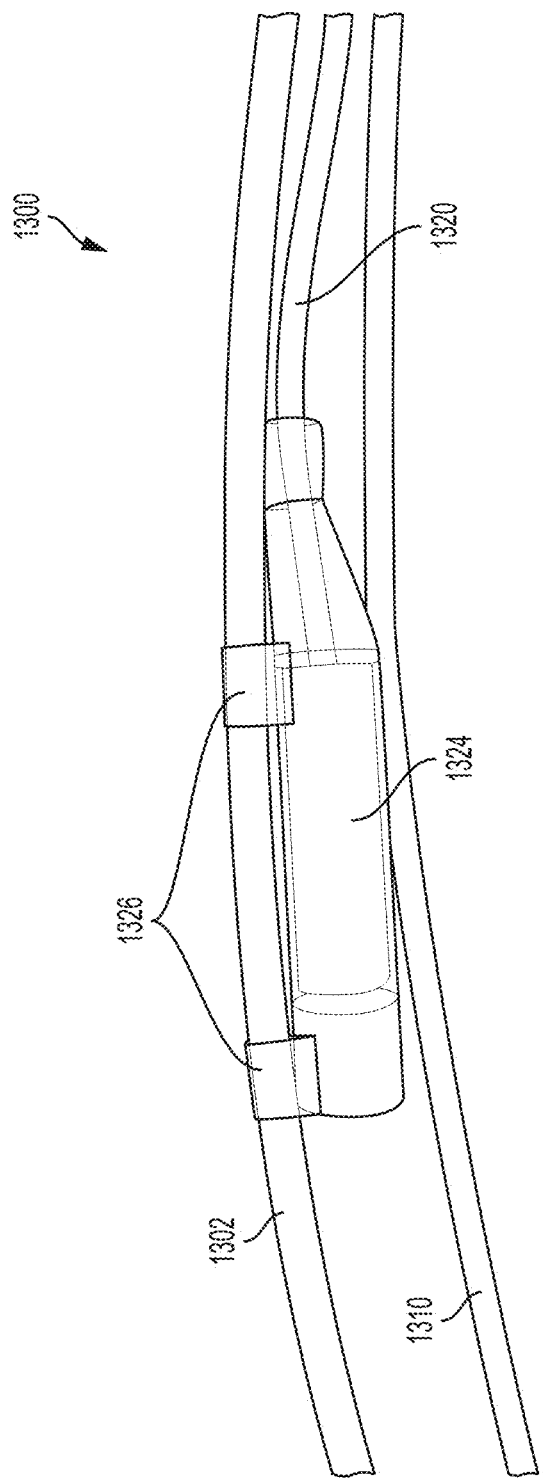

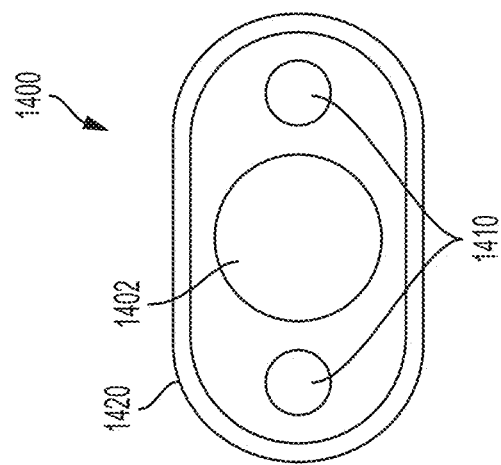
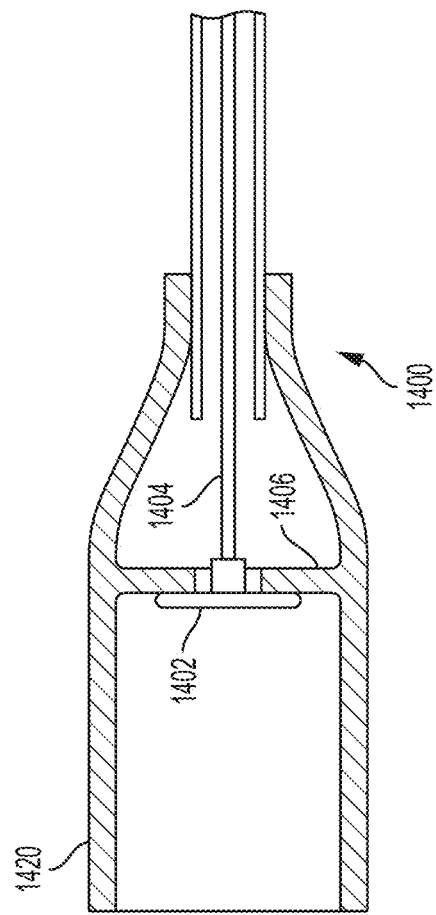
Fig. 14B
Fig. 14A

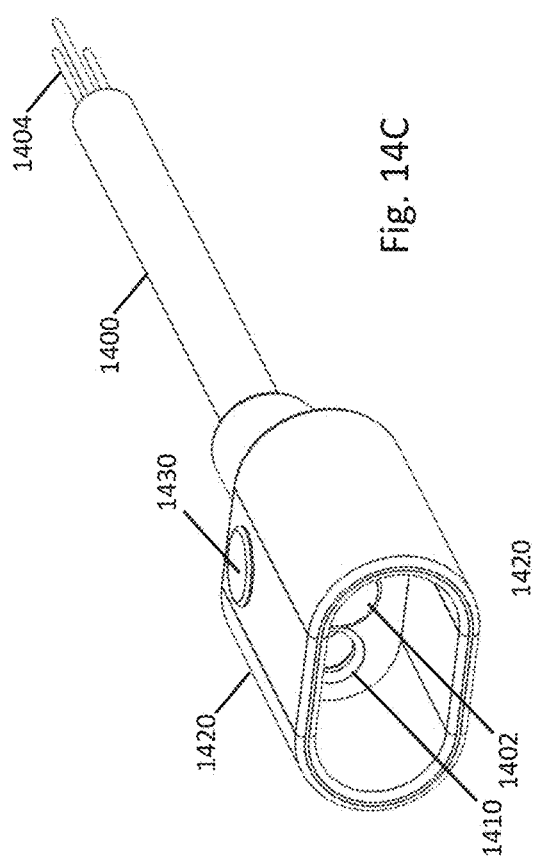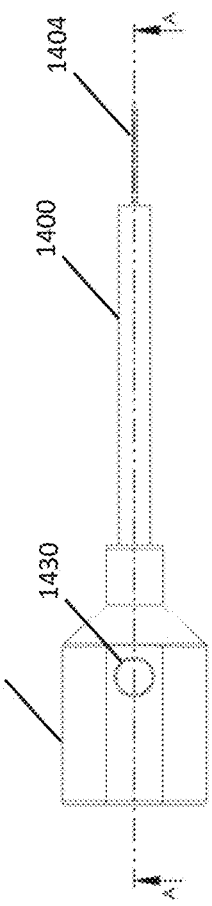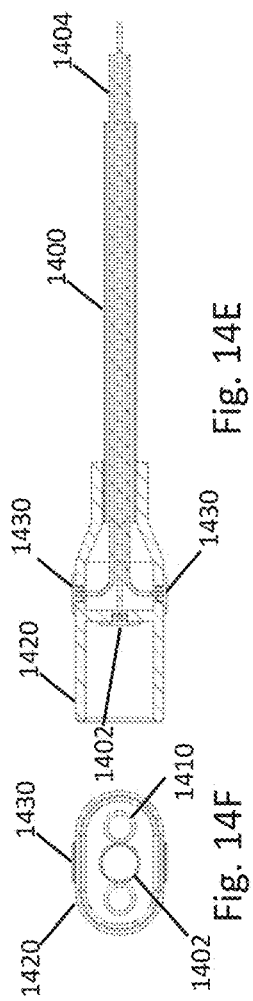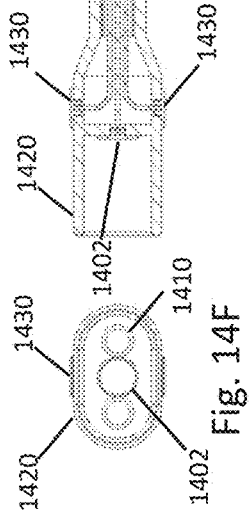

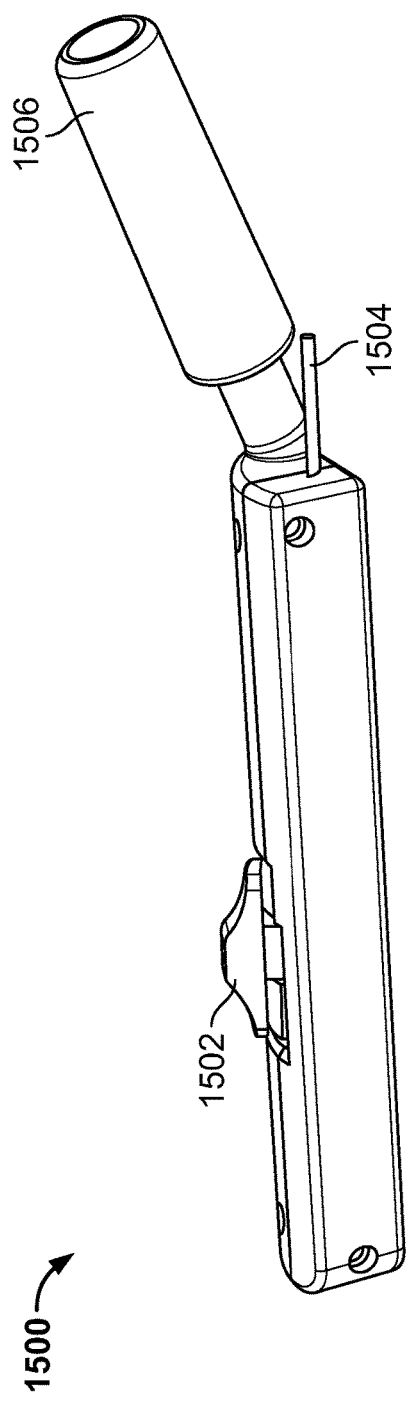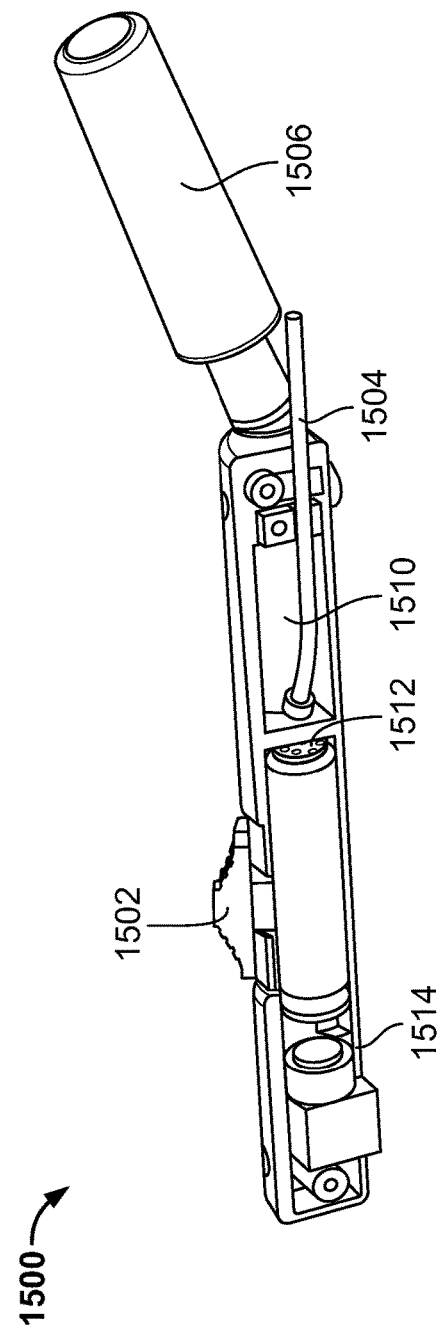

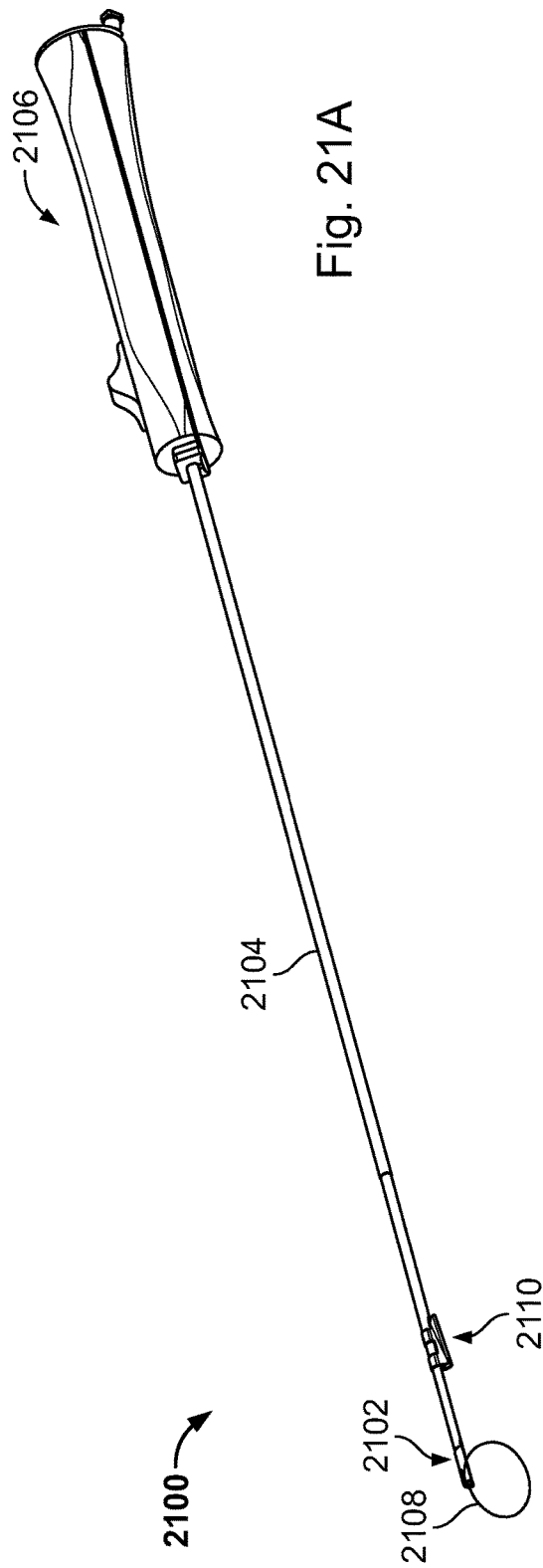
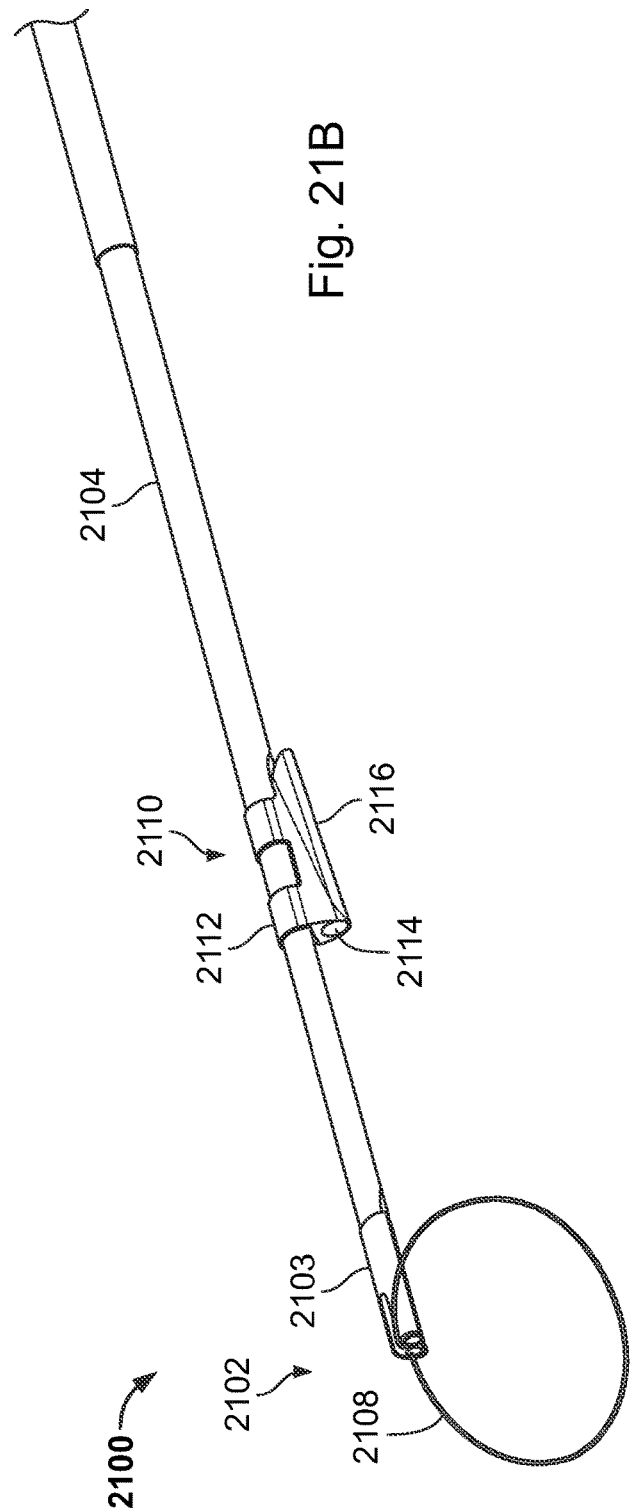

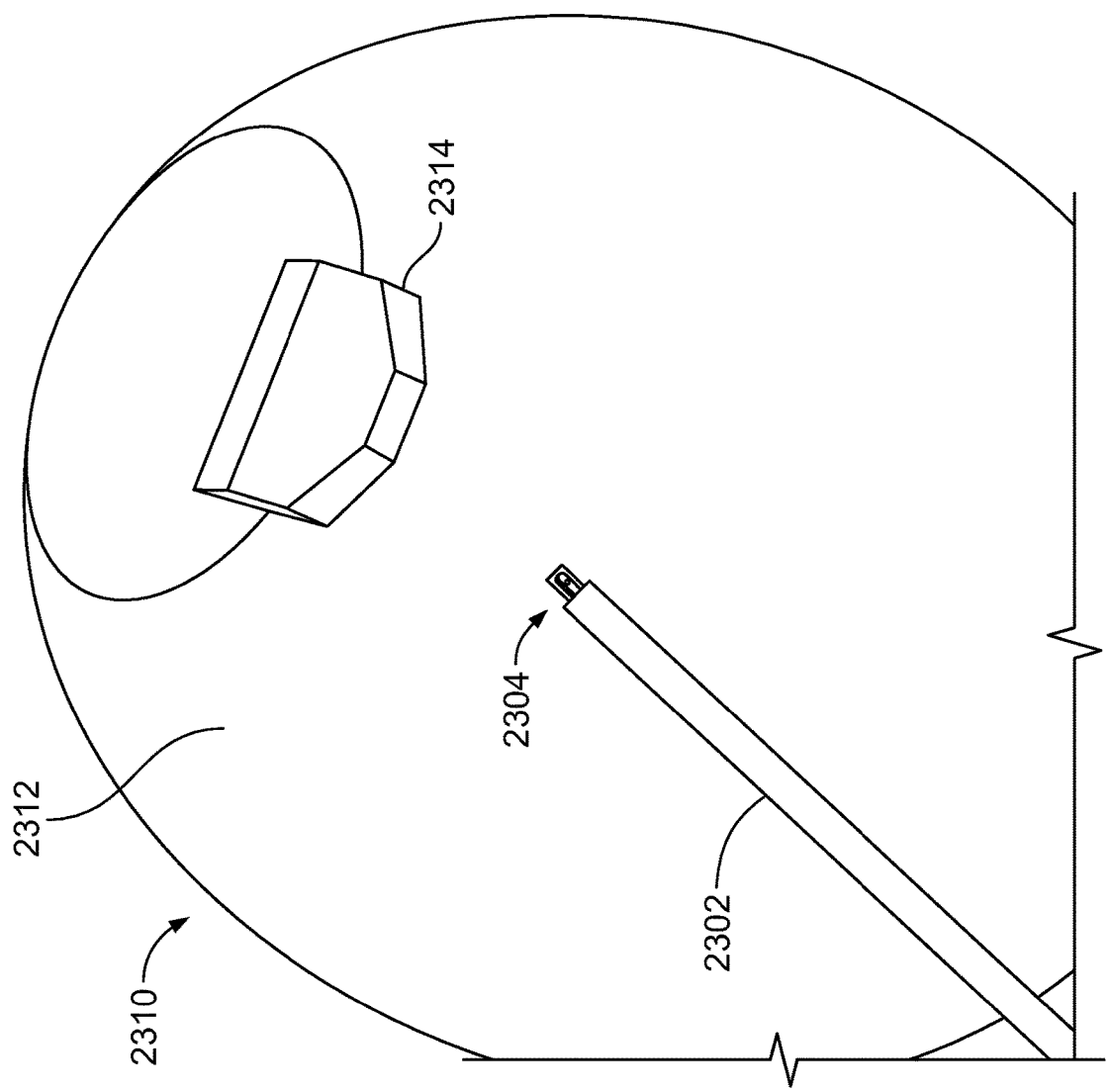

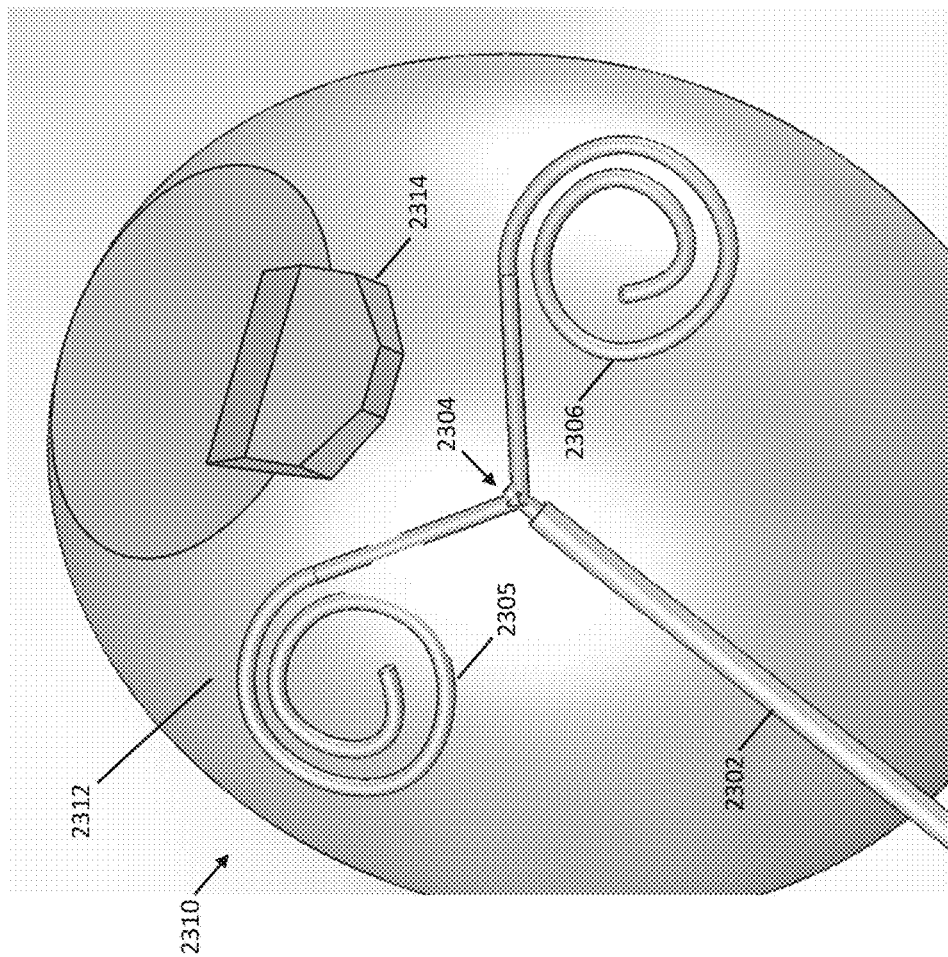

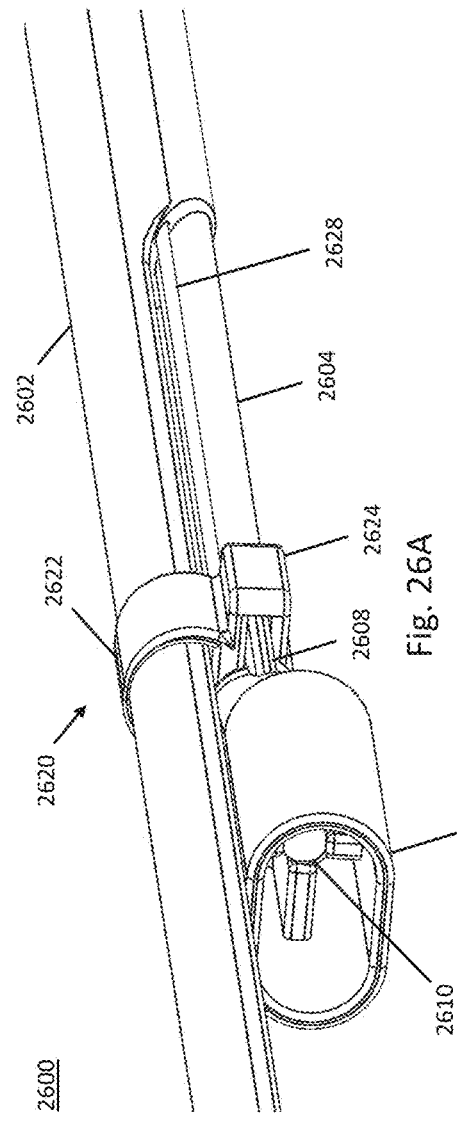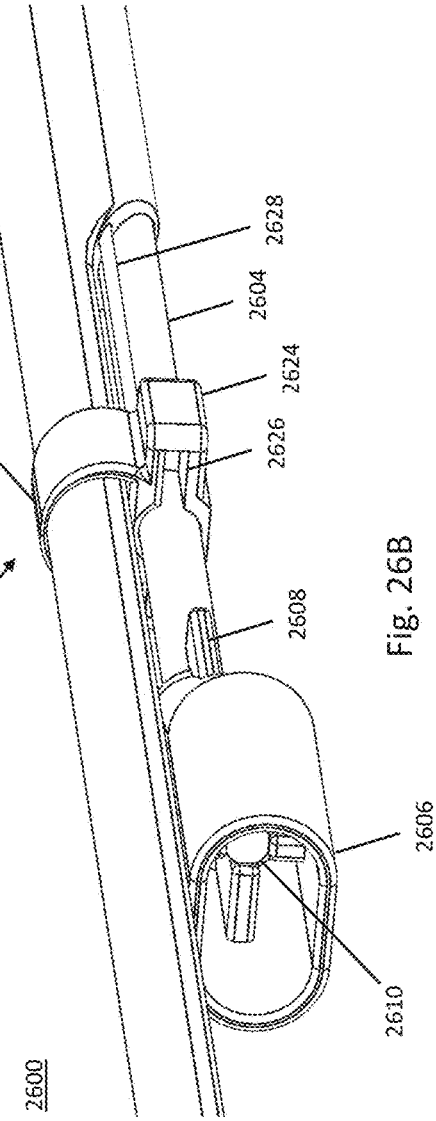

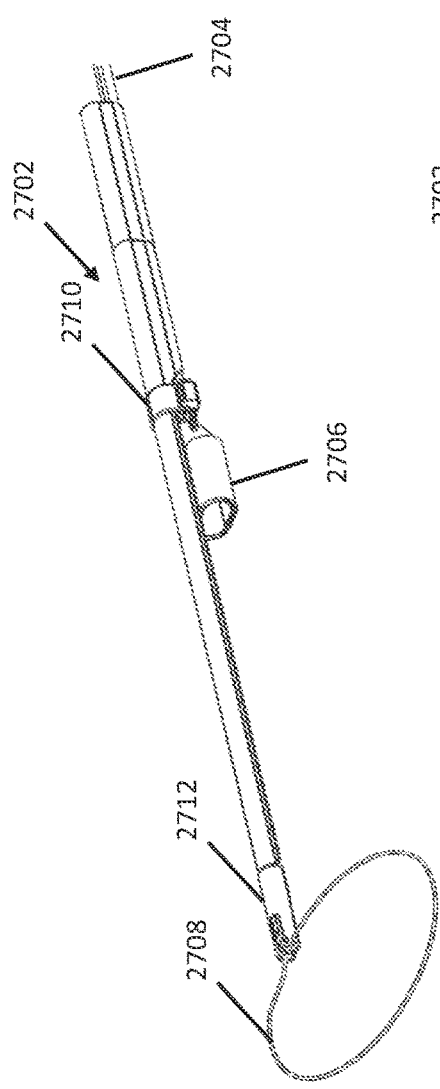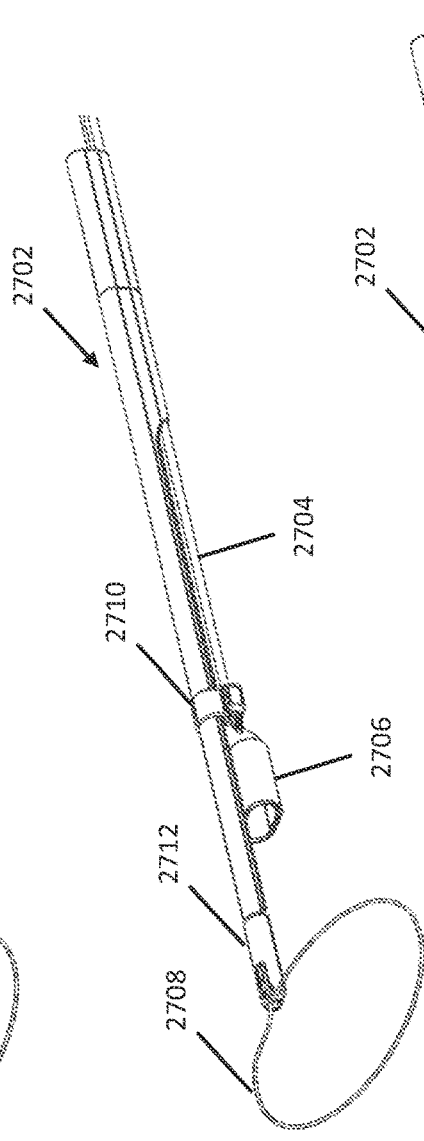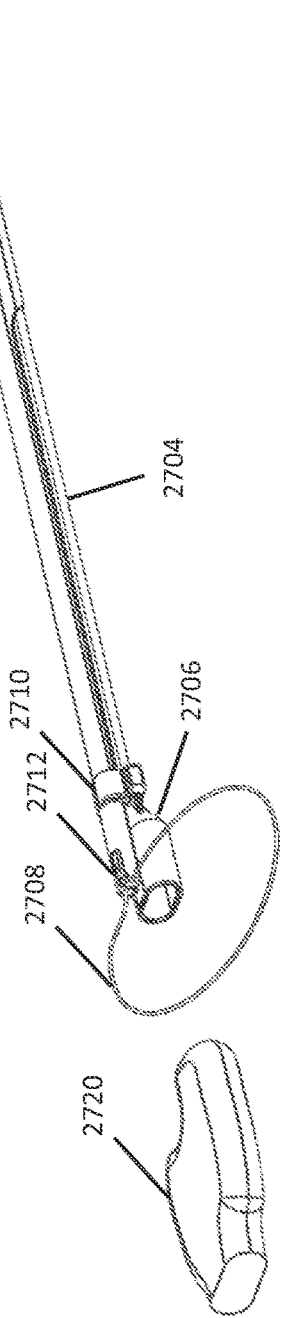
Fig. 27A
Fig. 27B
Fig. 27C

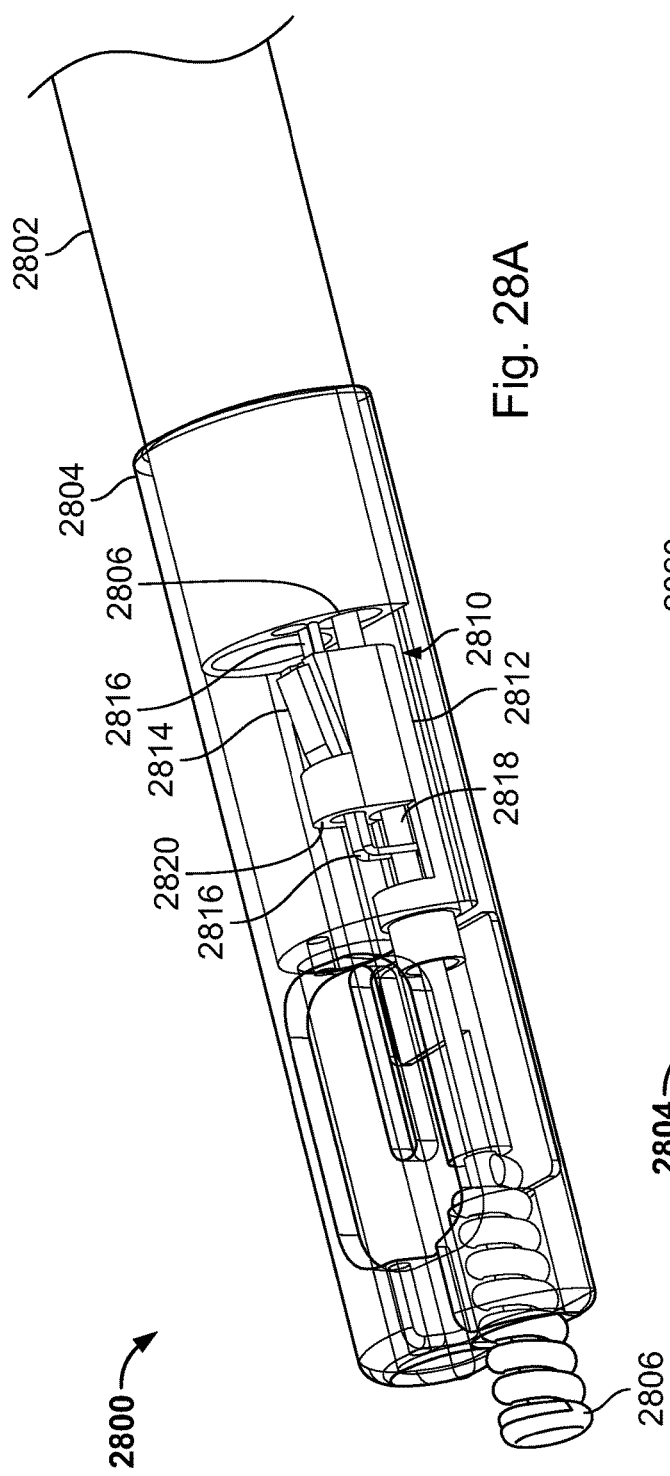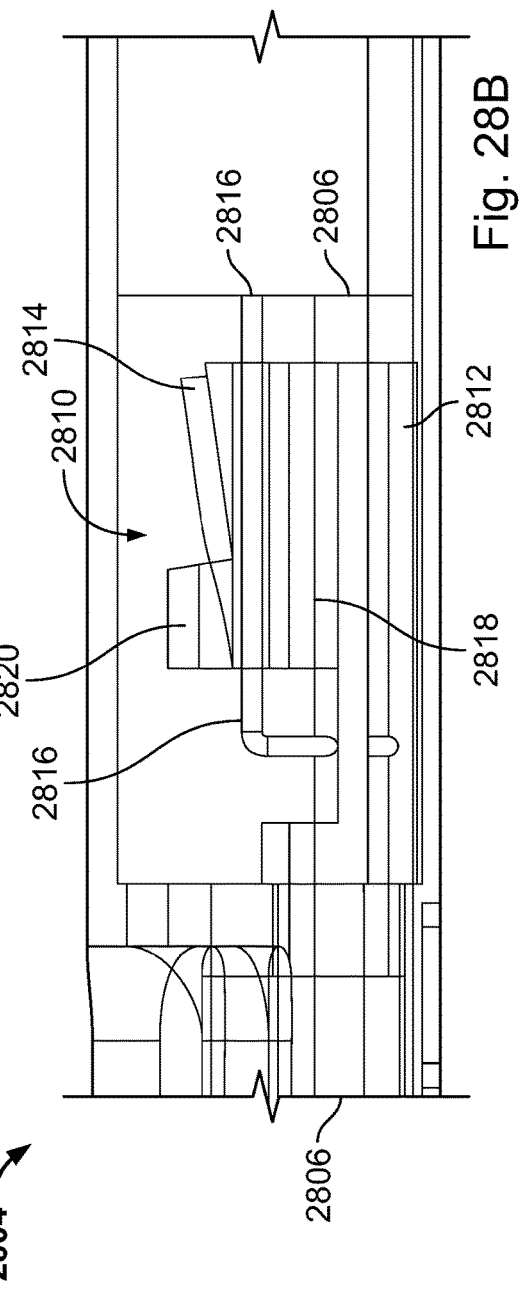

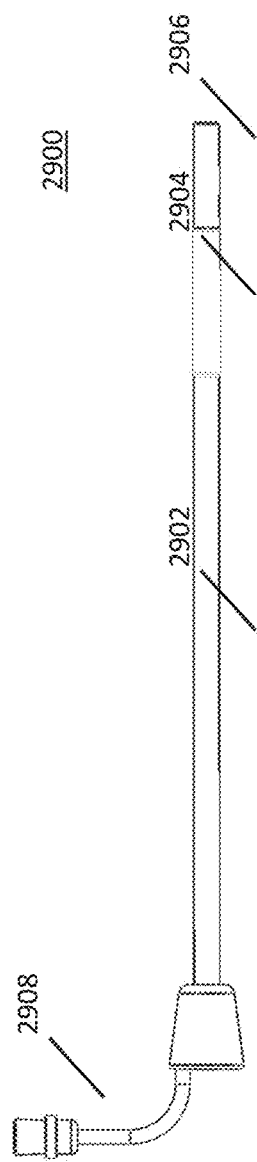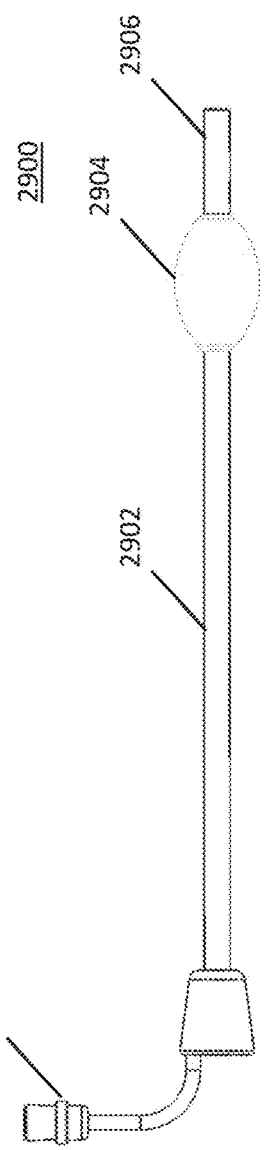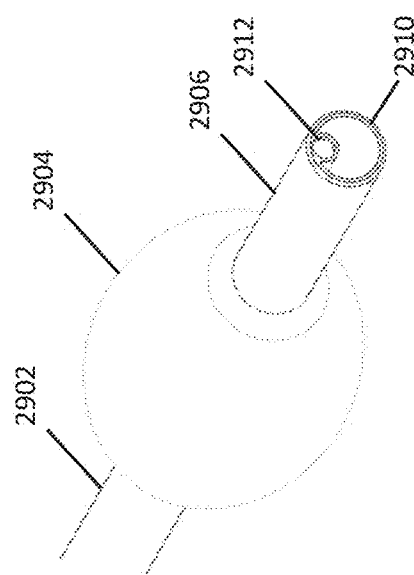

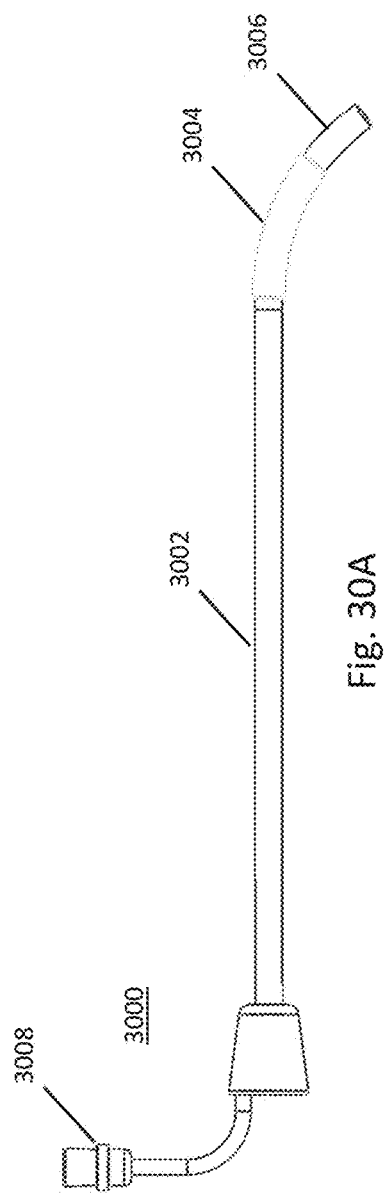
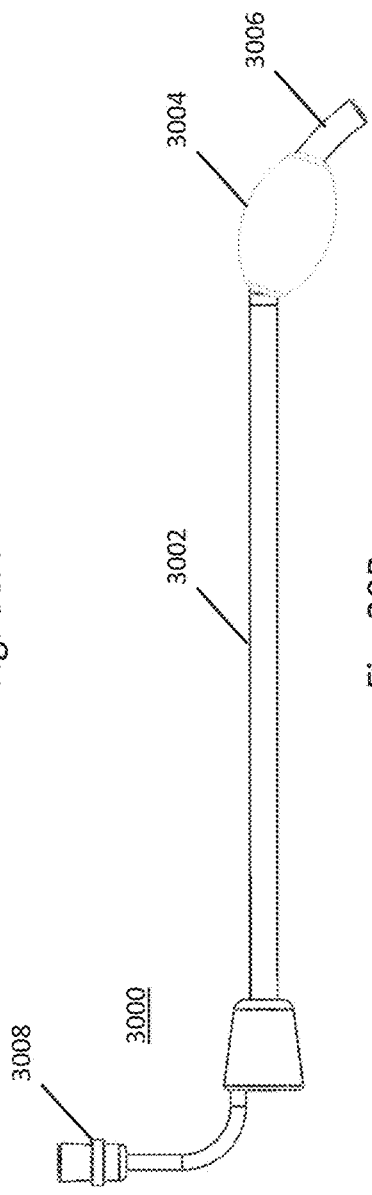
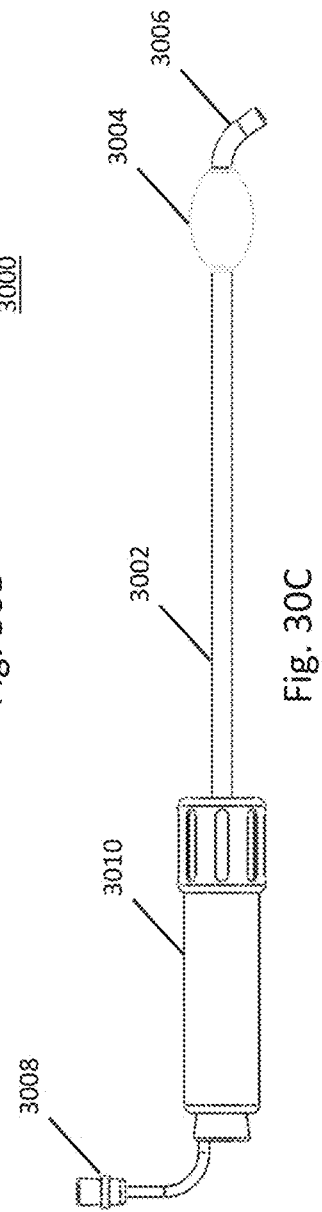

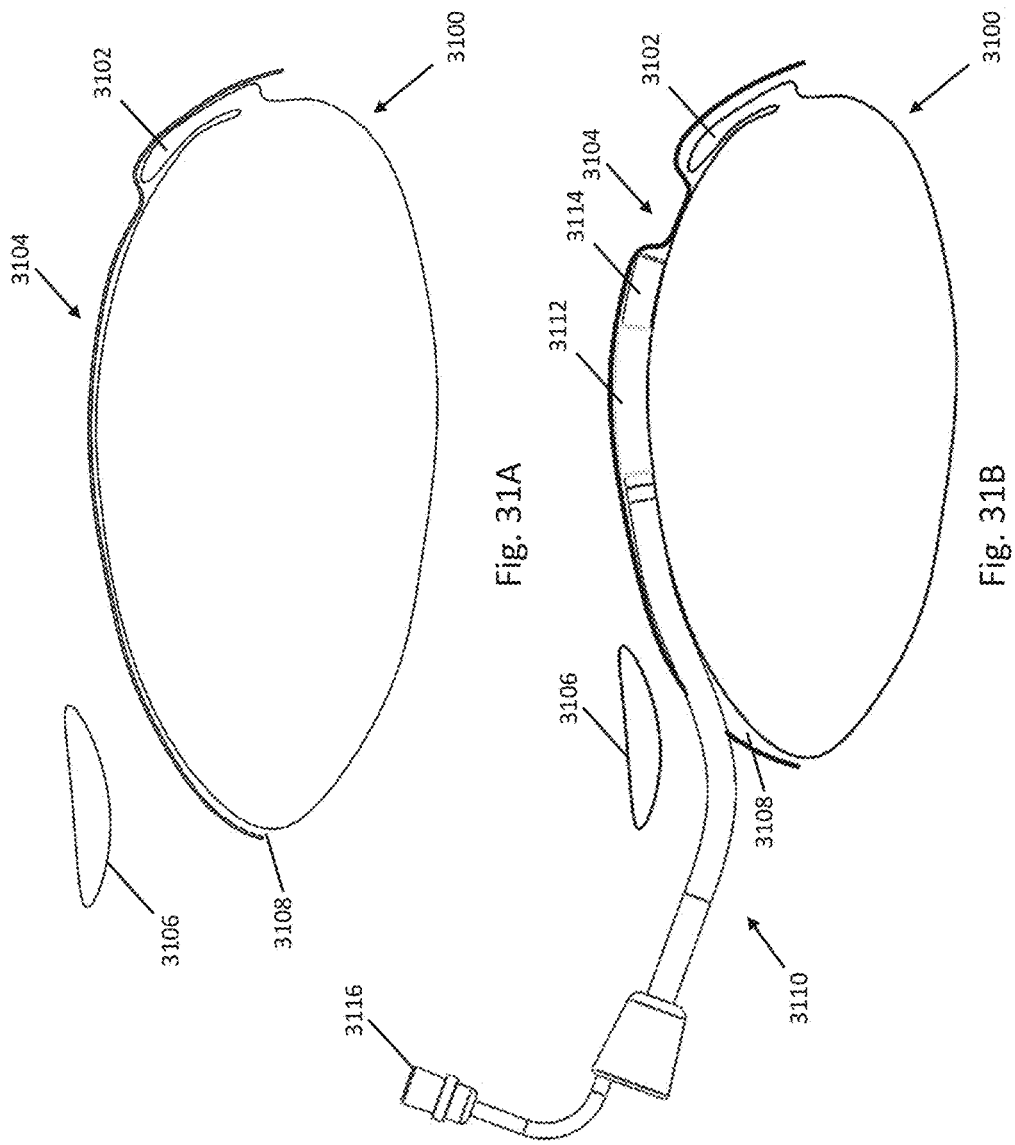

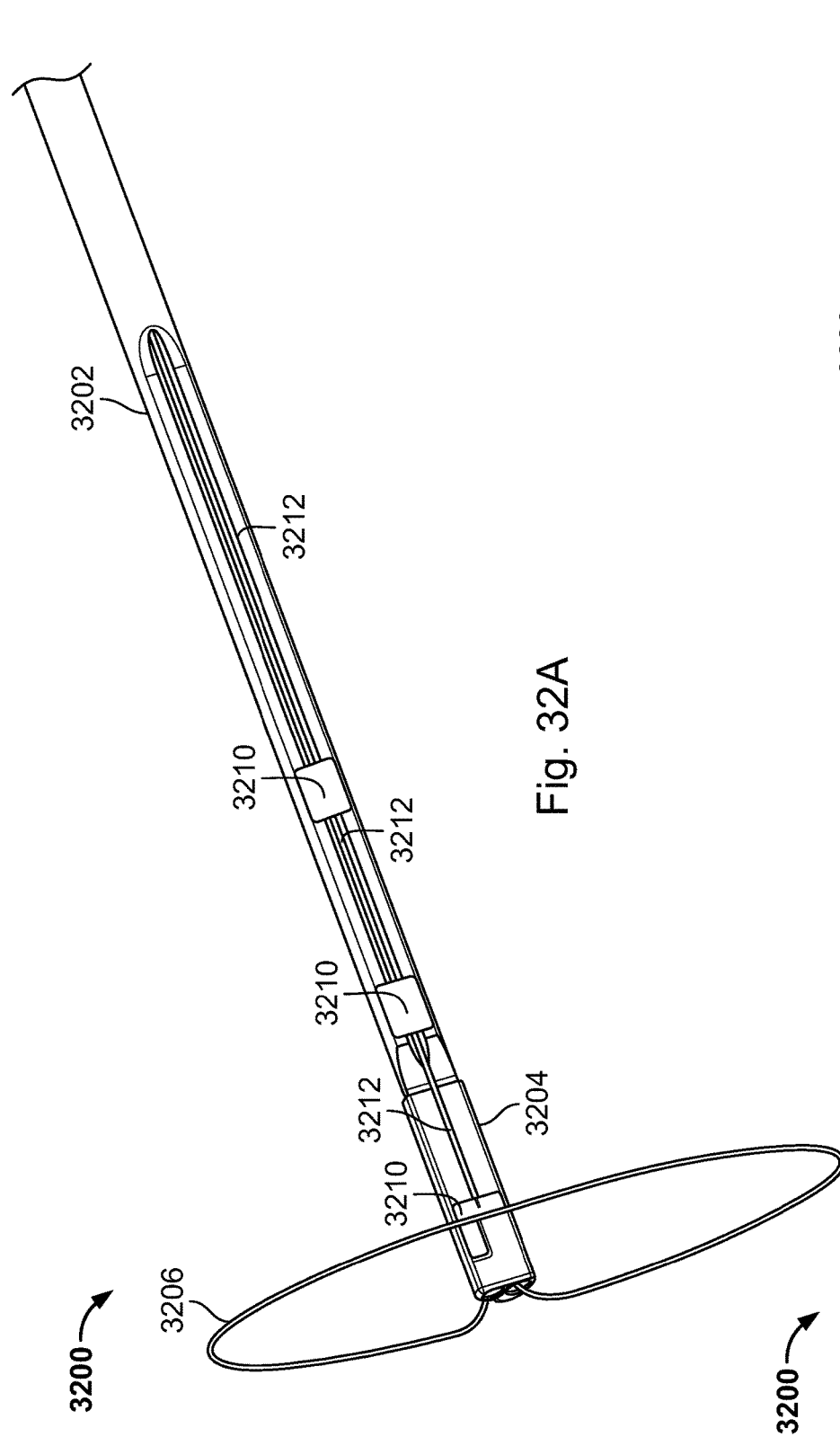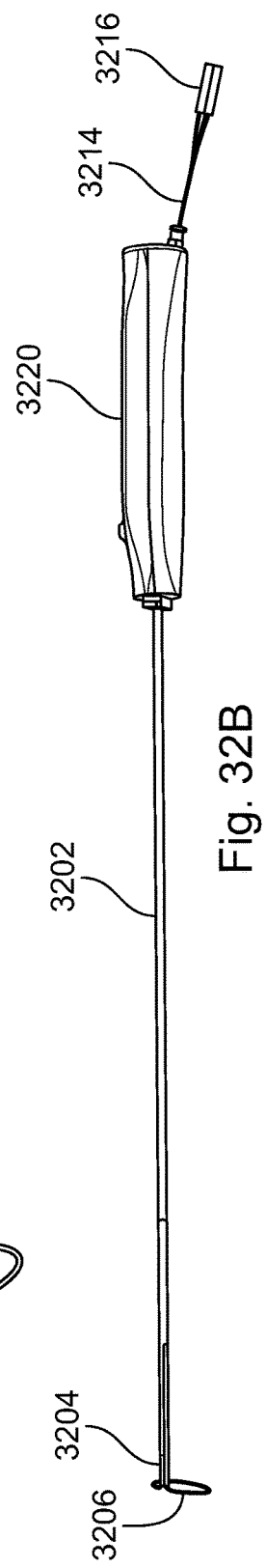

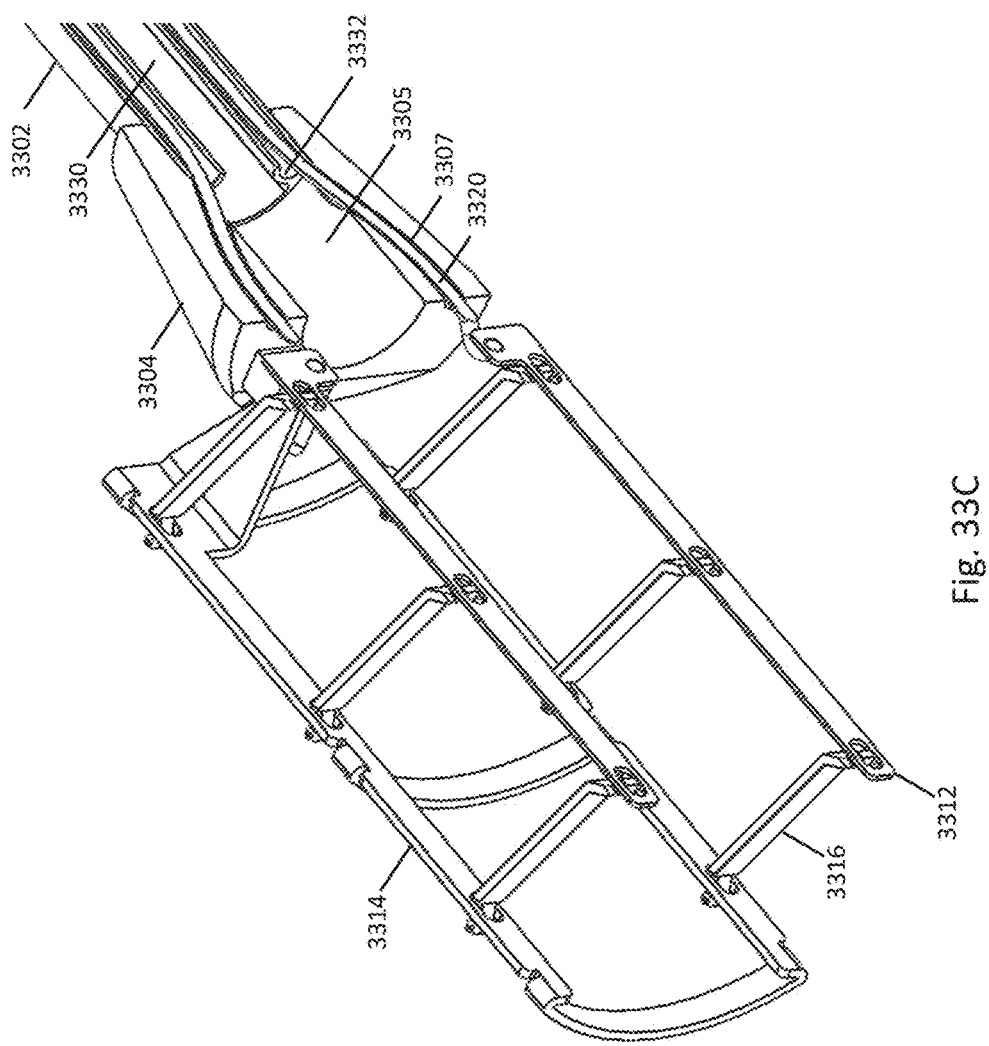

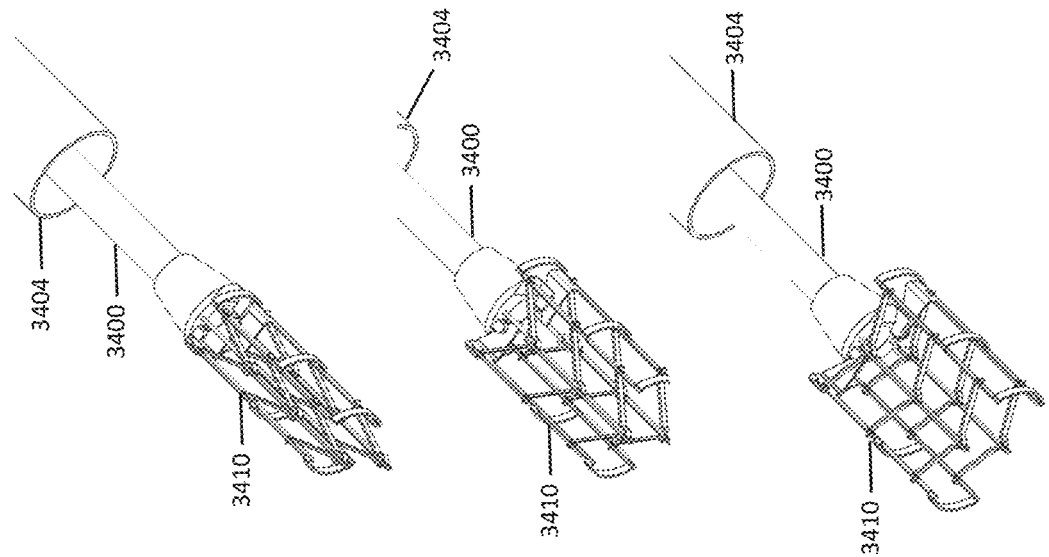
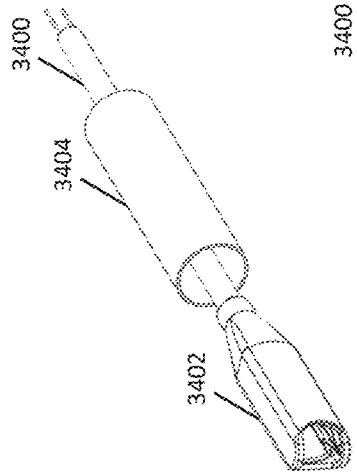
Fig. 34A
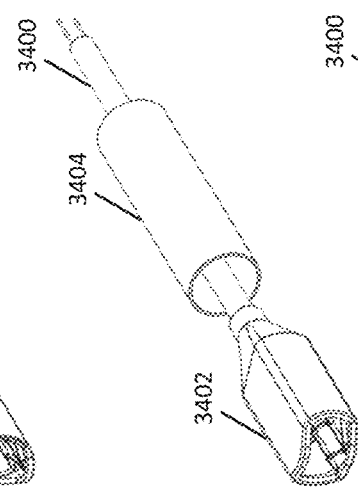
Fig. 34B
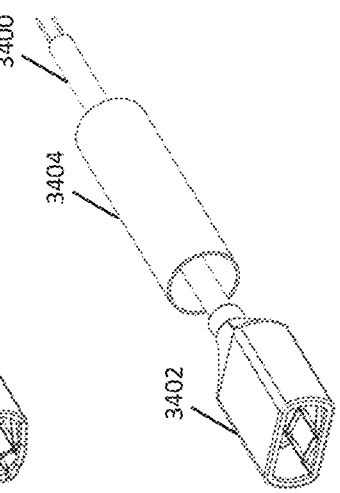
Fig. 34C

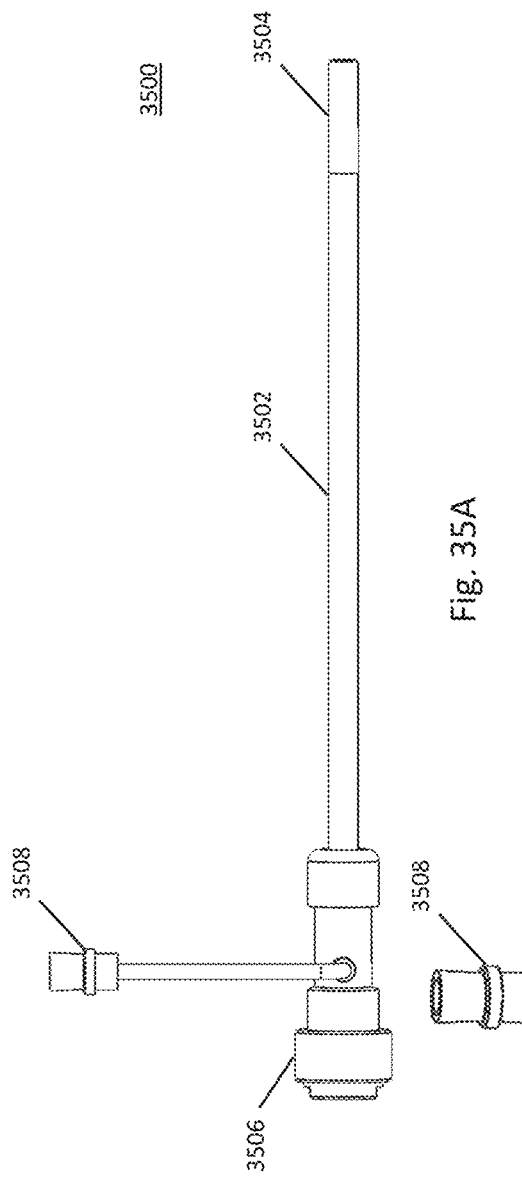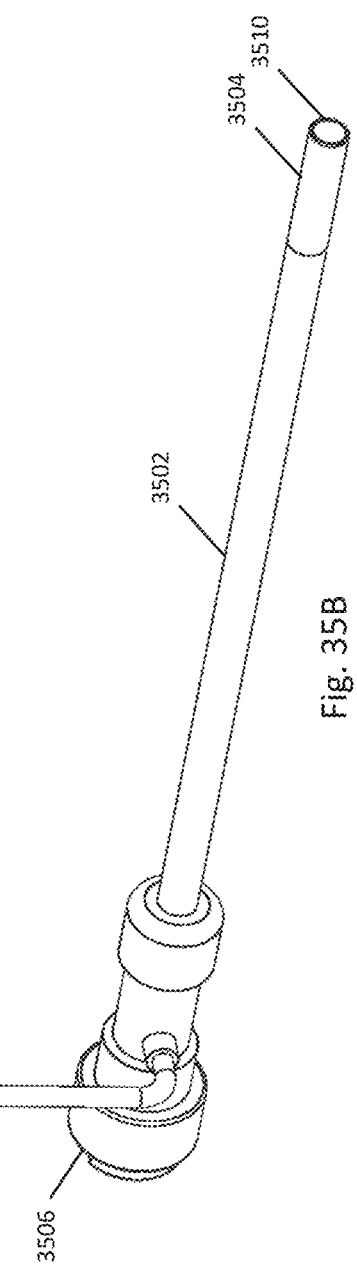
Fig. 35A
Fig. 35B

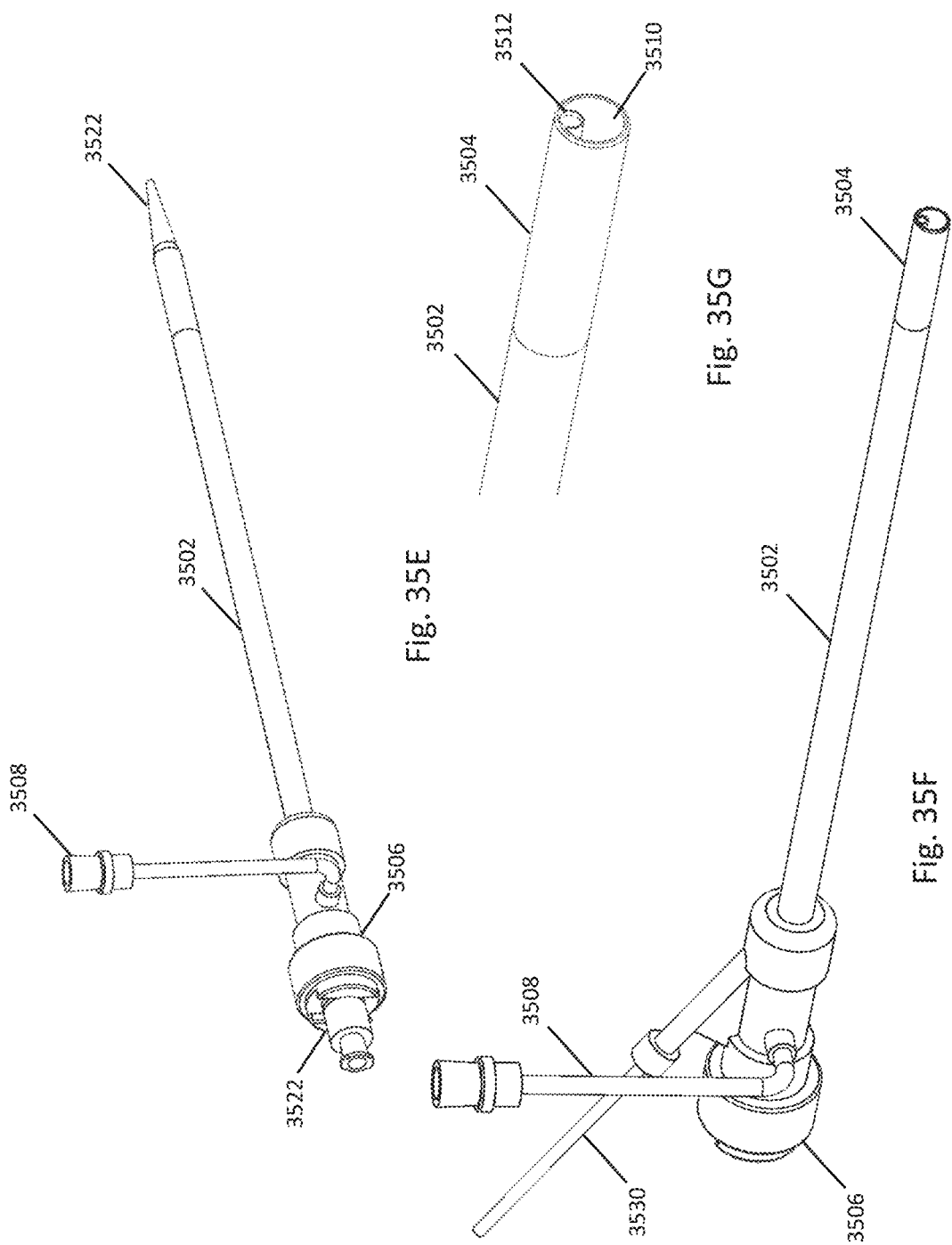

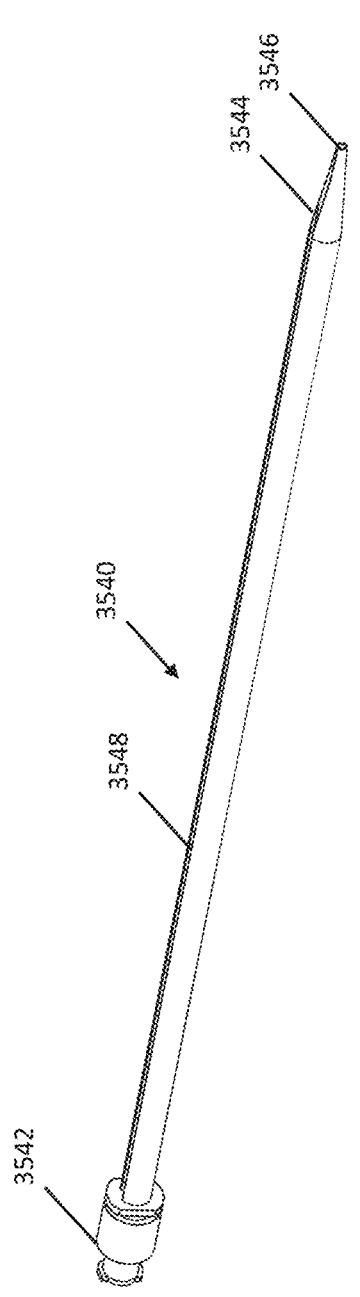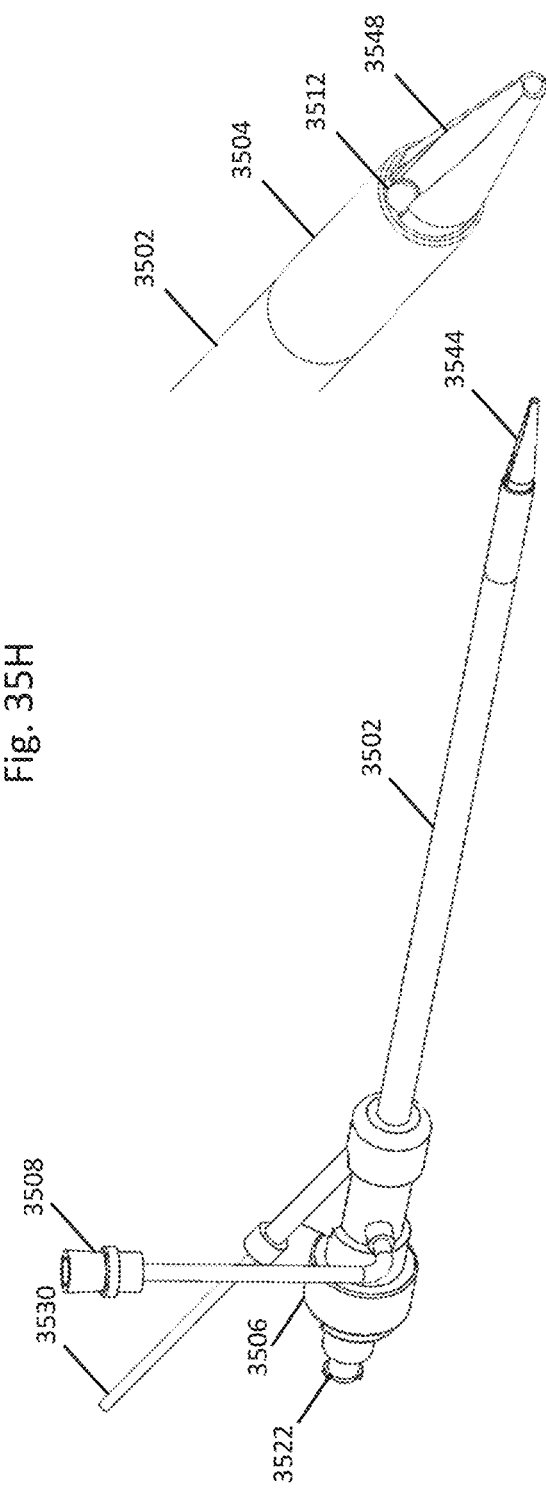

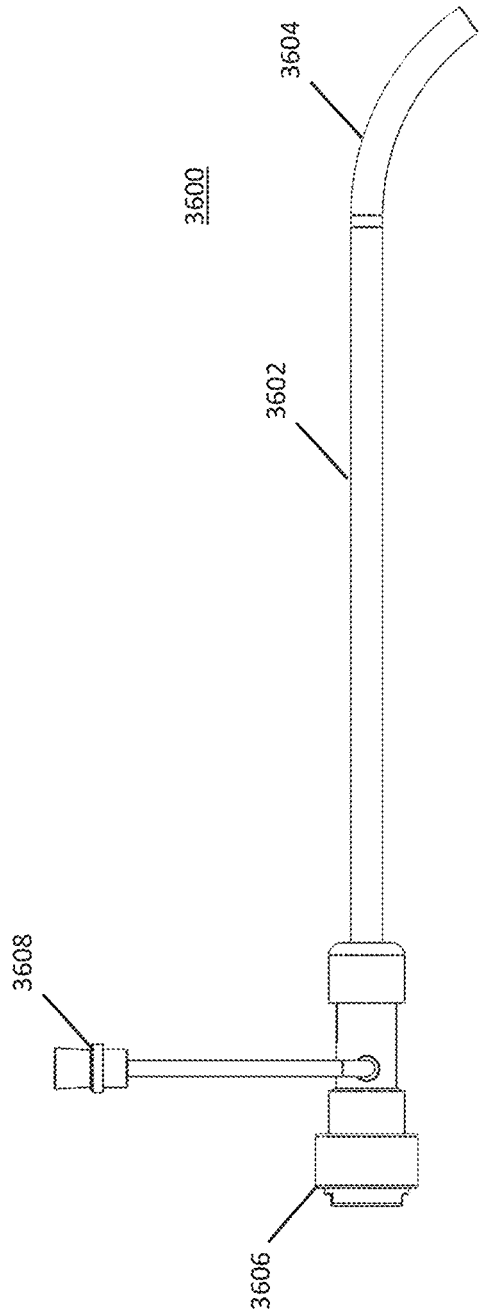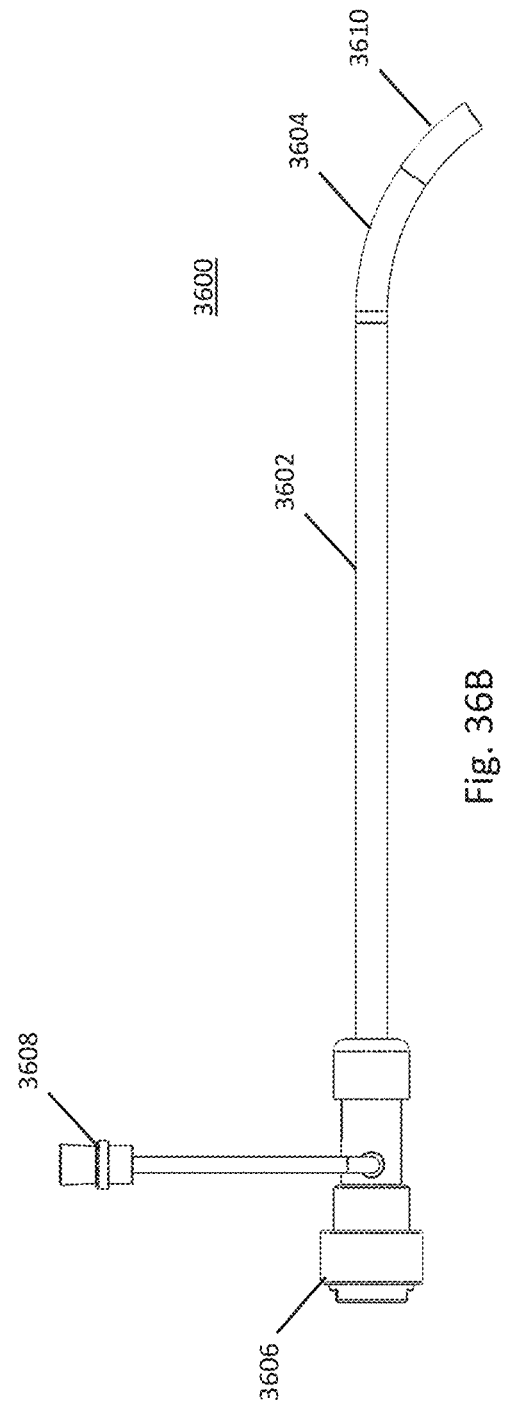
Fig. 36A
Fig. 36B

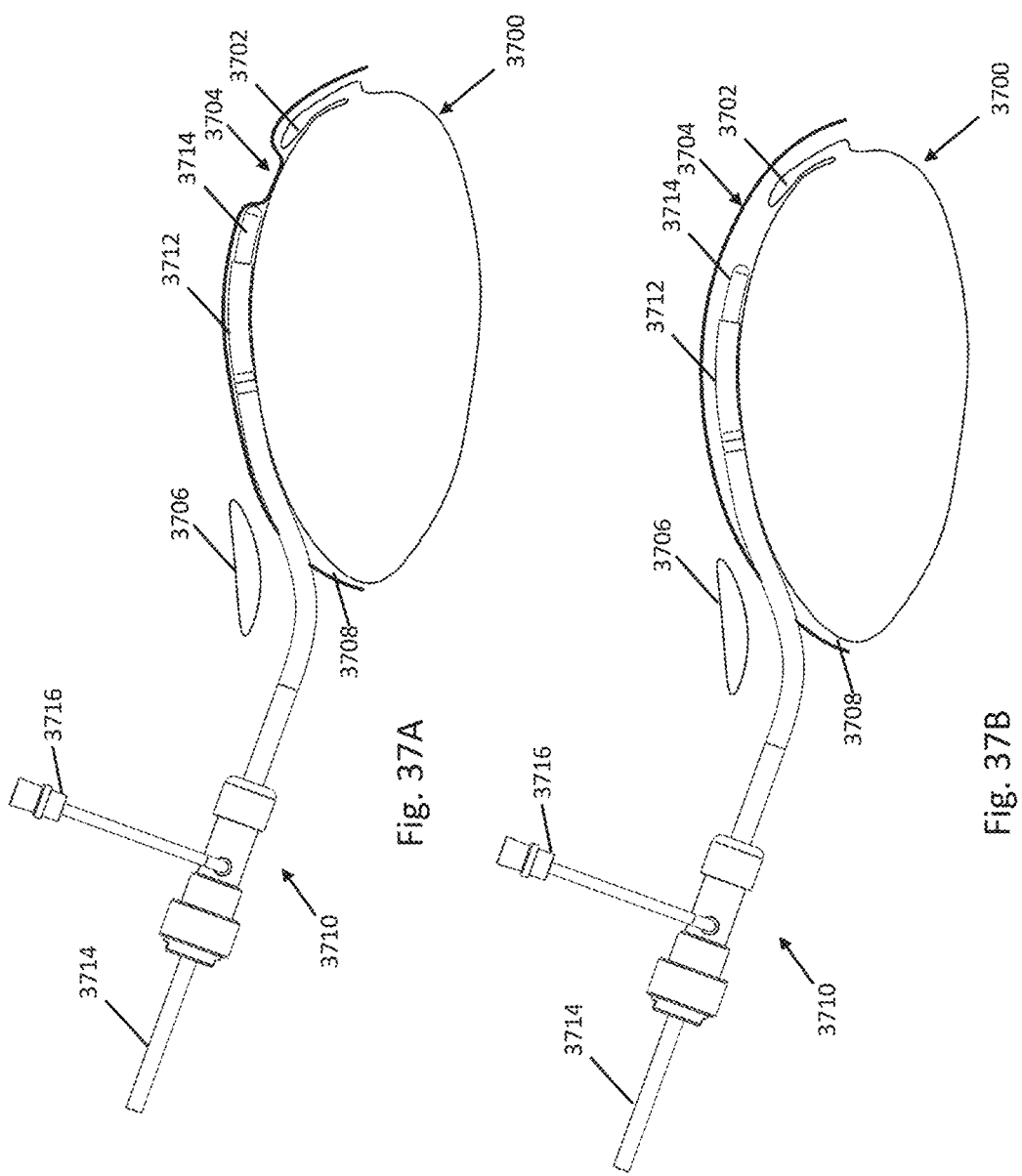

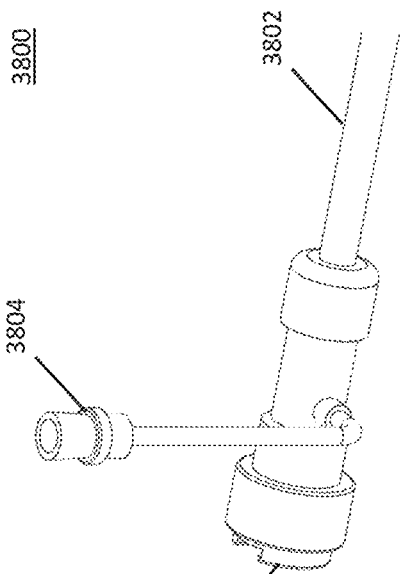
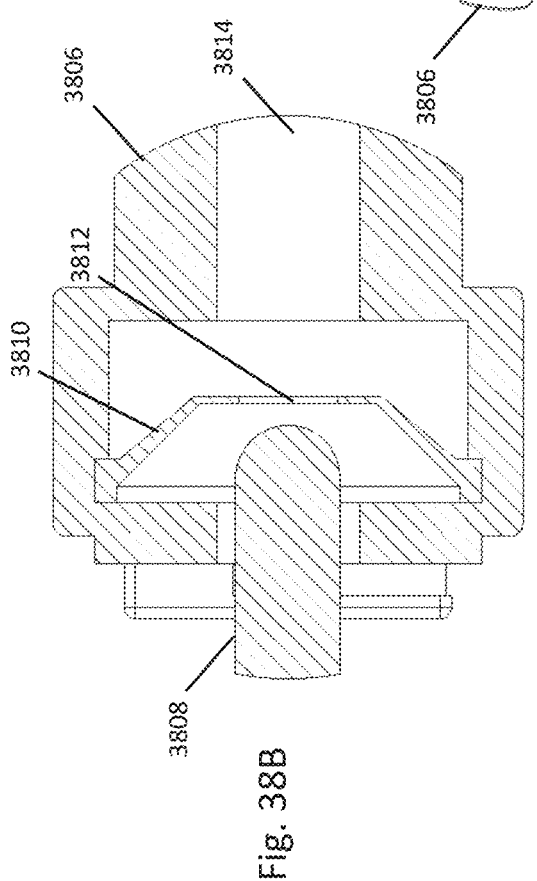
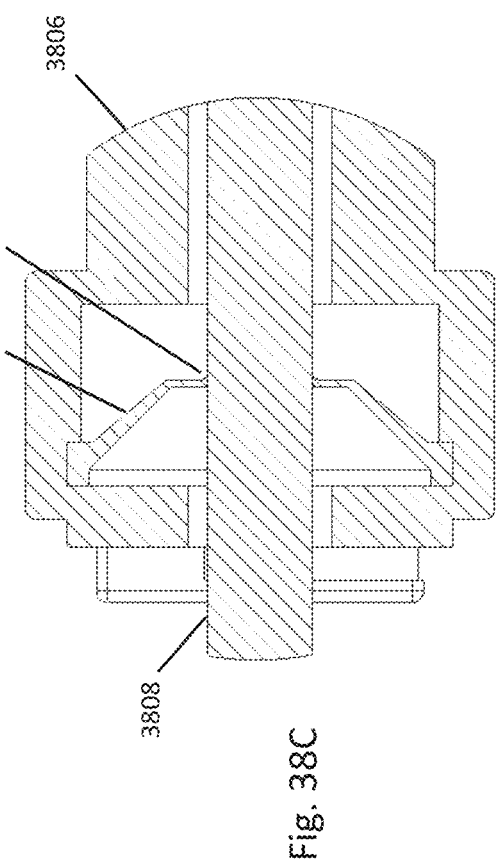

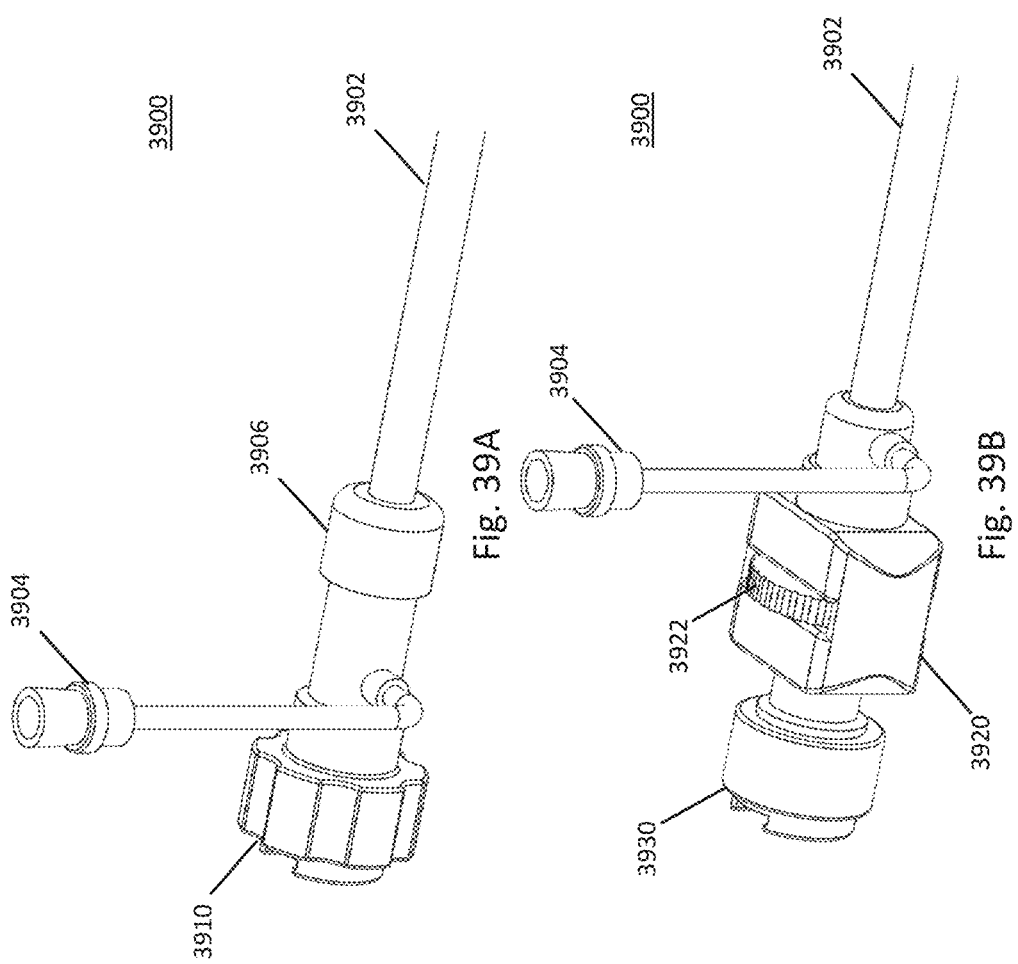

DEVICES AND METHODS FOR LEFT ATRIAL APPENDAGE CLOSURE

CROSS-REFERENCE TO RELATED APPLICATIONS

This application claims priority to U.S. Provisional Application Ser. No. 62/399,228, filed on Sep. 23, 2016, and titled "DEVICES AND METHODS FOR LEFT ATRIAL APPENDAGE CLOSURE," the content of which is hereby incorporated by reference in its entirety.

FIELD

Described here are devices and methods for ligating tissue, such as the left atrial appendage, using minimally invasive or intravascular approaches.

BACKGROUND

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage (LAA). One such method includes suturing the left atrial appendage along the base or ostial neck where it joins the atrial chamber. In this way, blood flow into the atrial appendage is cut off, eliminating the risk of thrombus formation therein. Other methods have also been investigated. These methods include stapling the base of the appendage and filling the appendage with a space-occupying or occluding member. Stapling is not preferred given the fragility of the appendage and its tendency to rupture, whereas occlusion devices may not effectively prevent all blood flow into the appendage.

Most of these procedures are typically performed through open-heart surgery; however, some may also be performed using minimally invasive techniques. Many procedures require multiple access sites (e.g., a first access site to access the internal structures of the heart and a second access site to access the pericardial space), advancing a first device through the vasculature and into the left atrial appendage to assist in guiding and/or positioning a ligating element carried by a second device that is positioned in the pericardial space. Those requiring only a single access point necessitate the use of at least one of a large surgical incision, a separate visualization tool (which may, for example, require the use of contrast), grasping the fragile left atrial appendage often with a tool prone to tearing the appendage, and puncturing the left atrial appendage. All of the foregoing may complicate the procedure and/or make it more dangerous. For example, many of the known procedures carry one or more following risks and/or complications: risk of tearing the LAA, complications with puncturing the LAA, complications using a large surgical incision, complications associated with advancing additional tools through the body, risk of perforation of the heart from internal components, risk of entrapment of internal components, and risks associated with transseptal access. In addition to increasing the danger of the procedures, these risks and complications may also necessitate increased recovery time, and/or may make the procedures more expensive. Therefore, improved epicardial devices and methods for closing the left atrial appendage using minimally invasive techniques would be desirable.

BRIEF SUMMARY

Described here are devices, systems, and methods for closing a target tissue, for example, the left atrial appendage. In general, the devices described here for closing a target tissue comprise an elongate body comprising a first lumen therethrough. A snare loop assembly may be provided and comprise a snare and a suture loop releasably coupled to the snare at least partially extending from a distal end of the elongate body. The device may further comprise a vacuum tube configured to apply vacuum to the target tissue. The vacuum tube may comprise a second lumen therethrough. The vacuum tube may be slidably positioned within the first lumen to extend through the snare loop assembly. An imaging device may be disposed within the second lumen.

In some variations, a vacuum pump may be operably connected to the second lumen and configured to provide suction at a distal end of the second lumen. In some variations, the device may comprise a fastener coupling the imaging device to the vacuum tube within the second lumen. In some of these variations, the fastener may comprise at least one radial aperture. In some of these variations, the vacuum pump may be configured to generate negative pressure at the distal end and through the radial aperture. In other variations, the distal end may comprise a surface configured to generate negative pressure. In another variation, the device may comprise a handle coupled to the elongate body and the vacuum tube. The handle may comprise one or more of a snare control, a vacuum tube control, an imaging device control, and a vacuum control.

The device may include additional variations. The imaging device may be configured to generate an image signal that is transmitted to a display. In some variations, the imaging device may comprise one or more of an endoscope, image sensor, and camera. In yet other variations, the device may comprise a sheath comprising a third lumen. The elongate body may be slidably positioned within the third lumen. In some variations, the vacuum tube may comprise a proximal end, a distal end, and an intermediate portion between the proximal and distal ends. A diameter of the distal end may be greater than a diameter of the intermediate portion.

In some variations, the distal end may be configured to transition between a collapsed configuration for passing through the first lumen and an expanded configuration for engaging at least a portion of the tissue.

In some other variations, the distal end of the elongate body may comprise a severing assembly configured to separate the suture loop from the elongate body. In yet other variations, a distal end of the vacuum tube may comprise a balloon. The balloon may define a third lumen operatively coupled to the second lumen. In still other variations, a slidable fastener may couple the elongate body to the vacuum tube.

In some variations, a distal end of the vacuum tube may comprise at least two elongate members. In some of these variations, the elongate members each define a set of apertures. In some other variations, one or more of the elongate body and the vacuum tube may comprise one or more electrodes configured to receive an electrocardiogram signal. In yet other variations, the sheath may comprise an expandable member. In still other variations, the sheath may comprise one or more proximal seals.

In some variations, a device for closing a target tissue is provided, comprising an elongate body comprising a first lumen therethrough. A snare loop assembly may be provided and comprise a snare and a suture loop releasably coupled to the snare at least partially extending from a distal end of the elongate body. The device may further comprise a sheath comprising a second lumen therethrough, an insufflation port, and one or more radial seals coupled to a proximal end of the sheath. The elongate body may be disposed within the second lumen.

In some variations, the sheath may comprise a third lumen therethrough and an imaging device disposed within the third lumen. In other variations, the device may further comprise a dilator configured to be releasably coupled to the sheath and disposed within the second lumen.

In some variations, a device for closing a target tissue is provided, having an elongate body comprising a first lumen therethrough. A snare loop assembly may be provided and comprise a snare and a suture loop releasably coupled to the snare at least partially extending from a distal end of the elongate body. The device may further comprise a sheath comprising a second lumen therethrough and an expandable member coupled to a distal portion of the sheath.

In some variations, the expandable member may be configured to transition between a collapsed configuration and an expanded configuration for increasing a spacing between a pericardium and an epicardium. In other variations, the device may further comprise a dilator configured to be releasably coupled to the sheath and disposed within the second lumen.

Also described here are methods of closing a target tissue. In general, the devices used in the method may comprise an elongate body comprising a first lumen therethrough. A snare loop assembly may be provided and comprise a snare and a suture loop releasably coupled to the snare. The device may further comprise a vacuum tube slidably positioned within the first lumen. The vacuum tube may comprise a second lumen therethrough. An imaging device may be disposed within a distal end of the second lumen.

In the method, a device may be advanced towards the target tissue. The vacuum tube may be advanced out of the elongate body through the snare loop assembly. The target tissue may be imaged using the imaging device. A vacuum may be applied to the target tissue through the second lumen. The snare loop assembly may be advanced around the target tissue. The suture loop may be tightened around the target tissue.

In some variations, the snare loop assembly may be closed around the target tissue, and the suture loop may be released from the snare loop assembly. In some other variations, the application of vacuum to the target tissue may draw the target tissue to a distal end of the second lumen. In some of these variations, the application of vacuum holds the vacuum tube against the target tissue. In yet other variations, the elongate body and the vacuum tube may be advanced through a sheath. In still other variations, the elongate body and the vacuum tube may be advanced through an access site into a pericardial space. In some of these variations, the elongate body and the vacuum tube may be advanced percutaneously.

The methods may include additional variations. In some variations, advancing the snare loop assembly around the target tissue may comprise advancing the elongate body towards the distal end of the vacuum tube. In some of these variations, tightening the suture loop may further comprise imaging the tightened suture loop around the target tissue using the imaging device. In some variations, the vacuum tube may be retracted into the elongate body. In further variations, the device may be withdrawn from the body.

In some variations, a sheath may be advanced into a pericardial cavity, and the pericardial cavity may be insufflated using the sheath. In some other variations, a distal end of the vacuum tube may be expanded after advancing the vacuum tube out of the elongate body. In yet other variations, an electrocardiogram signal may be received using one or more electrodes disposed on the device. In still yet other variations, the target tissue may comprise one or more of a left atrial appendage and myocardium.

BRIEF DESCRIPTION OF THE DRAWINGS

FIGS. 3B-3D are side views of the closure device shown in FIG. 3A.

FIGS. 4E-4H are cross-sectional views of the illustrative closure device depicted in FIG. 4D.

FIGS. 7A-7F are perspective views of illustrative variations of a portion of a vacuum tube. FIGS. 7A, 7C, and 7E show illustrative suction tips of the vacuum tube. FIGS. 7B, 7D, and 7F depict the suction tips in FIGS. 7A, 7C, and 7E coupled to tissue.

FIG. 11A is a side view of an illustrative variation of an echogenic vacuum tube. FIGS. 11B-11C depict illustrative variations of an echogenic surface.

FIG. 13A is a detailed side view of an illustrative variation of a closure device.

FIGS. 14A-14F are schematic views of illustrative variations of a vacuum tube. FIG. 14A is a cross-sectional side view of an illustrative variation of a vacuum tube. FIG. 14B is a front view of the vacuum tube depicted in FIG. 14A. FIG. 14C is a perspective view of another variation of a vacuum tube. FIGS. 14D-14F depict a plan view, a cross-sectional side view, and a front view, respectively, of the vacuum tube depicted in FIG. 14C.

FIG. 15A is a perspective view of an illustrative variation of a handle of a closure device. FIGS. 15B-15C are cross-sectional perspective views of the handle depicted in FIG. 15A.

FIG. 21A is a perspective view of an illustrative variation of a closure device. FIG. 21B is a perspective view of a distal portion of the closure device depicted in FIG. 21A.

FIGS. 23A-23D are perspective views of an illustrative variation of a vacuum device, closure device, and heart tissue.

FIG. 25A is a cross-sectional side view of a vacuum tube. FIG. 25B is a front perspective view of the vacuum tube depicted in FIG. 25A.

FIGS. 26A-26B are perspective views of an illustrative variation of a closure device.

FIGS. 27A-27F are perspective views of an illustrative variation of a closure device used in a tissue closing procedure.

FIGS. 28A-28B are schematic views of an illustrative variation of a closure device. FIG. 28A is a perspective view of a distal tip and FIG. 28B is a detailed side view of the distal tip depicted in FIG. 28A.

FIGS. 29A-29E are schematic views of an illustrative variation of a sheath. FIGS. 29A-29B are side views of the sheath. FIG. 29C is a front perspective view of the sheath depicted in FIG. 29B. FIGS. 29D-29E are detailed side views of a distal end of another illustrative variation of a sheath.

FIGS. 30A-30C are schematic side views of illustrative variations of a sheath.

FIGS. 31A-31C are schematic views of an illustrative variation of a sheath disposed in patient anatomy. FIG. 31A is a cross-sectional side view of patient anatomy. FIGS. 31B-31C are side views of the sheath in the patient anatomy.

FIGS. 32A-32B are a bottom perspective view and a side view, respectively, of an illustrative variation of a closure device.

FIGS. 33A-33C are perspective views of an illustrative variation of a vacuum tube.

FIGS. 34A-34C are perspective views of an illustrative variation of a vacuum tube in different configurations.

FIGS. 35A-35B are side and perspective views of an illustrative variation of a sheath. FIGS. 35C and 35H are front perspective views of illustrative variations of a dilator. FIG. 35E is a rear perspective view of the dilator depicted in FIG. 35C disposed in the sheath depicted in FIGS. 35A-35B. FIG. 35F is a front perspective view of an illustrative variation of a sheath and endoscope. FIG. 35G is a front perspective view of an elongate body of the sheath depicted in FIG. 35F. FIG. 35I is a front perspective view of the dilator depicted in FIG. 35H disposed in the sheath depicted in FIG. 35F. FIG. 35J is a front perspective view of the elongate body and dilator depicted in FIG. 35I.

FIGS. 36A-36B are side views of an illustrative variation of a sheath.

FIGS. 37A-37B are side views of an illustrative variation of a sheath in patient anatomy.

FIG. 38A is a perspective view, and FIGS. 38B-38C are cross-sectional side views, of an illustrative variation of a proximal end of a sheath.

FIGS. 39A-39B are perspective views of illustrative variations of a proximal portion of a sheath.

DETAILED DESCRIPTION

Figure 1:
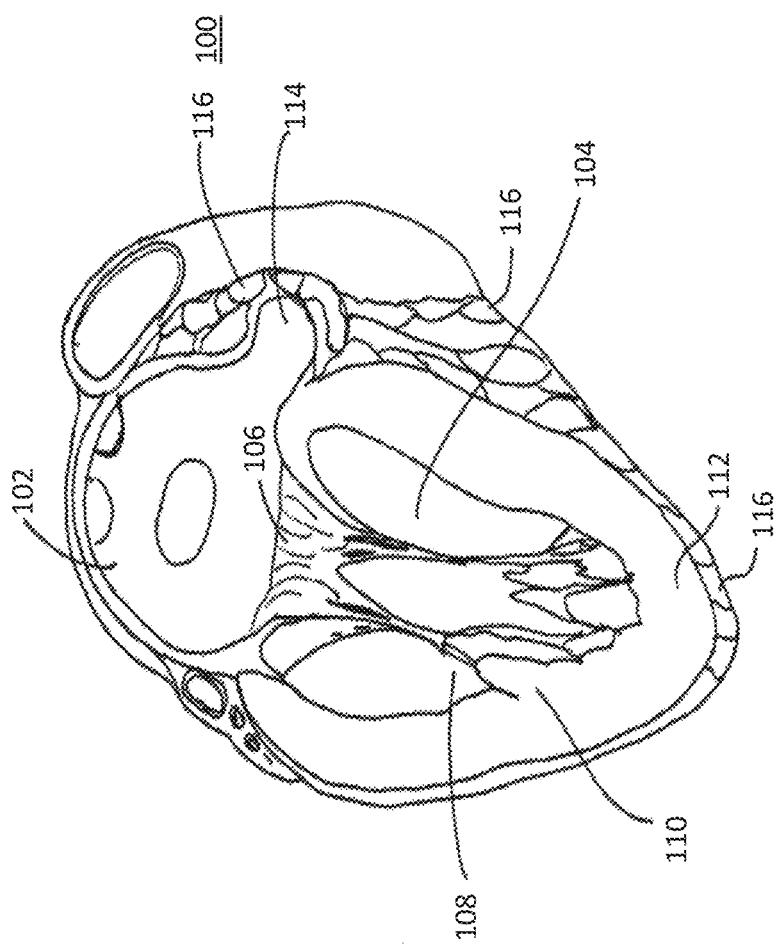
FIG. 1 provides a cross-sectional representation of a heart showing various anatomical structures.

Described here are devices, systems, and methods for closing tissue, for example, the left atrial appendage. In instances where the heart is the relevant anatomy, it may be helpful to briefly identify and describe the relevant heart anatomy. FIG. 1 is a cross-sectional view of the heart (100). Shown there is the left atrium (102) and the left ventricle (104). In between the left atrium (102) and the left ventricle (104) is the mitral valve (also known as the bicuspid valve), which is defined by a pair of mitral valve leaflets (106). The leaflets are connected to chordae tendinae (108) that are connected to papillary muscles (110). The papillary muscles join the ventricular wall (112). The left atrial appendage (114) is shown adjacent to, and is formed from, the wall of the left atrium (102).

As can be seen, the left atrial appendage (114) lies within the boundaries of the pericardium (116) and is in close proximity to the ventricular wall (112). The left atrial appendage typically has a tubular shape that approximates a cone, with a slight narrowing or neck in the plane of the orifice where it joins the left atrium (102). In patients with atrial fibrillation, the left atrial appendage (114) is the most common location for thrombosis formation, which, in time, may dislodge and cause a devastating stroke. Because stroke is the primary complication of atrial fibrillation, the left atrial appendage is frequently excluded from the left atrium in those patients undergoing procedures to treat atrial fibrillation, and is often removed or excluded at the time of other surgical procedures, such as mitral valve surgery, to reduce the risk of a future stroke. The devices and systems described here help ensure proper closure of the left atrial appendage at the neck or base of the left atrial appendage, along the anatomic ostial plane. In this way, exclusion of the entire left atrial appendage from systemic circulation may be facilitated.

I. Devices

Described here are closure devices and methods for closing a target tissue using the closure devices. Generally, the closure devices may comprise an elongate body and a snare loop assembly at least partially extending from a distal end thereof. The snare loop assembly may form a loop and may comprise a snare, and a suture loop releasably coupled to the snare. The closure devices described here may further comprise a first lumen and a vacuum tube slidably positioned within the first lumen. The vacuum tube may comprise a lumen therethrough, which, in some variations, may house and/or be coupled to an imaging device.

In some instances, the vacuum tube may assist in both visualization and stabilization of target tissue. For example, in some variations, the vacuum tube may be used to 1) view and identify the internal structures of a patient's body as the closure device is advanced to a target tissue and positioned relative to the target tissue and/or 2) apply vacuum to the target tissue to draw the target tissue toward the closure device and/or maintain contact with the target tissue to facilitate advancement of the snare loop assembly around the target tissue. This functionality may be provided through epicardial access without the need for endocardial access. For example, in variations in which the vacuum tube may assist in visualization, the vacuum tube may comprise an imaging device held with the vacuum tube and/or may be operably connected to an imaging device such that the images captured by the imaging device via the vacuum tube may be used to assist in advancing and/or positioning the vacuum tube relative to the target tissue (e.g., a camera positioned within or advanced through a vacuum tube lumen). The imaging device may further image the tissue drawn into the vacuum tube to confirm capture of the desired target tissue. In some variations, tissue may be identified and/or mapped using a set of electrodes disposed on one or more of the internal and external surfaces of a closure device, a vacuum tube, and/or an imaging device. The electrical signal received by the electrodes in contact with tissue may be used to identify the tissue and/or the location of the device. The electrode data may be further combined with other visualization data (e.g., from a mapping system) to generate a visual map of the heart. In some variations, other imaging methods, for example, fluoroscopy, fluorescence (near-infrared fluorescence, laser-induced fluorescence) may be employed. In instances in which the vacuum tube may assist with stabilization, the vacuum tube may provide suction to temporarily hold a portion of the target tissue against the suction tip of the vacuum tube and/or the closure device. The suction tip of the vacuum tube may be atraumatic so as to decrease the risk of damaging the tissue. The suction supplied by the vacuum tube may hold the target tissue in place relative to the closure device while a snare loop assembly is advanced or deployed around the left atrial appendage to temporarily or permanently close and/or ligate the target tissue. The visualization and/or stabilization of the target tissue provided by the vacuum tube may assist with effectively and efficiently advancing the closure device to the target tissue and positioning and holding the target tissue so that the snare loop assembly can be deployed and the suture loop can be placed at the desired location for tissue closure.

As mentioned above, the closure devices described here may be used to close and/or ligate a target tissue such as the left atrial appendage. In use in a left atrial appendage closure procedure, the closure device may be advanced, for example, percutaneously, toward a pericardial space. As mentioned above, in some variations, an imaging device disposed within the lumen of the vacuum tube may be used to assist in steering the closure device to the left atrial appendage. Once the closure device reaches the left atrial appendage, the imaging device may be used to visualize the left atrial appendage such that the vacuum tube may be advanced out of the elongate body and through the loop of the snare loop assembly towards a desired, visualized location on the left atrial appendage. The lumen of the vacuum tube may be used to apply a force (e.g., suction) to the left atrial appendage to pull the appendage toward the distal end of the vacuum tube lumen, thereby positioning the closure device for advancement of the snare loop assembly around the left atrial appendage. Once the vacuum tube and the closure device are positioned as desired relative to the appendage, the snare loop assembly may be advanced along the vacuum tube, which may be used as a guide, distally toward and around the target tissue. The snare loop assembly may then be closed around the target tissue and the suture loop may be released from the snare loop assembly to temporarily or permanently close or ligate the target tissue. The closure devices described here may be suitable for advancement to the left atrial appendage using a minimally invasive approach, e.g., through a small incision above, beneath, or through the rib cage, through an incision in the costal cartilage or the xiphoid, or the like. Because the closure devices described here provide for visualization and stabilization of the left atrial appendage during closure, only a single point of access (e.g., incision or port) to the left atrial appendage may be required. Put another way, the closure devices described here may be used to close the left atrial appendage from the pericardial space without accessing the internal structures of the heart through the vasculature or otherwise.

Figure 2:
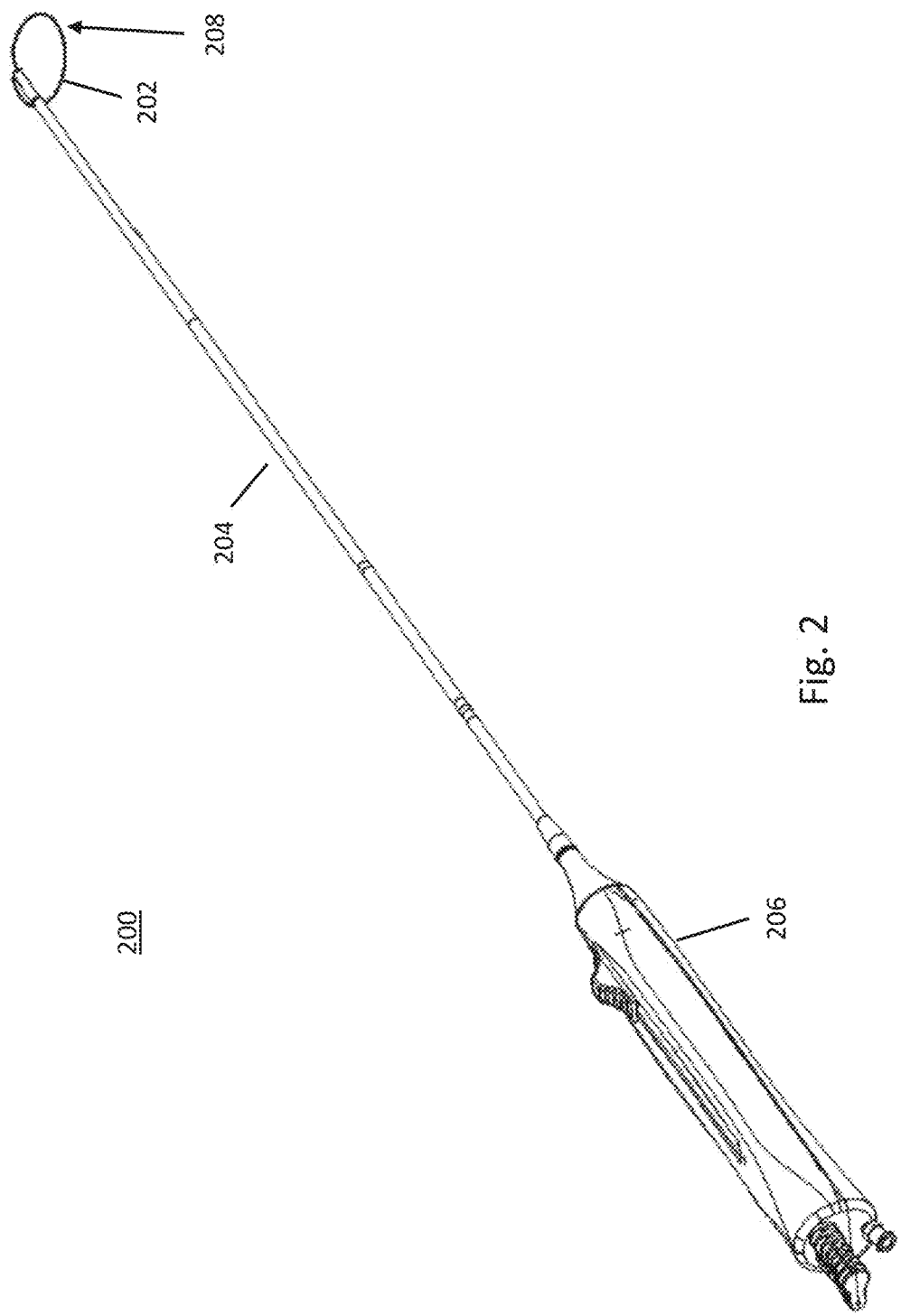
FIG. 2 is a perspective view of an illustrative variation of a closure device that may be used to close a target tissue.

FIG. 2 depicts one illustrative variation of closure device (200) that may be used to close the left atrial appendage. As shown in FIG. 2, the closure device (200) may comprise a snare loop assembly (202), an elongate body (204), and a handle (206). The handle (206) may be coupled to a proximal end of the elongate body (204) and may be used, among other things, to control and actuate the snare loop assembly (202), which may at least partially extend from a distal end of the elongate body (204). As will be discussed in more detail below, controls (e.g., a slider, a button, knob, switch, or the like) on the handle (206) may move the snare loop assembly (202) between a closed configuration and an open deployed configuration.

When in an open configuration, the snare loop assembly (202) and the elongate body (204) may form a continuous loop (208) (e.g., such that the snare loop assembly (202) and the elongate body (204) may fully encircle tissue placed in the loop (208)). When moved from the open configuration to the closed configuration, the size of the loop (208) may be reduced as some or all of the snare loop assembly (202) is withdrawn into the elongate body (204). In the closed configuration, the loop (208) may be provided entirely within the elongate body (204) or a substantial portion of the loop (208) may be provided within the elongate body (204) with a small portion of the loop (208) remaining outside of the elongate body (204). It should be noted that a vacuum tube is not shown in FIG. 2 for the sake of clarity and is described in more detail below.

Snare Loop Assembly

The snare loop assembly may be used to temporarily close and/or restrict one or more target tissues. Generally, the snare loop assembly comprises a closure element (e.g., a snare) and a suture loop releasably attached to the closure element. In some variations, the snare loop assembly may comprise a retention member at least temporarily coupling the closure element and the suture loop. The snare may be at least partially modifiable to move the snare loop assembly between the open, closed and retracted configurations. Generally, a portion of the snare may be housed in the elongate body, and another portion of the snare may extend outside of the distal end of the elongate body to at least partially define the loop and aperture of the snare loop assembly.

The snare loop assembly may be closed around tissue to temporarily or permanently close, ligate, or otherwise tighten tissue, and the suture loop may be tightened and released from the snare to hold or otherwise maintain the tissue in the closed configuration. Either before or after the suture loop is tightened, the snare loop assembly may be retracted into the elongate body to facilitate the removal of the closure device from confined body spaces. Once the suture loop is tightened around the left atrial appendage, the tissue suctioned from the suction tip of the vacuum tube may be released, which may allow for visual confirmation of the tissue closure by the imaging device.

Figure 3A:
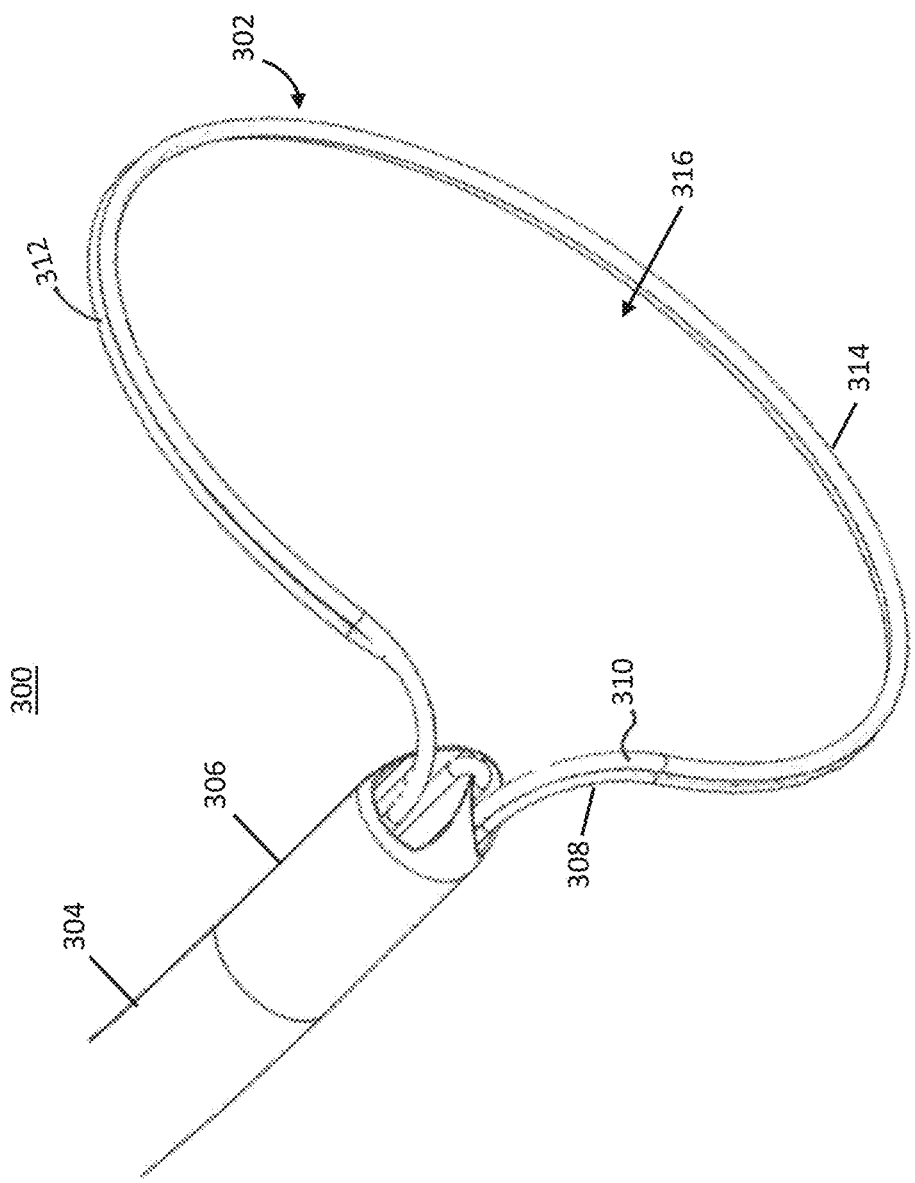
FIG. 3A is a perspective view of a distal end of an illustrative variation of a closure device having a snare loop assembly.

FIG. 3A shows a distal section of an illustrative variation of a closure device (300) comprising a snare loop assembly (302) and an elongate body (304) comprising a tip (306). As shown there, the snare loop assembly (302) may comprise a snare (308), a suture loop (310), and a retention member (312), and may be disposed relative to the elongate body (304) such that at least a portion of the snare loop assembly (302) extends from the distal end of elongate body (304) (e.g., via tip (306)). The snare loop assembly (302) is shown in FIG. 3A in an open configuration, and the portion of the snare loop assembly (302) extending out of the elongate body (304) may form a loop (314) having an aperture (316) therethrough. The loop (314) and the corresponding aperture (316) may be defined by one or more components of the snare loop assembly (302) (e.g., the snare) and the distal end of the elongate body (304), and may be suitable for encircling tissue such as the left atrial appendage. Generally, the snare (308) may be used to open and close the snare loop assembly (302). In some instances, the retention member (312) may be configured to release the suture loop (310) from the snare loop assembly (302) upon application of a sufficient force to suture loop (310).

As mentioned above, the snare (308) may be moveable to change the configuration (e.g., shape, diameter, circumference) of the snare loop assembly (302). In some variations, one end of the snare may be fixed relative to one or more portions of the closure device, while the other end may be coupled to a moveable portion of the handle such that it may be advanced or retracted through the elongate body. Movement of the free end of the snare may change the amount of the snare loop assembly that is disposed outside of the elongate body and around the vacuum tube (not shown), and thus may change the size (e.g., diameter, circumference, area) of the loop and the aperture defined thereby. Specifically, advancement of the snare through the elongate body may increase the size of the loop and the aperture of the snare loop assembly, while retraction of the snare through the elongate body may decrease the size of the loop and the aperture of the snare loop assembly. The free end of the snare may be directly attached to one or more portions of the handle (e.g., a slider, button, knob, switch, or the like), or may be coupled to the handle via a rigid structure, for example a hypotube, a rod, or the like. The rigid structure may be coupled to and moved by the handle, which may advance or retract the free end of the snare and thus may open and close the snare loop assembly. Although described as coupled to a portion of the handle, the free end of the snare need not be, and may be manipulated in any suitable manner. The fixed end of the snare may be coupled to any suitable portion of the closure device, for example, any portion of the elongate body (304) including the tip (306) or the handle. In some variations, the fixed end of the snare may be releasable, and in some instances retractable into a lumen of the elongate body, which may assist in releasing the target tissue from the aperture in the snare loop assembly after deployment of the suture loop. Utilizing a releasable or retractable snare may also assist with withdrawal of the closure device from body.

The closure element (e.g., snare) may be made of any suitable material or combination of materials. For example, in some variations, the snare may be made from a shape-memory material, such as a shape-memory alloy (e.g., a nickel titanium alloy, etc.), or may be made from stainless steel, polyester, nylon, polyethylene, polypropylene, combinations thereof, or the like. In variations where the snare is made from a shape-memory material, the snare may be configured to take on a particular shape or configuration when the snare loop assembly is placed in an open configuration, but may still be at least partially withdrawn into the elongate body to place the snare loop assembly in a closed configuration. For example, the snare may form a generally circular, teardrop-shaped, oval or ellipsoid, or triangular loop when the snare loop assembly is placed in an open configuration. In some instances, when the snare loop is in the closed configuration, it is at least partially withdrawn into the elongate body and tightened around the circumference of the vacuum tube that extends through the snare loop. In some variations, the snare may be radiopaque and/or comprise radiopaque materials and/or markers.

Moreover, in some variations, the snare loop assembly may be angled relative to the elongate body and/or the vacuum tube. Angling the snare relative to the elongate body and/or the vacuum tube may aid the snare in advancement over a vacuum tube and capturing tissue, as angling may better position the snare relative to tissue. As shown in FIG. 3B, the plane of snare loop assembly (302) is approximately perpendicular to the distal end of the elongate body (304), however, the plane of the snare loop assembly (302) may be varied over a wide range of angles (a), as depicted in FIGS. 3B-3D. In some variations, the angle (a) may be preset, while in other variations, the angle (a) is adjustable within a predetermined range. For example, the angle (a) formed between the plane of the snare loop assembly (302) and the distal end of the elongate body (304), may be between about 5 degrees and about 85 degrees (FIG. 3C), may be between about 5 degrees and about 45 degrees, may be about 90 degrees (FIG. 3B), or may be between about 95 degrees and less than 180 degrees (FIG. 3D). It should be noted that the angle (a) may be nearly 180 degrees so long as the vacuum tube (not shown) is configured to extend through an aperture (316) of the snare loop assembly (302).

Suture Loop

The snare loop assemblies described here may also comprise a suture loop for maintaining tissue in a closed manner. Generally, the suture loop may be releasably attached to the snare, for example, via a retention member, as will be described in more detail below. Furthermore, the suture loop may comprise a suture knot, but need not. This suture knot may be any suitable knot, including, but not limited to, a slip knot (e.g., a one-way slip knot) or a Meltzer knot. In some variations, at least a portion of the knot may be held within the tip of the elongate body. In other variations, the suture knot at least partially extends from the tip of the elongate body or may be positioned outside of the tip and may be temporarily held in fixed relation to the elongate body. When the suture loop comprises a suture knot, the suture loop may comprise a loop portion, a suture knot, and a tail extending from the suture knot. The suture tail may be pulled through the suture knot to reduce the diameter of the loop portion.

In variations where the suture loop comprises a slip knot, the suture may be advanced or withdrawn through the slip knot to change the size of the suture loop. In instances where the suture knot is held within or against a tip of the elongate body, the suture knot may not move while the size of the suture loop is changed. This may help prevent the closure device from damaging tissue. In some variations, the suture loop may comprise a unidirectional locking structure. In these variations, the unidirectional locking structure may be any structure capable of being advanced along the suture in one direction but resisting movement in a second direction.

In these variations, the locking structure may be advanced over a portion of the suture loop to help lock a suture knot in place. The locking structure may be advanced via one of the closure devices described here, or it may be advanced by a separate device after the suture loop has been released from the closure device.

The suture loop may be made from any suitable material useful in tissue exclusion or closure. For example, it may be made of a biodegradable material (e.g., polylactic acid, polyglycolic acid, polylactic-co-glycolic acid, etc.), or it may be made of a non-biodegradable material (e.g., metal, steel, polyester, nylon, propylene, silk, combinations thereof, etc.).

When the suture loop is tightened to close tissue, it may be possible for tissue to be pulled into the suture knot of the suture loop. If too much tissue is pulled into the suture knot, the suture knot may clog or jam in a way that prevents the suture loop from being further tightened. In some variations the suture loop may comprise one or more pledgets or tube sections to help shield a portion of the suture knot.

In some variations, a distal tip of an elongate body may comprise a suture loop severing assembly (e.g., a suture cutter) configured to separate a tightened suture loop from a closure device. For example, a portion of the suture disposed within the distal tip may be cut using a blade disposed in the distal tip to separate the suture loop from the closure device. Thus, in some variations, the closure devices described herein may deliver, tighten, and release a suture loop from the closure device (e.g., cut or otherwise sever the suture such that the suture loop may remain within the body after removal of the closure device) without additional devices. FIGS. 28A-28B depict a suture loop severing assembly (e.g., a suture cutter) (2810) disposed in a distal end, for example, in the distal tip (2804), of a closure device (2800). The closure device (2800) may comprise an elongate body (2802) coupled to the distal tip (2804). A suture (2806) may extend through respective lumens of the distal tip (2804) and elongate body (2802). The suture loop severing assembly (2810) may be disposed within a proximal portion of the distal tip (2804) and may comprise a severing assembly housing (2812). The severing assembly housing (2812) may define a first severing assembly lumen (2818) and a second severing assembly lumen (2820) that may be parallel to one another. At least a portion of a suture cutter (2814) (e.g., the edge of a blade) may be disposed within the second severing assembly lumen (2820). For example, the suture cutter (2814) may be mounted on a top surface of the severing assembly housing (2812) at an angle relative to a longitudinal axis of the distal tip (2804) and extend into the second severing assembly lumen (2820). In some variations, the suture cutter (2814) may have a length between about 0.5 mm and about 1.3 mm. The suture (2806) may extend through the first severing assembly lumen (2818). A control wire (2816) may extend through the second severing assembly lumen (2820) and be attached or otherwise coupled to the suture (2806) within the distal tip (2804). For example, the control wire (2816) may couple (e.g., loosely) to the suture (2806) distal to the suture cutter (2814) and proximal to the suture loop and the suture knot (not depicted). The control wire (2816) may extend through a control wire lumen in the elongate body (2802) and couple to an actuator in a handle (not shown). In some variations, heat or RF energy may be used to sever the suture instead of a blade. For example, the suture loop severing assembly (2810) may comprise an electrode or other device configured to generate heat or radiofrequency energy, which may be used to sever the suture (2806).

The suture loop severing assembly (2810) may be configured to cut the suture (2806) at a predetermined location (e.g., just distal to the attachment point with the control wire (2816) and proximal to the suture loop and suture knot) upon retraction of the control wire (2816) in a proximal direction. For example, a distal end of the control wire (2816) (e.g., a pull wire) may pull the suture (2806) up towards and into the second severing assembly lumen (2820). The suture cutter (2814) disposed within the second severing assembly lumen (2820) may thus contact and cut the portion of the suture (2806) drawn into the second severing assembly lumen (2820). When a retraction force (e.g., a pulling force) is not applied to the control wire (2816), the suture (2806) will not come into contact with the suture cutter (2814).

Retention Member

When the snare loop assemblies described here comprise a retention member releasably coupling a snare and a suture loop, the retention member may be any suitable member, such as dual-lumen tubing. In some variations, one lumen may have a slit, perforation, or other opening along its length, which may allow the suture to pass therethrough when it is ready to be deployed. The slit need not extend or be continuous along the entire length of the retention member. In some variations, the slit may have prongs or arms along its length to help capture and retain the suture in the retention member. In other variations, the slit may be covered at spaced-apart locations with a biodegradable polymer, which may temporarily tack or hold down the suture. Of course, in still other variations, the retention member may not comprise a slit, and may instead comprise some other type of retention mechanism, such as the prongs or tacks described just above. In yet other variations, there are no slits or openings in the retention member, and the suture loop may be released upon removing or withdrawing the retention member.

Elongate Body

The closure devices described here generally comprise an elongate body. The elongate body may house various components or portions thereof, for example, a portion of the snare, the suture loop, the retention member, imaging device, and the vacuum tube, and may provide a conduit to connect these elements to the handle. As described above, the snare and the vacuum tube may be slidable within the elongate body such that the snare and the vacuum tube may be advanced and retracted relative to the elongate body.

In some variations, at least a portion of the elongate body may be flexible and/or steerable (e.g., using pull wires or any other suitable steering mechanism), which may help facilitate navigation of the elongate body through the body to a target tissue. Utilizing an elongate body that is flexible and/or steerable may be especially useful in instances in which it is difficult to access the target tissue during a procedure because, for example, it may be underneath or covered by other anatomical structures.

In some variations, the elongate body may comprise various sections or portions with different characteristics, for example, different diameters, cross-sectional shapes, stiffnesses, materials, or the like, which may increase the steerability and maneuverability of the closure device. For instance, the elongate body may be braided, non-braided, tapered, non-tapered, or some combination thereof. In some instances, at least a portion of the elongate body may be shapeable, meaning that the elongate body may be manipulated (e.g., bent) and may retain the manipulated shape until a user or other applied force (e.g., from tissue within the body) further modifies it.

Figure 4A:
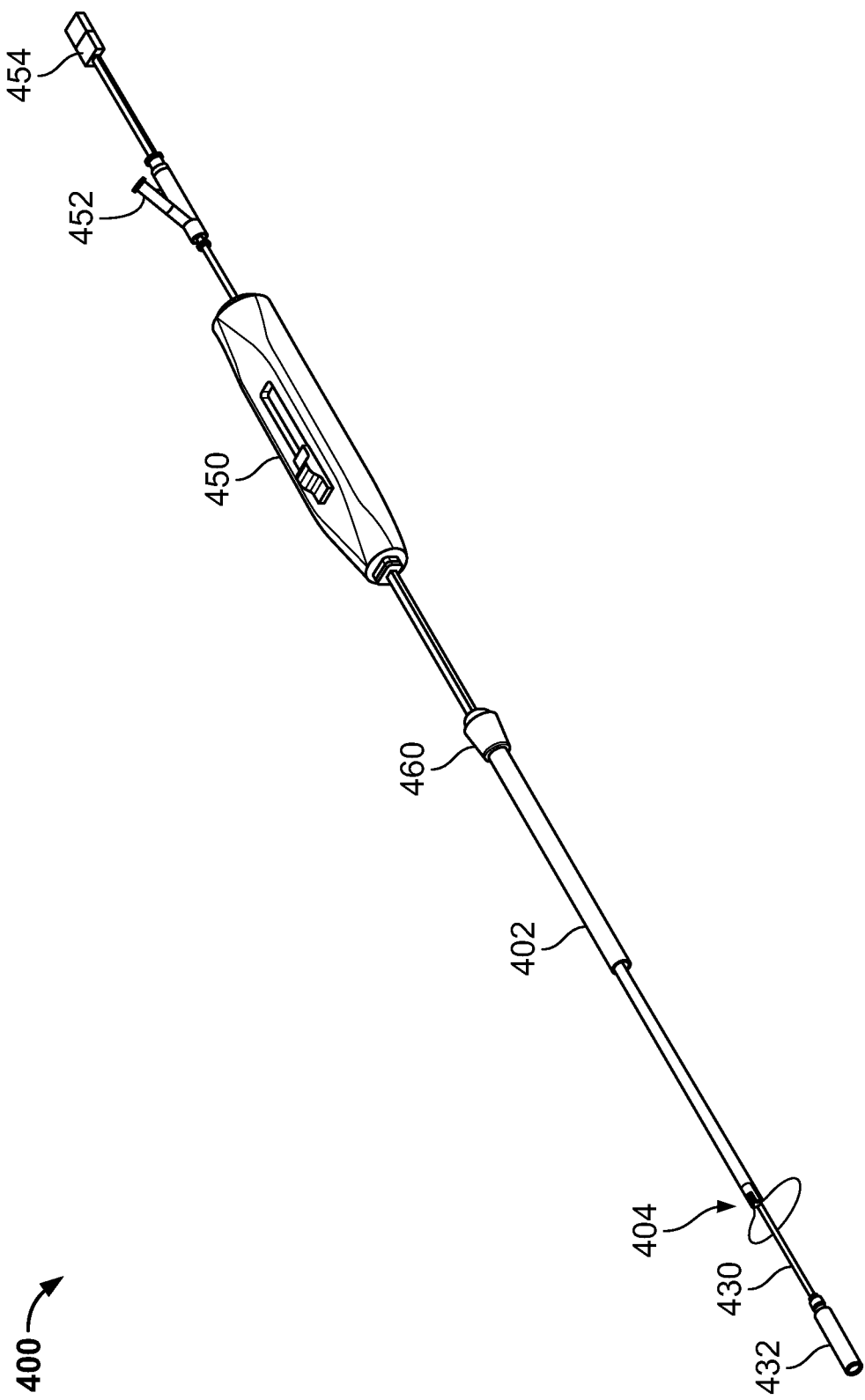
FIGS. 4A-4D are perspective views of an illustrative variation of a closure device.
Figure 4B:
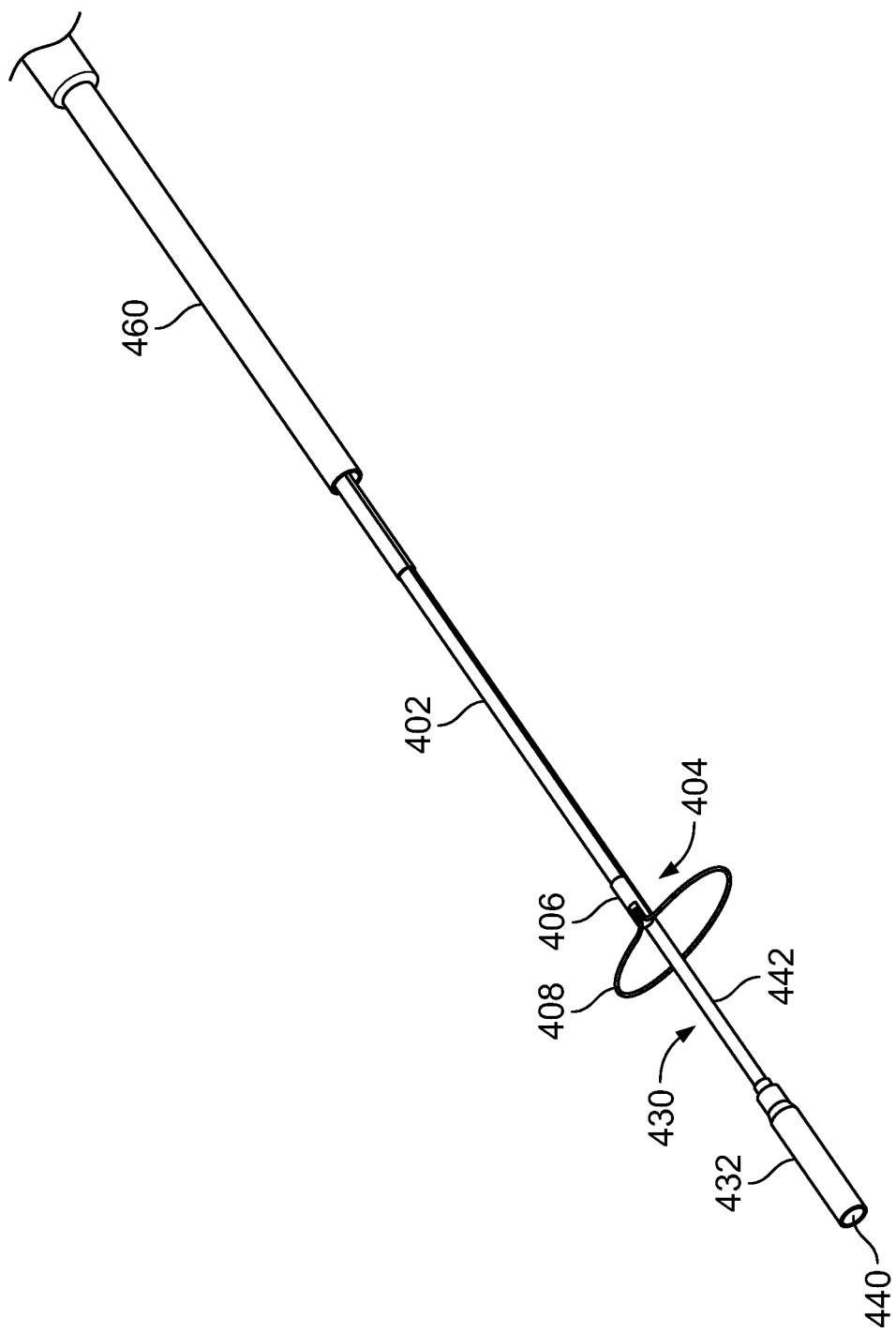
Figure 4C:
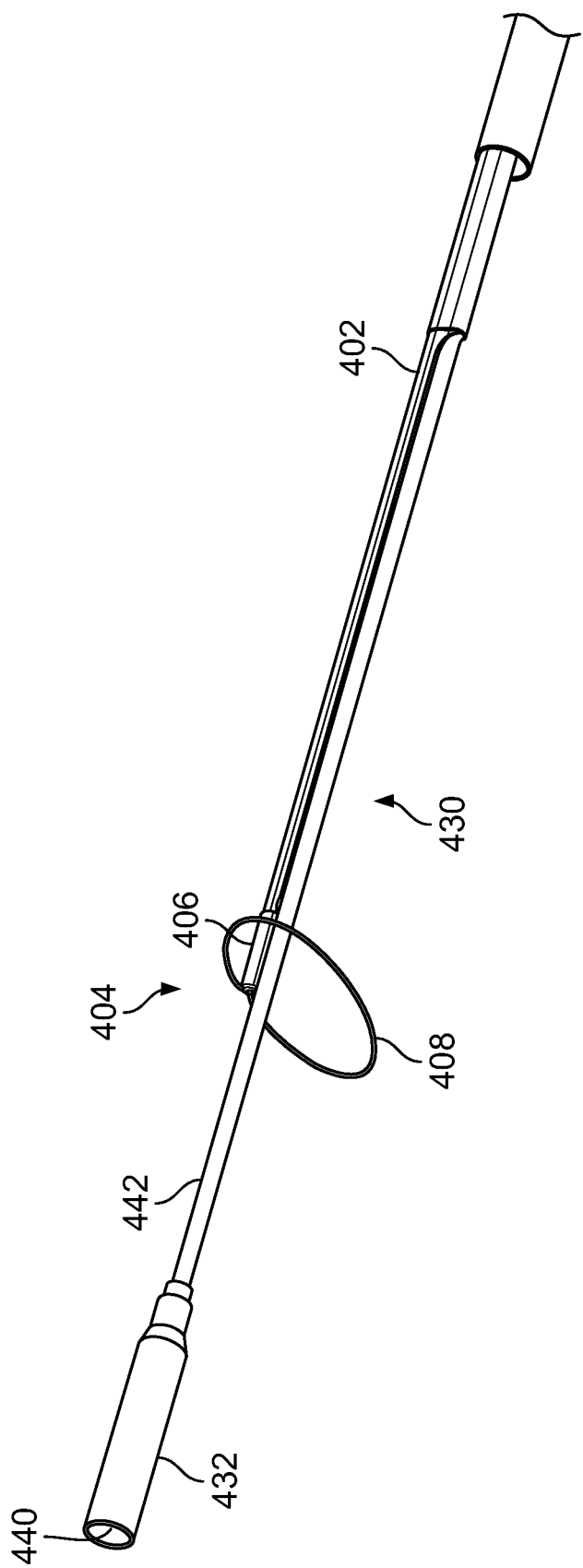

Turning to FIGS. 4B and 4C, as shown there, the elongate body (402) may comprise a tip (406) at the distal end thereof. In some variations, the tip (406) of the elongate body (402) may be formed separately from the elongate body (402), and may be attached to the elongate body (402) during assembly of the closure device using any suitable means (e.g., welded, using adhesive, using connectors). In other variations, the tip (406) may be integral with the elongate body (402). The tip (406) may have the same number of lumens as the elongate body (402), but need not. In some variations, the tip (406) may divide one or more lumens of the elongate (402) body into two or more sub-lumens. In other variations, the tip (406) may alter the size or shape of one or more lumens of the elongate body (402).

Figure 4D:
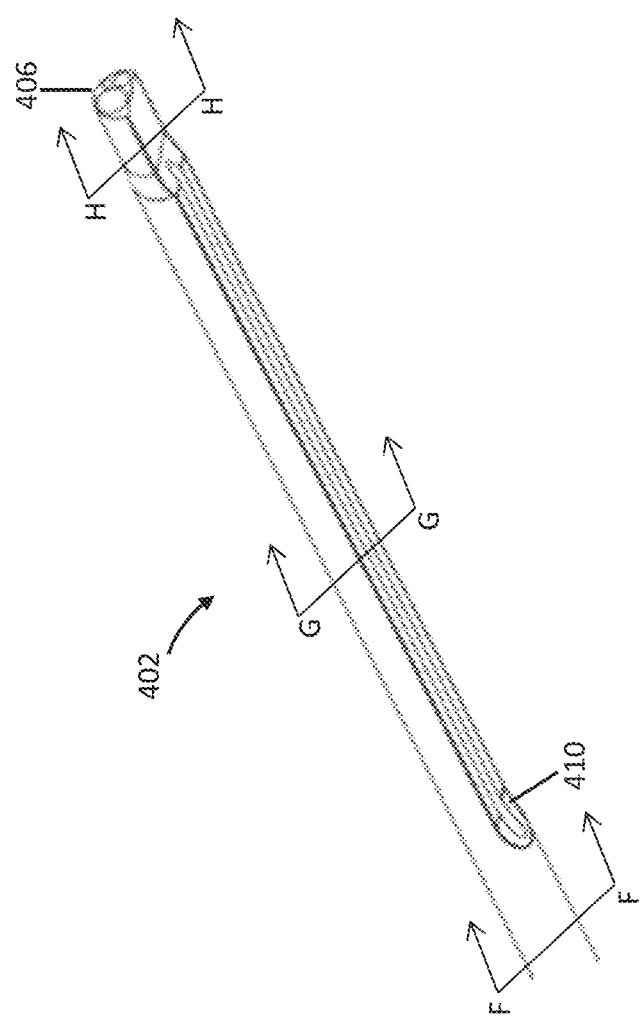

The elongate body may comprise any suitable cross-sectional shape, for example, circular, oval, D-shaped, triangular, or the like. In some variations, the cross-sectional shape of the elongate body may vary along its length. For example, FIG. 4D provides a perspective view of a distal end of the elongate body (402) having different portions. The elongate body may comprise a proximal portion with a first cross-sectional shape (e.g., circular) and a distal portion with a second cross-sectional shape (e.g., D-shaped). Of course, the elongate body may comprise any suitable number of portions, e.g., two, three, or four portions, and the length of each portion may be the same as or different from the other portions. The elongate body may further comprise one or more transitions connecting the portions of the elongate body comprising different diameters or different cross-sectional shapes. The elongate body and vacuum tube may have different shapes, sizes, components, portions, and other characteristics, as described in more detail below. The closure devices described here may include any of the features or elements, for example, any of the elongate body configurations, described in U.S. patent application Ser. No. 15/080,410, entitled "Devices and Methods for Left Atrial Appendage Closure" and filed on Mar. 24, 2016, the content of which is hereby incorporated by reference herein in its entirety. For instance, as described in more detail in U.S. patent application Ser. No. 15/080,410, the diameters and cross-sectional shapes of the elongate body may be different along each of the cross-sectional lines FF, GG, and HH, as shown in corresponding FIGS. 4F-4H and discussed in more detail below.

The elongate body described herein may comprise any suitable length and outer diameter, and the length and diameter of the elongate body may vary depending on the type of procedure being performed. For example, in some instances it may be desirable to limit the outer diameter of the elongate body such that it may fit through 18-French percutaneous tubing. In some variations, the outer diameter of the elongate body may also vary along its length. The elongate body may be made of any suitable material, for example, one or more polymers (e.g., polyether block amide, polyethylene, silicone, polyvinyl chloride, latex, polyurethane, PTFE, nylon, etc.).

Vacuum Tube

As mentioned briefly above, the closure devices described here may comprise a vacuum tube. The vacuum tube may be configured to be slidably positioned relative to an elongate body such that the vacuum tube may advance and retract with respect to the elongate body. For example, the vacuum tube may be configured to fit within a lumen of the elongate body or to slide adjacent the elongate body. The vacuum tube may assist with direct visualization of tissue structures (e.g., for appropriate placement of the vacuum tube relative to the tissue in order to guide a closure element), identification and/or mapping of tissue structures, and stabilization of the closure device relative to the target tissue for advancement of the closure element around the tissue. For example, an imaging device may be disposed within a lumen of the vacuum tube and vacuum may be applied to the tissue in contact with the vacuum tube to temporarily hold the left atrial appendage. In this manner, the closure device guided to the left atrial appendage and the closure element can be properly placed to effectuate tissue closure without a separate device, thereby improving safety and reducing complexity of the closure procedure.

FIG. 4A is a perspective view of an illustrative variation of a closure device (400) comprising an elongate body (402), a snare loop assembly (404), a vacuum tube (430), and a handle (450). The handle (450) may be coupled to the proximal ends of the elongate body (402) and the vacuum tube (430), and the vacuum tube (430) may be slidably positioned within a lumen of the elongate body (402) such that the handle (450) may be used to advance and retract the vacuum tube (430) relative to the elongate body (402). In some variations, the handle (450) may also be used to move the snare loop assembly (404) between open and closed configurations, control the vacuum pressure applied to the target tissue through the vacuum tube (430), control operation and/or advancement of an imaging device (not depicted) positioned within the vacuum tube, and/or release the suture loop from the snare loop assembly.

Turning back to FIGS. 4B-4C, in some variations, the vacuum tube (430) may comprise a proximal portion (not shown), an intermediate portion (442), a distal end (432), and a lumen therethrough (440). The lumen (440) may have any configuration sufficient to provide negative pressure at the distal end (432) when a proximal end of the lumen (440) is coupled to a vacuum source. As shown in FIGS. 4B and 4C, a diameter of the distal end (432) may be greater than a diameter of an intermediate portion (442) of the vacuum tube (430) (shown in FIGS. 4C, 4I), located between a distal end (432) and proximal end (not shown) of the vacuum tube (430). The intermediate portion (442) and proximal portion of the vacuum tube (430) may be sized to fit within a lumen of the elongate body (402) and hold within the lumen (440) one or more power and data conductors coupled to an imaging and/or sensing device as discussed in further detail below. The intermediate portion (442) of the vacuum tube (430) may further be flexible to steer the distal end (432) of the vacuum tube (430) towards a desired location. The distal end (432) may be sized to accept tissue when negative pressure is applied and may be atraumatic such that it does not lacerate, puncture, or otherwise damage the tissue when releasably coupled thereto. In some variations, the distal end (432) may comprise a cone, cup-shaped, or otherwise concave configuration. In some of these variations, the distal end (432) may be configured to releasably couple to the tissue surface via suction when pressed against the tissue (e.g., be a suction cup). In other of these variations, the distal end (432) may remain relatively rigid to aid in holding a target tissue. At least a portion of the proximal end of the vacuum tube (430) may be slidably disposed within the lumen of the elongate body (402).

In some variations, the distal end (432) of the vacuum tube (430) may comprise an atraumatic grasping element to physically engage and hold tissue adjacent to the vacuum tube (430) without damaging the tissue. In some instances, the distal end (432) of the vacuum tube (430) may be configured to grasp the tissue such that a seal is formed between the distal end (432) and the tissue. For example, the proximal end of the vacuum tube (430) may be coupled to a vacuum source and the distal end (432) may be sized and shaped such that a vacuum seal is temporarily formed when the distal end (432) of the vacuum tube (430) contacts tissue and the vacuum source is activated. The distal end of the vacuum tube (e.g., suction tip, vacuum cup) may comprise a shape and size configured to form a vacuum seal between the distal end of the vacuum tube and the tissue with predetermined attachment strength. For instance, the distal end of the vacuum tube may have an opening height substantially equal to a height of left atrial appendage tissue to fill the lumen of the distal end of the vacuum tube such that a vacuum seal may be formed. The strength of a vacuum force holding the distal end to heart tissue may be proportional to the area of the distal end's opening, assuming that the opening is substantially occluded by tissue to form a vacuum seal. In some variations, the suction tip of the vacuum tube may be configured to grasp and/or surround a left atrial appendage. In other variations, the suction tip of the vacuum tube may comprise one or more shapes and/or soft enclosures (e.g., bags, balloons) to surround at least a portion of the left atrial appendage. For example, an inflatable bag of the suction tip may be inflated to push the left atrial appendage against other heart tissue to hold the left atrial appendage in place therebetween.

Figure 19:
FIG. 19 is a perspective view of an illustrative variation of a vacuum tube.

In some variations, a suction tip of a vacuum tube may be configured to provide visualization via an imaging device disposed in the vacuum tube and stabilization through application of a vacuum suction force. FIG. 19 is a perspective view of another variation of a vacuum tube (1900) comprising a distal suction tip (1902), a vacuum tube (1904), a Y-arm (1906), and an imaging device (1912) (e.g., camera, endoscope, fiberscope, external light source and imaging sensor, ultrasonic catheter, or the like). The imaging device (1912) may be fixed relative to the vacuum tube or may be slidably positioned within a lumen of the vacuum tube (1904). The vacuum tube (1904) depicted in FIG. 19 may be slidably positioned within a lumen of an elongate body (not shown) of a vacuum tube as described herein. A proximal end of the Y-arm (1906) may be coupled to a first seal (e.g., Tuohy-Borst type seal) that may be configured to prevent vacuum leaks out of a proximal end of the vacuum tube (1900). The seal may allow an imaging device (e.g., a cable coupled to a distal end of the imaging device) to be disposed in the vacuum tube lumen, which may be used to communicate negative pressure to the suction tip. As described in more detail herein (e.g., FIGS. 38A-38C and 39A-39B), a second seal may be disposed proximal to the first seal to further improve a vacuum seal.

Although not shown, a handle may be coupled to the proximal end of the elongate body (1904). The handle may also be used to control one or more of the vacuum pressure applied to the target tissue through the elongate body (1904) and operation and/or advancement of the imaging device (1912) positioned within the elongate body (1904). The Y-arm (1906) may be used to couple a proximal end of the elongate body (1904) to a vacuum source (e.g., electronic or mechanical vacuum pump) as described in more detail herein. A proximal end of the imaging device (1912) may comprise an imaging device connector (1914) that may be configured to couple the imaging device (1912) to a device that may process and/or display images for use during a procedure (e.g., image processor and memory, user console, display, remote network, and/or the like).

Figure 20:
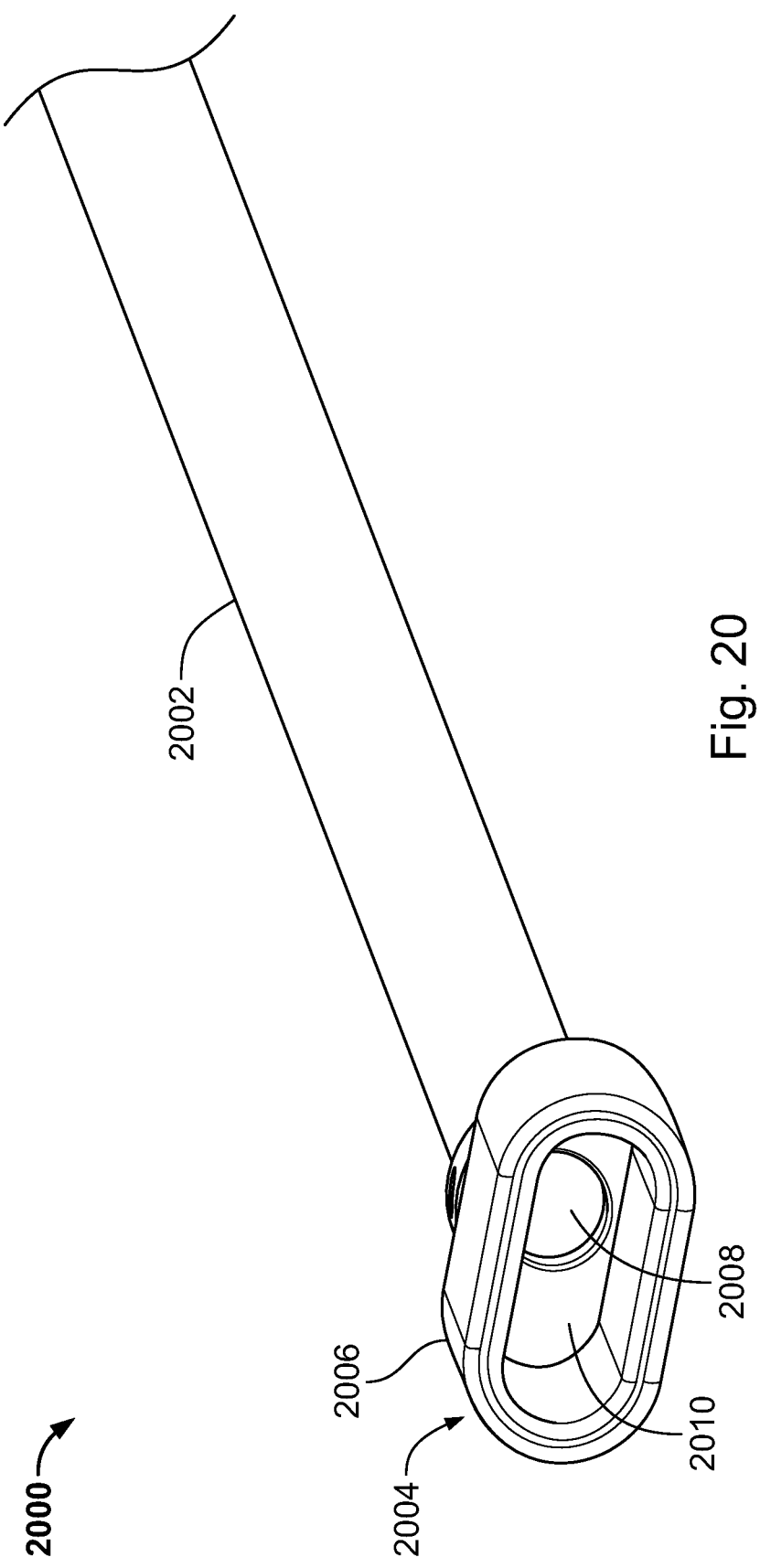
FIG. 20 is a perspective view of an illustrative variation of a suction tip of a vacuum tube.

In some variations, a suction tip of the vacuum tube may physically engage tissue adjacent to the vacuum tube by applying vacuum suction force to the tissue. FIG. 20 is a perspective view of a variation of a suction tip (2004) of a vacuum tube (2000). The vacuum tube (2000) may comprise an elongate body (2002) coupled to the suction tip (2004). The suction tip (2004) may be coupled to a distal end of the elongate body (2002). In some variations, the suction tip (2004) may be formed separately from the elongate body (2002), and may be attached to the elongate body (2002) during assembly of the vacuum tube (2000) using any suitable means (e.g., welded, using adhesive, using connectors). In other variations, the suction tip (2004) may be integral with the elongate body (2002). An imaging device (2008) may be slidably positioned or fixed within a lumen of the suction tip (2004) and elongate body (2002) as described herein. The suction tip (2004) may comprise an obround cup (2006). The obround cup (2006) may be configured to couple with tissue (not shown) by providing a vacuum seal around a circumference of an opening (2010) when a vacuum suction force is applied. A surface area of the suction tip (2004) may be increased by increasing a length of the opening (2010) relative to its width. The obround cup (2006) may comprise a height about equal to a thickness of the left atrial appendage or of target tissue to be suctioned. In some variations, an outer width of the obround cup (2006) may be less than about 20 French and an internal surface height of the obround cup (2006) may be between about 2 mm and about 3 mm. An obround cup (2006) within these dimensions may contact tissue along an entire circumference of the opening (2010) and thus provide increased vacuum holding force relative to an opening of a suction tip (2004) of an elongate body (2002) having a smaller surface area. In some variations, the obround cup (2006) may have a diameter of up to about 20 French.

In some variations, the obround distal tip (2006) may comprise a rigid polymer (e.g., stainless steel, plastic such as ultem, ABS, polycarbonate, a combination thereof, or the like) while one or more portions of the vacuum tube (2002) may comprise a more flexible material (e.g., reinforced pebax, polyimide, urethane, a combination thereof, or the like). Additionally or alternatively, in some variations, the vacuum tube (2002) may comprise braided polyimide and/or stainless steel wire braid having a relatively stiff wall configured to maintain its shape under negative pressure.

In some variations, a suction tip of a vacuum tube may be configured to transition between a collapsed configuration and an expanded configuration, which may aid in advancement of the vacuum tube through a lumen and may increase a cross-sectional area of tissue that may be suctioned. In the collapsed configuration, a cross-sectional area of the suction tip may be minimized to allow advancement of the vacuum tube through a sheath (e.g., cannula) for delivery of the vacuum tube into a pericardial cavity. Once the vacuum tube is advanced out of the sheath and into a pericardial space, the suction tip may transition to the expanded configuration having a larger diameter or transverse dimension than a lumen of the sheath. The expanded vacuum tube may be configured to draw a larger volume of tissue into a lumen of the suction tip. The suction tip may later transition back into the collapsed configuration for retraction and withdrawal from the patient. As described in detail herein, the suction tip may transition between collapsed or delivery/withdraw and expanded/deployed configurations using any suitable mechanism, for example, a fluid-based mechanism or a mechanical mechanism. In some variations, the suction tip may be self-expanding (e.g., naturally biased towards an expanded configuration). For example, the suction tip may comprise a shape memory material (e.g., a nickel titanium alloy) or other material that is biased toward an expanded configuration that may be advanced through and constrained within a lumen of an elongate body or sheath. When advanced out of the lumen, the suction tip may naturally transition to the expanded configuration. One or more portions (e.g., a proximal portion) of the suction tip may be angled in the expanded configuration such that the suction tip may be retracted back into the lumen and become constrained again (e.g., re-form a collapsed configuration).

Figure 25A:
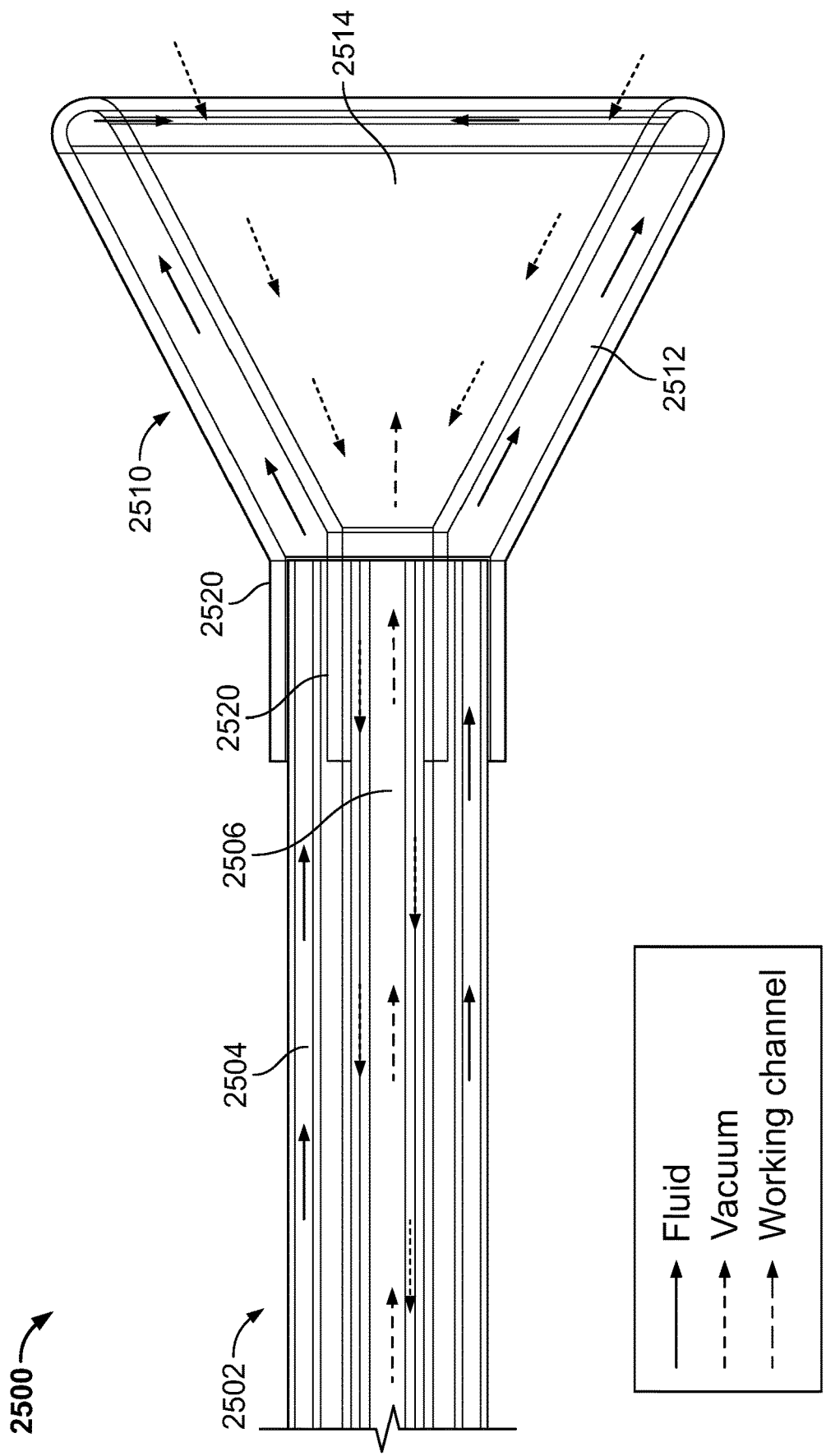
FIGS. 25A-25B are schematic views of an illustrative variation of a vacuum tube.
Figure 25B:
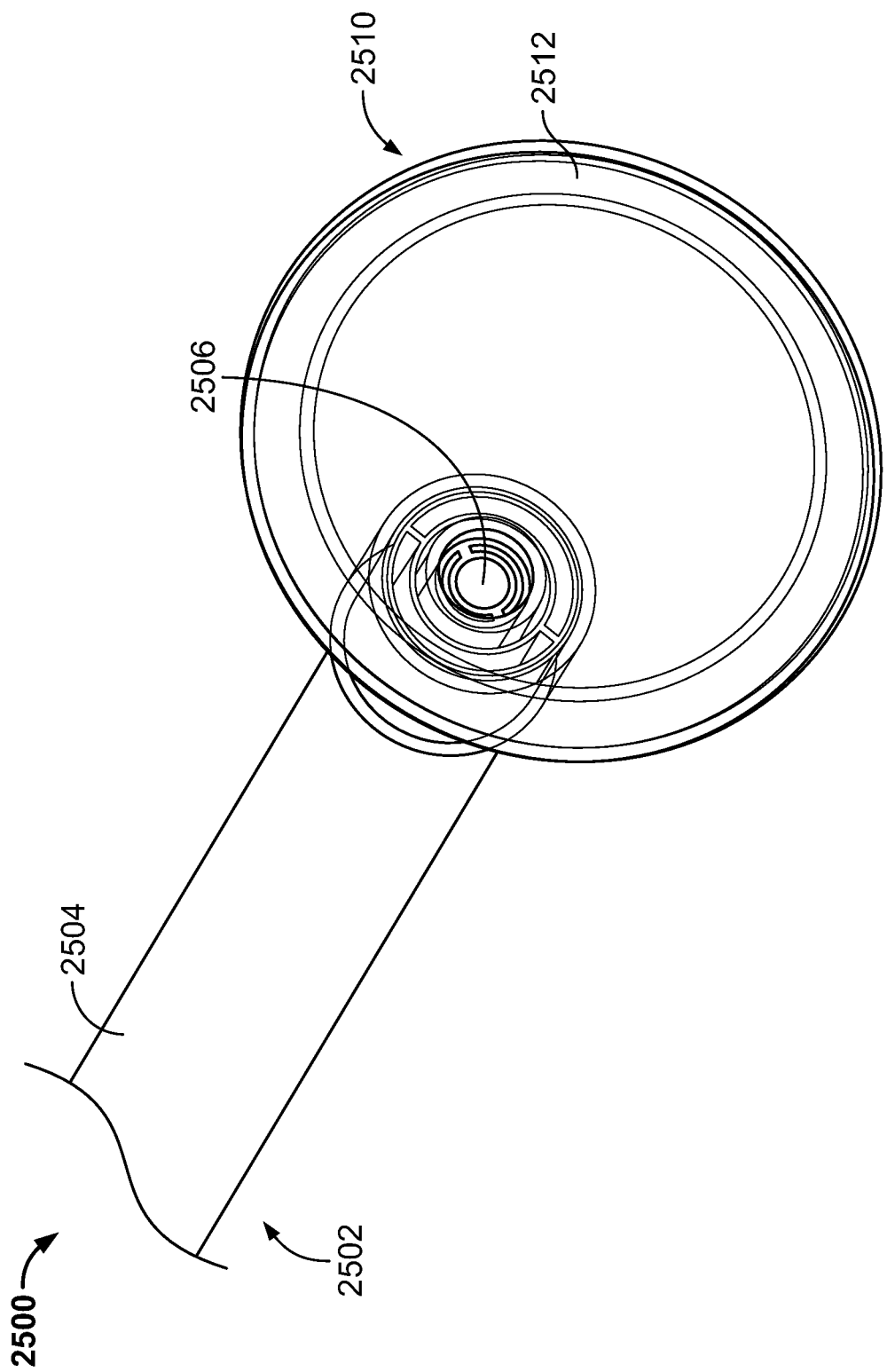

FIGS. 25A-25B depict a variation of a vacuum tube that may transition between a collapsed configuration and an expanded configuration using fluid. For example, the distal end (e.g., suction tip, vacuum cup) of the vacuum tube depicted in FIGS. 25A-25B may be filled with a fluid to rigidize the suction tip and allow tissue to be suctioned into a cavity formed in the suction tip. In some variations, at least a suction tip of a vacuum tube may be advanced in a first configuration (e.g., collapsed, compact, rolled-up, compressed, delivery) and then expanded into a second configuration (e.g., rigid, expanded, inflated, deployed) once a target tissue is reached, where the suction tip in the second configuration may be configured to physically engage tissue adjacent to the suction tip by applying vacuum suction force to the tissue. As shown in the cross-sectional side view of FIG. 25A, a vacuum tube (2500) may comprise an elongate body (2502) comprising a first lumen (2504) and a second lumen (2506). The second lumen (2506) may be disposed within the first lumen (2504) such that the second lumen (2506) has a smaller outer diameter than the first lumen (2504). That is, the second lumen (2506) may be concentric with or otherwise configured to nest within the first lumen (2504). In some variations, the second lumen (2506) may have internal diameter between about 2 mm and about 3 mm. A suction tip (2510) of the vacuum tube (2500) is shown in FIGS. 25A-25B in the second configuration, in which it may have a shape that is generally conical (e.g., funnel, cup), cylindrical, obround, polygonal, and/or the like. The suction tip (2510) may comprise an opening (2514) having a distal diameter greater than that of the second lumen (2506). In some variations, the first and second lumens need not be concentric with each other. For example, the second lumen may comprise a set of two crescent-shaped lumens disposed around a central first lumen. In some variations, the crescent-shaped lumens may be on opposite sides of the first lumen (e.g., on top and bottom, on left and right).

In some variations, the suction tip (2510) may comprise a soft enclosure (e.g., bag, balloon) that comprises a third lumen (2512) (e.g., distal lumen). A distal end of the first lumen (2504) may be coupled to and in fluid communication with the third lumen (2512) such that the third lumen (2512) may be inflated using fluid directed through the first lumen (2504). A distal end of the second lumen (2506) may be coupled to the opening (2514) of the suction tip (2510). In some variations, a proximal end of the elongate body (2502) may be coupled to a Y-arm (not shown) and configured to slidably position the second lumen (2506) relative to the first lumen (2504). In some variations, the position of the second lumen (2506) may be fixed relative to the first lumen (2504) using, for example, a proximal portion (2520) of the suction tip (2510). Additionally or alternatively, the first lumen (2504) and second lumen (2506) may be fixed relative to each other at a handle. For example, in the first configuration, the second lumen (2506) may be withdrawn from a distal end of the elongate body (2502).

As mentioned above, the suction tip may transition from the first configuration to the second configuration using fluid. The first lumen (2504) and the third lumen (2512) in the first configuration may be empty of fluid (e.g., gas, liquid). In this manner, the suction tip (2510) may comprise a compressed or low-profile shape having a smaller volume of space and may thus easily advance through a sheath and/or elongate body (not shown). For example, the suction tip (2510) in the first configuration may compress such that a distal portion of the suction tip (2510) may fold over on itself or otherwise form lower profile such that it may fit within a lumen of a smaller sheath. That is, the suction tip (2510) may be in a collapsible state. Once the first lumen (2504) and suction tip (2510) are positioned at a predetermined location (e.g., at or adjacent a target tissue), the second lumen (2506) may be slidably advanced within the first lumen (2504) to couple to the suction tip (2510) (e.g., such that the second lumen (2506) is flush with a proximal end of the suction tip). The first lumen (2504) may be coupled to a fluid source (e.g., a syringe filled with fluid) and may then be filled with a fluid (e.g., saline, contrast agent, $CO_2$, and combinations thereof) that flows into and fills the third lumen (2512) of the suction tip (2510) with the fluid, thereby transitioning the suction tip (2510) from the first delivery configuration to the second deployed configuration, in which it may be rigid, expanded, and/or inflated. Fluid flow through the first lumen (2504) and into the third lumen (2512) is depicted by a solid arrow in FIG. 25A. Small air bubbles may be present in one or more of the first lumen (2504) and third lumen (2512) without negative consequence to the rigidity of the vacuum tube (2500). The second lumen (2506) and opening (2514) may form a working channel through which suction may be applied and/or a device (e.g., imaging device) may be advanced. For example, FIG. 25A depicts a vacuum suction force being applied within the opening (2514) and second lumen (2506).

In some variations, the first lumen (2504) and third lumen (2512) in the second configuration may have a pressure (e.g., fluid pressure) at least equal to a suction force applied through the second lumen (2506) and opening (2514) of the suction tip (2510). In some variations, the suction tip (2510) may be configured to withstand a pressure of up to about 400 psi (or 27 atm) before failure (e.g., before the soft enclosure leaks and/or bursts). The suction tip may be made of any suitable material or combination of materials. For example, in some variations, the suction tip may comprise a balloon made from nylon, polyethylene terephthalate, combinations thereof, or the like. The suction tip may be configured to take on a particular shape or configuration when the suction tip is inflated in the second configuration. For example, the suction tip may form a shape that is generally conical, diamond, spherical, pyramidal, or the like, when in the second configuration. In some variations, the suction tip may be translucent, opaque, and/or colored (e.g., as a visual marker for an imaging device). In some variations, one or more portions of the suction tip and/or elongate body may be radiopaque and/or comprise radiopaque material and/or markers.

Figure 33A:
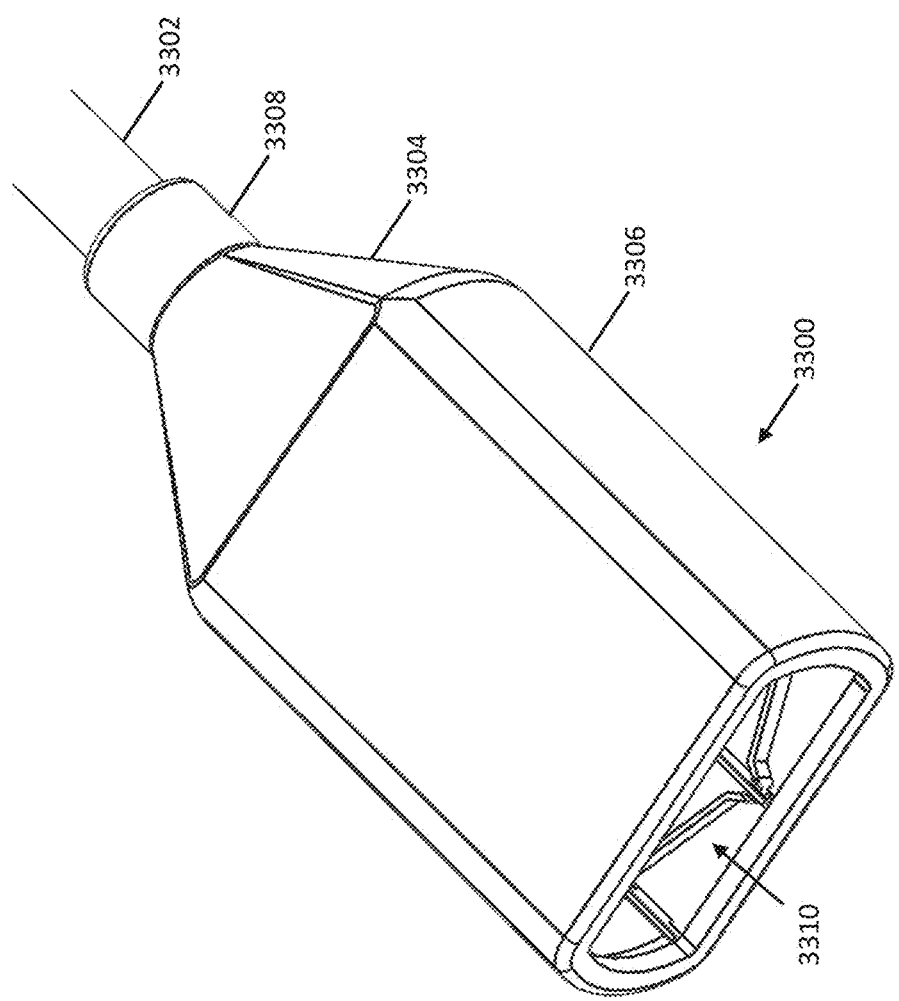

In some variations, an operator may use a vacuum tube that may transition between collapsed and expanded configurations mechanically. FIGS. 33A-33D depict variations of a suction tip of a vacuum tube that may be mechanically operated to transition between collapsed and expanded configurations. FIG. 33A illustrates a suction tip (3300) coupled to a vacuum tube (3302). The suction tip (3300) may comprise a distal hub (3304) (hidden in FIG. 33A under the cover (3306)) coupled to a frame (3310) covered by a cover (3306). The distal hub (3304) and/or cover (3306) may be coupled to the vacuum tube (3302) via a seal (3308).

Figure 33B:
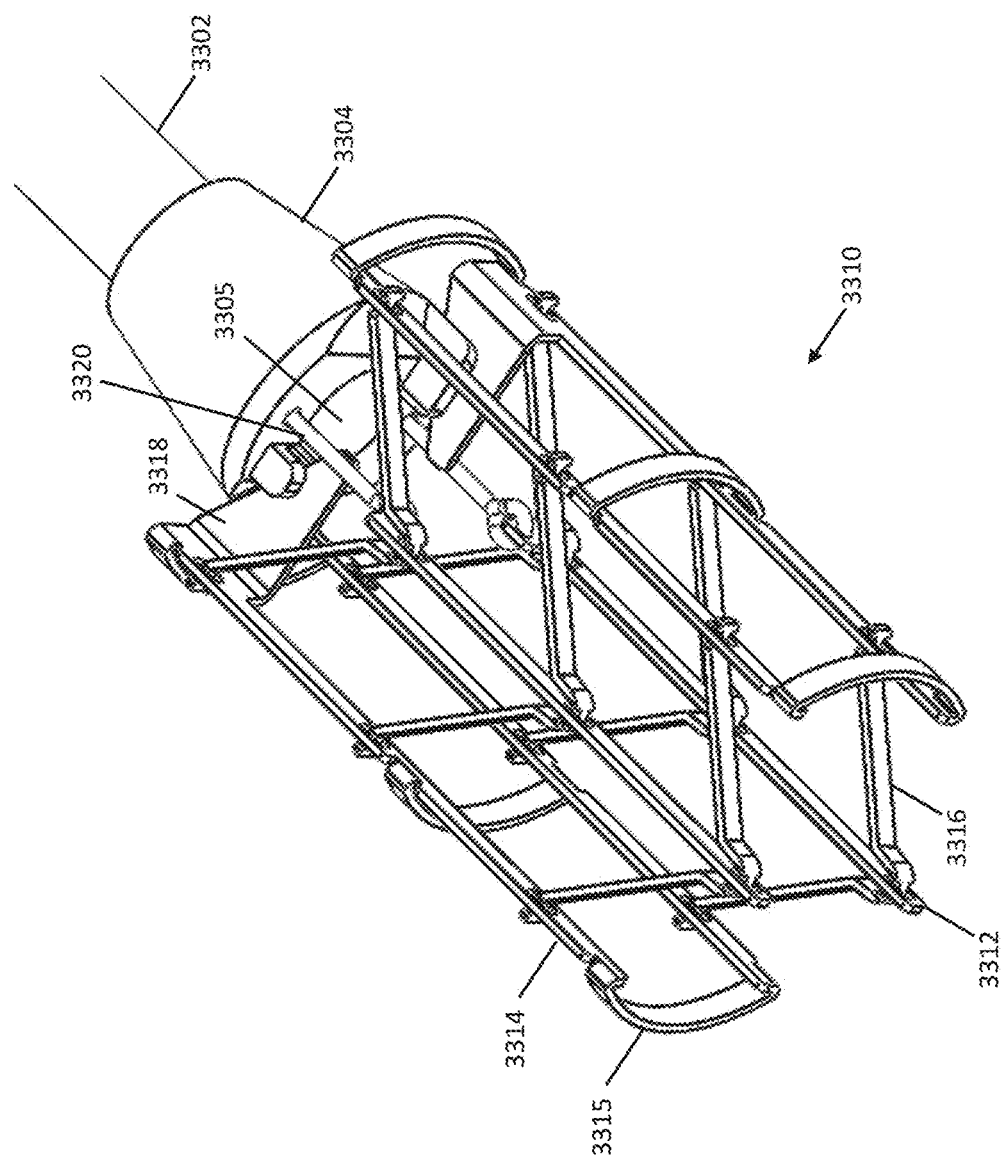

FIG. 33B depicts the suction tip with the cover (3306) removed for clarity. As shown in FIG. 33B, the hub (3304)

may be fixed to the outside diameter of the vacuum tube (3302). The hub (3304) may comprise a first hub lumen (3305) operatively coupled to a lumen of the vacuum tube (3302). The frame (3310) may comprise a set of first support members (3312) (e.g., a pair of longitudinal struts) and a set of second support members (3314) (e.g., a pair of longitudinal struts). The support members (3312, 3314) may be parallel to a longitudinal axis of the suction tip (3300). The second support members (3314) may comprise one or more curved portions (3315) along a length of the suction tip. The first support members (3312) may advance and retract along the longitudinal axis of the suction tip (3300) while the second support members (3314) may move laterally relative to the longitudinal axis of the suction tip (3300). A set of support connectors (3316) may be coupled between adjacent first and second support members (3312, 3314). For example, the support connectors may comprise elongate metal or hard plastic struts that are angled relative to the longitudinal axis. One or more control wires (3320) (e.g., a pair of pull wires) may extend through (e.g., positioned within a lumen or corresponding lumens of) the vacuum tube (3302) and distal hub (3304) and be coupled to the first support members (3312) of the frame (3310). In variations using a plurality of control wires (3320), the control wires (3320) may be operated independently. As shown in FIG. 33B, the distal ends of the control wires (3320) may be coupled to the proximal ends of the first support members (3312). Advancement and retraction of the control wires (3320) may change a configuration of the frame (3310) and thus the suction tip by moving the first support members (3312) longitudinally and the second support members (3314) laterally, as described in more detail herein. The geometry of the frame components are such that the second support members (3314) remain parallel to the first support members (3312) as the second support members (3314) move laterally.

A proximal portion of each of the second support members (3314) may be coupled to a ramp (3318) (e.g., a triangular or wedge shaped plate) configured to slide along a distal face of the hub (3304). As the frame (3310) transitions into an expanded configuration, each ramp (3318) may force the second support members (3314) to displace laterally relative to the longitudinal axis of the suction tip (3300). As the frame (3310) transitions into an expanded configuration, the support connectors (3316) may flex away from the first support members (3312) and store spring energy. The control wires (3320) may be released, thus allowing the second support members (3314) to relax and come together, thereby drawing the second support members (3314) back into the collapsed configuration.

Figure 33D:
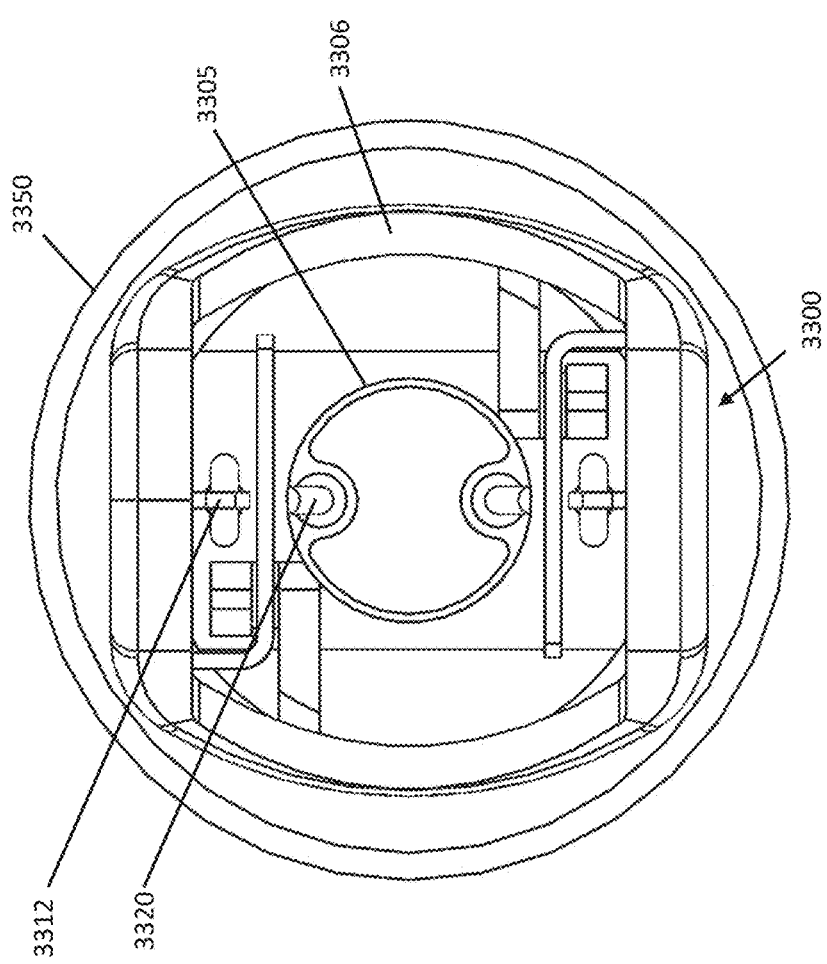
FIG. 33D is a front view of a variation of a vacuum tube.

FIG. 33C is a cross-sectional perspective view of the suction tip (3300) and vacuum tube (3302) without the cover (3306). The vacuum tube (3302) may comprise a plurality of lumens including a first vacuum tube lumen (3330) and a second vacuum tube lumen (3332). In some variations, an imaging device (e.g., camera, endoscope, fiberscope, ultrasonic catheter, or the like) may be disposed within the first vacuum tube lumen (3330) and a vacuum suction force may be applied through the first vacuum tube lumen (3330). The control wire (3320) may be disposed in the second vacuum tube lumen (3332). The distal hub (3304) may comprise a first hub lumen (3305) and a second hub lumen (3307). The first hub lumen (3305) may be operatively coupled to the first vacuum tube lumen (3330) and the second hub lumen (3307) may be operatively coupled to the second vacuum tube lumen (3307). The control wire (3320) may be slideable within the second hub lumen (3307). One or more control wires (3320) may extend to a proximal end of the vacuum tube (3302) and be coupled to an actuator (not shown) (e.g., an actuator disposed in a handle). FIG. 33D is a front view of the suction tip (3300) of a vacuum tube (3302) in a collapsed configuration sized to slide within a lumen of a sheath (3350).

FIGS. 34A-34C illustrate the suction tip (3402) of the vacuum tube (3400) (with and without a cover) advanced out of a sheath (3404) in various configuration states. FIG. 34A depicts the suction tip (3402) in a collapsed configuration, in which it is configured (e.g., sized) to slide within a lumen of the sheath (3404). A control wire of the suction tip may be in the fully distal position. In FIG. 34B, suction tip (3402) is partially expanded into an intermediate configuration. In this configuration, a width of the suction tip (3402) may be larger than a diameter of the sheath (3404) and the control wire may be in the partially retracted position. In FIG. 34C, the suction tip (3402) is in the fully expanded configuration. In this configuration, the control wire is in the fully proximal position and the suction tip (3402) is in the fully expanded configuration. The fully expanded configuration has the largest cross-sectional area (length and width) relative to the collapsed and intermediate configurations, thereby providing a larger surface area for tissue contact. A vacuum suction force may be applied to the vacuum tube (3400) and suction tip (3402) in any of the aforementioned configurations, however, it may be most effective in the fully expanded configuration in which the vacuum tip is configured to contact the largest surface are of tissue relative to the other configurations.

In some variations, the suction tip may comprise any suitable length, and the length of the suction tip may vary depending on the type of procedure being performed. In some variations, the suction tip may have a length between about 10 mm and about 25 mm. In some variations, an expanded to collapsed ratio of a width of the suction tip may be about 2 to 1 (i.e., the width of the suction tip may be about twice as large in the expanded configuration than in the collapsed configuration). The cover of the suction tip may be made of any suitable material, for example, one or more compliant, flexible materials including, but not limited to, low-durometer silicone, thermoplastic elastomers, a combination thereof, or the like. The frame of the suction tip may be made of any suitable material, for example, one or more rigid materials including, but not limited to, stainless steel, a nickel titanium alloy, a rigid polymer (e.g., polyimide, polyetherimide), a combination thereof, or the like.

Figure 7B:
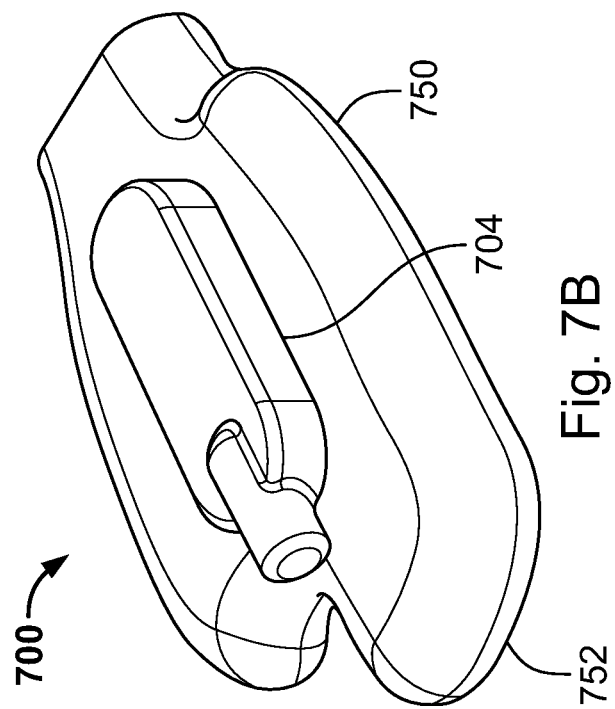
Figure 7A:
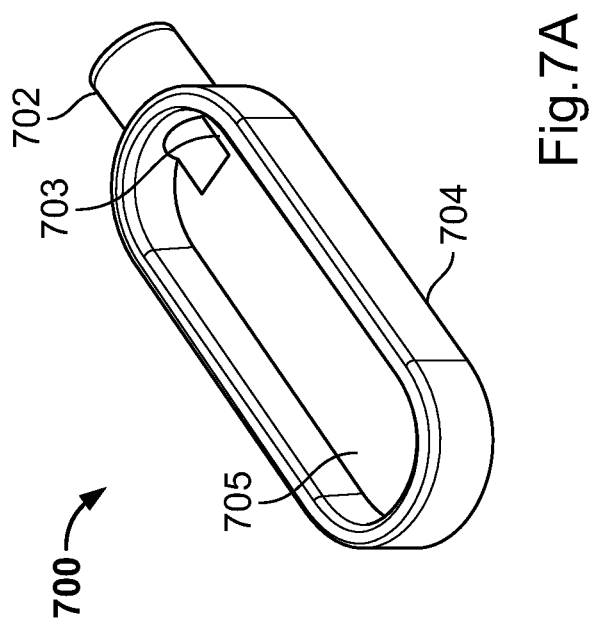

FIG. 7A is a perspective view of a variation of a suction tip (700) of a vacuum tube and FIG. 7B depicts the suction tip (700) coupled to tissue (750). In this variation, the suction tip (700) may comprise an obround cup (704) and a connector (702) configured to couple to a vacuum tube (not shown). The obround cup (704) may be configured to couple with tissue (750) by providing a vacuum seal around a circumference of an opening (705). A surface area of the suction tip (700) of a vacuum tube may be increased by increasing a length of an opening relative to its width. For instance, the obround cup (704) may have a length-to-width ratio of between about 4:1 and about 1.5:1. In one variation, the obround cup (704) may have a length-to-width ratio of about 3:1. An obround cup (704) within these ratios may contact tissue (750) along an entire circumference of the opening (705) and thus provide increased vacuum holding force relative to an opening of a suction tip of a vacuum tube having a smaller surface area. A connector opening (703) may be perpendicular to an obround opening (705) such that suction may be provided in a direction perpendicular to a lumen of the connector (702). This configuration may bring the closure device close to tissue (750), which may decrease the distance that the snare loop assembly needs to travel to be advanced over the tissue (750). For example, a suction tip (700) configured to couple to a lengthwise side of tissue (750), such as a lengthwise side of the left atrial appendage shown in FIG. 7B, may bring the closure device closer to the left atrial appendage than if coupled to an apex (752) of the left atrial appendage. In some variations, the obround suction tip (700) may comprise a rigid polymer having a height between about 0.20 cm and about 1.0 cm, a width between about 0.20 cm and about 1.50 cm, and a length between about 1.0 cm and about 3.0 cm. In other variations, the obround suction tip (700) may have a length-to-width ratio of between about 15:1 and about 1.5:1. In one variation, the obround suction tip (700) may have a length-to-width ratio of about 5:1. In another variation, the obround suction tip (700) may have a length-to-width ratio of about 2:1. In yet another variation, the obround suction tip (700) may have a length-to-width ratio of about 2.5:1. In some variations, the obround suction tip (700) may comprise a height of about 0.60 cm, a width of about 0.80 cm, and a length of about 2.0 cm.

Figure 7D:
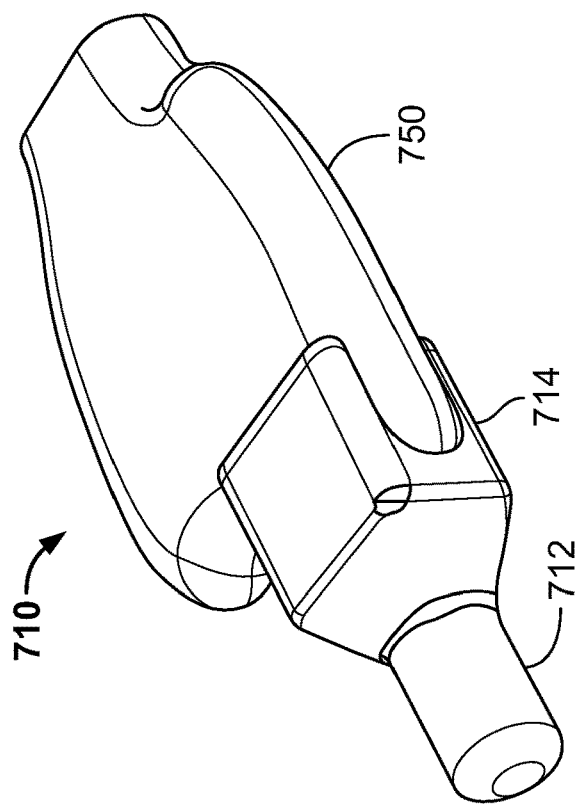
Figure 7C:
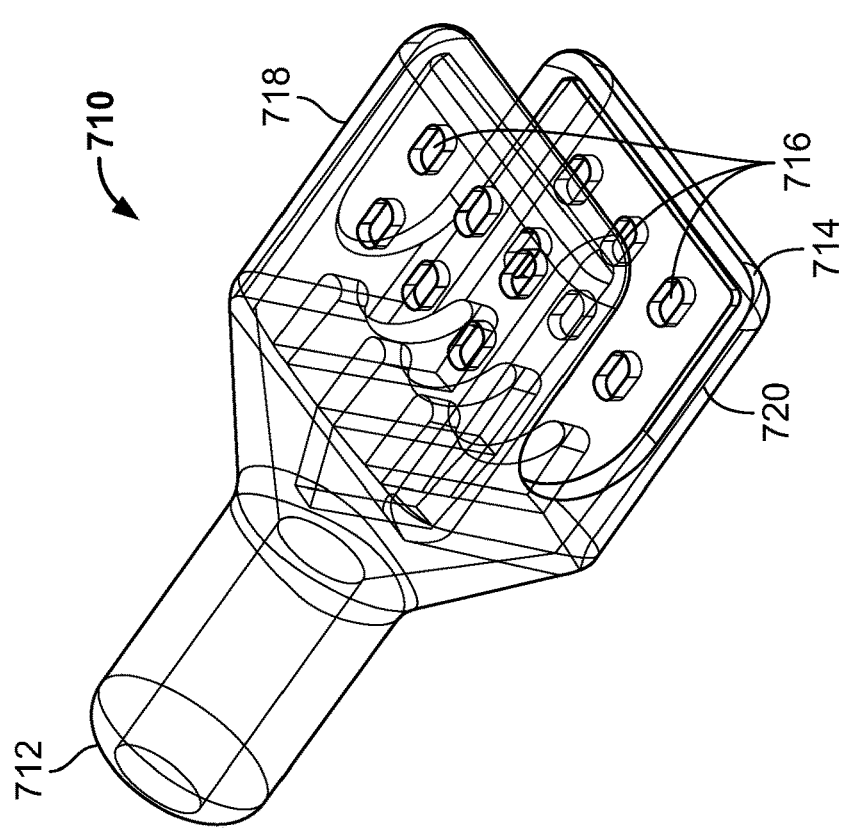

In other variations, a suction tip of the vacuum tube may physically engage tissue adjacent to the vacuum tube through physically grasping tissue and the optional application of a vacuum suction force to the tissue. FIG. 7C is a perspective view of a suction tip (710) of a vacuum tube and FIG. 7D depicts the suction tip (710) of the vacuum tube coupled to tissue (750). In this variation, the suction tip (710) of the vacuum tube (700) is in the form of a gripper comprising a U-shaped portion (714) and a connector (712) configured to be coupled to a vacuum tube (not shown). The U-shaped portion (714) may comprise a first arm (718), a second arm (720), and a plurality of protrusions (716) disposed along an interior surface of the U-shaped portion (714). The first and second arms (718, 720) and protrusions (716) are configured to hold tissue (750) but not lacerate, puncture, or damage the tissue (750) by forming atraumatic surfaces and edges (e.g., rounded, blunt) to enclose tissue without causing damage. For example, as shown in FIG. 7D, an opening of the U-shaped portion (714) (i.e., the distance between the first and second arms (718, 720)) may be about equal to a height of the tissue (750). The U-shaped portion (714) may be advanced such that the first arm (718) is on a first side of the tissue and the second arm (720) is on a second, opposite side of the tissue. In this way, the U-shaped portion (714) may enclose a portion of the tissue (750) and may temporarily couple to the tissue (750) using the suction force provided through the connector (712). Once tissue has been captured by the suction tip (710), the U-shaped portion (714) and the protrusions (716) may hold the tissue and provide resistance to movement of tissue (750). In some instances, the suction tip (710) may have a width and height about equal to a width and height of the left atrial appendage. The U-shaped portion (714) may further comprise rounded edges to reduce trauma to tissue. In other variations, the length of the U-shaped portion (714) may be shorter so as to form a C-shape or V-shape. In some variations, the suction tip gripper (710) may comprise an elastomeric polymer having a hardness (Shore) of about 50 A. It should be appreciated that an imaging device may be provided in the vacuum tube or connector (712) and may provide visualization of tissue (750) captured by U-shaped portion (714).

In yet other variations, a suction tip of the vacuum tube may be advanced in a first configuration (e.g., compact, rolled up, compressed) and then expanded into a second configuration (e.g., expanded, inflated), where the second configuration of the suction tip of the vacuum tube is configured to physically engage tissue adjacent to the vacuum tube by applying vacuum suction force to the tissue. For example, at least a portion of a suction tip of a vacuum tube may be expanded to press one side of tissue such as the left atrial appendage against heart tissue on an opposite side of the left atrial appendage. FIG. 7E is a perspective view of a deformable suction tip (720) of the vacuum tube comprising a connector (722) coupled to a base (724), and a vacuum portion (726). The suction tip (720) may be configured to couple to a vacuum tube (not shown). FIG. 7F depicts the deformable suction tip (720) coupled to tissue (750). The vacuum portion (726) and a ring portion (728) may be disposed in the base (724). In some variations, the base (724) of the deformable suction tip (720) may comprise an elastomeric polymer having a hardness (Shore) of about 27 A. This allows the base (724) to be deformed into a smaller volume (not shown) (e.g., rolled up, compressed), such as during advancement of the vacuum tube in the body. Once in a desired position, pressure may be applied to a ring portion (728) to expand and/or rigidize the deformable suction tip. Negative pressure may then be applied to the vacuum portion (726) to suction tissue. While depicted in FIGS. 7E and 7F as having a circular cross-sectional shape, it should be appreciated that the base (724) may have any suitable cross-sectional shape, such as rectangular, square, oval, triangular, diamond, or the like. In this variation, the connector (722) may be coupled to an intermediate portion of a vacuum tube that may comprise at least a first vacuum tube lumen to provide negative pressure and a second vacuum tube lumen to provide positive pressure. The connector (722) may comprise at least a first suction tip lumen (730) operably coupled to the first vacuum tube lumen of the vacuum tube and a second suction tip lumen (732) operably coupled to the second vacuum tube lumen of the vacuum tube. Thus, in this variation, the first suction tip lumen (730) may provide negative pressure to the vacuum portion (726) and the second suction tip lumen (732) may provide positive pressure to the ring portion (728) of the base (724). As depicted in FIG. 7E, the connector (722) of the suction tip (720) may also comprise a third suction tip lumen (734), which may provide positive pressure to the ring portion (728). Positive pressure may be provided to the suction tip (720) and ring portion (728) by a positive pressure source having fluid comprising gas and/or liquid. In some variations, the vacuum portion (726) may suction to tissue.

Figure 24A:
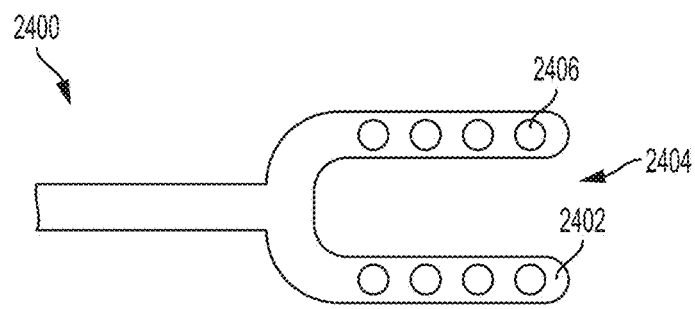
FIGS. 24A-24D are side views of illustrative variations of a vacuum tube.
Figure 24B:
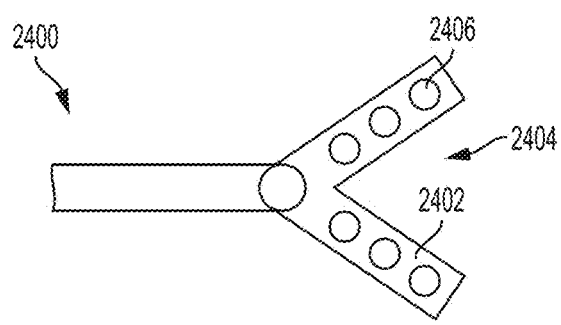
Figure 24C:
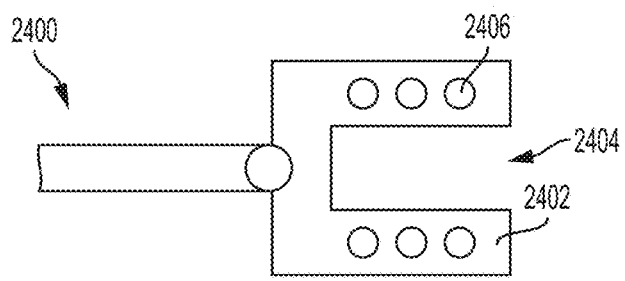

FIGS. 24A-24D depict variations of vacuum tubes comprising apertures and suction tips. A vacuum tube (2400) may comprise a plurality of apertures (2406) at a suction tip (2404). FIGS. 24A-24C illustrate vacuum tubes (2400) having a suction tip (2404) comprising a pair of elongate members (2402) each defining a plurality of apertures (2406) configured to apply a vacuum/suction force to tissue (not shown). FIGS. 24A and 24C illustrate U-shaped distal ends while FIG. 24B illustrates a V-shaped distal end. The suction tip (2404) in FIG. 24A is rounded while the suction tip (2404) in FIG. 24C forms right angles. In some variations, the spacing between the elongate members (2402) may be configured to surround a left atrial appendage to hold it in place relative to the vacuum tube (2400) without compressing and/or squeezing the left atrial appendage. In some variations, the suction tips may be disposed above and/or below the left atrial appendage to hold tissue (e.g., the left atrial appendage may rest on the suction tip or the suction tip may rest on the left atrial appendage). Alternatively, the elongate members (2402) may be disposed to lie on top of tissue (e.g., left atrial appendage, pericardium) such that the tissue may be suctioned into contact with the apertures (2406) and thus the suction tip.

In some variations, the suction tip (2404) may have a length-to-width ratio of between about 4:1 and about 1.5:1. In one variation, the suction tip (2404) may have a length-to-width ratio of about 3:1. In other variations, the suction tip (2404) may have a length-to-width ratio of between about 15:1 and about 1.5:1. In one variation, the suction tip (2404) may have a length-to-width ratio of about 5:1. In another variation, the suction tip (2404) may have a length-to-width ratio of about 2:1. In yet another variation, the suction tip (2404) may have a length-to-width ratio of about 2.5:1. In some variations, the suction tip (2404) may comprise a height of about 0.60 cm, a width of about 0.80 cm, and a length of about 2.0 cm. In some variations, the suction tip (2404) may have a height between about 0.20 cm and about 1.0 cm, a width between about 0.20 cm and about 1.50 cm, and a length between about 1.0 cm and about 3.0 cm.

Figure 24D:
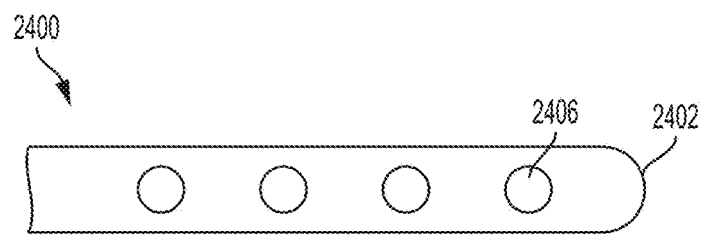

FIG. 24D shows a vacuum tube (2400) comprising a single elongate member (2402) and a plurality of apertures (2406). For example, the suction tip may comprise two, three, four, five, six, seven, eight apertures, or more, including all values and sub-ranges in between. The vacuum tube (2400) of FIG. 24D may be configured to generate suction through a set of selected apertures to suction myocardium tissue near the left atrial appendage. Additionally or alternatively, the vacuum tube (2400) may suction the left atrial appendage itself.

In some embodiments, the suction tip (432) of the vacuum tube (430) may comprise a different material than the intermediate portion (442) of the vacuum tube (430). For example, in some variations, the suction tip (432) of the vacuum tube (430) may be formed from a material that is more rigid than the material used to form a more proximal portion of the vacuum tube. In these variations, a proximal and/or intermediate portion of the vacuum tube (430) may be flexible (e.g., configured to bend), which may assist in steering the suction tip (432) of the vacuum tube (430) to a desired location, while the suction tip (432) of the vacuum tube (430) may be rigid such that the suction tip (432) of the vacuum tube (430) remains open and configured to accept tissue when vacuum is applied. For instance, the suction tip (432) of the vacuum tube (430) may be formed from a rigid material (e.g., stainless steel, plastic such as ultem, ABS, polycarbonate, or the like) and a proximal and/or intermediate portion of the vacuum tube (430) may comprise a more flexible material (e.g., reinforced pebax, polyimide, urethane, or the like). In another example, the proximal and/or intermediate portion of the vacuum tube may comprise braided polyimide and/or stainless steel wire braid having a relatively stiff wall configured to maintain its shape under negative pressure.

In some variations, the vacuum tube (430) may comprise various sections or portions with different characteristics, for example, stiffness, cross-sectional shape, diameter, or the like, to assist in maneuvering the vacuum tube and/or closure device within a confined space such as a body cavity. For example, in some variations, the vacuum tube may comprise a proximal portion and/or intermediate portion (442) comprising walls of reduced thickness relative to the suction tip of the vacuum tube. This may result in a proximal portion and/or intermediate portion (442) of the vacuum tube that is pliable, which may aid advancement through a pericardial space. It should be appreciated that the vacuum tube (430) may be steerable (e.g., using pull wires) regardless of whether an imaging device is used.

The vacuum tube may be slidably positioned within a lumen of the elongate body. In particular, the lumen of the elongate body may at least partially surround the vacuum tube. As shown in FIG. 4C, the vacuum tube (430) may extend from the elongate body (402). It should be appreciated that the lumen of the elongate body through which the vacuum tube may extend may form a partial lumen (e.g., groove, channel, recess) at a distal end of the elongate body (as shown in FIG. 4D) or may extend up to and/or beyond the tip (406) of the elongate body. The partial lumen as shown in FIGS. 4C-4D may in some instances improve flexibility to assist in steering and/or guiding the closure device along the vacuum tube.

Figure 4I:
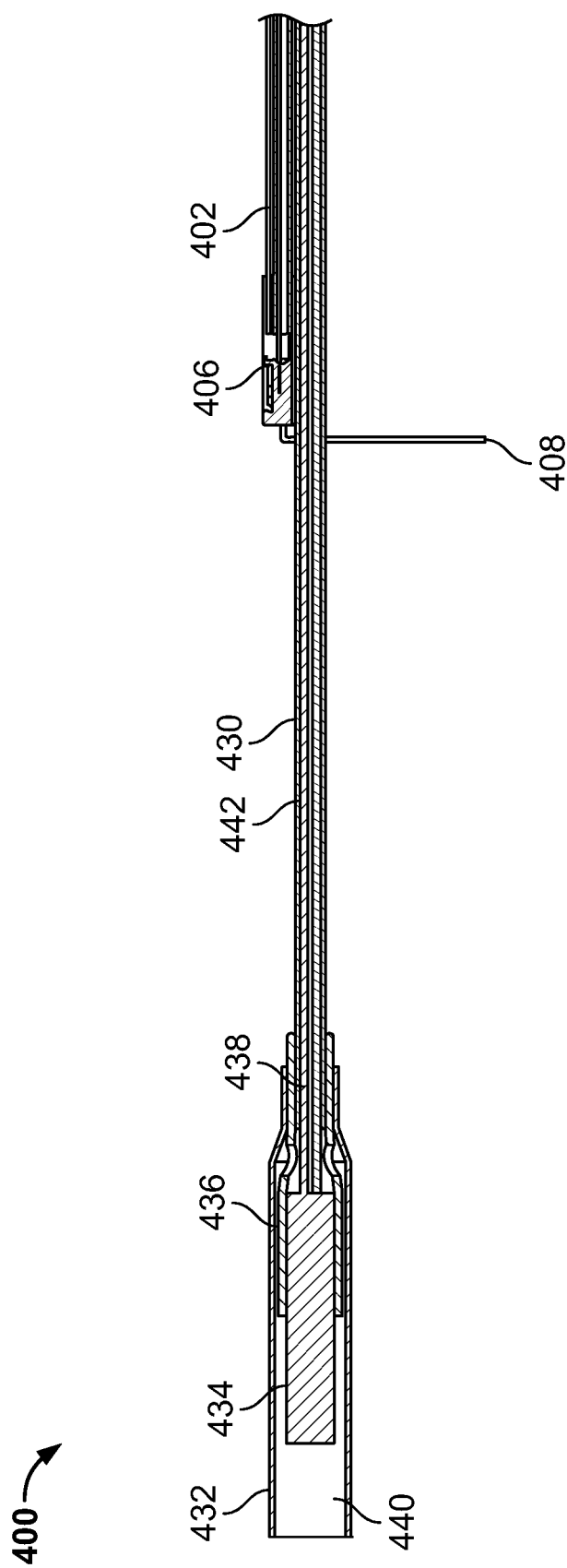
FIG. 4I is a cross-sectional side view of a variation of the closure device.

FIG. 4I is a cross-sectional side view of a variation of the vacuum tube (430) and elongate body (402). As shown there, the elongate body (402) may comprise a tip (406) and a snare loop assembly (404) extending from a distal end thereof. The vacuum tube (430) is shown extended through the snare loop assembly (404). In some instances, the vacuum tube (430) may be advanced out of the elongate body (402) through the aperture (408) formed by the snare loop assembly (404). In some variations, at least a portion of the vacuum tube may already be positioned through the snare loop (e.g., the snare loop may be positioned around the vacuum tube) prior to insertion of the closure device into the body. As mentioned above, the vacuum tube (430) may comprise a lumen (440) extending from a suction tip (432) to a proximal end of the vacuum tube (430) and the proximal end of the lumen (440) may be operably connected to a vacuum pump (not shown) configured to generate negative pressure in the lumen (440) and provide a suction force at the suction tip (432) of the vacuum tube (430).

Any suitable vacuum pump may be used, for example, an electric vacuum pump (e.g., an aspirator), a mechanical vacuum pump, or the like. In some instances, the vacuum pump may be part of a central vacuum system that is integrated into a medical facility, where the central vacuum system utilizes a large vacuum pump and a vacuum reservoir to provide negative pressure to a plurality of rooms. In these variations, the proximal end of the lumen (440) may be coupled to a wall outlet that may provide negative pressure generated by the central vacuum system. The force generated within the vacuum tube (430) may be at least sufficient to pull tissue towards the suction tip (432) of the lumen (440) such that the vacuum tube (430) may be held against the tissue. For example, a vacuum pump may generate a negative pressure between about 480 mmHg and about 635 mmHg. In some instances, the vacuum pump may generate a negative pressure of about 560 mmHg. A tissue holding force may be between about 0.25 lbf to about 1.0 lbf. For instance, in one variation, a vacuum tube comprising a suction tip having an area of about 0.06 in$^2$ may be used with a vacuum pump to generate a negative pressure of about 560 mmHG, which may result in a tissue holding force of about 0.65 lbf.

Figure 5A:
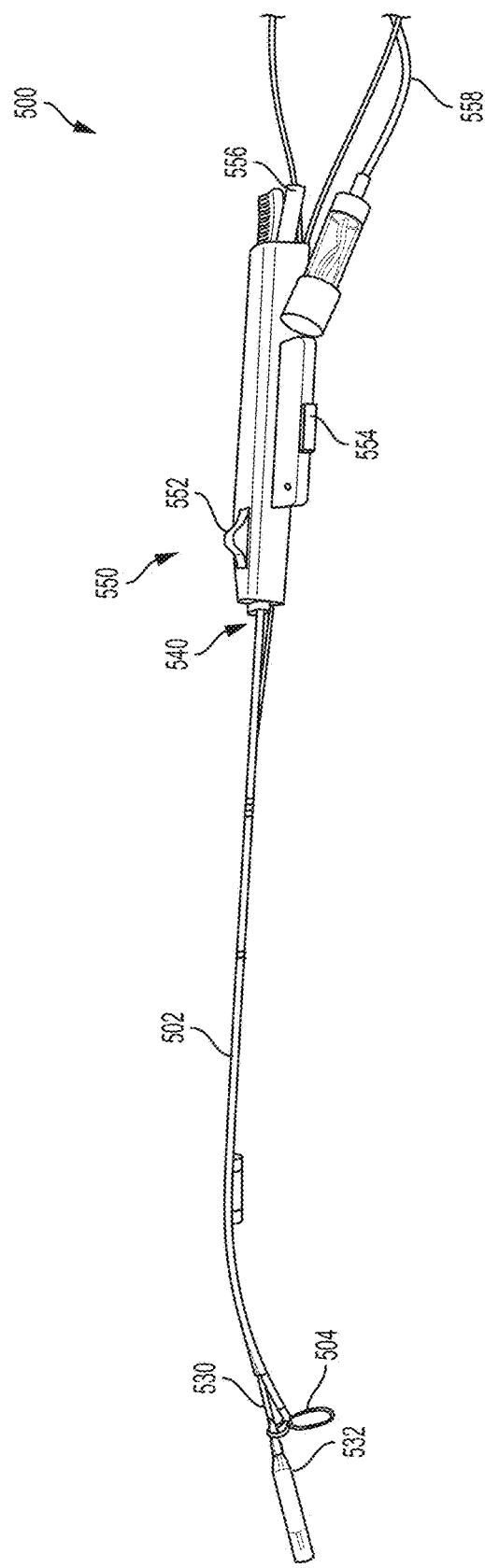
FIGS. 5A-5B are side views of an illustrative variation of a closure device.
Figure 5B:
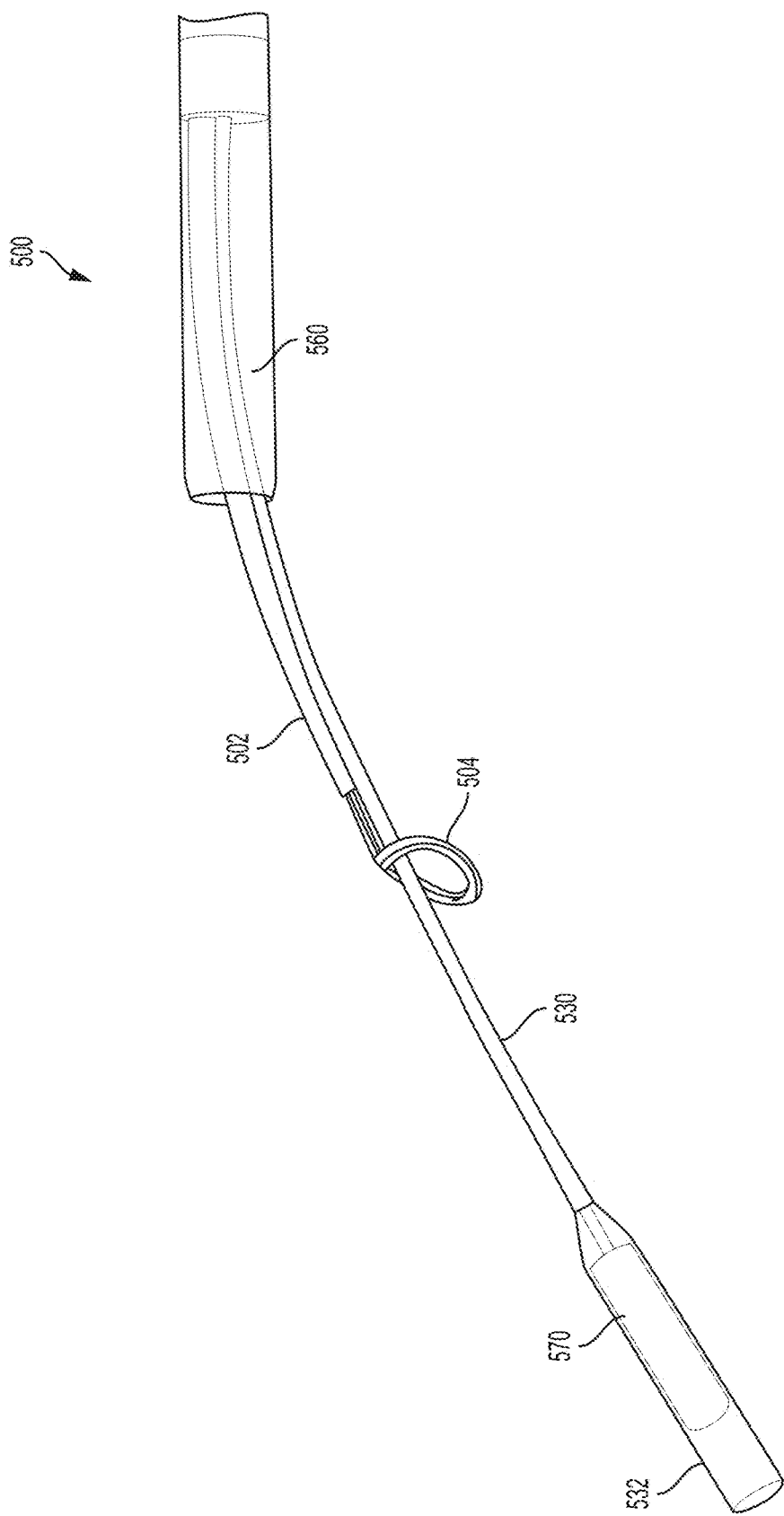

In some variations, a vacuum tube and elongate body may be coupled to a handle of a closure device without the vacuum tube being disposed in a lumen of the elongate body. FIGS. 5A-5B depict side views of a closure device (500) comprising an elongate body (502), a snare loop assembly (504), a vacuum tube (530), and a handle (550). The handle (550) may be coupled to the proximal ends (540) of the elongate body (502) and the vacuum tube (530). In contrast with the closure device (400) depicted in FIGS. 4A-4I, a portion of the vacuum tube (530) is not disposed within a lumen of the elongate body (502). Instead, the vacuum tube (530) may be slidably positioned adjacent the elongate body (502) such that the handle (550) may be used to advance and retract the vacuum tube (530) relative to the elongate body (502). For example, the vacuum tube (530) may extend through and exit from a proximal end of the handle (550). An operator may grasp a proximal end of the vacuum tube (530) to advance and/or retract the vacuum tube (530). The handle (550) may comprise a snare control (552) and a vacuum tube control (554) to operate the snare and to control a vacuum function of the closure device (500), respectively. In some variations, the vacuum tube control (554) may also control advancement and/or retraction of the vacuum tube (530) (e.g., using a slider, knob, button, switch, or the like). As discussed in more detail below, the handle (550) may be used to move the snare loop assembly (504) between open and closed configurations, steer the elongate body (502) and vacuum tube (530), control the vacuum pressure applied to the target tissue through the vacuum tube (530), control operation and/or advancement of the imaging device (570) (as best shown in FIG. 5B) positioned within the vacuum tube (530), and/or release the suture loop from the snare loop assembly (504). A proximal end of the handle (550) may comprise a vacuum connector (556) and an imaging device connector (558), as discussed in further detail below.

Figure 6:
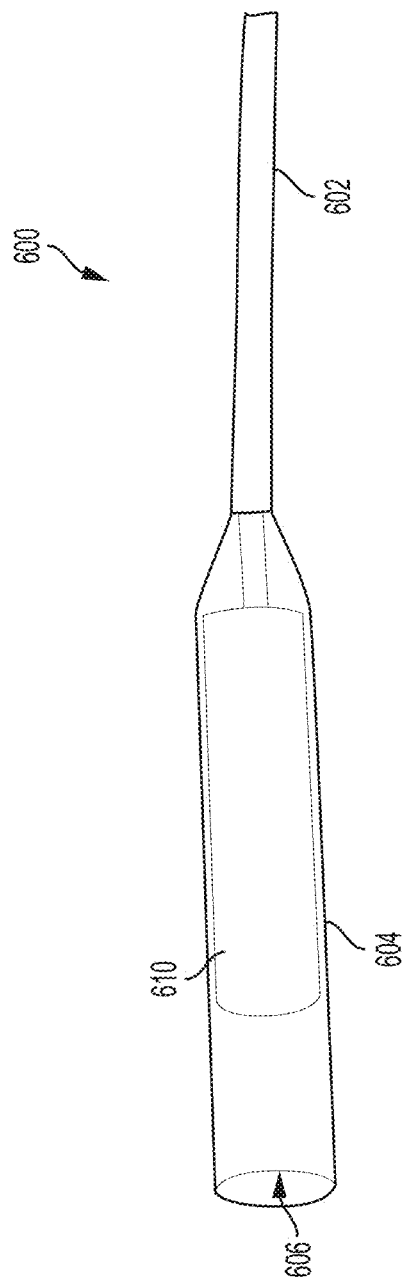
FIG. 6 is a side view of an illustrative variation of a vacuum tube.

FIG. 6 is a side view of an illustrative variation of a vacuum tube (600) comprising an intermediate portion (602) and a suction tip (604). The suction tip (604) of the vacuum tube (600) may be coupled to the intermediate portion (602) of the vacuum tube (600) in any suitable manner. For example, as depicted in FIG. 6, a proximal side of the suction tip (604) of the vacuum tube (600) may taper and be coupled (e.g., welded, using adhesive, using connectors) to a suction tip of the intermediate portion (602) of the vacuum tube (600). In other variations, the suction tip (604) of the vacuum tube (600) and the intermediate portion (602) of the vacuum tube (600) may be integrally formed. An imaging device (610) may be disposed within a lumen (606) of the suction tip (604) of the vacuum tube (600) and may be configured to provide visualization of tissue (not shown). The imaging device (610) may be located at a predetermined distance from an opening of the suction tip (604) of the vacuum tube (600) to provide a buffer between the tissue (e.g., heart tissue) pulled into the opening of the suction tip (604) of the vacuum tube (600) and positioned within the lumen (606) of the vacuum tube (600) and the imaging device (610). Power and data conductors (not shown) may extend from the imaging device (610) through the vacuum tube (600) to at least a handle (not shown). The lumen (606) of the vacuum tube (e.g., the intermediate portion (602) and the suction tip (604)) may be sufficiently sized such that the imaging device (610) and the power and data conductors may be positioned within the lumen (606) of the vacuum tube (600) and vacuum may still be transmitted from a vacuum pump through the lumen (606) of the vacuum tube (600) to a suction tip (604) of the vacuum tube (600).

In some variations, a vacuum tube may be slidably adjacent to an elongate body and may be coupled together using a coupling element (e.g., fastener) configured to slidably hold a portion of the vacuum tube relative to a corresponding portion of the elongate body. This may help ensure that a snare loop and vacuum tube are aimed in the same direction and may assist in positioning the devices relative to one another. FIGS. 26A-26B depict perspective views of a closure device (2600) comprising an elongate body (2602), a vacuum tube (2604), an imaging device (2610), and a fastener (2620). The elongate body (2602) may define a plurality of lumens therethrough where a snare loop may extend out of a first lumen and the vacuum tube (2604) may be slideably disposed within and extend out of a second lumen of the elongate body (2602). The cross-sectional shape of the elongate body (2602) may vary along its length as described in more detail above. For example, a distal portion of the elongate body (2602) may comprise a D-shaped cross-section and a proximal portion of the elongate body (2602) may comprise a circular cross-section. The vacuum tube (2604), for example, may extend out of the lumen of the elongate body (2602) (e.g., of the circular-cross section in FIG. 26A). An operator may grasp a proximal end of the vacuum tube (2604) to advance and/or retract the vacuum tube (2604). In some variations, the elongate body (2602) and the vacuum tube (2604) may be coupled to a handle (not shown) comprising a snare control and a vacuum tube control as described herein. For example, a vacuum tube control may be configured to control advancement and/or retraction of the vacuum tube using an actuator (e.g., slider, a knob, button, switch, or the like).

A suction tip (2606) of the vacuum tube (2604) may be coupled to or otherwise configured to hold an imaging device (2610) and may further comprise a shape to aid in suctioning tissue, as shown in the tissue closing process of FIGS. 27A-27F, which will be described in more detail below. The imaging device (2610) may be disposed within a lumen of the suction tip (2606) of the vacuum tube (2604) and may be configured to provide visualization of tissue. The imaging device (2610) may be located at a predetermined distance from an opening of the suction tip (2606) to provide a buffer or gap between the tissue pulled into the opening of the suction tip (2606). The imaging device (2610) may comprise power and data conductors (e.g., electrical connectors, lead wires) that extend from the imaging device (2610) through the vacuum tube (2604) and into a handle. The lumen of the vacuum tube (2604) may be sufficiently sized to hold the imaging device (2610) and still transmit a vacuum force through the vacuum tube (2610). In some variations, the suction tip (2606) may comprise a shape such as those described with respect to FIGS. 20, 25A-25C, and 33A-34C.

The closure device (2600) may further comprise a fastener (2620) configured to slidably hold portions of the elongate body (2602) and the vacuum tube (2604) relative to one another. The fastener (2620) may comprise a first body portion (2622) and a second body portion (2624) configured to couple to the elongate body (2602) and vacuum tube (2604), respectively. As shown in FIGS. 26A-26B, the first body portion (2622) may comprise a D-shape body defining a corresponding D-shape lumen that mimics or corresponds to the D-shape of the elongate body (2602) over which it is disposed. Similarly, the second body portion (2624) may comprise a circularly-shaped body defining a corresponding circularly-shaped lumen configured to slide over the circular vacuum tube (2604).

The fastener (2620) may be coupled to a control wire (2628) (e.g., pull wire) that may be coupled at a proximal end to a handle (not shown) and at a distal end to one or more of the body portions (2622, 2624) of the fastener (2620). The control wire (2628) may be advanced and retracted to slidably position the fastener (2620) along a length of the closure device (2600) (e.g., elongate body (2602)). The control wire (2628) may be fixed to the fastener (2620) and may extend through a lumen of the elongate body (2602) (e.g., the same as or separate from lumens for the snare loop assembly and vacuum tube) and into a handle. In some variations, an operator may advance or retract the control wire (2682) relative to the elongate body (2602), thereby slidably positioning the fastener (2620) along a length of the closure device (2600). For example, the control wire (2628) may extend from a proximal end of a handle or may be coupled to an actuator (e.g., slider, knob, button, switch, or the like) of the handle. In some variations, the vacuum tube (2604) and the fastener (2620) may be moved independently.

In some variations, the suction tip (2606) may be locked to the fastener (2620) using a mating assembly. For example, the suction tip (2606) may comprise a first mating feature (2608) (e.g., a male connector) configured to engage a second mating feature (2626) (e.g., a female connector) (best shown in FIG. 26B) of the fastener (2620). For example, the first mating feature (2608) may comprise a projection extending from a proximal end of the suction tip (2606) that may be configured to fit within a recess in the second fastener (2624).

In some variations, the fastener (2620) may be a slidable constraint attached to a distal portion of the elongate body (2602) and vacuum tube (2604). The first and second body portions (2622, 2626) of the fastener (2620) may comprise a diameter sufficient to allow the fastener (2620) to slide along a length of the closure device (2620) (e.g., elongate body (2602). The fastener (2620) may be fixed relative to the suction tip (2606) of the vacuum tube (2604) using the mating assembly (2608, 2626) on the suction tip (2606) and fastener (2620). When mated, a consistent orientation may be maintained between the elongate body (2602) and the vacuum tube (2604), even as a distal portion of the closure device (2600) is maneuvered within a pericardial space of a patient.

Figure 8:
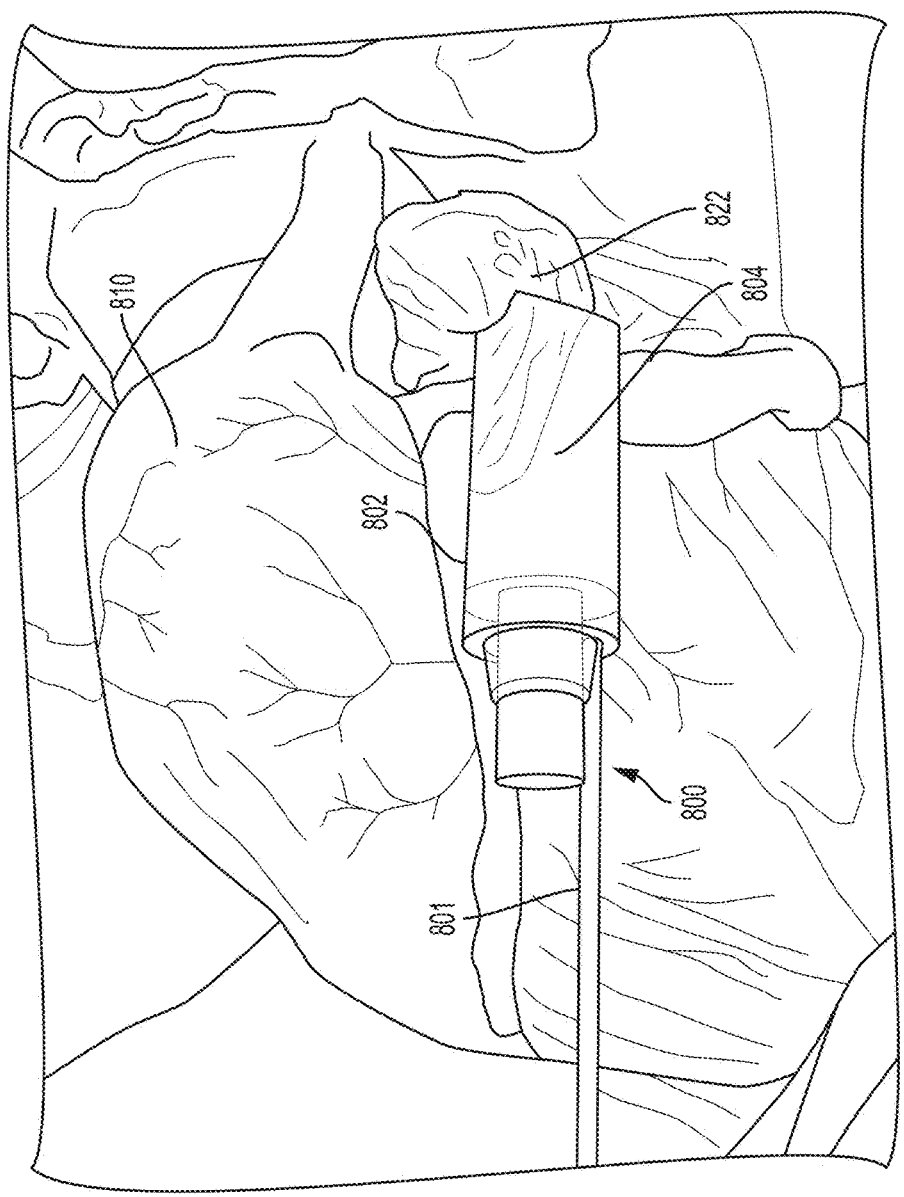
FIG. 8 is a side view of an illustrative variation of a vacuum tube coupled to heart tissue.

As mentioned above, the suction tip of the vacuum tube may comprise an atraumatic element that may physically engage and hold tissue adjacent to or within the vacuum tube without damaging the tissue. FIG. 8 depicts a variation of a vacuum tube (800) in use. As shown there, the suction tip (802) of the vacuum tube (800) is coupled to heart tissue (810) including a left atrial appendage (820). Generally, an intermediate portion (801) and the suction tip (802) of the vacuum tube (800) may be advanced over the anterior surface of the heart in a generally inferior-to-superior direction. In particular, the suction tip (802) of the vacuum tube (800) is advanced over left atrial appendage (822) tissue such that a portion of the left atrial appendage tissue (822) is disposed in a lumen (804) of the suction tip (802) of the vacuum tube (800) (e.g., the tissue (822) makes contact with an opening of the lumen (804)). In some variations, the suction tip (802) of the vacuum tube (800) may first make contact with an apex of the left atrial appendage (822). As heart tissue occludes an opening of the lumen (804) of the suction tip (802) of the vacuum tube (800), the soft left atrial appendage (822) may compress together. In order for the vacuum tube (800) to position and stabilize the left atrial appendage (822) in a desired position, a lumen (804) of the suction tip (802) of the vacuum tube (800) must be substantially occluded by the left atrial appendage tissue (822) so as to form a vacuum seal. Once occluded, pressure within the lumen (804) of the suction tip (802) of the vacuum tube (800) may be reduced by applying negative pressure (e.g., turning on a vacuum) to quickly draw tissue (822) further into the lumen (804) of the suction tip (802).

Figure 9A:
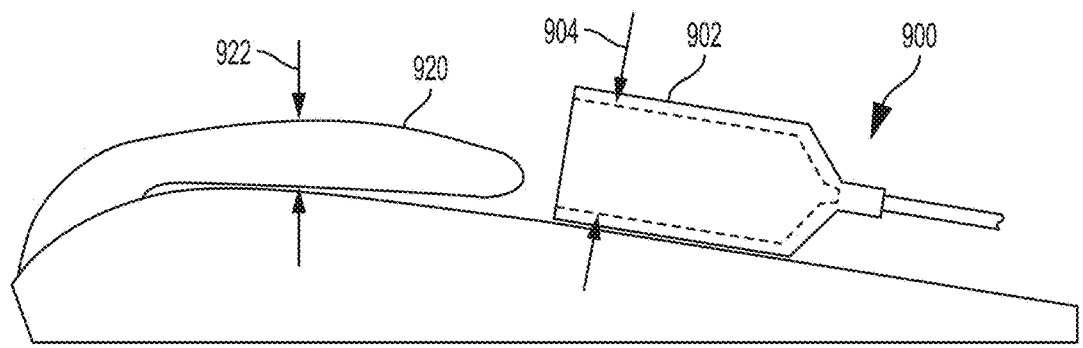
FIG. 9A is a schematic side view of an illustrative variation of a vacuum tube and heart tissue.
Figure 9B:
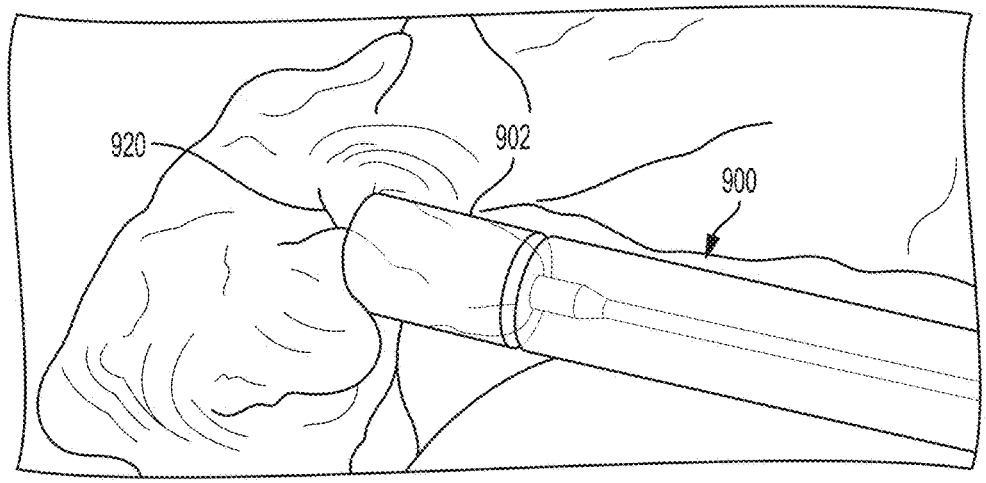
FIG. 9B is a perspective view of the vacuum tube depicted in FIG. 9A coupled to a left atrial appendage.

As depicted further in FIGS. 9A-9B and 10A-10B, the configuration of the suction tip of the vacuum tube may determine an amount of tissue suctioned into the suction tip. FIG. 9A is a schematic side view of an illustrative variation of a vacuum tube (900) and left atrial appendage (920). As shown there, the vacuum tube (900) may comprise a suction tip (902) having an opening with a diameter/height (904) greater than that of a height (922) of the left atrial appendage (920). FIG. 9B is a perspective view of the vacuum tube (900) depicted in FIG. 9A coupled to the left atrial appendage (920). FIGS. 9A-9B illustrate a round suction tip opening of the vacuum tube.

Figure 10A:
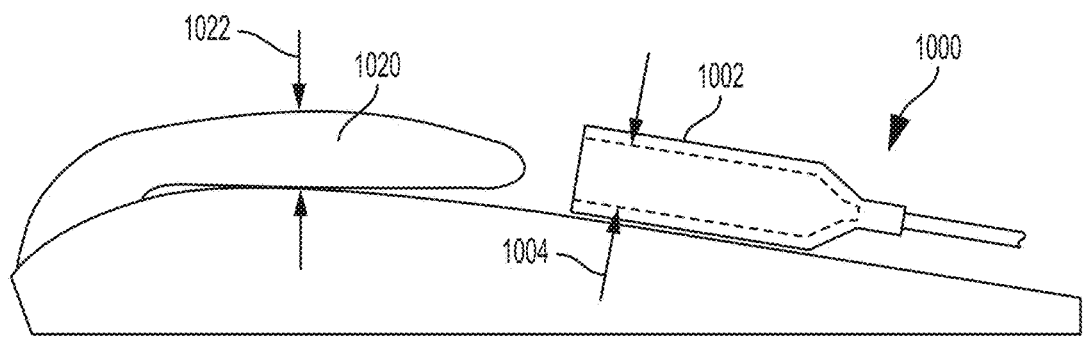
FIG. 10A is a schematic side view of an illustrative variation of a vacuum tube and heart tissue.
Figure 10B:
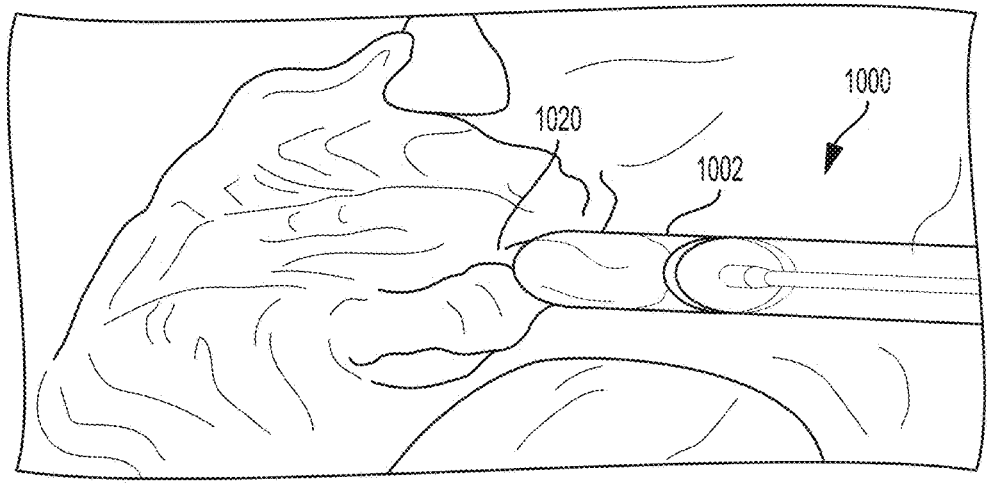
FIG. 10B is a perspective view of the vacuum tube depicted in FIG. 10A coupled to a left atrial appendage.

FIG. 10A is a schematic side view of an illustrative variation of a vacuum tube (1000) and the left atrial appendage (1020). FIG. 10B is a perspective view of the vacuum tube (1000) depicted in FIG. 10A coupled to the left atrial appendage (1020) using vacuum. FIGS. 10A-10B illustrate an obround suction tip opening of the suction tip (1002) of the vacuum tube (1000) having a height less than a diameter (904) of the round suction tip opening of the suction tip (902) of the vacuum tube (900). Due to the diameter/height difference between the suction tip (902) of the vacuum tube (900) and left atrial appendage (920), a lumen of the suction tip (902) has a greater volume to fill with the left atrial appendage before forming a vacuum seal via negative pressure. By contrast, a suction tip (1002) of the vacuum tube (1000) having a height substantially equal to a height of heart tissue may result in less tissue bunching in the suction tip (1002) of the vacuum tube (1000). For example, FIG. 9B shows a greater amount of heart tissue bunched up and suctioned into the suction tip (902) of the vacuum tube (900) than in FIG. 10B. A suction tip (1002) of the vacuum tube (1000) comprising an opening having a height (1004) about equal to a height (1022) of the left atrial appendage (1020) may aid in establishing a vacuum seal and may reduce potential damage to the left atrial appendage. For example, the height of the suction tip (1002) favorably matches the generally flat and/or wide shape of the left atrial appendage (1020) to cover the suction tip (1002) to establish the vacuum. If the height of a suction tip of a vacuum tube is substantially greater than the height of a left atrial appendage, then a gap is formed between the suction tip of the vacuum tube and left atrial appendage when they contact, thereby inhibiting a vacuum seal. A vacuum suction force holding a suction tip of a vacuum tube to heart tissue is proportional to the area of the distal opening of the vacuum tube. Thus, a holding force of the vacuum tube may be increased by increasing a width of the suction tip opening of the vacuum tube.

In some variations, the closure devices described here may comprise a vacuum tube configured to stabilize the closure device relative to myocardium tissue around the left atrial appendage (as opposed to stabilizing the closure device using a vacuum tube suctioned to the left atrial appendage itself). The vacuum tube may assist with stabilization of the closure device to aid advancement of the closure element to ligate tissue. For example, the vacuum tube may be advanced toward myocardial tissue near the left atrial appendage and vacuum (e.g., negative pressure) may be applied to the myocardial tissue in contact with the vacuum tube to temporarily hold the closure device in place relative to the myocardium. That is, the vacuum tube may anchor the closure device to the heart. Generally, myocardial tissue is firmer than the fragile left atrial appendage such that a stronger suction may be applied to the myocardium than to the left atrial appendage. In some variations, this may allow for additional stability and for a stronger coupling between the closure device and heart tissue, while minimizing the risk of damage to the left atrial appendage. In some variations, the vacuum tube may be anchored near (but not on) the left atrial appendage such that a snare loop assembly disposed within or extending from an elongate body may be more easily advanced (e.g., guided) around a target tissue (e.g., left atrial appendage).

As shown in FIG. 23A, a vacuum tube (2304) may be slidably positioned within a lumen of a sheath (2302). As described herein, the closure device (2300) may be advanced using an epicardial approach towards a heart (2310) of a patient, and in particular, towards myocardial tissue (2312) and/or a left atrial appendage (2314). The vacuum tube (2304) may be slidably positioned within a lumen of the sheath (2302). For example, the vacuum tube (2304) may have a size that fits within a lumen of the sheath (2302). Additionally or alternatively, the vacuum tube (2304) may slide adjacent to an external surface the sheath (2302). The vacuum tube (2304) may comprise one or more lumens as described in more detail with respect to FIGS. 23B-24D. Vacuum (e.g., suction, negative pressure) may be applied to the myocardial tissue (2312) in contact with the vacuum tube (2304) to temporarily hold the myocardium (2312) in place relative to the sheath (2302). That is, the vacuum tube (2304) may anchor the sheath (2302) (as well as any other devices extending from the sheath) to the heart (2310).

Figure 23C:
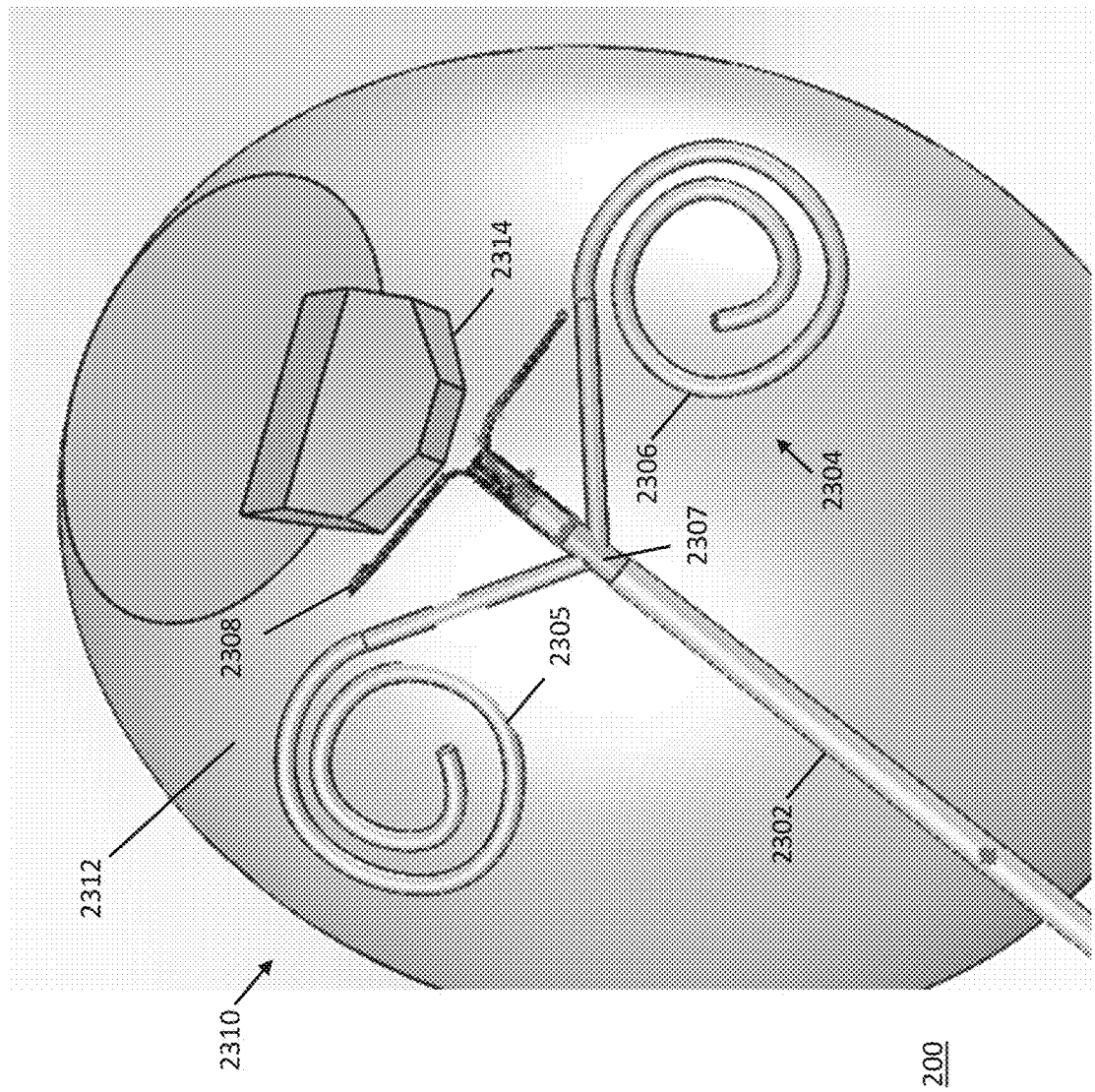
Figure 23D:
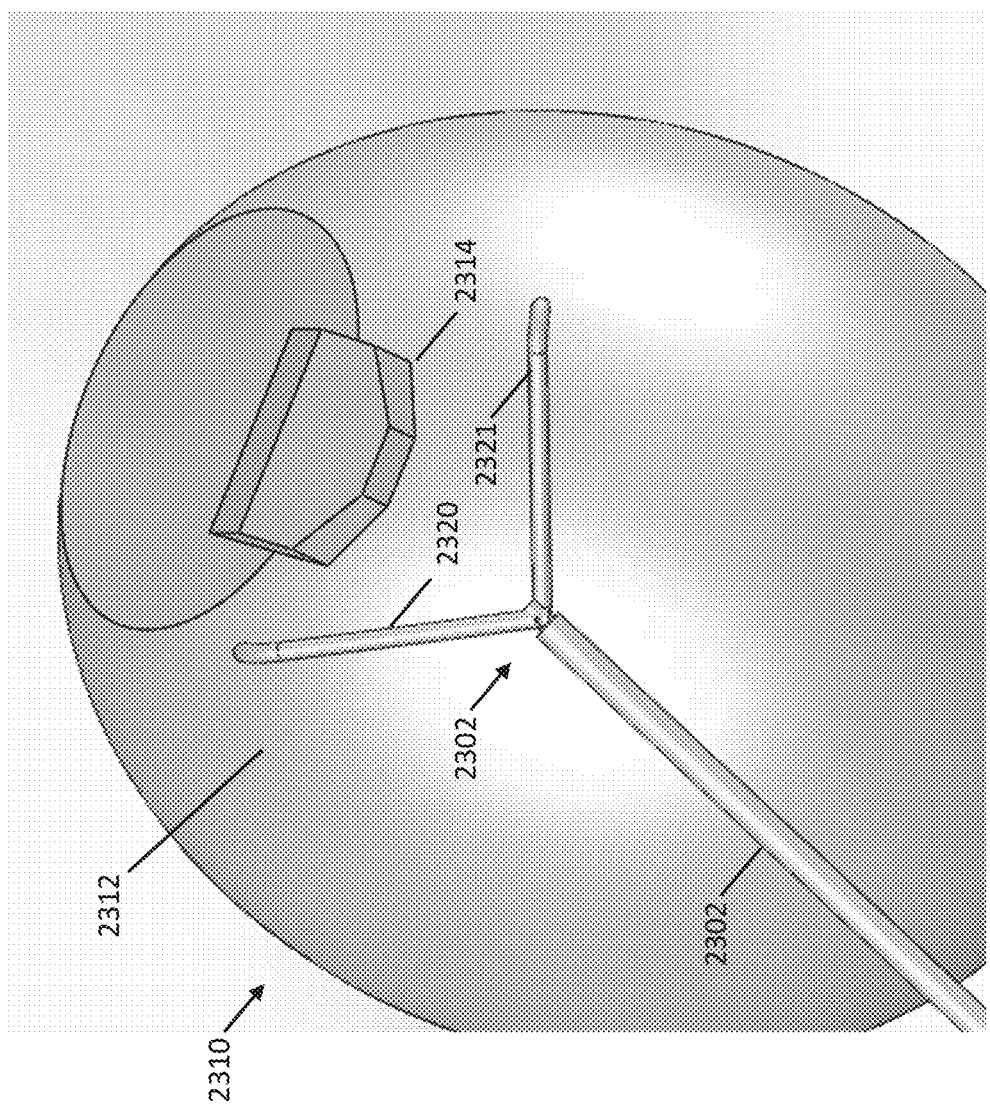

The vacuum tube (2304) may be advanced out of a lumen of the sheath (2304) and may be expandable such that it may transition from a first configuration (e.g., collapsed, delivery configuration) to a second configuration (e.g., expanded, deployed configuration). In the second configuration, the vacuum tube (2304) may comprise a suction tip configured to apply vacuum suction force to tissue in contact with the suction tip. In some variations, as shown in FIGS. 23B-23D, a vacuum tube (2304) may comprise one or more elongate members (2305, 2306) each defining a lumen therethrough. In some variations, the elongate members (2305, 2306) comprising a lumen and one or more apertures may be disposed on either side of the left atrial appendage (2314) (e.g., disposed to the left and right of an apex of the left atrial appendage). For example, the elongate members (2305, 2306) may extend laterally from a longitudinal axis of a distal end of the sheath (2302). This placement of the vacuum tube (2304) may increase stability of the closure device (2300) relative to the left atrial appendage (2314) when a snare loop assembly is used to manipulate tissue (e.g., ligate the left atrial appendage (2314)). In some variations, the intersection of the elongate members (2305, 2306) may form an angle of between about 30 degrees and about 150 degrees relative to each other. In some variations, the intersection of the elongate members (2305, 2306) may form an angle of between about 80 degrees and about 130 degrees. In some variations, fluoroscopy and CT image data may be used to guide placement of the vacuum tube (2304).

As shown in FIG. 23B, a distal portion of a first elongate member (2305) and/or the second elongate member (2306) may comprise a spiral shape and may each comprise one or more spaced-apart side and/or radial apertures (e.g., openings) (not shown) disposed along the portion configured to contact myocardium (e.g., along a spiral of the elongate member). For example, the apertures may be defined in a sidewall of the elongate member (2305, 2306). A spiral shape of the elongate members (2305, 2306) may permit a large surface area of the myocardium (2312) to be suctioned such that a stronger coupling force may be formed between the closure device (2300) and the myocardium (2312). In some variations, the elongate members (2305, 2306) may form a shape different than a spiral, e.g., a circle, a triangle, a V-shape, a C-shape, a -P-shape, a Y-shape, or the like. For example, FIG. 23D depicts a variation of the first and second elongate members (2320, 2321) comprising a curved suction tip configured to contact the myocardium (2312) at a distal end of the elongate members (2320, 2321). For example, vacuum may be applied to the myocardium (2312) through a single distal end aperture of the first and second elongate members (2320, 2321). In some variations, one or more of the elongate members may have a length between about 2 cm and about 30 cm.

In some variations, the apertures (not shown) may be defined on a side of the elongate member (2305, 2306) configured to directly oppose (e.g., face) the myocardium (2312). A vacuum force may be applied to the myocardial tissue through one or more of the apertures in one or more of the elongate members (2305, 2306) to anchor the closure device (2300) to the myocardium (2312). The apertures may have any suitable pattern and shape such as circular, elliptical, polygonal, rectangular (e.g., slit), cross-shaped, a combination thereof, or the like. The apertures may vary in size and/or shape along a length of the elongate member (2305, 2306). For example, distal apertures may define a larger opening than proximal apertures. One or more of the elongate members may comprise any suitable number of apertures, for example, one, two, three, four, five, six, seven, eight, or more, and the apertures may be located at any suitable location along the lengths of one or more of the elongate members. In some variations, the elongate members may comprise between two and four apertures, and in other variations, between three and five apertures. For example, a number, size (e.g., surface area), and location of apertures may be based on the suction power generated by a vacuum pump. For example, an aperture having a surface area of about 0.06 in$^2$ may be used with a vacuum pump, as described herein, to generate a negative pressure of about 560 mmHG, which may result in a tissue holding force of about 0.65 lbf.

In some variations, as shown in FIG. 23C, the elongate body (2307) may be configured to slide adjacent to the vacuum tube (2304) and within a lumen of the sheath (2302) such that the elongate body (2307) may advance and retract relative to the vacuum tube (2304) or vice-versa. For example, the vacuum tube (2304) may be configured to slide adjacent the elongate body (2307) (and within a lumen of the sheath (2302) or to fit within a lumen of the elongate body (2307). The elongate members (2305, 2306) of the vacuum tube (2304) may extend out of corresponding apertures in the elongate body (2307) at a predetermined angle with respect to a longitudinal axis of the elongate body (2307). The elongate body (2307) may comprise a snare loop assembly (2308) and an imaging device (not shown) as described herein. The elongate body (2307) and snare loop assembly (2308) may be configured to extend out of the sheath (2302) and advance towards and/or over the left atrial appendage (2314) as described herein for left atrial appendage (2314) capture and/or ligation.

Additionally or alternatively, the vacuum tube may comprise a cardiac electrophysiology diagnostic device configured to receive electrophysiology data (e.g., electrocardiogram signals) of cardiac tissue (e.g., myocardium, pericardium, left atrial appendage). For example, the vacuum tube may comprise one or more electrodes and may be configured to receive/measure electrical signals from tissue. For example, one or more electrodes may be disposed between and/or be adjacent to the apertures illustrated in FIGS. 23A-24D. The signal data received from the electrodes may be used to determine which portions of the vacuum tube (2400) are in contact with tissue, and which tissue the vacuum tube (2400) is in contact with. The signal data may be received and processed by a controller comprising a processor and memory. In some variations, suction may be inhibited unless signal data from one or more electrodes indicates contact between the vacuum tube and tissue. Alternatively, the suction force provided to or at apertures in different portions of the vacuum tube/suction tip may be different based on which electrodes, if any, are measuring electrical signals. For example, an electrode disposed on a distal portion of the vacuum tube may receive an electrical signal corresponding to tissue contact. In turn, the suction force of one or more apertures in the distal portion (e.g., near, on either side, or adjacent to the electrode receiving the electrical signal indicating tissue contact) of the vacuum tube may be increased such that suction is efficiently applied. Conversely, the suction force of apertures adjacent to electrodes that do not receive an electrical signal from tissue may be reduced.

The force applied to the tissue via the vacuum tube may assist in appropriately positioning and stabilizing the closure device to ligate tissue. Thus, the closure devices described here may ligate tissue without the need for a separate positioning and/or stabilization devices, for example, balloons, wires, magnets, or the like. In variations in which the closure devices are used to close the left atrial appendage, closure may be effectuated from the pericardial space using only a single access point to percutaneously access the external surface of the left atrial appendage. Thus, components such as balloons, wires, and/or magnets advanced through an atrial chamber or otherwise within the left atrial appendage are not needed. In this manner, an epicardial, single access site (e.g., sub-xiphoid) procedure is sufficient to ligate a left atrial appendage using the closure devices described herein, which may make the left atrial appendage procedure more simple, less costly, and safer.

In some variations, one or more of the vacuum tube (e.g., suction tip of the vacuum tube), elongate member, elongate body, and sheath may also comprise markers that may provide an indication of the location of the closure device in the body and advancement of the closure device. The markers may comprise any suitable marker, for example, a visual, radiopaque, or echogenic marker, and may be attached to the elongate body and/or vacuum tube in any suitable manner (e.g., printed on, adhesive, rings, or the like). One or more of the elongate body and the vacuum tube may comprise any suitable number of markers, for example, one, two, three, four, or more, and the markers may be located at any suitable location along the lengths of one or more of the elongate body, vacuum tube, and other tube (e.g., an imaging tube as described in more detail below).

In some variations, a vacuum tube may comprise an echogenic surface that may assist in visualizing the location of the vacuum tube within the body. FIG. 11A is a side view of a vacuum tube (1100) comprising a suction tip (1102) having a first echogenic surface (1104). The suction tip (1102) of the vacuum tube (1100) may be visualized under transesophageal echocardiography (TEE) and/or fluoroscopy to provide location and position information of the closure device within the body. The echogenic suction tip (1102) of the vacuum tube (1100) may thus facilitate indirect visualization of the portion of the vacuum tube (1100) that is in contact with tissue, for example, the left atrial appendage. The suction tip (1102) may comprise any echogenic surface texture. For example, FIG. 11A illustrates a first echogenic surface (1104) comprising a spiral groove pattern. FIG. 11B depicts a second echogenic surface (1106) comprising a round dimpled pattern, and FIG. 11C depicts a third echogenic surface (1108) comprising a diamond dimpled pattern. It should be appreciated that that the echogenic surface may comprise one or more geometric shapes, written characters, and repeating patterns thereof. The echogenic surface may comprise one or more protrusions and indentations that may be distinguished for indirect visualization. In some variations, indentations and protrusions may comprise one or more lines and line intersections forming an identifiable image contrast.

In some variations, the closure devices described here may comprise an elongate body, a vacuum tube having an echogenic suction tip, and an imaging device disposed in the suction tip of the vacuum tube. The imaging device may directly visualize tissue from a lumen of the vacuum tube. The echogenic suction tip of the vacuum tube may be indirectly visualized to aid in orienting and locating the vacuum tube relative to body structures. The advancement, stabilization, and closure procedures described herein may be performed using one or more direct and indirect visualization techniques. In some variations, the vacuum tube may comprise a port and/or lumen configured to form saline bubbles out of a suction tip of the vacuum tube to aid visualization of the suction tip of the vacuum tube using TEE.

In other variations, the closure device may comprise a vacuum tube having an echogenic suction tip, and one or more imaging devices (as described in further detail below) disposed in the suction tip of the vacuum tube and slidably adjacent the vacuum tube and elongate body. It should be appreciated that the vacuum tube having an echogenic suction tip may be provided without an imaging device disposed in the vacuum tube or used without another imaging modality, thus reducing the number of elements in the imaging device and the number of steps in a closure procedure. The echogenic surface patterns illustrated and described above may be applied to any surface of the closure device, such as an outer surface of the vacuum tube and/or the elongate body. The vacuum tube and elongate body may have different surface patterns to aid differentiation of closure device elements.

The vacuum tube described herein may comprise any suitable length, and the length of the vacuum tube may vary depending on the type of procedure being performed. The vacuum tube may be made of any suitable material, for example, one or more polymers (e.g., reinforced pebax, polyimide, urethane, etc.). The vacuum tube may be braided, non-braided, tapered, non-tapered, or some combination thereof. In some variations, the cross-sectional shape of the vacuum tube may vary along its length, but need not. As shown in FIG. 6, an intermediate portion (602) of the vacuum tube (600) may comprise polyimide and a stainless steel wire braid. In some variations, an outer diameter of the vacuum tube may be between about 0.10 cm and 0.30 cm. In some cases, an outer diameter of the vacuum tube may be about 0.203 cm.

Imaging Device

The closure devices described here may also comprise an imaging device that may be used to facilitate advancing and placing the closure device relative to the target tissue. Providing an imaging device within a lumen of the vacuum tube may assist a user in visualizing tissue in front of and/or around the suction tip of the vacuum tube, which may be useful throughout a closure procedure. For example, in a left atrial appendage closure procedure, as a closure device is advanced percutaneously to the pericardial space, the imaging device may provide useful information to assist in guiding the closure device towards the left atrial appendage. Moreover, the left atrial appendage may be imaged to guide the vacuum tube towards, for example, an apex of the left atrial appendage prior to and during application of a vacuum through the vacuum tube to assist in placing the vacuum tube for use as a guide for the closure element to a desired location on the tissue. After suction has been released, the left atrial appendage may be imaged to confirm ligation of the left atrial appendage and to assist in withdrawal of the closure device from the body. In some cases, the imaging device may confirm that the snare loop assembly transitions to an open configuration and that the vacuum tube advances through the open snare loop assembly.

FIG. 4I depicts a variation of a closure device (400) comprising an imaging device (434). In some variations, and as depicted in FIG. 4I, the imaging device (434) may be coupled to or otherwise positioned at the suction tip (432) of the vacuum tube (430). In the variation shown in FIG. 4I, the imaging device (434) is housed within the lumen (440) of the vacuum tube (430), but it need not be and may instead be coupled to any suitable portion of the vacuum tube (430) (e.g., coupled to a side external surface, front facing portion of the suction tip) or the elongate body (402). In some instances, it may be desirable for the imaging device (434) to be positioned on or within the vacuum tube because this may allow a user to better visualize the location of the target tissue relative to the vacuum tube and may make it easier to guide or otherwise position the suction tip (432) of the vacuum tube (430) at a location at or on the tissue that will properly position the snare loop assembly for advancement to the desired location on the tissue for closure. Furthermore, positioning the imaging device (434) within the vacuum tube may allow the operator to image tissue being drawn into the vacuum tube, which may assist in confirming the capture of the desired tissue (e.g., left atrial appendage tissue).

The imaging device (434) may have any suitable diameter and length. For example, the imaging device (434) may have a diameter of up to about 6 mm, including a diameter of about 3 mm, about 3.5 mm, about 4 mm, about 4.5 mm, about 5 mm, about 5.5 mm, between about 3 mm and about 5 mm, between about 4 mm and about 6 mm, or between about 5 mm and about 6 mm. The imaging device (434) may comprise any suitable length, for example, about 20 mm, about 23 mm, about 25 mm, between about 20 mm and about 25 mm, between about 20 and 23 mm, or between about 23 mm and about 25 mm. In one variation, the imaging device (434) may have a diameter of about 5.5 mm and a length of about 23 mm.

The imaging device (434) may be configured to allow a user to view the suction tip (432) of the vacuum tube (430), the snare loop assembly (404), and/or the tissue in front of or surrounding it during a procedure. The suction tip (432) of the imaging device (434) may be positioned within the suction tip (432) of the vacuum tube (430) such that tissue may be drawn into the vacuum tube (430) and may be distinguishable using imaging when drawn into the vacuum tube (430). The imaging device (434) may be any device that assists a user in viewing the elongate body (402), the snare, suture loop, and/or tissue. For example, in some variations, the imaging device (434) may comprise a camera with an image sensor (e.g., a CMOS or CCD array with or without a color filter array and associated processing circuitry), which may be positioned at the suction tip of the vacuum tube (430). An external light source (e.g., laser, LED, lamp, or the like) may generate light that is carried to the suction tip of the vacuum tube via fiber optic cables or the imaging device (434) may comprise one or more LEDs to provide illumination. For example, the imaging device may comprise a bundle of flexible optical fibers (e.g., a fiberscope) having a diameter of up to about 2 mm. The fiberscope may be configured to receive and propagate light from an external light source. The fiberscope may comprise an image sensor configured to receive light reflected from pericardial anatomy. The image sensor may detect the reflected light and convert it into image signals that may be processed and transmitted for display. The camera may also comprise optics (e.g., lenses). In other variations, the imaging device (434) may comprise an endoscope slidably positioned within the lumen (440) of the vacuum tube (430). The endoscope may have any suitable configuration, for example, it may be a chip-on-the-tip camera endoscope, a three camera endoscope, or the like. In yet other variations, the imaging device (434) may comprise an ultrasonic catheter. It should be appreciated that the imaging device (434) may comprise any device that allows for or facilitates visualization of any portion of the closure device and/or of the internal structures of the body.

As a vacuum tube and imaging device are advanced through the pericardial space, tissue pressed against an opening of the suction tip of the vacuum tube may compress. The imaging device, including any light sources for illumination, may be housed in a sealed (waterproof) housing. This tissue may press against the imaging device and obscure the view from the imaging device. For example, a distal end of a housing of an imaging device may be located between about 0.20 cm and about 2.0 cm from an opening of the suction tip of the vacuum tube. In some variations, the distance between the imaging device and the opening of the vacuum tube may reduce and/or prevent contact between tissue and the imaging device. For example, the space between a distal end of the imaging device and the opening of the vacuum tube may provide a minimum field of view of the imaging device. With a clear field of view, tissue such as left atrial appendage tissue may be more readily distinguishable from myocardial and pericardial tissue.

In some variations, a connector (438) may connect the imaging device (434) to a power supply, processor, and/or display to provide power, control signals, and/or transmit the image signals. The image signals may be transmitted by wire or wirelessly to a display for viewing by a user. In some variations, the imaging device (434) may be separate from the closure device and may be advanced through a lumen of the vacuum tube prior to or during a procedure, or advanced along a rail formed along an external surface (e.g., the top, bottom, side) of the closure device. In still other variations, the closure device may comprise an imaging device (434) as described above and a separate imaging device (e.g., endoscope, ultrasonic catheter, or the like) may also be advanced through a different access site to supplement the visualization provided by the imaging device (434) of the closure device (400).

During a procedure using the closure devices described here, a user may view the images generated by the imaging device (434) in real-time on a display and use them to assist with the tissue closing process. For example, the images generated by the imaging device (434) may help a user identify the location of the closure device within the body and ensure that the procedure is applied to the correct anatomy. For example, when the target tissue is the left atrial appendage, it may be useful to view the left atrial appendage as the closure device, and more specifically, the vacuum tube approach the appendage. This is because it is important to ligate the left atrial appendage at the proper location (e.g., at the base) to attain effective closure and minimize leakage. The ability to view the appendage as the closure device and in particular, the vacuum tube, approach it may allow a user to better position the suction tip of the vacuum tube relative to the appendage for tissue closure, which prepares the closure element to be advanced to the proper location. For example, because the relative locations of the vacuum tube and the snare loop assembly are known, the vacuum tube may be used as a guide to advance the snare loop assembly to and around the appendage to the desired location once the vacuum tube is positioned properly.

More particularly, in some instances, the imaging device (434) may visualize an anterior lobe (apex) of the left atrial appendage, which may assist in guiding the vacuum tube (430) toward a desired contact position with the appendage, which, in some variations, may be on an anterior lobe of the left atrial appendage. Placing the vacuum tube (430) at the desired contact position may allow the snare loop assembly (404) to be advanced around and over the anterior lobe of the left atrial appendage and towards a base or ostial neck of the left atrial appendage.

In the embodiment depicted in FIG. 4I, when the vacuum tube (430) is releasably coupled to tissue (i.e., using suction), the imaging device (434) within the lumen (440) of the vacuum tube (430) may be unable to visualize the advancement of the snare loop assembly (404) over and around the left atrial appendage, as the tissue may be partially or fully blocking the imaging device (434). However, releasably coupling the vacuum tube (430) to the left atrial appendage may ensure that the snare loop assembly (404) is appropriately placed for advancement over the apex of the left atrial appendage to the ostium.

Figure 12B:
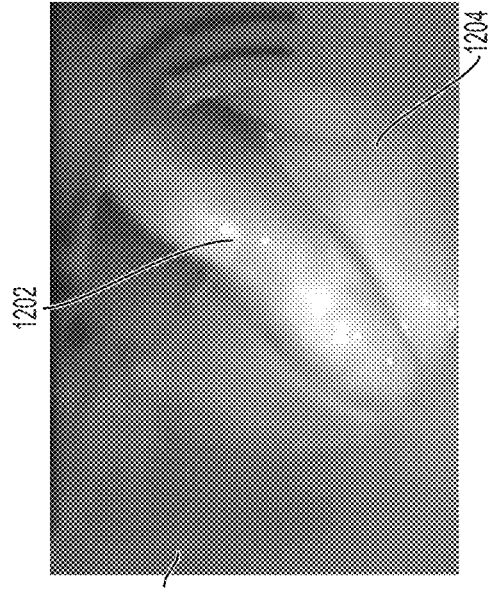
FIGS. 12A-12D are images taken from a distal end of a variation of a closure device.
Figure 12D:
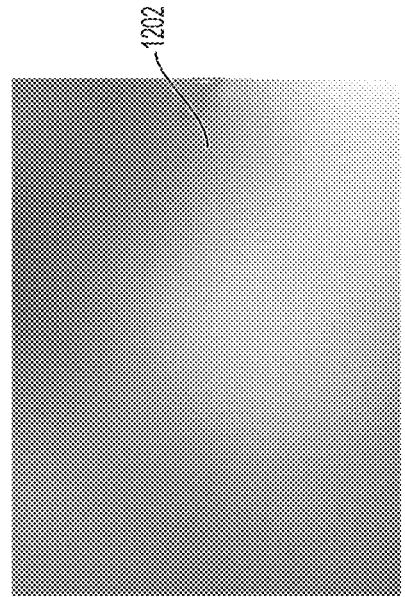
Figure 12A:
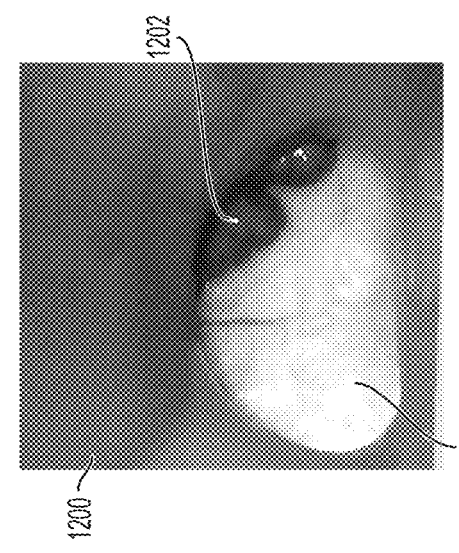
Figure 12C:
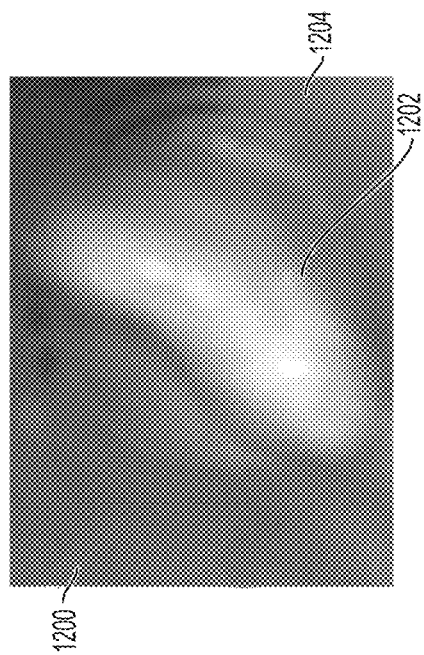

FIGS. 12A-12D are illustrative images from an imaging device disposed in a closure device. FIG. 12A shows an image taken by the imaging device from within a lumen (1200) of a suction tip of a vacuum tube. The heart tissue (left atrial appendage tissue (1202) and pericardial tissue (1204)) is in contact with an opening of the lumen (1200). In FIG. 12A, the left atrial appendage (1202) may be readily distinguishable from pericardial tissue (1204) due to its deep red color and pulsating movement. The images from the imaging device may thus aid in visually locating the left atrial appendage for guiding the closure device. FIG. 12B is an image from the imaging device as left atrial appendage tissue (1202) is drawn into the distal lumen (1200) by one or more of vacuum and advancement of the vacuum tube. The image may confirm that the vacuum tube has drawn in left atrial appendage tissue (1202) and not pericardial tissue (1204). FIG. 12C is a subsequent image from the imaging device as left atrial appendage tissue (1202) is further drawn into the distal lumen (1200) and begins to provide an obscured image. FIGS. 12A-12C show left atrial appendage tissue (1202) drawn into the distal lumen (1200) without application of negative pressure vacuum suction, although a vacuum may be generated when the left atrial appendage is first visualized and/or located.

Once the left atrial appendage tissue (1202) has been drawn into the distal lumen, preferably with minimal gaps between the left atrial appendage tissue (1202) and an inner wall of a suction tip of the vacuum tube, the vacuum may be activated. FIG. 12D is an image of left atrial appendage tissue (1202) drawn into a distal end of the lumen (1200) such that the image is obscured by left atrial appendage tissue (1202), thereby providing confirmation of the capture and hold of tissue (1202) to the vacuum tube.

It should be appreciated that the closure devices described herein may use additional visualization devices including direct and indirect visualization techniques. As briefly mentioned above, in some variations, a second imaging device may be coupled to the elongate body or an external surface of the vacuum tube to allow visualization of the snare loop assembly as it is advanced around the left atrial appendage. In these variations, the second imaging device may be coupled to the elongate body or an external surface of the vacuum tube fixedly or releasably, using any suitable means (e.g., adhesive, bonding, snap fit elements, a combination thereof, or the like.) In some instances, an additional imaging device (i.e., in addition to the first or second imaging devices described above) may be separately advanced to assist in visualizing the snare loop assembly advancing around the left atrial appendage and/or placement of the suture loop around the left atrial appendage. Additionally, other visualization techniques may also be used to assist in visualizing a closure procedure, as described below.

In some variations, the closure devices described herein may be used with additional visualization devices and/or visualization techniques including, but not limited to, CT, intracardiac echocardiography (ICE), magnetic resonance imaging (MM), 3 mensio, guided tracking (e.g., mapping data merged with CT data), fluoroscopy, direct optical imaging (e.g., a camera), transesophageal electrocardiogram (TEE), EKG, fusion (e.g., fluoroscopy data merged with CT data), fluorescence, and ultrasound. In some variations, the closure devices described herein may be used in conjunction with visualization catheters positioned in one or more of the coronary sinus and pulmonary artery. For example, a multi-polar catheter may be disposed in the coronary sinus (running just inferior to the base of the appendage) and may be used to locate an apex of the left atrial appendage. A second catheter may be disposed in the pulmonary artery and may be used to locate an internal edge of the heart. These catheters may be configured as fluoroscopic landmarks that may indicate that the ostium of the LAA is located between the acute angle formed by intersection of the two catheters. In some variations, one or more of ICE, fluoroscopy, optical imaging, EKG, mapping, and fusion may be used during capture of the LAA and/or to confirm capture of the LAA. In some instances, fluoroscopy, optical imaging, EKG, mapping, and fusion may be used during advancement.

In some variations, fluorescence (e.g., near-infrared fluorescence, laser-induced fluorescence (LIF)) may be used to assist in determining the location of particular cardiac tissues and/or of one or more of the devices described herein. For example, in some variations, the imaging device may comprise a light source configured to generate one or more of near-infrared light (NIL) and light that is used for laser-induced fluorescence (LIF), or it may comprise one or more optical fibers configured to transmit such light generated by an external light source (e.g., on or more lasers, light-emitting diodes (LEDs), or the like). The imaging device may further comprise one or more optical sensors configured to receive emission spectra reflected from the tissue. Because different types of cardiac tissue (e.g., left atrial appendage, myocardium, aorta, ventricles, fatty tissue) may generate different and unique emission spectra when excited by NIL and/or light used for LIF, it may be possible to differentiate between different types of cardiac tissue (and thus determine positioning of one or more of the devices described herein relative to that tissue) based on the emission spectra detected. The received emission spectra data may be analyzed by a processor (contained within or external to the imaging device) to classify one or more of the tissue, vacuum tube, and closure device being imaged. In some variations, the received emission spectra data may be used to determine a location and/or orientation of the closure device relative to the left atrial appendage.

FIGS. 21A-21B are perspective views of a closure device (2100) comprising an elongate body (2104) and an imaging assembly (2110) disposed outside the elongate body (2104), which may aid in visualization of heart tissue. In particular, the imaging assembly (2110) disposed outside of the elongate body (2104) may aid visualization of a snare loop and/or tissue as the snare loop is advanced towards a left atrial appendage. In some variations comprising a vacuum tube, the imaging device may visualize one or more of the snare loop, tissue, and vacuum tube. Furthermore, the imaging assembly (2110) may aid a user in confirming that a suction tip of the vacuum tube is stabilized against the left atrial appendage. The snare loop may be imaged as it is advanced over the left atrial appendage. As shown in FIG. 21A, the closure device (2100) may comprise a distal end (2102), an elongate body (2104), a handle (2106), and a snare loop assembly (2108). The handle (2106) may be coupled to the proximal end of the elongate body (2104) and the handle (2106) may be used to move the snare loop assembly (2108) between open and closed configurations, control the imaging device (2114), release a suture loop from the snare loop assembly, and/or control vacuum pressure applied to the target tissue through the vacuum tube. The handle (2106) may further comprise an imaging device control, which may control operation of the imaging device (and movement of the imaging device relative to the vacuum tube and/or elongate body (2104)).

As can be seen in FIG. 21B, the imaging assembly (2110) may comprise one or more fasteners (2112), an assembly housing (2216), and an imaging device (2114). The imaging device (2114) (e.g., camera, endoscope, fiberscope, external light source and image sensor, ultrasonic catheter, or the like) may be disposed in the assembly housing (2116). In some variations, the imaging device (2114) may be battery powered or be connected to a power source via a set of electrical conductors (e.g., insulated lead wires). The imaging assembly (2110) may be slidably coupled to the elongate body (2104) by the fasteners (2112). For example, the fasteners (2112) may encircle the elongate body (2104) and may allow the imaging device (2114) to be slidably positioned while maintaining a consistent orientation relative to the elongate body (2104). The imaging device (2114) may be disposed in a lumen of the assembly housing (2116) such that the imaging device (2114) is angled relative to a longitudinal axis of the elongate body (2104). For example, the assembly housing lumen may be angled such that an imaging device disposed in the lumen is also angled relative to the longitudinal axis of the elongate body (2104). Alternatively, the assembly housing lumen may be substantially parallel to the longitudinal axis of the elongate body while the imaging device may be disposed in the lumen at an angle relative to the longitudinal axis. This may allow the imaging device (2114) to have a field-of-view that is less obstructed by the elongate body (2104) and may allow a greater portion of the snare loop to be imaged.

In some variations, the imaging device (2114) may be between about 2 cm and about 8 cm away from the distal tip (2103). In some variations, the imaging device (2114) may form an angle with the elongate body (2104) of up to about 10 degrees. In some variations, the imaging device (2114) may have a field-of-view of about 90 degrees to about 120 degrees. In some variations, the imaging assembly (2110) may have a length of between about 1 cm and about 3 cm and a height of between about 6 mm to about 9 mm. In some variations, the imaging assembly (2110) may be coupled to a control wire (e.g., pull wire) (not shown), which may be advanced/retracted (e.g., using an actuator coupled to handle) by an operator to slidably position the imaging assembly (2110) along a length of the elongate body (2104).

Figure 22:
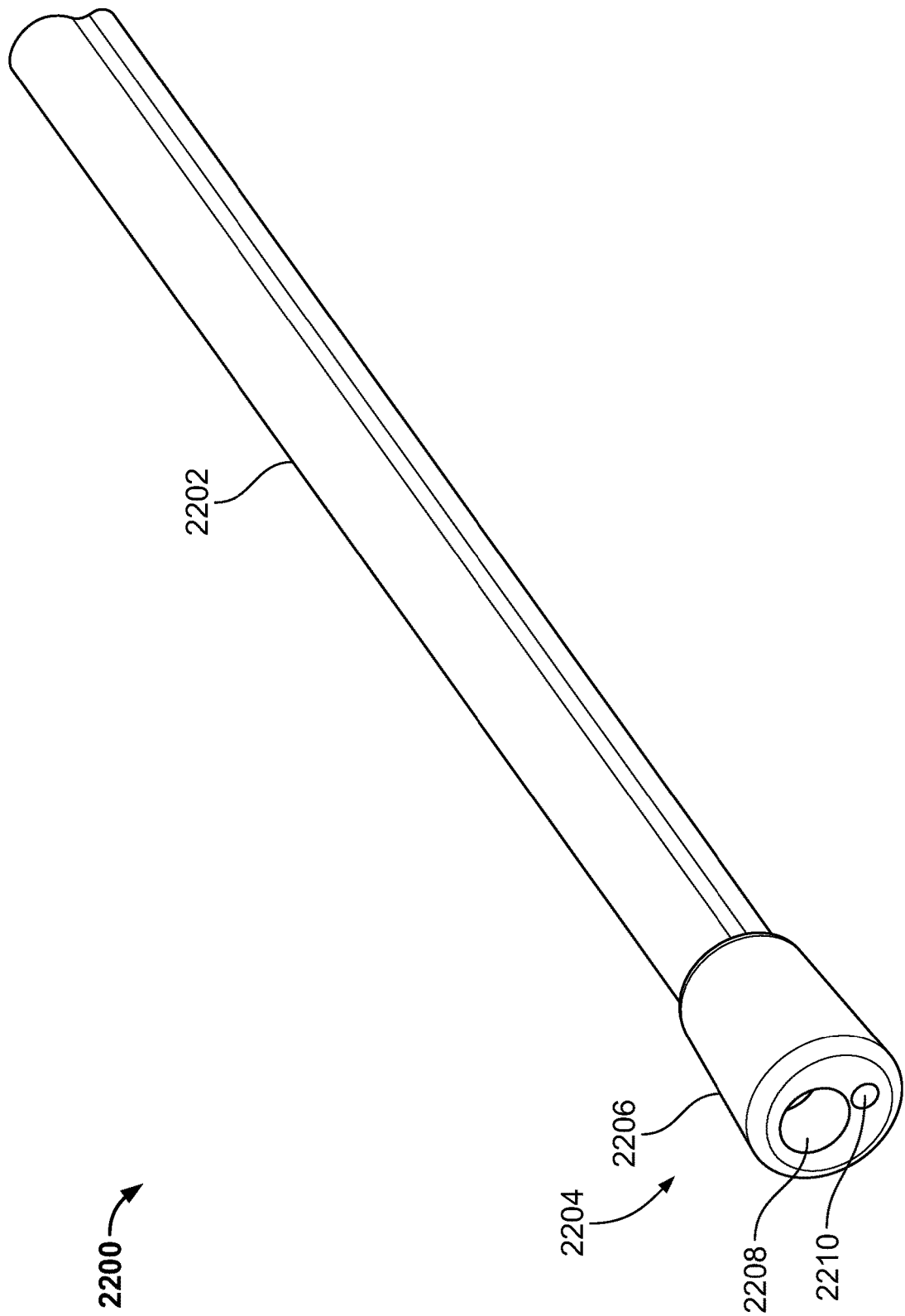
FIG. 22 is a perspective view of an illustrative variation of a sheath.

FIG. 22 is a perspective view of another variation of a sheath (2200) comprising an elongate body (2202) having a plurality of lumens (e.g., two). A distal end (2204) of the sheath (2200) may comprise a distal tip (2206) as described herein. The elongate body (2202) and the distal tip (2206) may each comprise at least a first lumen (2208) and a second lumen (2210). The sheath (2200) may be used in conjunction with a closure device comprising a snare loop assembly and/or a vacuum tube (both not shown) slidably positioned within the first lumen (2208) of the elongate body (2202). In some variations, the snare loop assembly may be slidably advanced or retracted over the vacuum tube disposed within the first lumen (2208). An imaging device (not shown) (e.g., endoscope) may be slidably positioned within the second lumen (2210) of the elongate body (2202). In some variations, a distal opening of the second lumen (2210) may be positioned up to about 1.0 cm away from a distal end of an imaging device to set a minimum field-of-view and serve as a buffer (e.g., empty space) against tissue that may be inadvertently drawn into the second lumen (2210) of the elongate body (2202). That is, the buffer may prevent contact between the tissue and a distal end of the imaging device. In some variations, the distal opening of the second lumen (2210) may be between about 0.2 cm and 2.0 cm away from the distal end of an imaging device. In some variations, the imaging device may be fixed relative to the elongate body (2202).

As shown in FIG. 13A, a closure device (1300) may comprise an imaging device (1324) disposed outside a vacuum tube (1310) to aid in visualization of heart tissue, the vacuum tube (1310), and the elongate body (1302) of the closure device (1300). In particular, an imaging device (1324) disposed outside of the vacuum tube (1310) may aid visualization of a snare loop as it is advanced over the vacuum tube (1300) towards the left atrial appendage. Furthermore, the imaging device (1324) may aid a user in confirming that a suction tip of the vacuum tube is stabilized against the left atrial appendage. Then, the snare loop may be imaged as it is advanced over the left atrial appendage. The imaging device (1324) may be coupled to an imaging tube (1320) and may extend proximally to couple to a handle (not shown). An imaging device control disposed in the handle may control operation of the imaging device (1324) and movement relative to the vacuum tube (1310) and elongate body (1302). A snare loop (not shown) may be advanced over one or more of the vacuum tube (1310), imaging tube (1320), and imaging device (1324). In some variations, an opening of the imaging tube (1320) may be positioned up to about 1.0 cm away from the distal end of the imaging device (1324) to set a minimum field of view and serve as a buffer against tissue that may be inadvertently drawn into the lumen of the imaging tube (1320). In some variations, the opening of the imaging tube may be between about 0.2 cm and 2.0 cm away from the distal end of the imaging device (1324). In some cases, the opening of the imaging tube may be about 1.0 cm away from the distal end of the imaging device (1324).

The imaging device (1324) may be slidably coupled to one or more of the elongate body (1302) and the vacuum tube (1310) by fasteners (1326). The fasteners (1326) may encircle the elongate body (1302) and may allow the imaging device (1324) to be slidably positioned while maintaining a consistent orientation relative to the elongate body (1302). The fasteners (1326) may couple the imaging device (1324) to a skived region (1314) of the elongate body (1302).

The imaging tube (1320) may extend through a lumen in the elongate body (1302) and couple to a handle of the closure device. The imaging tube (1320) may be advanced and/or retracted in a manner similar to that of the vacuum tube. For example, the imaging tube (1320) may couple to a sliding actuator in the handle, such as a slider, or any other suitable control in handle (e.g., a button, knob, switch, or the like). The imaging tube (1320) may comprise a lumen that may house signal and power conductors. For example, in some variations, the conductors may comprise 32 AWG wires. The imaging tube (1320) may comprise any suitable material, for example, spring-tempered stainless steel wire, and any suitable diameter, for example, between about 0.25 cm and about 0.50 cm. In some variations, it may be beneficial to use spring-tempered stainless steel wire to increase the kink resistance of the imaging tube (1320). Additionally or alternatively, a stainless steel wire (e.g., between about 0.25 mm to 0.50 mm diameter and spring tempered) may extend through the imaging tube (1320) to increase kink resistance. In another variation, that imaging tube (1320) may be identical to the vacuum tube. For example, the imaging tube (1320) may comprise a 2 mm polyimide tubing reinforced with stainless steel wire braid, and have a diameter between about 0.10 cm and about 0.50 cm. It should be appreciated that the closure device may comprise one or more of an imaging device disposed in a lumen of the vacuum tube and an imaging device disposed externally of the vacuum tube.

Although it may be useful to position an imaging device within the lumen of the vacuum tube to assist in visualizing the tissue and/or tools within the field of view of the lumen (440), it may also be useful to use the lumen of the vacuum tube to apply negative pressure (suction) to assist in holding and/or stabilizing the closure device relative to the target tissue. Thus, the closure devices described here may be configured such that the imaging device may be disposed within the lumen of the vacuum tube and the vacuum tube may still provide suction to pull the target tissue into the vacuum tube (or advance the vacuum tube (430) toward the target tissue). For example, in some variations, the imaging device (434) may be positioned such that it does not block or otherwise adversely affect the ability of a vacuum pump/vacuum tube to apply negative pressure to the target tissue. In some instances, the imaging device (434) may comprise an outer diameter or dimension that is sufficiently smaller than the inner diameter of the suction tip (432) of the vacuum tube (430) such that vacuum may be pulled around the imaging device (434). For instance, the clearance between the vacuum tube and the imaging device may form a small passageway while still allowing a vacuum to be communicated to an opening of the suction tip of the vacuum tube. In some variations, an outer diameter of a suction tip (432) of the vacuum tube (430) may be up to about 1.0 cm. In some cases, an outer diameter of a suction tip (432) of the vacuum tube (430) may be about 0.635 cm.

As shown in FIG. 4I, in some variations, the closure device (400) may further comprise a fastener (436) that couples the imaging device (434) to the lumen (440) of the vacuum tube (430) to keep the imaging device (434) stationary during a procedure (i.e., hold it in place). In some instances, the fastener (436) may comprise one or more side and/or radial apertures that allow transmission of the vacuum pressure therethrough. The fastener (436) may be positioned within the lumen (440) of the vacuum tube (430) and may be parallel with, and in some instances, concentric with the vacuum tube (430). For example, the fastener (434) may be positioned within the intermediate portion (442), the suction tip (432), or partially within each of the intermediate portion (442) and the suction tip (432) of the vacuum tube (430). The fastener (436) may comprise any suitable means for attaching the imaging device (434) to the lumen (440), including but not limited to adhesive, bonding, snap fit elements, a combination thereof, or the like. For instance, in one variation, the imaging device (434) may be advanced through the second lumen (440) until a snap fit fastener secures the imaging device in place within the second lumen (440). It should be appreciated that the closure devices described herein need not comprise a fastener coupling the imaging device (434) and the vacuum tube (430). For example, as described above, the imaging device (434) may be slidably disposed in the vacuum tube such that it may be advanced and retracted therethrough (e.g., an endoscope advanced through the vacuum tube).

As mentioned briefly above and depicted in FIG. 4I, in some instances, the imaging device (434) may comprise a connector (438) that may couple the imaging device (434) to a power supply, a processor, and/or a display. The connector (438) may include one or more wires and/or cables that may be positioned within and extend through the lumen (440) of the vacuum tube (430) to/or through the handle for connection to a power storage device therein and/or an external device. For example, in some variations, the closure device may comprise a power storage device (e.g., disposable and/or rechargeable batteries) for the imaging device within its handle and the connector (438) may couple the imaging device (434) to the power storage device. In other variations, the connector (438) may couple the imaging device (434) to an external power source. Additionally, the connector (438) may couple the imaging device (434) to a processor or other control system such that control signals may be sent to the imaging device (434) and image signals may be received from the imaging device (434). The connector (438) may also be used to couple the imaging device (434) to a monitor to display the images or a recording device to store the images for later use.

Electrode

The closure devices described herein may additionally, or alternatively, comprise an electrode that may be used to facilitate advancing and placing the closure device relative to the target tissue. Providing an electrode within a lumen of the vacuum tube may assist a user in identifying the type of tissue captured within a suction tip of the vacuum tube, which may be useful throughout a closure procedure. For example, in a left atrial appendage closure procedure, a closure device may be advanced percutaneously to the pericardial space using indirect visualization techniques such as fluoroscopy. The electrode may be disposed within a lumen of the vacuum tube at a location that does not contact non-suctioned tissue. For instance, the electrode may be disposed deep enough into the suction tip of the vacuum tube such that tissue that enters into the lumen of the vacuum tube during advancement of the vacuum tube within pericardial space does not contact the electrode. Once positioned as desired on the tissue, for example, the left atrial appendage, vacuum may be applied to pull tissue further into the lumen of the suction tip of the vacuum tube. Once pulled inside of the lumen, the tissue may contact the electrode. Once tissue contacts the electrode, the electrode may generate a signal (e.g., electrocardiogram signal) that may be used to determine the type of tissue inside the lumen of the suction tip of the vacuum tube. For example, in the left atrial appendage closure procedure, the electrode may generate a signal that may be used to determine whether the tissue inside the lumen of the vacuum tube is myocardium, pericardium, fat tissue, or the left atrial appendage. For instance, a user may review the signal on an external display to determine if the closure device is coupled to the left atrial appendage. If the signal indicates that the left atrial appendage is not positioned within the vacuum tube, then the vacuum may be released, the vacuum tube may be repositioned, and the process may be repeated until the left atrial appendage is captured. After vacuum has been released, the left atrial appendage may be imaged (e.g., using TEE, fluoroscopy) to confirm ligation of the left atrial appendage and to assist in withdrawal of the closure device from the body.

In some variations, a closure device may additionally, or alternatively, comprise a cardiac electrophysiology diagnostic device configured to receive electrophysiology data (e.g., electrocardiogram signals) of cardiac tissue (e.g., myocardium, pericardium, left atrial appendage). For example, a distal surface of the closure device may comprise one or more electrodes. The electrodes may be configured to receive a signal when in contact with tissue and the signal may be used to determine the type of tissue and/or the location of the closure device relative to tissue. In particular, a mapping system may be coupled to the closure device and may be used to process the received signals to generate an anatomical map of the patient. The mapping system and/or closure device may be used to map and locate the closure device relative to mapped cardiac structures such as the pericardium, myocardium, and/or left atrial appendage. The electrodes may not necessarily be used to generate a cardiac map. For example, after the closure device is advanced into the pericardium (e.g., through a percutaneous subxiphoid access site), one or more electrode connectors disposed proximal to a handle may be connected to a mapping system. The electrodes may be moved into contact with tissue and the electrodes of the closure device may receive electrical signals from the tissue in contact with the electrodes. This data may then be used to map a location of the device relative to the mapped cardiac anatomy. In some variations, a user may review the generated map on a display to guide advancement of the closure device towards a predetermined cardiac structure such as the left atrial appendage. The located left atrial appendage may be subsequently ligated using the same closure device. This may allow the closure device to both map and ligate tissue, thereby reducing cost, complexity, and procedure time as compared with when separate mapping catheter is used.

In some variations, electrode signal data may be used to locate the closure device using a real-time, three-dimensional cardiac map. For example, a set of impedance sensors disposed on a patient may allow a mapping system to determine a set of coordinates of one or more electrodes of the closure device. In some variations, a three-dimensional cardiac map generated by a mapping system may be combined (e.g., merged) with image data generated from a pre-procedure CT scan of the heart. In some variations, the electrodes may receive signals from tissue simultaneously with application of a vacuum suction force or those steps may be performed serially in a predetermined sequence. In some variations, the devices and/or vacuum tube may comprise electrodes used to aid advancement of a closure device in place of other visualization devices such as imaging devices (e.g., camera, endoscope, fiberscope, external light source and imaging sensor, ultrasonic catheter, or the like). That is, additional imaging (e.g., from fluoroscopy or a camera) may not be necessary.

FIG. 14A is a cross-sectional side view of an illustrative variation of a vacuum tube (1400) comprising a suction tip (1420) with an electrode (1402) disposed therein. FIG. 14B is a front view of the suction tip (1420) of the vacuum tube (1400) depicted in FIG. 14A. A conductor (1404) (e.g., electrical lead wire) may be coupled to the electrode (1402) and may extend through the vacuum tube (1400). The electrode (1402) may be coupled to the suction tip (1420) of the vacuum tube (1400) via one or more fasteners (1406). Vacuum may be communicated through the vacuum tube (1400) and the suction tip (1420) of the vacuum tube (1400) through one or more apertures (1410) in the fasteners (1406). The apertures (1410) may comprise any shape, size, or number suitable to communicate a vacuum to an opening of the suction tip (1420). For example, the apertures (1410) may comprise a diameter of between about 0.1 cm and about 0.3 cm. The electrode (1402) may comprise an atraumatic shape that does not lacerate, puncture, or otherwise damage tissue drawn into a lumen of the suction tip (1420) of the vacuum tube (1400). In some variations, the electrode (1402) may be disposed radially along an inner wall of the suction tip (1420) of the vacuum tube (1400). In such a configuration, an imaging device (not shown) may be disposed in the lumen of the suction tip (1420) of the vacuum tube (1400). Alternatively, an electrode (1402) may be disposed on a housing of the imaging device (1400). In some variations, the electrode (1402) may be disposed between about 0.20 cm and about 2.0 cm from an opening of the suction tip (1420) of the vacuum tube (1400). For instance, the electrode (1402) may be disposed about 1.0 cm from an opening of the suction tip (1420) of the vacuum tube (1400).

FIGS. 14C-14E depict a variation of vacuum tube (1400) comprising one or more exterior electrodes (1430) disposed on a surface of the suction tip (1420) of the vacuum tube (1400). Each of the electrodes (1402, 1430) may be coupled to its own conductor (1404), which may extend through a length of the vacuum tube (1400). During advancement of the vacuum tube (1400) through a pericardial space, the exterior electrodes (1430) may make contact with surrounding tissue and receive electrical signals (e.g., ECG signals). Changes in the received signals may indicate movement of the vacuum tube (1400) through the pericardial space and may assist an operator in determining a location of the vacuum tube (1400) relative to cardiac tissue.

FIGS. 32A-32B depict a variation of a closure device (3200) comprising one or more electrodes (e.g., ECG receiving electrodes). A closure device (3200) may comprise an elongate body (3202), a distal tip (3204), and a snare loop assembly (3206). As shown in FIG. 32B, a proximal end of the elongate body (3202) may be coupled to a handle (3220). A cable (3214) may extend from a proximal end of the handle (3220) and comprise one or more electrical connectors (3216). The electrical connectors may be coupled to, for example, a mapping system. Turning to FIG. 32A, one or more electrodes (3210) may be disposed on a surface of the distal tip (3204) and/or elongate body (3202) and configured to receive electrophysiology signals. For example, one or more electrodes (3210) may be disposed on a skived portion of the closure device (3200) (e.g., a bottom or underside surface of the elongate body). However, one or more of the electrodes (3210) may be disposed on any distal portion of the closure device (3200). Each of the electrodes (3210) may be electrically coupled to a corresponding conductor (3212) (e.g., lead wire) such that the electrodes (3210) may be independently wired. The conductor (3212) may extend through a lumen of the elongate body (3202) and handle (3220) to the electrical cable (3214). In some variations, the electrodes (3210) may assist in identifying a location of the closure device (3200) relative to the patient anatomy, as described above. The electrodes (3210) may comprise an atraumatic shape that does not lacerate, puncture, or otherwise damage tissue. In some variations, a snare loop may comprise one or more electrodes. In some variations, the electrodes may be sized to match a diameter and/or width of one or more of the elongate body (3202) and distal tip (3204). In some variations, the closure device (3200) may include up to about 10 electrodes. The electrodes may be made of any suitable material or combination of materials. For example, in some variations, the electrodes may be made from a conductive material such as stainless steel, platinum, copper, combinations thereof, or the like.

Lumens

The vacuum tubes and elongate bodies described here may have any suitable number of lumens. As used herein, "lumen" may refer to any bore or passageway extending through a length of the vacuum tube, elongate body, or other portion of the closure device (e.g., through a handle). It should be appreciated that a lumen need not be entirely enclosed (i.e., the lumen may comprise one or more slots, slits, gaps, or other openings along some or all of the length of the lumen). The vacuum tube and elongate body may comprise one, two, three, four, or five or more lumens. For example, the vacuum tube may comprise one or more lumens configured for aspiration and/or injection of fluid to aid imaging device cleaning (e.g., optical sensor, lens). Some or all of the lumens may extend entirely through the vacuum tube and/or elongate body (e.g., from the proximal end of the elongate body to the distal end of the elongate body). Other lumens may pass through only a portion of the closure device (e.g., from one end to an intermediate point along a length of the device, or between two intermediate points along the length of the device).

The various components of the imaging device may be housed within any lumen of the vacuum tube. The various components of the snare loop assembly may be housed within any lumen or lumens of the elongate body. For example, in some variations, all of the components of the snare loop assembly may be housed in a single lumen. In other variations, different portions of the snare loop assembly may be at least partially housed in different lumens. In some variations, there may be excess suture housed within the elongate body, and this excess suture may be housed in any suitable lumen.

Referring now to FIG. 4D, shown there is a variation of an elongate body (402) comprising a tip (406) and a first lumen (410) including portions having different heights. The elongate body (402) may in some portions be angled, ramped, tapered, and/or beveled, which may assist in preventing the elongate body (402) from kinking or getting caught on tissue when advanced through the body. In the variation depicted in FIG. 4E, different portions of the elongate body (402) may correspond to a particular cross-sectional shape or diameter of the elongate body (402) and, in some instances, to both a particular cross-sectional shape and a particular diameter.

FIGS. 4F-4H depict cross-sectional views of the elongate body (402) along lines FF, GG, and HH of FIG. 4D, respectively. As shown in FIGS. 4F-4H, the FF cross-section comprises a cylindrical cross-section having a first height (424), the GG cross-section comprises a D-shaped cross-section having a second height (426), and the HH cross-section comprises a D-shaped cross-section having a third height (428). In this variation, the first height (424) may be greater than the second and third heights (426, 428). Moreover, as depicted here, the second height (426) may be greater than the third height (428); however, in some instances the third height (428) may be greater than the second height (426).

FIG. 4E depicts a cross-sectional view of the elongate body (402) comprising a first lumen (412) through which a vacuum tube may be slidably disposed. The elongate body (402) may further comprise a first snare loop assembly lumen (414), a second snare loop assembly lumen (416), a third snare loop assembly lumen (418), a first skive line (420), and a second skive line (422). As mentioned above and depicted in FIGS. 4G and 4H, in some instances, the elongate body may comprise a D-shaped cross-sectional shape. In order to fabricate an elongate body with a D-shaped cross-sectional shape, a portion of the elongate body may be cut or otherwise removed.

In some variations, the first and second skive lines (420, 422) may indicate where to cut the elongate body (i.e., at what height) to remove a bottom section of it to create a portion or portions of the elongate body comprising a D-shaped cross-sectional shape. Cutting the elongate body (402) at the first and second skive lines (420, 422) may yield an elongate body (402) with the cross-sectional shapes depicted in FIGS. 4G and 4H, respectively. Thus, the first and second skive lines (420, 422) may correspond to the heights for the second and third heights (426, 428) of the elongate body (402), respectively.

In removing the bottom section of the elongate body (402) as shown in FIG. 4H, a section of the elongate body forming all or part of the first lumen (412) may be removed. For example, when the elongate body (402) is cut at the first skive line (420), all of the first lumen (412) may be removed (as shown in FIG. 4H), and when the elongate body is cut at the second skive line (422), only a portion of the first lumen (412) may be removed (as shown in FIG. 4G) such that the elongate body (402) may comprise a lumen in the form of a groove, as can be seen in FIG. 4D.

Figure 13C:
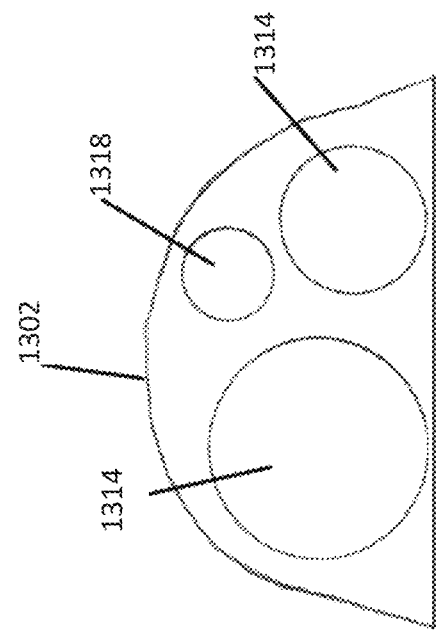
FIGS. 13B-13C are cross-sectional views of the illustrative closure device depicted in FIG. 13A.
Figure 13B:
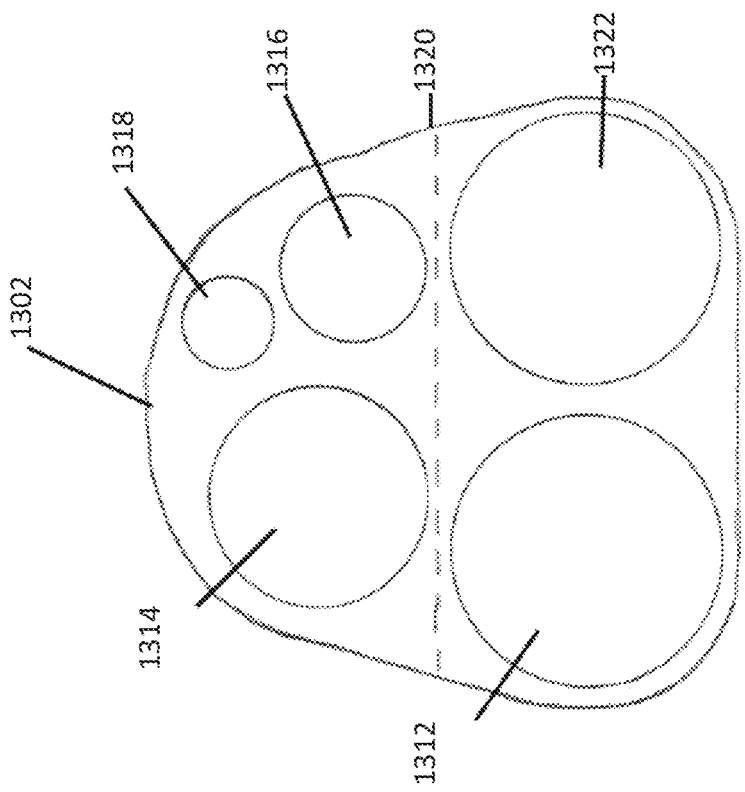

Referring now to FIG. 13B, shown there is a variation of an elongate body (1302) comprising a first lumen (1312) through which a vacuum tube may be slidably disposed and a second lumen (1322) through which an imaging device may be disposed. The elongate body (1302) may further comprise a first snare loop assembly lumen (1314), a second snare loop assembly lumen (1316), a third snare loop assembly lumen (1318), and a skive line (1320). For example, the first snare loop assembly lumen (1314) may comprise a snare loop actuator lumen, the second snare loop assembly lumen (1316) may comprise a suture lumen, and the third snare loop assembly lumen (1318) may comprise a snare release lock wire lumen. In some instances, the elongate body may comprise a D-shaped cross-sectional shape. In order to fabricate an elongate body with a D-shaped cross-sectional shape, a portion of the elongate body may be cut or otherwise removed.

In some variations, the skive line (1320) may indicate where to cut the elongate body (i.e., at what height) to remove a bottom section of it to create a portion or portions of the elongate body comprising a D-shaped cross-sectional shape. Cutting the elongate body (1302) at the skive line (1320) may yield an elongate body (1302) with the cross-sectional shape depicted in FIG. 13C. In removing the bottom section of the elongate body (1302) as shown in FIG. 13C, a section of the elongate body (1302) forming all or part of the first lumen (1312) and second lumen (1322) may be removed. In some instances, the elongate body (1302) may be cut at the skive line (1320) between about 2.5 cm and about 25 cm from a distal end of the elongate body (1302), for example, between about 5 cm and about 15 cm, between about 7.5 cm and about 12.5 cm, and at about 10 cm. The first and second lumens (1312, 1322) may have different diameters or the same diameters.

As described above, the snare loop assembly described here may be advanced to the left atrial appendage over the vacuum tube. By aligning the suction tip of the vacuum tube with the left atrial appendage, the vacuum tube may serve as a guide for the snare loop assembly and elongate body, among other functions. In some variations, cutting the elongate body along the first and/or second skive lines may allow the closure device to more easily access the neck of the left atrial appendage while utilizing the vacuum tube as a guide. For example, in order to advance the snare loop assembly or closure loop around the left atrial appendage and to its neck for closure, the distal tip of the elongate body, from which the snare loop assembly extends, may need to be advanced past the suction tip of the vacuum tube while the suction tip of the vacuum tube remains engaged with (through suction) or otherwise aligned with the left atrial appendage. Removing the first lumen (412) from a distal end of the elongate body (402), as shown in FIG. 4H, may allow the tip of the elongate body (402) and the snare loop assembly to travel along and past the enlarged distal end of the vacuum tube and the apex of the left atrial appendage, to the neck of the left atrial appendage. After the suture loop is deployed, the elongate body (402) may then be retracted also using the vacuum tube as a guide. Thus, the vacuum tube need not be repositioned to allow the distal tip of the elongate body, and the snare loop assembly attached thereto, to access the neck of the left atrial appendage for closure.

Turning back to the variation depicted in FIG. 4E, the first lumen (412), the first snare loop assembly lumen (414), the second snare loop assembly lumen (416), and the third snare loop assembly lumen (418) may be circular. While all the lumens are depicted as circular, this need not be the case, and the lumens may have any suitable shape. The lumens may have different diameters or the same diameters. While the lumens are depicted in specified locations within the elongate body (402), the lumens may be positioned in any location within the elongate body (i.e., their centers may be moved and their locations shifted).

Additionally, in some variations, the lumens may comprise a lining or a coating designed to reduce the frictional forces between the internal surface of the lumens and the components housed within them. The small size of the lumens, their relative locations, the materials used, and the precision required to fabricate the elongate bodies may result in manufacturing variations (e.g., different frictional characteristics inside the lumens) between different lots and/or different manufacturers. These variations may lead to an inconsistent user experience and may result in frustration with the closure device and/or improper usage. For example, if the frictional forces between the internal surface of a lumen and a suture vary, the user may be required to apply different amounts of force to tighten the suture each time the device is used. This may result in over or under tightening of the suture around the tissue. Accordingly, in some variations, the suture lumen may comprise a friction-reducing lining or coating (e.g., a polytetrafluoroethylene (PTFE)). It may be desirable to include a friction-reducing lining in any and/or all of the lumens of the elongate body and/or vacuum tube, as doing so may result in a more consistent and predictable user experience.

Handle

In addition to having an elongate body, a vacuum tube, and a snare loop assembly, the closure devices typically comprise one or more mechanisms for controlling manipulation and advancement of the elongate body, vacuum tube, and/or the snare loop assembly. For example, a handle or other control mechanism (e.g., a surgical master-slave robotic system) may be used to control and actuate the vacuum tube and the snare loop assembly through the elongate body.

As shown in FIGS. 2 and 4, the closure devices described here may comprise a handle or other control mechanism. The handle may serve many purposes. For instance, the handle may provide an interface between the device and the user as the user may hold onto and control the device and its components using the handle. Additionally, the handle may be used to control and advance the vacuum tube through the elongate body, steer and/or guide the vacuum tube, actuate a grasping element, advance an imaging device through the vacuum tube, control an imaging device, and/or control the vacuum pressure applied through the vacuum tube. For instance, the handle may also include one or more of a snare control, suture control, elongate body control, vacuum tube control, imaging device control, and a vacuum control. These controls (e.g., actuators) may take any suitable form, for example, a slider, a button, a knob, a fob, a switch, a latch, a combination thereof, or the like. For example, in some variations, the imaging device control may comprise a switch to activate and deactivate the imaging device and/or a slider to slidably position (e.g., advance, retract) the imaging device. The vacuum control may comprise a slider to advance the vacuum tube into and out of the elongate body and a button, switch, knob, or the like, may be used to control negative pressure of a vacuum source.

In some instances, the handle or other control mechanism may change the snare loop assembly between a delivery, or "closed," configuration and a deployed, or "open," configuration, and vice versa. For example, the handle or control mechanism may be used to increase or decrease the diameter and circumference of the snare loop assembly. Placing the snare loop assembly in a closed configuration may allow for a low-profile advancement of the snare loop assembly over the vacuum tube to a target location and/or may allow the snare loop assembly to close around a target tissue. Conversely, placing a snare loop assembly in an open configuration may allow the snare loop assembly to be placed around one or more target tissues and/or may allow the snare loop assembly to release one or more target tissues previously closed by the snare loop assembly.

In addition, the handle or other control mechanism may steerably advance the vacuum tube from a lumen of the elongate body. Activation and control of an imaging device within a suction tip of the vacuum tube may allow for visualization of tissue structures and improved positioning of the closure device for a procedure. Activation and control of a vacuum pump may generate vacuum pressure within the second lumen sufficient to provide suction at the suction tip of the vacuum tube that may allow for pressure attachment of the closure device to tissue. The imaging device may also be positioned by a handle to confirm closure of the left atrial appendage by imaging the closed suture loop.

As shown in the variation of the closure device (400) depicted in FIG. 4, a vacuum connector (452) may comprise a Y-arm and an imaging device connector (454). In some variations, the vacuum connector (452) may be used to couple the proximal end of the vacuum tube (430) to a vacuum source (e.g., electronic or mechanical vacuum pump). The imaging device connector (454) may be used couple the imaging device to device that may process and/or display the images for use during a procedure (e.g., a computer, a television, or the like).

Figure 15C:
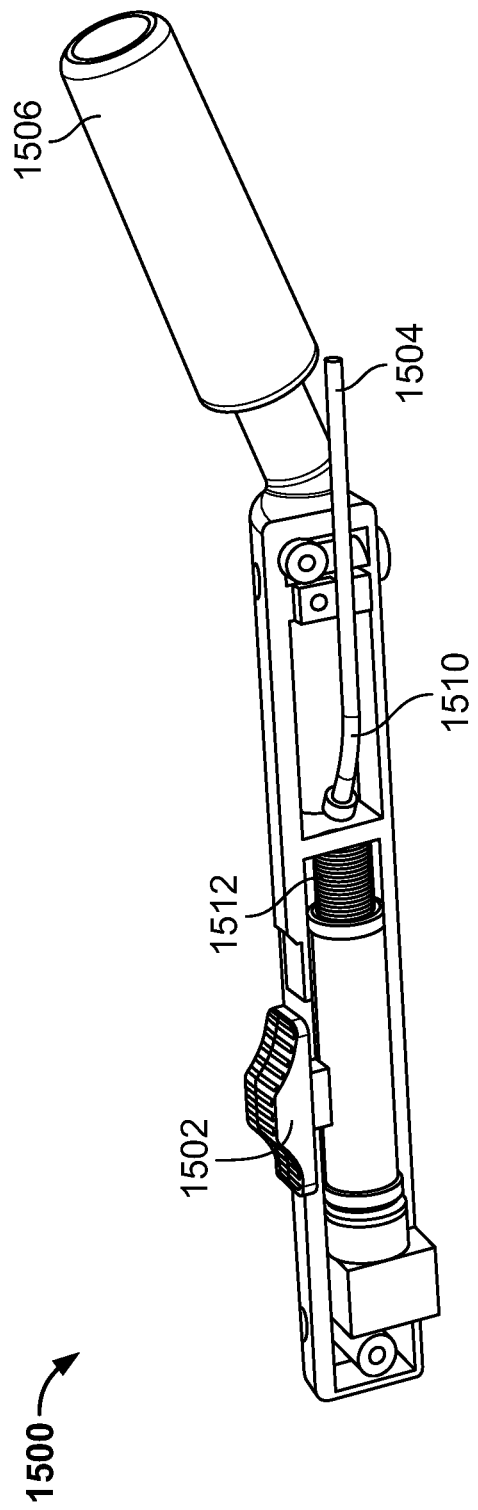

FIG. 15A is a perspective view of an illustrative variation of a vacuum control (1500) of a closure device. A portion of the handle of the closure device may comprise the vacuum control (1500). The vacuum control (1500) may comprise a switch (1502), which may be in the form of a finger slidable control knob. The switch (1502) may actuate a connection between a vacuum source (through vacuum source connector (1506)) and the vacuum tube (1504), thereby activating vacuum through the vacuum tube. The vacuum source connector (1506) may couple the vacuum control (1500) to the vacuum source such as a vacuum pump, and the vacuum tube (1504) may extend distally. FIGS. 15B-15C are cross-sectional perspective views of the vacuum control (1500) depicted in FIG. 15A. For instance, the vacuum control (1500) may further comprise a vacuum chamber (1510) having a compression spring (1512) and a control opening (1514) disposed therein. FIG. 15B depicts the vacuum control (1500) with the switch (1502) in a vacuum disconnection position. In this position, a control opening (1514) is separated from the switch (1502) and the compression spring (1512). The switch (1502) may comprise a detent to lock the switch (1502) in the vacuum disconnection position. The vacuum control (1500) comprises a chamber (1510) that provides common vacuum communication between an external vacuum source, control opening (1514), and vacuum tube (1504). FIG. 15C depicts the vacuum control (1500) with the switch (1502) in a vacuum connection position. For example, a user may slide the switch (1502) proximally to release the detent and rotate the switch (1502) to allow the compression spring (1512) to slide the switch (1502) distally. The switch (1502) may comprise an elastomeric gasket configured to occlude the control opening (1514), thus sealing the chamber (1510) and establishing a vacuum in the vacuum tube (1504).

Figure 16:
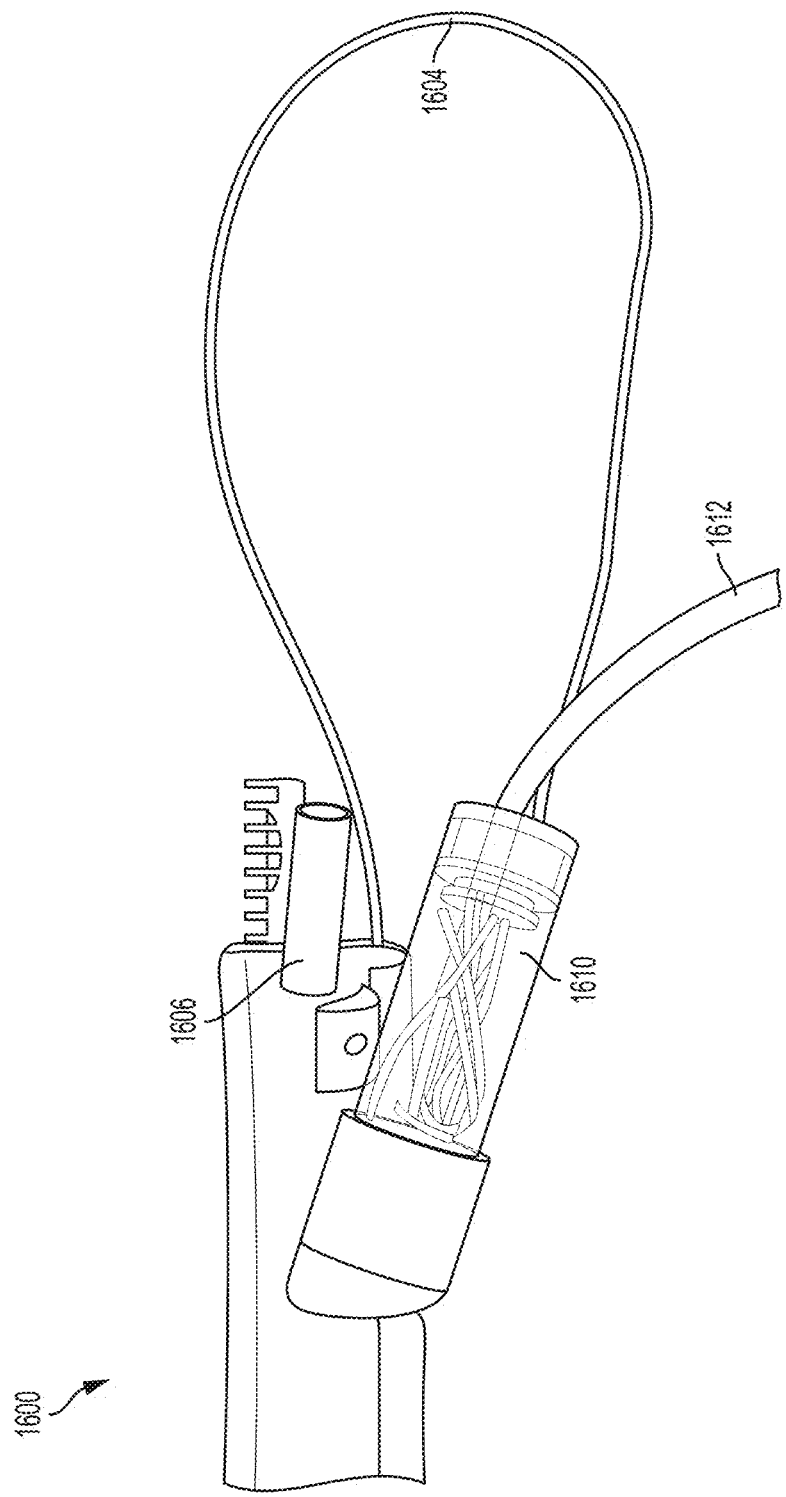
FIG. 16 is a side view of an illustrative variation of a handle of a closure device.

FIG. 16 is a side view of an illustrative variation of a proximal end of a handle (1600) comprising a vacuum source connector (1606) and a plenum (1610). The plenum (1610) provides a sealed chamber for separating power and data conductors (e.g., for an imaging device, electrode) from a proximal end of the vacuum tube (1604). The plenum (1610) is sealed in order to communicate the vacuum from the handle (1600) through a suction tip of the vacuum tube (1604). A proximal end of the plenum (1610) may be connected to a closed vacuum chamber in the handle (not shown) as discussed in FIGS. 15A-15C. A vacuum tube (1604) may extend into the plenum (1610) with its lumen open to the plenum (1610), thus allowing negative pressure to be applied through the vacuum tube (1604). Signal and power conductors from the imaging device may be coupled to an imaging device connector (1612) from inside the plenum (1610). The vacuum tube (1604) and imaging device connector (1612) may be sealed to the plenum (1610) to prevent vacuum leaks.

The vacuum tube (1604) may have sufficient length to form a loop from an end of a handle (1600) and back into the plenum (1610). Accordingly, the relatively heavy and stiff imaging connector (1612) may be coupled to the handle (1600) rather than coupled to the vacuum tube (1604), thus preserving tactile control of the vacuum tube (1604) for a user. For example, when the left atrial appendage is stabilized against the vacuum tube, a user may hold the vacuum tube at the handle to maintain stabilization of the left atrial appendage.

The handle may be further used to control and actuate the snare loop assembly through the elongate body, steer and/or guide the elongate body, and/or modify the shape of the elongate body using a pull wire controlled through the handle. The handle may enable a user to control the release of the suture loop from the snare, and it may be used to house electronic or other related components for one or more imaging devices. In some variations, the closure devices described here may comprise a tensioning mechanism for managing the tension applied to a portion of the suture loop (e.g., a tail of the suture loop) of the closure device. When the closure devices are used to place and tighten a suture loop around a tissue, it may be desirable to manage the tension applied to the suture as the suture loop is tightened. The handle may comprise any suitable elements to facilitate use of the device for the closure of tissue, including sliders, knobs, switches, latches, push buttons, or the like, which may be coupled to any component to maneuver, pull, push, open, close, deploy, activate, de-activate, or otherwise use the component.

Sheath

As shown in FIG. 4A, the closure device (400) may be used with a sheath (460) (e.g., cannula) comprising a lumen therethrough. The closure device (400) including the elongate body (402) and the vacuum tube (430) may be slidably positioned within and advanced through the sheath (460) for introduction into the body. In another variation shown in FIG. 5B, the closure device (500) may be used with a sheath (560) comprising a lumen therethrough. The closure device (500) including the elongate body (502) and the vacuum tube (530) may be slidably adjacent to each other and advanced through the sheath (560) for introduction into the body. The elongate body (500) may include a snare loop assembly (504) which may be advanced and closed around tissue. The vacuum tube (530) may include a suction tip (532) of the vacuum tube (530) having an imaging device (570) disposed in a distal end (532) lumen. As discussed above, a suction tip (532) of the vacuum tube (530) may provide stabilization of the closure device (500) relative to target tissue, and the imaging device (570) disposed in the suction tip (532) may provide direct visualization of heart tissue.

As discussed herein, a sheath may be used to help advance one or more components (e.g., closure device, imaging device, vacuum tube) into a desired portion of the pericardial cavity. In some variations, the sheath may additionally be configured to create separation between the pericardium and the epicardium, which may assist in increasing a field-of-view and thus aid in visualization of a procedure. The sheath may create separation through inflation of a portion of the sheath or through insufflation of the pericardial cavity using the sheath. The pericardial cavity is an example of potential space that is formed between adjacent structures that are normally pressed together. FIG. 31A is a cross-sectional side view of patient anatomy including the pericardial cavity (3108). FIG. 31A depicts the heart (3100) comprising a left atrial appendage (3102) and a pericardium (3104) covering the heart (3100). The xiphoid process (3106) is adjacent the heart (3100). The fibrous pericardium (3104) comprises a flexible membranous sac adjacent to the epicardium that comprises a layer of the heart (3100) immediately exterior to the myocardium. The pericardium (3104) is normally in contact with the epicardium. When a device such as a sheath is introduced into the pericardial cavity (3108), the sheath may be advanced and maneuvered fairly freely through the pericardial cavity (3108). However, the pericardium generally conforms to the sheath (e.g., drapes over the sheath) such that a field-of-view from a distal end of the sheath may be limited. In some variations, the sheaths described herein may be configured to increase separation between the pericardium and epicardium in order to increase a field-of-view from a distal end of the sheath for imaging devices advanced through the sheath. Thus, advancement and visualization of cardiac structures may be improved.

Figure 29D:
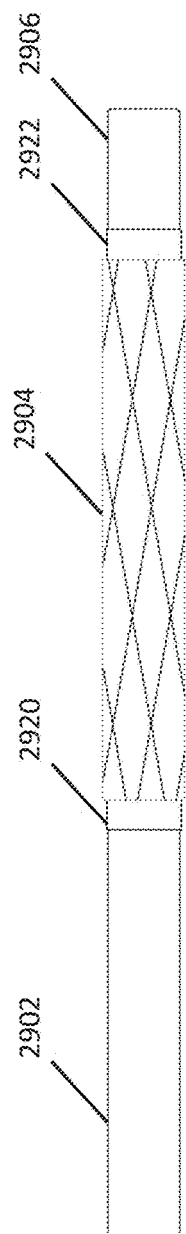

In some variations, a sheath may be used to create an access site and create separation in a pericardial cavity. As shown in FIGS. 29A-29E, a sheath (2900) may comprise an elongate body (2902) having a distal end (2906). The elongate body (2902) may be coupled to an expandable member (2904). The distal end (2906) may comprise a soft tip as described herein. A proximal end of the elongate body (2902) may be coupled to a port (2908) configured as a conduit for fluid (e.g., gas, liquid) to travel through the elongate body (2902) and expandable member (2904). The elongate body (2902) may comprise a semi-flexible polymer material as described herein and may comprise a plurality of lumens. FIG. 29C illustrates a first lumen (2910) configured to receive a closure device or ablation device and a second lumen (2912) configured to receive or hold an imaging device (e.g., endoscope, fiberscope, camera). However, the elongate body (2902) may comprise additional lumens such as a third lumen fluidly coupling the port (2908) to the expandable member (2904). The number, size, and configuration of the lumens may vary based on the procedure to be performed.

In some variations, the expandable member (2904) may transition between first and second configurations. For example, a fluid source (e.g., a syringe filled with liquid) may be coupled to the port (2908) and may be used to introduce and/or remove fluid from the sheath (2900). In variations comprising a syringe, an operator may depress a plunger of the syringe to fill (e.g., inflate) the expandable member (2904) into the second configuration as shown in FIGS. 29B-29C. A valve of the port (2908) may be closed to allow the syringe, or other fluid source, to be removed. When transitioning the expandable member (2904) from the second configuration to the first configuration, the fluid source may be coupled to the port (2908) and, for example, the plunger of a syringe may be withdrawn to remove fluid from the expandable member (2904).

In some variations, the expandable member (2904) may comprise a soft enclosure (e.g., bag, balloon). The balloon may be made of any suitable material or combination of materials. For example, in some variations, the balloon may be made from nylon, polyethylene terephthalate, combinations thereof, or the like. The balloon may be configured to take on a particular shape or configuration when inflated in the second configuration.

Figure 29E:
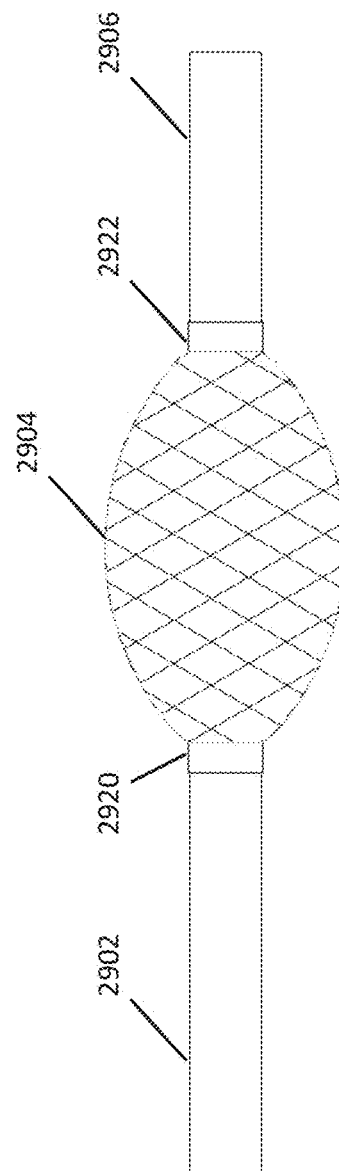

FIGS. 29D-29E depict a variation of the expandable member (2904) comprising a set of deformable wires. The wires may be made of any suitable material such as stainless steel, a nickel titanium alloy, or the like. The expandable member (2904) may comprise a proximal ring (2920) and a distal ring (2922) coupled to the ends of the wires. In some variations, one of the rings may be fixed to the elongate body (2902) while the other ring (e.g., sliding ring) may be slidably positioned along a length of the elongate body (2902). For example, a control wire (e.g., pull wire) (not shown) may be coupled to the sliding ring through a lumen of the elongate body (2902). An operator may advance and retract the control wire to transition the expandable member (2904) between the first configuration (FIG. 29D) and the second configuration (FIG. 29E).

In some variations, a sheath may comprise a curved and/or deflectable portion. FIGS. 30A-30B depict a sheath (3000) comprising a portion with a predetermined curved shape that may aid an operator in aiming the sheath (3000) towards a left atrial appendage at a desired angle. The sheath (3000) may comprise an elongate body (3002) having a distal end (3006) and an expandable member (3004) coupled thereto. A proximal end of the elongate body (3002) may be coupled to a port (3008) as described herein. One or more of the elongate body (3002), expandable member (3004), and distal end (3006) may comprise a curved shape. As described herein, the expandable member (3004) may transition between a first configuration (FIG. 30A) and a second configuration (FIG. 30B). The curved shape of the sheath (3000) may allow the sheath (3000) to be steered, by rotating the sheath (3000), as it is advanced through a body cavity (e.g., pericardial cavity). Furthermore, the curved shape of the sheath (3000) may be configured to conform or correspond to the curvature of one or more portions of the heart, which may aid in the advancement of one or more devices to a superior aspect of the heart.

In some variations, the elongate body of a sheath may comprise various sections or portions with different characteristics, for example, different diameters, cross-sectional shapes, stiffnesses, materials, or the like, which may increase the steerability and maneuverability of the sheath. For instance, the elongate body may be braided, non-braided, tapered, non-tapered, or some combination thereof. Braiding may increase the torsional stiffness of the sheath while allowing the sheath to remain relatively flexible, thus improving overall steerability and maneuverability of the sheath. In some instances, at least a portion of the elongate body may be shapeable, meaning that the elongate body may be manipulated (e.g., bent) and may retain the manipulated shape until a user or other applied force (e.g., from tissue within the body) further modifies it.

In some variations, a distal end (3006) of a sheath (3000) may be adjustably deflectable, thus allowing a field-of-view from the distal end (3006) to be modified without otherwise moving the sheath (3000). A proximal end of the elongate body (3002) may be coupled to a handle (3010). The handle (3010) may comprise a deflection actuator (e.g., slider, knob, button, switch, or the like) comprising a control wire (e.g., pull wire) (not shown) coupled to the deflectable distal end (3006). For example, the control wire may extend through a control wire lumen of the elongate body (3002). The distal end (3006) may be deflected in one or more directions. For example, the distal end (3006) may be deflectable in one direction by up to about 120 degrees.

In some variations, a sheath may be used to insufflate a gas (e.g., $CO_2$ gas) into a pericardial cavity to create a separation between the pericardium and epicardium. As depicted in FIGS. 35A-35B, a sheath (3500) may comprise an elongate body (3502) having a distal end (3504). A proximal end of the elongate body (3502) may be coupled to a hub (3506) and a port (3508) configured as a conduit for fluid (e.g., $CO_2$ gas) to travel through a first lumen (3510) of the elongate body (3502). The elongate body (3502) may comprise a semi-flexible polymer material and may comprise a plurality of lumens. FIG. 35G illustrates the first lumen (3510) configured for one or more of a closure device, ablation device, a dilator, or the like. A second lumen (3512) may be configured for or to receive an imaging device (e.g., endoscope, fiberscope, camera). The number, size, and configuration of the lumens may vary based on the procedure to be performed. The hub (3506) may comprise a radial seal coupled to a proximal end of the elongate body (3502). The radial seal is disposed within the hub (3506), as shown for example, in FIGS. 38A-38B. The seal may circumferentially surround a shaft of a device disposed within a lumen of the sheath (3500) such that $CO_2$ introduced into one or more lumens of the sheath (3500) may exit only through the distal end (3504) of the sheath (3500), thus allowing a pericardial cavity to be insufflated.

FIGS. 38A-38C and 39A-39B depict illustrative variations of a sheath comprising a radial seal. FIG. 38A illustrates a proximal end of a sheath (3800) comprising an elongate body (3802), a hub (3806) coupled to a proximal end of the elongate body (3806), and a port (3804). FIGS. 38B-38C are cross-sectional side views of the hub (3806) coupled to the proximal end of the elongate body (3802). The hub (3806) may define a hub lumen (3814) operatively coupled to a lumen of the elongate body (3802). A radial seal (3810) may be disposed within the hub lumen (3814), may comprise a flexible material, and may define a seal aperture (3812). A device (3808) may be advanced through the radial seal (3810) and hub lumen (3814), into a lumen of the elongate body (3802). Device (3808) as used herein may refer to any of the devices described herein such as the closure device, vacuum tube, imaging device, dilator, catheter, combinations thereof, or the like. The radial seal may be made of any suitable material or combination of materials. For example, in some variations, the radial seal may be made from silicone, thermoplastic elastomer, combinations thereof, or the like.

The seal aperture (3812) may be sized to have a diameter smaller than that of an outer diameter of the device (3808). For example, the seal aperture (3812) may be sized to be just slightly smaller than a diameter of the device (3808) to create a fluid seal while adding minimal frictional drag to the device (3808) guided through the sheath (3800). For example, the radial seal (3810) may be minimally deformed (e.g., stretched) as the device (3808) extends through the seal (3810). The radial seal (3810) may thus reduce, if not prevent escape of $CO_2$ gas from a proximal end of the sheath (3800). In some variations, an outer surface of the device (3808) may comprise a low-friction coating (e.g., PTFE) disposed on portions of the device (3808) in slidable contact with the radial seal (3810).

FIGS. 39A-39B depict additional variations of a proximal hub of a sheath. FIG. 39A illustrates a sheath (3900) comprising an elongate body (3902), a hub (3906) coupled to a proximal end of the elongate body (3902), and a port (3904). The hub (3906) may comprise a Tuohy-Borst seal system. For example, a seal control actuator (3910) may be disposed over the hub (3906). An operator may adjust the seal control actuator (3910) (e.g., slider, knob, button, switch, or the like) in order to modify a diameter of the seal within the hub (3906), thus providing an adjustable seal that may accommodate devices of different diameters that are otherwise configured to move within the sheath (3900). Once a seal is formed between the hub (3906) and device (not shown), the knob (3910) may be further adjusted to modify the friction applied by the seal to the device.

In some variations, a hub of a sheath may comprise at least two seals. This may allow one or more devices to be removed from a lumen of the sheath while minimizing $CO_2$ loss from a proximal end of the sheath when the device is withdrawn proximally from the sheath. FIG. 39B illustrates a sheath (3900) comprising an elongate body (3902), a hub (3920) coupled to a proximal end of the elongate body (3902), and a port (3904). The hub (3920) may comprise a first seal controlled by a seal control actuator (3922) (e.g., slider, knob, button, switch, or the like) and a second seal (3930) disposed proximal to the first seal. The second seal (3930) may comprise any suitable seal such as the fixed diameter seal described with respect to FIGS. 38A-38C, a Tuohy-Borst seal, or the like. The first seal may be configured to form a seal around a device disposed within a lumen of the hub and to close the lumen of the hub (e.g., form a complete seal) when a device is not present in a lumen of the hub. This may allow a device to be advanced and retracted from the sheath (3900) with minimal loss of fluid (e.g., $CO_2$ gas). For example, when a device is disposed in a lumen of the hub (3920) and the elongate body (3902), at least the second seal (3930) may form a seal between the hub (3920) and the device. The port (3904) may be used to introduce $CO_2$ gas into the sheath (3900) and the gas may exit a distal end of the sheath (3900) to insufflate a body cavity such as the pericardial cavity. When it is desired to remove the device from the sheath, the device may be partially withdrawn such that a distal end of the device is disposed between the first and second seals. The seal control actuator (3922) may then fully close the hub (3920) such that an aperture diameter of the seal is zero or nearly zero. The device may then be retracted out of the second seal (3930) and the hub (3920) with minimal fluid loss. A device may be introduced into the sheath by advancing a distal end of the device between the second seal (3930) and the first seal (3920) of the hub (3920). That is, the distal end of the device may pass through the second seal (3930) but not the first seal of the hub (3920). The first seal may be in the fully closed state when the device is introduced into the hub (3920). Once the second seal (3930) forms a seal around the device, the seal control actuator (3922) may be used to open the first seal to allow the device to be advanced into a lumen of the elongate body (3902). Thus, introduction of a device into the sheath (3900) may be performed with minimal fluid loss.

Figure 35C:
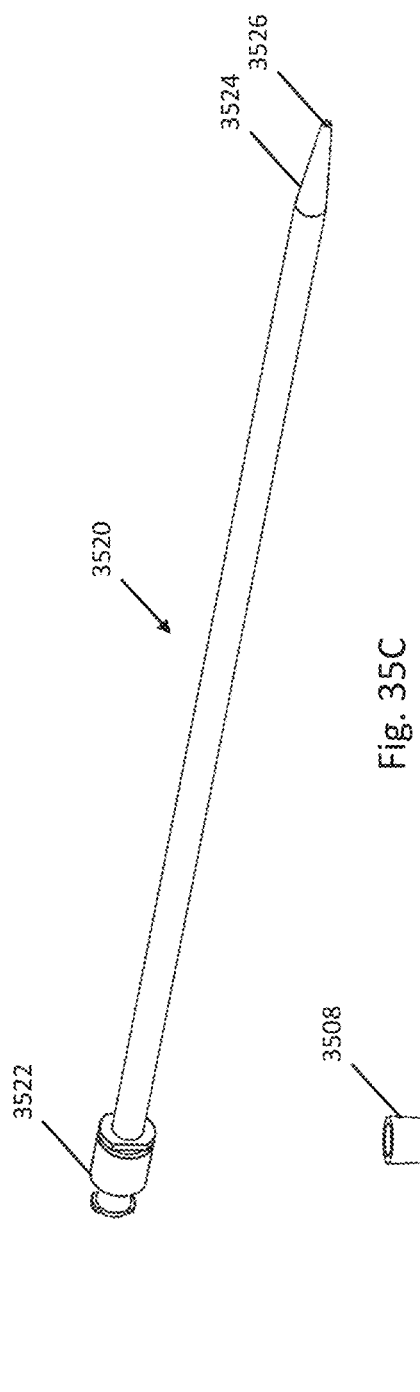
Figure 35D:
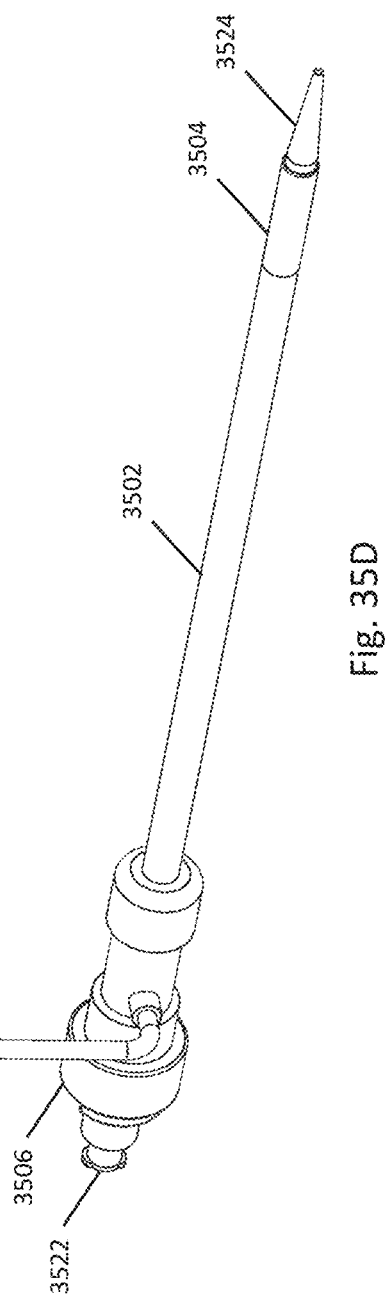
FIG. 35D is a front perspective view of the dilator depicted in FIG. 35C disposed in the sheath depicted in FIGS. 35A-35B.

In some variations, a dilator may be advanced through a sheath to aid in creation of an access site. FIG. 35C depicts an illustrative variation of a dilator (3520) comprising a tapered distal end (3524) and defining a guidewire lumen (3526). The tapered distal end (3524) may reduce the force necessary to advance the dilator (3520) and/or sheath (3500) assembly through tissue. A proximal end of the dilator (3520) may be coupled to a dilator hub (3522) configured to releasably connect the dilator (3520) to the sheath (3500). As shown in FIGS. 35D-35E, the dilator (3520) coupled to the sheath (3500) may be handled as a single unit during procedures involving a guidewire, thus improving ease of use for an operator. The dilator hub (3522) may be releasably connected to the hub (3506). The dilator (3520) may comprise a semi-flexible polymer material such as FEP, polypropylene, or the like. In some variations, the dilator (3520) may be configured to fit within a lumen of the sheath (3500). For example, an outer diameter of the dilator (3520) may be just smaller than a diameter of a sheath lumen. In some variations, a diametric clearance between the dilator and sheath may be between about 0.02 mm and about 0.2 mm. This may provide additional strength to a wall of the sheath (3500) when the sheath (3500) is inserted into and through tissue. The guidewire lumen (3526) may extend through a length of the dilator (3520) and may have a diameter configured for a guidewire. In some variations, the sheath and/or dilator may have a diameter between about 12 Fr and about 27 Fr. In some variations, the guidewire may have a diameter between about 0.35 mm and about 1.05 mm.

In some variations, as shown in FIG. 35F-35G, the sheath (3500) may comprise a plurality of lumens including a first lumen (3510) and a second lumen (3512). An imaging device (e.g., a flexible endoscope) may be disposed in a distal end of the sheath (3500) and may be coupled to a cable (3530) that extends through a length of the elongate body (3502). The cable (3530) may extend out of the hub (3506). In some variations, an imaging device may be fixed or removably disposed within the second lumen (3512). In some variations, the hub (3506) may comprise a radial seal configured to seal the cable (3530) and minimize fluid loss from a proximal end of the sheath (3500).

In some variations, a dilator (3540) may be configured to fit within a sheath (3500) and the sheath (3500) may comprise a plurality of lumens (e.g., FIG. 35G). As shown in FIG. 35H, a dilator (3540) may comprise a tapered distal end (3544) and a guidewire lumen (3546). The tapered distal end (3544) may reduce the force necessary to advance the dilator (3540) and/or sheath (3500) assembly through tissue. The dilator (3540) may define a channel (3548) (e.g., recess, groove) that may extend through a length of the dilator. The channel (3548) may mimic a shape of the second lumen (3512) of the sheath (3500) (e.g., have a similar radius of curvature and/or corresponding shape) such that the channel (3548) may slide over the second lumen (3512). For example, FIGS. 35I-35J illustrate the dilator (3540) disposed within a first lumen (3510) of the elongate body (3502). As shown in FIG. 35J, the dilator (3540) may be disposed in the elongate body (3502) of the sheath (3500) such that a second lumen (3512) of the elongate body (3502) may be slideably disposed within the channel (3548) of the dilator (3540). Thus, the channel (3548) of the dilator (3540) may accommodate the second lumen (3512) of the sheath (3502) and an imaging device disposed within the second lumen (3512). A proximal end of the dilator (3540) may be coupled to a dilator hub (3542) and may be configured to releasably connect the dilator (3540) to the sheath (3500). The dilator (3540) may be configured to fit within a lumen of the sheath (3500). The guidewire lumen (3546) may extend through a length of the dilator (3540) and may have a diameter configured for a guidewire.

In some variations, a sheath configured for gas insufflation of the pericardial cavity may comprise a curved portion and/or deflectable portion. FIGS. 36A-36B depict a sheath (3600) having a predetermined curved shape that may aid an operator in aiming the sheath (3600) towards a target cardiac structure (e.g., pericardium, left atrial appendage) at a desired angle. The sheath (3600) may comprise an elongate body (3602) having a distal end (3604). A proximal end of the elongate body (3602) may be coupled to a port (3608) as described herein. One or more of the elongate body (3602) and distal end (3604) may comprise a curved shape. The curved shape of the sheath (3600) allows the sheath (3600) to be steered, by rotating the sheath (3600), as it is advanced through a body cavity (e.g., pericardial cavity). Furthermore, the curved shape of the sheath (3600) may conform to the curvature of one or more portions of the heart, thus aiding the advancement of one or more devices to a superior aspect of the heart. In some variations, the sheath (3600) may comprise a soft tip (3610) that may be made of any suitable material or combination of materials softer and/or more flexible than other portions of the elongate body (3602). The soft tip (3610) may reduce the likelihood of trauma to tissue as the sheath (3600) is advanced within a pericardial cavity.

Additionally or alternatively, in some variations, a closure device may comprise an expandable member coupled to a distal portion of the device. The expandable member (e.g., balloon, wire mesh) may be configured to create space within a pericardial cavity to improve a field-of-view from a distal end of the closure device.

It should be appreciated that the sheaths, vacuum tube devices, imaging devices, closure devices, dilators, and combinations thereof may each be deflectable. That is, the devices described herein may be articulable so as to allow an operator to steer one or more devices during a procedure through a body cavity. In some variations, one or more control wires (e.g., pull wire) may be disposed through a lumen of a sheath and/or an elongate body and coupled at a proximal end to a handle comprising a deflection control actuator. A distal end of the control wire may be coupled to the deflectable device such that movement of the control wire deflects at least a portion of the device in a desired direction. For example, one or more of a closure device, vacuum tube, imaging device, sheath, and dilator, may be deflectable along multiple planes using one or more control wires.

II. Kits

The devices described herein may be combined in various kits. Generally, a kit may comprise one or more of a closure device, vacuum tube, imaging device, electrophysiology diagnostic device, sheath, and dilator as described herein. The kits may be packaged with one or more of the devices assembled together, or may be packaged with one or more of the devices provided separately. Any of the kits described may further comprise instructions for use. In some variations, a kit for closing tissue may comprise a closure device, a vacuum tube disposed in a lumen of the closure device, and an imaging device disposed in a lumen of the vacuum tube and/or coupled externally to the closure device or vacuum tube. In some variations, a kit for closing tissue may comprise a closure device and a vacuum device disposed in a lumen of the closure device. In some of these variations, the closure device and/or vacuum tube may comprise a mounting assembly (e.g., fasteners within a lumen of the vacuum tube, fastener couplable to the closure device) configured to couple to an imaging device where the imaging device may be provided separately.

In other variations, a kit for closing tissue may comprise a closure device, a vacuum tube, and an electrophysiology diagnostic device integrated with one or more of the closure device and vacuum tube. An imaging device may optionally be included that may be disposed within a lumen of the vacuum tube and/or closure device or may be separate from the vacuum tube and/or closure device but configured to be disposed within a lumen of either. In yet other variations, a kit for closing tissue may comprise a closure device, vacuum tube, and an expandable sheath (e.g., a balloon sheath, for example, as depicted FIG. 31C, and an insufflation sheath in FIG. 37B) configured to increase spacing in a pericardial cavity. An imaging device may optionally be included that may be disposed within a lumen of the sheath and/or closure device. The sheaths may optionally include a dilator. Some variations may include multiple imaging devices such as a vacuum tube and sheath each including separate imaging devices.

III. Methods

The closure devices described here may be useful for closing tissue, for example, the left atrial appendage. The closure devices may access the left atrial appendage using minimally invasive approaches, for example, percutaneously or through a small subxiphoid window. In use, a distal end of the closure device may be advanced into the body toward a target tissue (e.g., the left atrial appendage) using a sheath. During advancement, the snare loop assembly may be in a closed configuration to help prevent the snare loop assembly from snagging or catching on tissue or other obstructions. Likewise, the vacuum tube may be at least partially retracted into a first lumen of the elongate body (or a sheath) to ease advancement of the closure device through confined body spaces. Once the distal end of the elongate body has reached a location at or near the target tissue, the snare loop assembly may be moved into the opened configuration and the vacuum tube may be advanced through the aperture of the snare loop assembly such that the snare loop assembly (and a small portion of the tip of the elongate body) form a loop around the vacuum tube. In some variations, the diameter of the aperture of the snare loop assembly during advancement may be larger than an outer diameter of the suction tip of the vacuum tube. In these variations, the vacuum tube may be positioned such that the snare loop assembly may encircle, surround, or otherwise form a loop around the suction tip of the vacuum tube during advancement. In variations in which the closure device comprises an imaging device, the imaging device may be used during advancement to confirm the position of the closure device within the body cavity and provide visualization to assist in guiding the closure device to the target tissue, to assess the condition of the target tissue, and to determine a contact location to engage with and/or releasably couple the vacuum tube to the target tissue.

In order to engage a target tissue to assist in stabilizing the closure device and properly positioning the snare loop assembly for closure, a distal opening of the vacuum tube may be advanced to contact and draw a portion of tissue into a lumen of the vacuum tube. A vacuum may be generated in the lumen of the vacuum tube using negative pressure to hold tissue in place relative to the vacuum tube, which may reduce the need for additional stabilization or guide elements in the pericardial space or inside the heart. More particularly, releasably coupling the vacuum tube to a target tissue using suction may properly position the snare loop assembly for advancement over and/or around the target tissue such that the use of additional guides or positioning elements (e.g., a balloon, magnets, or the like) may not be required. Thus, the methods described herein may allow for closure of tissue using a single-access point.

After advancement around a target tissue, the snare loop assembly may be closed around the encircled tissue to close, ligate, or otherwise restrict the target tissue. The snare loop assembly may be re-opened, repositioned, and re-closed as necessary. In some instances, a suture loop or other restricting device may be tightened and released from the closure device to maintain closure of the target tissue. In variations in which the closure device comprises a tensioning device or mechanism, the tensioning device or mechanism may be used to release the suture loop from the snare loop assembly and/or tighten the suture loop. The suture loop may be tightened before and/or after removal of the closure device from the body.

To remove the closure device from the body, the snare loop assembly may again be opened to release the target tissue (the suture loop or other restricting device may remain in place) such that the snare loop assembly, vacuum tube, and the elongate body may be withdrawn. In some variations, the fixed end of the snare may be releasably attached to the elongate body such that the snare loop assembly may be released and retracted into the elongate body after the suture loop is deployed. In these variations, a retraction device or mechanism may be used to release the fixed end of the snare from the elongate body and retract the snare and in some variations, the retention member, into the elongate body.

In variations in which the snare is not releasable, the snare loop assembly (without the suture loop which may have already been deployed around the target tissue) may be opened to facilitate removal of the snare loop assembly from around the target tissue. Once the snare loop assembly is withdrawn from around the target tissue, it may be closed to facilitate a low-profile withdrawal from the body. The suction applied via the vacuum tube may be released before or after deployed of the suture loop and/or opening of the snare loop assembly for withdrawal. Once the vacuum tube disengages and/or decouples from the target tissue, the imaging device may be used to view and confirm the placement and tightening of the suture loop around the target tissue and may assist in withdrawing the closure device from the body. In some variations, the vacuum tube may be partially or fully retracted into the elongate body to facilitate withdrawal of the closure device from the body.

Figure 17:
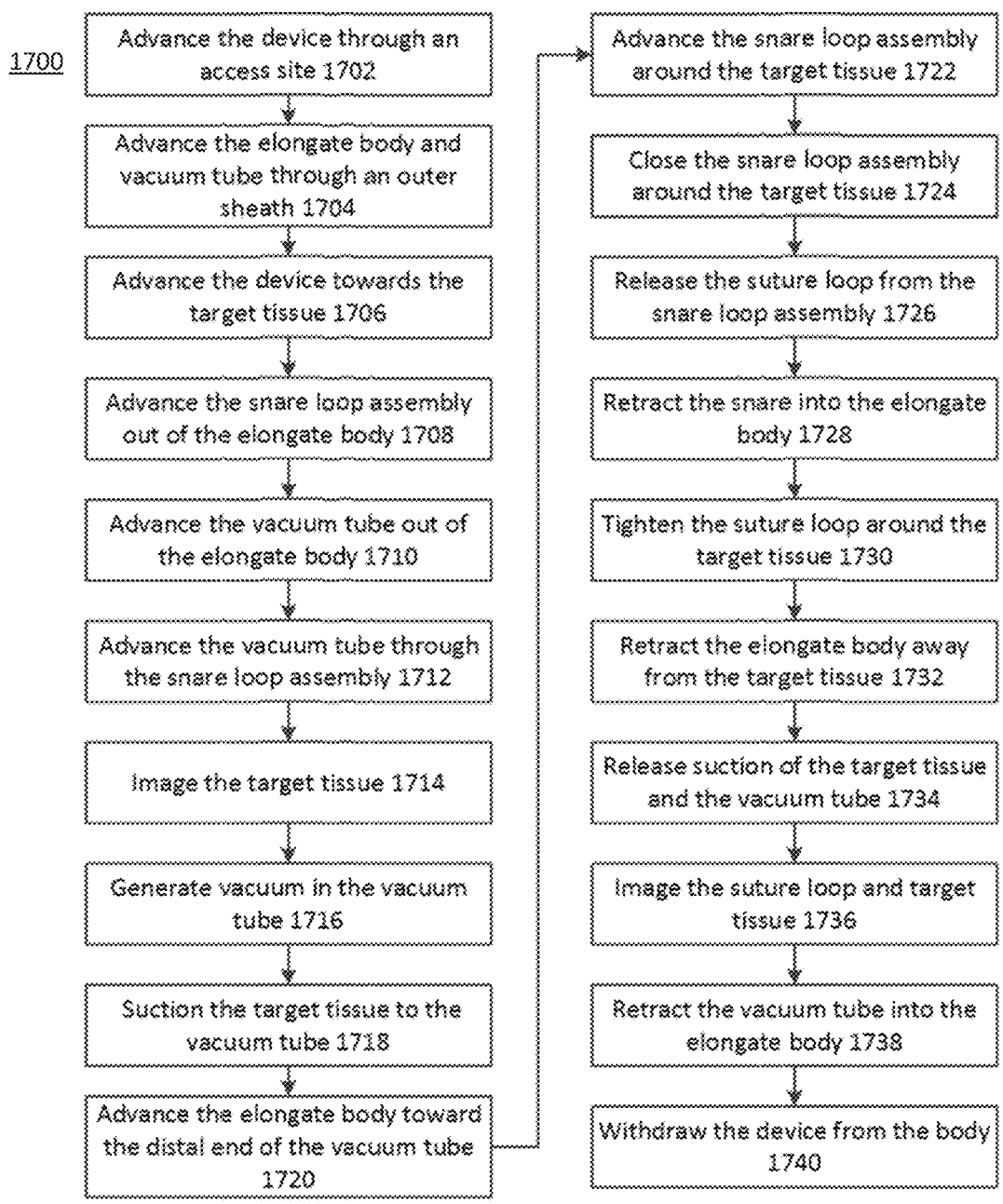
FIG. 17 is a flowchart describing a variation of a method of closing tissue.

FIG. 17 is a flowchart (1700) of an illustrative variation of a method of closing a target tissue. The method (1700) may begin with advancement of a closure device through an access site into the pericardial space (1702). The closure device may be advanced using a minimally invasive technique, for example, percutaneously or through a small window. In some variations, a sheath may be used to introduce the closure device, vacuum tube, and/or imaging device into the body. For example, a distal end of the elongate body and vacuum tube may be advanced through a lumen of the sheath into a body cavity (1704) such as a pericardial cavity. As another example, a closure device and vacuum tube may be advanced through a first lumen in a sheath while an imaging device may be advanced through a second lumen in the sheath. In some variations, a sheath as described herein may be advanced through a pericardial cavity to advance devices such as a dilator, closure device, vacuum tube, electrophysiology diagnostic device (e.g., ECG receiving electrodes, mapping catheter), imaging device (e.g., endoscope, fiberscope, camera), combinations thereof, or the like towards cardiac structures such as the left atrial appendage.

In FIG. 31B, a sheath (3110) is shown advanced into a pericardial cavity (3108) between the pericardium (3104) and the epicardium of the heart (3100). The sheath (3110) may be introduced into the pericardial cavity (3108) using a sub-xiphoid access, for example. In some variations, the sheath (3110) may be inserted percutaneously, or via a small incision, over a guidewire into the pericardial cavity (3108). Access to the pericardial cavity may include inserting a needle into the midline inferior to the xiphoid process (3106). The needle may be advanced in the superior direction (using fluoroscopic imaging), until the needle pierces the pericardium (3104). A guidewire may then be inserted through the needle and into the pericardial cavity (3108). The needle may be withdrawn and one or more sheaths and in some variations, dilators, (e.g., FIGS. 35C-35E, 35H-35J) may be advanced over the guidewire and into the pericardial cavity (3108). The dilator may be withdrawn from the sheath such that a lumen of the sheath is made available for advancement of devices such as a closure device, vacuum tube, imaging device, combinations thereof, or the like.

Figure 31C:
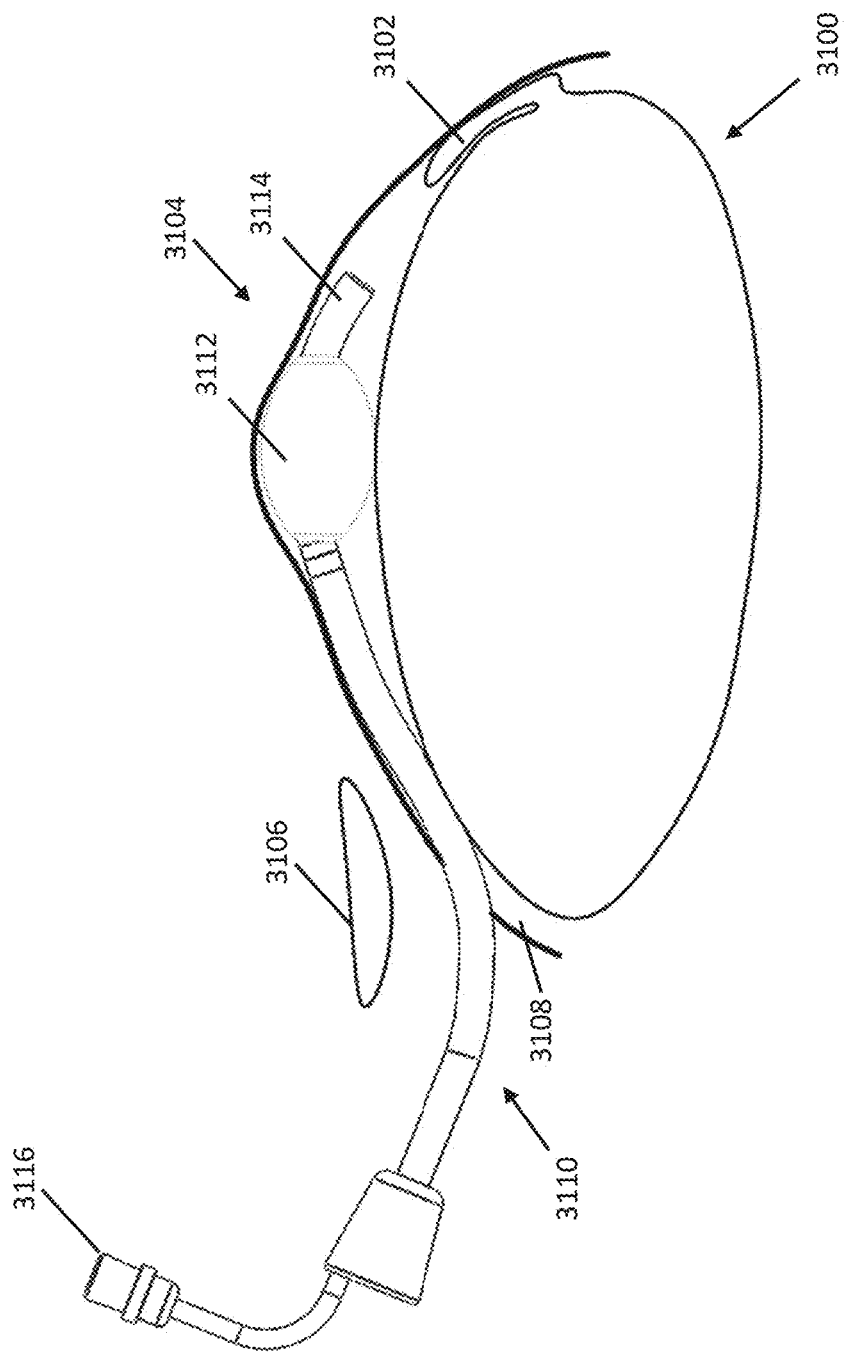

In some variations, the sheath (3110) may be used to increase separation between a pericardium and endocardium (e.g., a space in the pericardial cavity), which may increase a field-of-view for a distal end of the sheath (3110). The sheath (3110) may be advanced towards the left atrial appendage (3102). An expandable member (3112) of the sheath (3110) may be in a first configuration such that the pericardium (3104) drapes over the distal end (3114) of the sheath (3110). An expandable member (3112) may transition from the first configuration (FIG. 31B) to a second configuration (FIG. 31C) where the expandable member (3112) is inflated, which may lift up a distal portion of the sheath (3110) relative to the heart (3100). As shown in FIG. 31C, once the expandable member (3112) is in the second configuration, the distal end (3114) of the sheath (3110) may have a clear line-of-sight to the left atrial appendage (3102)

and surrounding anatomy to aid advancement of the sheath (3110) and devices advanced through the sheath (3110).

Additionally or alternatively, a sheath may be used for $CO_2$ insufflation of a pericardial cavity to increase separation between the pericardium and epicardium, which may increase a field-of-view of a distal end of the sheath (3710). FIG. 37A is a cross-sectional side view of a sheath (3710) disposed in the pericardial cavity (3708) and depicts the heart (3700) comprising a left atrial appendage (3702) and a pericardium (3704) covering the heart (3700). The xiphoid process (3706) is adjacent the heart (3700). A sheath (3710) is shown advanced into a pericardial cavity (3708) between pericardium (3704) and epicardium of the heart (3700). The sheath (3710) may be advanced towards the left atrial appendage (3702). A device (3714) (e.g., closure device, vacuum tube, imaging device) may be disposed in and extend out of a distal end of the sheath (3712). FIG. 37A illustrates the pericardium (3704) draped over sheath (3712) and the device (3714) prior to $CO_2$ insufflation. A $CO_2$ gas source may be coupled to the port (3716) and may be used to insufflate the pericardial cavity with $CO_2$ so as to separate the pericardium (3704) from the epicardium of the heart (3700), as shown in FIG. 37B. A field-of-view from within the pericardial cavity may thus be improved. Generally, creation of an access site using a piercing needle through the pericardium creates an opening that creates a natural seal between the pericardium (3704) and sheath (3710) such that $CO_2$ leakage out of the pericardial cavity (3708) is minimized. Of course, additional $CO_2$ may be insufflated as necessary into the pericardial cavity (3708) to maintain a desired spacing in the pericardial cavity (3708).

The vacuum tube and elongate body of the closure device may then be advanced toward a target tissue (1706), such as the left atrial appendage. It should be appreciated that one or more imaging devices may be used to assist in guiding the closure device toward the target tissue. For example, as described above, one or more imaging devices on the closure device may be used and/or other imaging methods, for example, fluoroscopy, fluorescence (near-infrared fluorescence, laser-induced fluorescence) may be employed.

Once the closure device approaches the target tissue, the snare loop assembly, being in some variations retracted within a first lumen of the elongate body, may be advanced out of the elongate body (1708) so as to form and/or enlarge the aperture formed by the snare loop assembly. The vacuum tube may be advanced out of the first lumen of the elongate body (1710) and through the aperture of the snare loop assembly (1712). Once in a desired position, the target tissue within a field-of-view of a suction tip of the lumen of the vacuum tube may be directly imaged (1714). In some variations, the apex of the left atrial appendage and/or another desired contact location may be identified in the images generated by the imaging device.

Once a user identifies a desired contact location, the user may advance and steer the vacuum tube towards the desired contact location on the target tissue, for example, the apex of the left atrial appendage. For example, in some variations, the vacuum tube may be curved and a user may rotate (torque) the proximal end of the vacuum tube to steer the distal end to a desired location. Additionally or alternatively, the vacuum tube may be retracted into or otherwise positioned relative to the elongate body (e.g., with the distal end within a closed snare loop assembly) such that the vacuum tube may be maneuvered with or using the elongate body of the closure device. For example, the elongate body may comprise a curved distal region that may be steered by rotating (torqueing) a handle clockwise and/or counterclockwise. Rotation of the body may also result in rotation of the vacuum tube such that the elongate body may be used to steer the vacuum tube. The vacuum tube may be maneuvered to contact the tissue and draw a portion of the tissue into a lumen of the vacuum tube. In some variations, the vacuum tube may be aimed to contact the left atrial appendage while in other variations, the vacuum tube may be aimed to contact myocardial tissue near the left atrial appendage. The vacuum pump may be activated to generate a negative pressure in the vacuum tube (1716) to provide suction from the suction tip of the lumen of the vacuum tube based on the type of tissue in contact with the suction tip. When a vacuum is generated, the suction tip will tend to indiscriminately suction any soft tissue adjacent an opening of the vacuum tube, so long as the opening is sufficiently occluded by tissue that a vacuum seal is established. Therefore, generation of vacuum as the vacuum tube is advanced may undesirably suction tissue other than the left atrial appendage (e.g., pericardium, fat tissue). The target tissue may be pulled toward the vacuum tube (1718) and/or the vacuum tube may be pulled toward the target tissue and the target tissue may be releasably coupled to the suction tip of the vacuum tube at the contact location. The negative pressure applied to the target tissue via the vacuum tube may hold the target tissue in place relative to the vacuum tube (1718). The desired contact location may be selected to result in the appropriate positioning of the snare loop assembly relative to the target tissue to effectuate closure of the target tissue. The imaging device may provide the ability to visualize the target tissue to identify the desired contact location and to place the vacuum tube at the desired contact location. It should be appreciated that, in some variations, the vacuum tube may contact and stabilize the target tissue using negative pressure in combination with the use of mechanical force, e.g., a grasping element, while in other variations the vacuum tube may contact and stabilize the target tissue using only mechanical force.

In some variations, the vacuum tube may be advanced out of the elongate body and advanced to contact myocardial tissue near a left atrial appendage (e.g., on either side of an apex of the left atrial appendage using two or more elongate members). A suction force may be applied through the vacuum tube to hold the vacuum tube and closure device relative to the myocardium. The snare loop assembly and elongate body may be advanced toward the apex of the left atrial appendage.

Once the vacuum tube is positioned as desired relative to the target tissue (e.g., coupled to the desired contact location on the target tissue), the elongate body and the snare loop assembly extending therefrom may be advanced along the vacuum tube toward the target tissue and the suction tip of the vacuum tube (1720). In some variations, the vacuum tube may be used as a guide to advance the elongate body toward and retract the elongate body from the target tissue. The snare loop assembly may be advanced out of the elongate body before or after advancing the elongate body toward the suction tip of the vacuum tube. In some variations, advancement and deployment of the elongate body, vacuum tube, and the snare loop assembly may be indirectly visualized using any appropriate imaging method, for example, fluoroscopy and/or transesophageal echocardiography (TEE). Additionally or alternatively, advancement and deployment of the elongate body, vacuum tube, and the snare loop assembly may use an electrophysiology diagnostic device such as one or more electrodes disposed on a surface of one or more of the elongate body, vacuum tube, and snare. Electrophysiology data received from the electrodes may be used to identify tissue and locate the closure devices relative to cardiac structures. In some variations, the received data from an electrophysiology diagnostic device may be used in conjunction with other mapping data (e.g., CT data) to generate a map of cardiac structures. The generated cardiac map may be displayed to an operator to guide the procedure.

The snare loop assembly may be advanced around the target tissue (1722). As the elongate body is advanced toward and over the target tissue, the snare loop assembly extending from a distal end of the elongate body will also be advanced around the target tissue. For instance, in variations in which the procedure is a left atrial appendage closure procedure, the snare loop assembly may be advanced around the left atrial appendage to the base or ostial neck of the left atrial appendage. Once advanced to a desired position, the snare loop assembly may be closed around the target tissue (1724), for example, the base or ostial neck of the left atrial appendage.

The snare loop assembly may be opened and closed by a snare control on the handle as necessary to ensure that the target tissue is properly ligated. After the snare loop assembly is determined to be positioned properly, the suture loop may be released from the snare loop assembly (1726) by, for instance, pulling a suture fob on the handle. The snare may be retracted into the elongate body (1728) and the suture loop may be tightened around the target tissue (1730). The elongate body may be retracted away from the target tissue (1732). The vacuum pump may be disabled or otherwise disconnected such that the target tissue is released and the vacuum tube is decoupled from the target tissue (1734). Once the vacuum pump is disabled and the tissue is released, the imaging device in the closure device may optionally be used to view the suture loop and target tissue (1736) or any other area of interest. The vacuum tube may then be at least partially retracted into the elongate body (1738), the closure device may be withdrawn from the body (1740), and the tail of the suture may be cut.

Figure 18A:
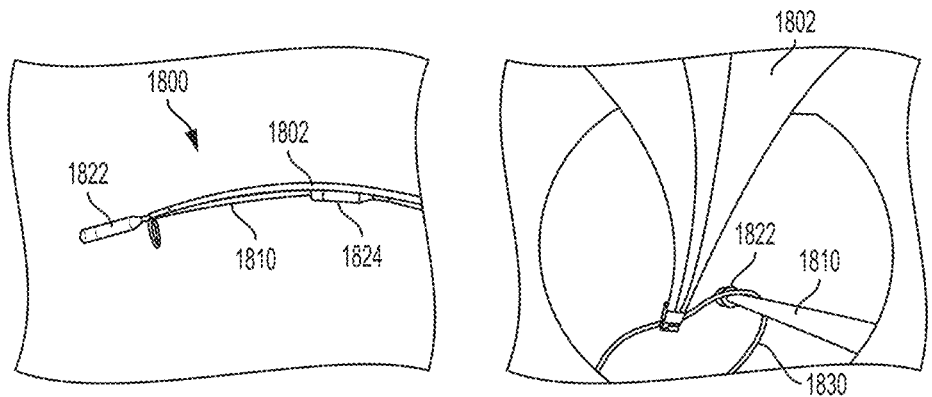
FIGS. 18A-18C depict an illustrative variation of a closure device and corresponding images generated by the closure device.
Figure 18B:
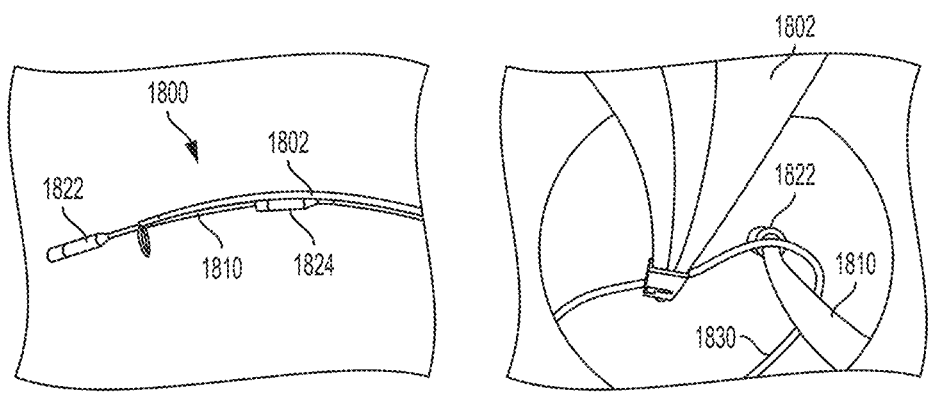
Figure 18C:
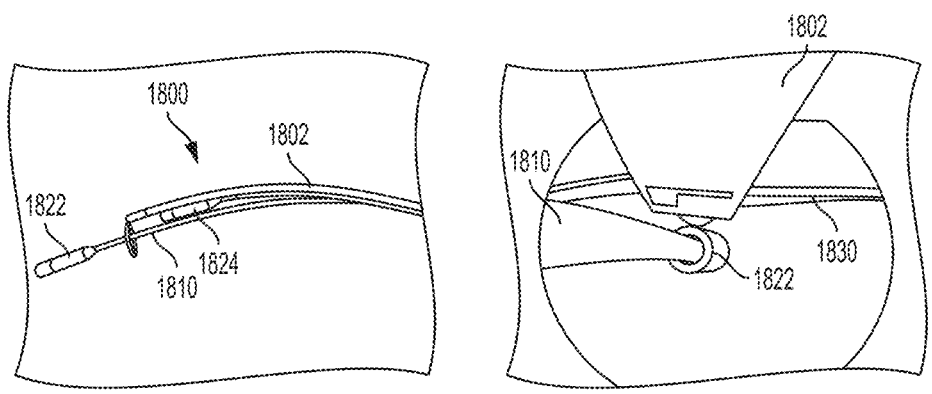

As shown in FIGS. 18A-18C, a closure device (1800) may comprise an imaging device (1824) disposed outside a vacuum tube (1810) configured to be advanced relative to the vacuum tube (1810) and elongate body (1802) to aid in visualization of the closure device (1800). In particular, an imaging device (1824) disposed outside of the vacuum tube (1810) may aid visualization of a snare loop (1830) as it is advanced over the vacuum tube (1810). FIG. 18A depicts the imaging device (1824) in a proximal position relative to the elongate body (1802) and vacuum tube (1810) adjacent the corresponding image from the imaging device showing the elongate body (1802), vacuum tube (1810), suction tip (1822) of the vacuum tube (1810), and snare loop (1830). As the imaging device (1824) is advanced distally to an intermediate position in FIG. 18B, the elongate body (1802), vacuum tube (1810), suction tip (1822) of the vacuum tube (1810), and snare loop (1830) are more clearly distinguishable. In a distal position shown in FIG. 18C, the imaging device (1824) is able to obtain a close-up image of the elongate body (1802), vacuum tube (1810), suction tip (1822) of the vacuum tube (1810), and snare loop (1830).

Figures 27D, 27E, 27F:
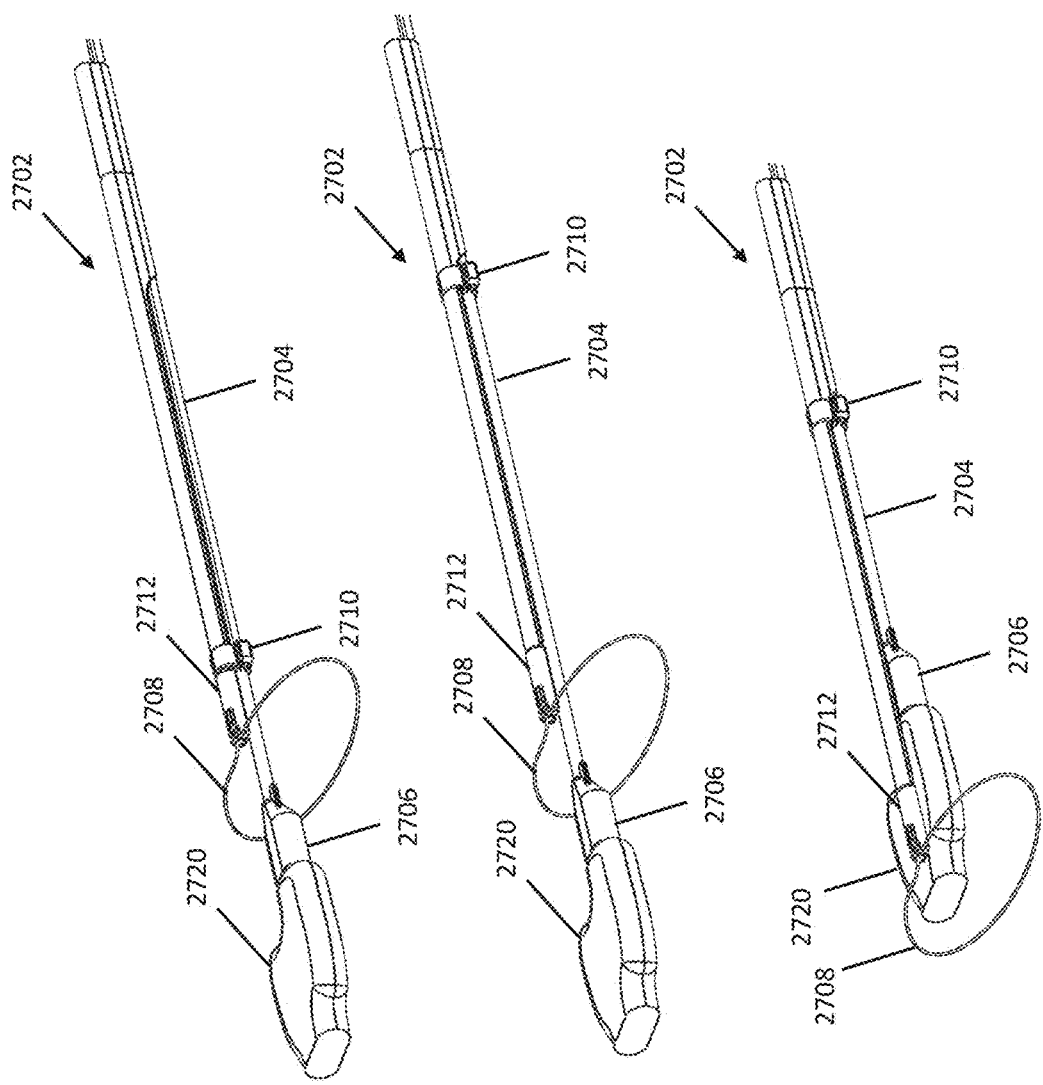

In some variations, a closure device comprising a vacuum tube slidably adjacent to an elongate body and held together by a fastener may be used in a tissue closure procedure. As depicted in FIGS. 27A-27F, a closure device (2700) may comprise a vacuum tube (2704) slidably positioned relative to an elongate body (2702). The elongate body (2702) may comprise a distal tip (2712) and a snare loop assembly (2708) extending therefrom. The vacuum tube (2704) may extend from a lumen of the elongate body (2702) and may comprise a suction tip (2706) (e.g., vacuum/imaging cup) and a lumen extending therethrough. An imaging device may be disposed within a lumen of the vacuum tube (2704) and may be configured to be advanced relative to the elongate body (2702) to aid in visualization of the closure device (2700) (e.g., snare loop) and tissue (e.g., left atrial appendage). FIG. 27A depicts the suction tip (2706) of the vacuum tube (2704) and fastener (2710) in a first position (e.g., most proximal position) relative to the elongate body (2702). In the first position, the vacuum tube (2704) and fastener (2710) may be at a most retracted position with respect to the elongate body (2702). The suction tip (2706) of the vacuum tube (2704) may be mated with the fastener (2710) to maintain an orientation and distance between the suction tip (2706) and a portion of the elongate body (2702). In some variations, the closure device (2700) may be advanced into a pericardial space of a patient with the vacuum tube (2704) and fastener (2710) in the first position. An imaging device disposed in the suction tip (2706) may be used to visually guide the advancement of the closure device (2700). A snare loop of the snare loop assembly (2708) is shown forming a loop in FIGS. 27A-27B for the sake of illustration.

As the vacuum tube (2704) and fastener (2710) are advanced distally to a second position (e.g., an intermediate position) in FIG. 27B, the vacuum tube (2704) mated with the fastener (2710) may move together with the fastener (2710) along a length of the elongate body (2702). That is, the fastener (2710) may fix a position of the suction tip (2706) of the vacuum tube (2704) relative to a portion of the elongate body (2702) such that the elongate body (2702) and vacuum tube (2702) may be steered together to efficiently advance the closure device (2700) through a body cavity. Moreover, an operator may position the vacuum tube (2704) and fastener (2710) at a desired location relative to the elongate body (2702) based on a desired viewpoint of an imaging device disposed within a lumen of a suction tip (2706) the vacuum tube (2704). This allows operator to visually guide the advancement of the closure device (2700) (e.g., to locate a left atrial appendage (2720)). As the closure device (2700) is advanced through a pericardial space, a distal tip (2712) of the elongate body (2702) may contact and push the pericardium to create an open space under the distal tip (2712) of the elongate body (2702) and in front of the suction tip (2706) of the vacuum tube (2704). This may improve a field-of-view of the imaging device and make it easier for an operator to locate anatomical features such as the left atrial appendage.

In a third position (e.g., flush position) of the vacuum tube (2704) and fastener (2710) shown in FIG. 27C, the suction tip (2706) of the vacuum tube (2704) may be in contact with and disposed under the distal tip (2712). The suction tip (2706) may also be aligned with or disposed within an aperture of the snare loop assembly (2708). The fastener (2710) in the third position may be slidably positioned to contact the proximal ends of each of the distal tip (2712) and suction tip (2706). In some variations, a user may transition the closure device (2700) from the second position to the third position upon identification and visual confirmation of the left atrial appendage (2720) within a predetermined distance. An imaging device disposed within the vacuum tube (2704) in the third position may be configured to obtain a close-up image of the left atrial appendage (2720). For example, image data of the left atrial appendage (2720) may be used to identify specific features such as the lobes of the appendage (2720).

As depicted in FIG. 27D, the vacuum tube (2704) may be advanced distal of the distal tip (2712) and through a snare loop of the snare loop assembly (2708). The position of the fastener (2710) abutting the distal tip (2712) may help ensure that the vacuum tube (2704) and distal tip (2712) are closely held together, which may make it more probable that the vacuum tube (2704) will successfully pass through the aperture of the snare loop (2708) as the vacuum tube (2704) is advanced. As the vacuum tube (2704) is advanced, the imaging device may be used by the operator to confirm that the vacuum tube (2704) is advanced through the snare loop. The fastener (2710) decouples from the suction tip (2706) when the vacuum tube (2704) is advanced in FIG. 27D because the distal tip (2712) prevents further distal advancement of the fastener (2710). The vacuum tube (2704) may be further advanced to contact the left atrial appendage (2720). The imaging device may be used to guide advancement of the vacuum tube and may generate images such as those described herein (e.g., FIG. 12A). A vacuum suction force may be applied to the left atrial appendage as the left atrial appendage is imaged by the imaging device. For example, the operator may confirm that the vacuum tube (2704) has drawn in left atrial appendage tissue (e.g., FIG. 12B) using the imaging device. As tissue is drawn further into the vacuum tube (2704), the operator may confirm the capture and hold of tissue within a lumen of the vacuum tube (2704) (e.g., FIGS. 12C-12D).

FIG. 27E depicts the fastener (2710) slidably positioned in the first position while the vacuum tube (2706) holds the left atrial appendage (2720). This allows the elongate body (2702) to be advanced toward the left atrial appendage (2720) and distal to the suction tip (2706) of the vacuum tube (2704) without interference from the fastener (2710). For example, as shown in FIG. 27F, as the elongate body (2702) is advanced distal to the suction tip (2706) of the vacuum tube (2704) and over the left atrial appendage (2720), the snare loop assembly (2708) may encircle the left atrial appendage (2720). The fastener (2710) may move relative to the left atrial appendage (2720) but does not interfere with a tissue closure procedure. The remaining steps may follow a tissue closure procedure as described herein (e.g., FIG. 17).

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination. The description of certain elements or characteristics with respect to a specific figure are not intended to be limiting or nor should they be interpreted to suggest that the element cannot be used in combination with any of the other described elements.

We claim:

1. A method of closing a target tissue comprising:
   advancing a device towards the target tissue, wherein the device comprises an elongate body comprising a first lumen therethrough, a snare loop assembly comprising a snare and a suture loop releasably coupled to the snare, a vacuum tube slidably positioned within the first lumen, the vacuum tube comprising a second lumen therethrough, and an imaging device fixed within a distal end of the second lumen;
   advancing the vacuum tube out of the elongate body and through the snare loop assembly;
   imaging the target tissue using the imaging device;
   applying vacuum to the target tissue through the second lumen;
   advancing the snare loop assembly around the target tissue; and
   tightening the suture loop around the target tissue.

2. The method of claim 1 further comprising closing the snare loop assembly around the target tissue and releasing the suture loop from the snare loop assembly.

3. The method of claim 1 wherein the application of vacuum to the target tissue draws the target tissue to a distal opening of the vacuum tube.

4. The method of claim 3 wherein the application of vacuum releasably couples the vacuum tube to the target tissue.

5. The method of claim 4 wherein the application of vacuum releasably couples the vacuum tube to an anterior lobe of the left atrial appendage.

6. The method of claim 1 further comprising advancing the elongate body and the vacuum tube through a sheath.

7. The method of claim 1 further comprising advancing the elongate body and the vacuum tube through an access site into a pericardial space.

8. The method of claim 7 wherein the elongate body and vacuum tube are advanced percutaneously.

9. The method of claim 1 wherein advancing the snare loop assembly around the target tissue comprises advancing the elongate body towards the distal end of the vacuum tube.

10. The method of claim 9 wherein tightening the suture loop further comprises imaging the tightened suture loop around the target tissue using the imaging device.

11. The method of claim 1 further comprising expanding a distal end of the vacuum tube after advancing the vacuum tube out of the elongate body.

12. The method of claim 1 further comprising receiving an electrocardiogram signal using one or more electrodes disposed on the device.

13. The method of claim 1 wherein the target tissue is a left atrial appendage.

14. The method of claim 1 wherein the device further comprises a fastener fixing the imaging device to the vacuum tube.

15. The method of claim 14 wherein the fastener comprises a side aperture configured to allow transmission of vacuum therethrough.

16. The method of claim 14 wherein the fastener is concentric with the vacuum tube.

17. The method of claim 1 wherein the imaging device is offset from a distal opening of the vacuum tube.

18. The method of claim 17 wherein a distal end of a housing of the imaging device is positioned between about 0.20 cm and about 2.0 cm from the distal opening of the vacuum tube.

19. The method of claim 1 wherein imaging the target tissue with the imaging device comprises imaging the target tissue being drawn into the second lumen of the vacuum tube.

20. The method of claim 1, wherein advancing the device towards the target tissue comprises utilizing the imaging device during advancement to: confirm the position of the device within a body cavity, assist in guiding the device to the target tissue, assess the condition of the target tissue, and/or determine a contact location for releasable engagement with the vacuum tube.

* * * * *